US012685787B2

(12) United States Patent
Lau et al.

(10) Patent No.: US 12,685,787 B2
(45) Date of Patent: Jul. 21, 2026

(54) LIPID NANOPARTICLES WITH RNA FOR COSMETIC TREATMENT

(71) Applicant: Lipovectra Inc., San Antonio, TX (US)

(72) Inventors: Frank Ho Pak Lau, River Ridge, LA (US); Jason Bourgeois, San Antonio, TX (US)

(73) Assignee: Lipovectra Inc., San Antonio, TX (US)

( * ) Notice: Subject to any disclaimer, the term of this patent is extended or adjusted under 35 U.S.C. 154(b) by 0 days.

(21) Appl. No.: 19/431,261

(22) Filed: Dec. 23, 2025

(65) Prior Publication Data

US 2026/0115326 A1        Apr. 30, 2026

Related U.S. Application Data

(63) Continuation-in-part of application No. PCT/US2025/031590, filed on May 30, 2025.

(60) Provisional application No. 63/868,661, filed on Aug. 22, 2025, provisional application No. 63/771,940, filed on Mar. 14, 2025, provisional application No. 63/653,319, filed on May 30, 2024.

(51) Int. Cl.
| *C07H 21/02* | (2006.01) |
| *A61K 38/17* | (2006.01) |
| *A61K 48/00* | (2006.01) |

(52) U.S. Cl.
CPC .......... *A61K 48/0058* (2013.01); *A61K 38/17* (2013.01); *A61K 48/0041* (2013.01)

(58) Field of Classification Search
CPC ..................... A61K 48/0058; A61K 48/0041
See application file for complete search history.

(56) References Cited

U.S. PATENT DOCUMENTS

| | | | |
|---|---|---|---|
| 8,058,069 | B2 | 11/2011 | Yaworski et al. |
| 8,158,601 | B2 | 4/2012 | Chen et al. |
| 8,492,359 | B2 | 7/2013 | Yaworski et al. |
| 8,822,668 | B2 | 9/2014 | Yaworski et al. |
| 8,969,353 | B2 | 3/2015 | Mahon et al. |
| 9,364,435 | B2 | 6/2016 | Yaworski et al. |
| 9,738,593 | B2 | 8/2017 | Ansell et al. |
| 10,155,945 | B2 | 12/2018 | Knopov et al. |
| 10,189,802 | B2 | 1/2019 | Mahon et al. |
| 10,385,106 | B2 | 8/2019 | Bancel et al. |
| 10,406,113 | B2 | 9/2019 | Frederick et al. |
| 10,413,618 | B2 | 9/2019 | Guild et al. |
| 10,501,513 | B2 | 12/2019 | Bancel et al. |
| 10,703,789 | B2 | 7/2020 | De Fougerolles et al. |
| 10,821,175 | B2 | 11/2020 | Gindy et al. |
| 10,844,028 | B2 | 11/2020 | Mahon et al. |
| 11,141,378 | B2 | 10/2021 | Yaworski et al. |
| 11,291,631 | B2 | 4/2022 | Shah |
| 11,400,109 | B2 | 8/2022 | Karve et al. |
| 11,414,393 | B2 | 8/2022 | Mahon et al. |
| 11,583,504 | B2 | 2/2023 | Brader |

| | | | |
|---|---|---|---|
| 11,744,801 | B2 | 9/2023 | Schariter et al. |
| 11,786,607 | B2 | 10/2023 | Hoge et al. |
| 11,814,640 | B2 | 11/2023 | Harashima et al. |
| 12,011,507 | B2 | 6/2024 | Kurek et al. |
| 12,064,479 | B2 | 8/2024 | Drummond et al. |
| 12,077,501 | B2 | 9/2024 | Benenato et al. |
| 12,090,235 | B2 | 9/2024 | Horhota et al. |
| 12,151,029 | B2 | 11/2024 | Hennessy et al. |
| 12,286,625 | B2 | 4/2025 | Thibonnier |
| 12,357,575 | B2 | 7/2025 | Schariter et al. |
| 12,383,508 | B2 | 8/2025 | Almarsson et al. |
| 2013/0150625 | A1 | 6/2013 | Budzik et al. |
| 2023/0277457 | A1 | 9/2023 | Shepard et al. |
| 2023/0366001 | A1 | 11/2023 | Li et al. |
| 2024/0050908 | A1 | 2/2024 | Mitchell et al. |
| 2024/0261381 | A1 | 8/2024 | Bevers et al. |
| 2025/0049954 | A1 | 2/2025 | Karve et al. |
| 2025/0115872 | A1 | 4/2025 | Pourquie et al. |
| 2025/0152518 | A1 | 5/2025 | Hennessy et al. |

FOREIGN PATENT DOCUMENTS

| | | | |
|---|---|---|---|
| CN | 102423493 | B | 8/2013 |
| CN | 116875603 | A | 10/2023 |
| CN | 117551183 | A | 2/2024 |
| CN | 118453868 | A | 8/2024 |
| CN | 118496341 | A | 8/2024 |
| CN | 118549656 | A | 8/2024 |
| CN | 118557595 | A | 8/2024 |
| CN | 118638750 | A | 9/2024 |
| CN | 118662636 | A | 9/2024 |
| CN | 118879889 | A | 11/2024 |
| CN | 118909932 | A | 11/2024 |
| CN | 119302966 | A | 1/2025 |
| CN | 119679688 | A | 3/2025 |
| CN | 119732889 | A | 4/2025 |
| EP | 4509118 | A2 | 2/2025 |
| EP | 3638678 | B1 | 12/2025 |
| JP | 2024138266 | A | 10/2024 |
| JP | 2025005946 | A | 1/2025 |
| KR | 102512998 | B1 | 3/2023 |
| WO | 2006095837 | A1 | 8/2008 |
| WO | 2019046809 | A1 | 3/2019 |
| WO | 2020061284 | A1 | 3/2020 |

(Continued)

OTHER PUBLICATIONS

Kim et al., "Tongue Fat and its Relationship to Obstrucitve Sleep Apnea", Sleep, vol. 37, No. 10, 2014, pp. 1639-1648D.

(Continued)

*Primary Examiner* — Amy Rose Hudson
(74) *Attorney, Agent, or Firm* — LEASON ELLIS LLP

(57) ABSTRACT

A method for directing a change in cell state of white adipose tissue (WAT) which involve treating WAT cells with mRNA encapsulated inside lipid nanoparticles (LNPs). The mRNA encodes UCP1 or other proteins that may transition WAT to brown adipose tissue (BAT). The LNP may contain (C14-4:NCL:Cholesterol:PEG/Lipid Conjugate) at the molar ratio of (35:16:46.5:2.5), (50:10:38.5:1.5) or (56.5:10:31.8:1.7).

15 Claims, 33 Drawing Sheets

Specification includes a Sequence Listing.

(56) References Cited

FOREIGN PATENT DOCUMENTS

| WO | 2023118450 A1 | 6/2023 |
| WO | 2024005157 A1 | 1/2024 |
| WO | 2024130374 A1 | 6/2024 |
| WO | 2024159175 A2 | 8/2024 |
| WO | 2025085373 A1 | 4/2025 |

OTHER PUBLICATIONS

"Beige is all the Rage: Drug Treatment Stimulates Beige Fat Formation Resulting in Metabolic Health Benefits in People with Obesity", National Institute of Diabetes and Digestive and Kidney Diseases, News, May 1, 2020, 2 pages.

Wang et al., "Effect of Weight Loss on Upper Airway Anatomy and the Apnea-Hypopnea Index", American Journal of Respiratory and Critical Care Medicine, 2020, vol. 201, No. 6, pp. 718-727.

Xue et al., "LNP-RNA-engineered adipose stem cells for accelerated diabetic wound healing", Nature Communications, 2024, vol. 15:739. 13 pages.

Gavin, Kathleen M., "Origins of Adult Adipose Progenitors", Encyclopedia of Tissue Engineering and Regenerative Medicine, vol. 2, 2019, pp. 299-312.

Carrière et al., "Browning of White Adipose Cells by Intermediate Metabolites: An Adaptive Mechanism to Alleviate Redox Pressure", Diabetes, 2014, vol. 63, pp. 3253-3265.

An et al., "Adipose Tissue and Metabolic Health", Diabetes and Metabolism Journal, 2023, 47, pp. 595-611.

Arch, Jonathan R. S., "Challenges in b3-adrenoceptor agonist drug development", Therapeutic Advances in Endocrinology and Metabolism, 2011, 2(2), pp. 59-64.

Bartesaghi et al., "Subcutaneous delivery of FGF21 mRNA therapy reverses obesity, insulin resistance, and hepatic steatosis in diet-induced obese mice", Molecular Therapy: Nucleic Acids, 2022, vol. 28, pp. 500-513.

Baskaran et al., "TRPV1 Activation Antagonizes High-Fat Diet-Induced Obesity at Thermoneutrality and Enhances UCP-1 Transcription via PRDM-16", Pharmaceuticals, 2024, vol. 17, No. 1098, 16 pages.

Carpentier et al., "Brown Adipose Tissue—A Translational Perspective", Endocrine Reviews, 2023, 44, pp. 143-192.

Chen et al., "CPEB2-dependent translation of long 3'-UTR Ucp1 mRNA promotes thermogenesis in brown adipose tissue", The EMBO Journal, 2018, 37: e99071. 15 pages.

Choe et al., "Adipose Tissue Remodeling: its Role in energy Metabolism and Metabolic Disorders", Frontiers in Endocrinology, 2016, vol. 7, article 30, 16 pages.

Cohen et al., "Cell biology of fat storage", MBoC Perspective on Cell Biology and Human Health, 2016, vol. 27, p. 2523-2527.

Cohen et al., "The cellular and functional complexity of thermogenic fat", Nat Rev Mol Cell Biol., 2021, vol. 22, No. 6, pp. 393-409. 47 pages.

Cojocaru et al., "Mitochondrial Dysfunction, Oxidative Stress, and Therapeutic Strategies in Diabetes, Obesity, and Cardiovascular Disease", Antioxidants, 2023, 12, 658, 19 pages.

Fedorenko et al., "Mechanism of Fatty-Acid Dependent UCP1 Uncoupling in Brown Fat Mitochondria", Cell, 2012, vol. 151, No. 2, pp. 400-413. 26 pages.

El-Araby et al., "Adiponectin mRNA Conjugated with Lipid Nanoparticles Specifically Targets the Pathogenesis of Type 2 Diabetes", Aging and Disease, 2025, vol. 16, No. 2, pp. 1059-1079.

Emont et al., "A single-cell atlas of human and mouse white adipose tissue", Nature, 2022, vol. 603:926-933. 37 pages.

Hu et al., "Nanoparticles Targeting Macrophages as Potential Clinical Therapeutic Agents Against Cancer and Inflammation", Frontiers in Immunology, 2019, vol. 10, Article 1998, 14 pages.

Galmozzi et al., "ThermoMouse: an in vivo model to identify modulators of UCP1 expression in brown adipose tissue", Cell Rep., 2014, vol. 9, No. 5: 1584-1593. 19 pages.

Gaspar et al., "An update on brown adipose tissue biology: a discussion of recent findings", American Journal of Physiology, Endocrinology and Metabolism, 2021, 320, pp. E488-E495.

Gong et al., "Keys to the switch of fat burning: stimuli that trigger the uncoupling protein 1 (UCP1) activation in adipose tissue", Lipids in Health and Disease, 2024, 23:322, 27 pages.

Ikeda et al., "UCP1 Dependent and Independent Thermogenesis in Brown and Beige Adipocytes", Frontiers in Endocrinology, 2020, vol. 11, article 498, 6 pages.

Kim et al., "Brown Fat and Browning for the Treatment of Obesity and Related Metabolic Disorders", Diabetes and Metabolism Journal, 2016; 40(1), pp. 12-21.

Kissig et al., "Brown and Beige Adipose Thermogenesis" Cell, 2016, 116(1), 3 pages.: 258-258.e1. 3 pages.

Kurylowicz et al., "Induction of Adipose Tissue Browning as a Strategy to Combat Obesity", International Journal of Molecular Sciences, 2020, vol. 21: 6241. 28 pages.

Laursen et al., "Neuronal UCP1 expression suggests a mechanism for local thermogenesis during hibernation", PNAS, vol. 112, No. 5, pp. 1607-1612.

Lee et al., "Strategies for targeted gene delivery using lipid nanoparticles and cell-derived nanovesicles", Nanoscale Adv., 2023, vol. 5, pp. 3834-3856.

Liu et al., "An update on brown adipose tissue and obesity intervention: Function, regulation and therapeutic implications", Frontiers in Endocrinology, 2023, 13:1065263. 14 pages.

Liu et al., "The secretory function of adipose tissues in metabolic regulation", Life Metabolism, 2024, 3(2), loae003. 15 pages.

Lu et al., "Alternative Polyadenylation and Differential Regulation of Ucp1: Implications for Brown Adipose Tissue Thermogenesis Across Species", Frontiers in Pediatrics, 2021, vol. 8, Article 612279, 8 pages.

Luo et al., "Adipose tissue in control of metabolism", J Endocrinol., 2016, vol. 231, No. 3, pp. R77-R99. 39 pages.

McNeill et al., "Human brown adipose tissue as a therapeutic target: warming up or cooling down?" Eur J Endocrinol. 2021; 184(6), R243-R259.

Norota et al., "Lipid nanoparticle delivery of the CRISPR/Cas9 system directly into the mitochondria of cells carrying m.7778G>T mutation in MtDNA (mt-Atp8)", Scientific Reports, 2025, vol. 15, Article No. 18717, 13 pages.

O'mara et al., "Chronic mirabegron treatment increases human brown fat, HDL cholesterol, and insulin sensitivity", The Journal of Clinical Investigation, 2020, vol. 130, No. 5, pp. 2209-2219.

Poher et al., "Brown adipose tissue activity as a target for the treatment of obesity/insulin resistance", Frontiers in Physiology, 2015, vol. 6, article 4, 9 pages.

Porter et al., "The therapeutic potential of brown adipocytes in humans", Frontiers in Endocrinology, 2015, vol. 6, article 156, 8 pages.

Richard et al., "Adipose Tissue: Physiology to Metabolic Dysfunction", Endotext, Apr. 2020, 67 pages.

Ricquier, Daniel, "Uncoupling Protein 1 of Brown Adipocytes, the Only Uncoupler: A Historical Perspective", Frontiers in Endocrinology, 2011, vol. 2, Article 85. 7 pages.

Rosen et al., "What We Talk About When We Talk About Fat", Cell 2014, 156(0):20-44. 46 pages.

Sakaguchi, Masaji, "Adipose Tissue Dynamics, Thermogenesis, and Interorgan Connections for Preventing Obesity and Metabolic Disorders", JMA Journal, 2024, vol. 7, Iss. 2, pp. 172-177.

Schachner-Nedherer et al., "Lipid Nanoparticles as a Shuttle for Anti-Adipogenic miRNAs to Human Adipocytes" Pharmaceutics. 2023, vol. 15, 1983. 20 pages.

Schirinzi et al., "Browning of Adipocytes: A Potential Therapeutic Approach to Obesity", Nutrients, 2023, vol. 15, 2229, 20 pages.

Sidossis et al., "Brown and beige fat in humans: thermogenic adipocytes that control energy and glucose homeostasis", The Journal of Clinical Investigation, 2015, vol. 125, No. 2, pp. 478-486.

Solmonson et al., "Uncoupling Proteins and the Molecular Mechanisms of Thyroid Thermogenesis", Endocrinology. 2016;157(2):455-462.

(56) References Cited

OTHER PUBLICATIONS

Wang et al., "Specific muscle targeted delivery of miR-130a loaded lipid nanoparticles: a novel approach to inhibit lipid accumulation in skeletal muscle and obesity", Journal of Nanobiotechnology, 2025, 23:159, 18 pages.

Vegiopoulos et al., "Adipose tissue: between the extremes", The EMBO Journal, 2017, vol. 36, No. 14, pp. 1999-2017.

Yamada et al., "Mitochondrial drug delivery systems for macromolecule and their therapeutic application to mitochondrial diseases", Adv. Drug Deliv. Rev. 2008; 60, pp. 1439-1462.

Yamada et al., "MITO-Porter: A liposome-based carrier system for delivery of macromolecules into mitochondria via membrane fusion", Biochim. Biophys. Acta. 2008; 1778: pp. 423-432.

Yamada et al., "Dual Function MITO-Porter, a Nano Carrier Integrating Both Efficient Cytoplasmic Delivery and Mitochondrial Macromolecule Delivery", Molecular Therapy, 2011, vol. 19, No. 8, pp. 1449-1456.

Yasuzaki et al., Mitochondrial matrix delivery using MITO-Porter, a liposome-based carrier that specifies fusion with mitochondrial membranes, Biochem. Biophys. Res. Commun. 2010; 397(2):181-186. 38 pages.

Zhou et al., "Functional Attenuation of UCP1 as the Potential Mechanism for a Thickened Blubber Layer in Cetaceans", Mol Biol Evol., 2022, vol. 39, No. 11: msac230. 12 pages.

International Search Report and Written Opinion for PCT/US2025/031590 mailed Dec. 4, 2025. (9 pages).

Christian, Mark, "The browning of white fat", Endocrinologist, Issue 126, 2017, 6 pages.

Kahn et al., "Keeping It Local in Metabolic Disease: Adipose Tissue Paracrine Signaling and Insulin Resistance", Diabetes, vol. 71, 2022, pp. 599-609.

06 10µg

SEQUENCE LISTING

```
Sequence total quantity: 130
SEQ ID NO: 1           moltype = RNA   length = 2837
FEATURE                Location/Qualifiers
source                 1..2837
                       mol_type = other RNA
                       organism = synthetic construct
SEQUENCE: 1
ggagaattcg tcgactggat ccggtaccga ggagatctgc cgccgcgatc gccatgggcg    60
ggctgacagc cagcgacgtg cacccaaccc tgggagtgca gctgtttttcc gccggcattg   120
ctgcctgtct ggctgatgtg atcactttcc cactggacac agctaaagtg cggctgcagg   180
tgcagggcga gtgcccaaca agctctgtga tcaggtacaa gggcgtgctg gggaccatca   240
ccgccgtggt gaagaccgag ggcagaatga aactgtatag tggtcttccc gccggcctgc   300
agagacagat ttctagcgcc tcactgcgca ttggcctgta tgatacagtg caggagtttc   360
tgactgccgg caaggaaact gctccatccc tgggcagcaa aatcctggcc ggactcacaa   420
ctggcggcgt ggccgtcttc atcgggcagc ccactgaggt ggtgaaggtg cgcctgcagg   480
cccagagcca cttgcatggg atcaaaccca gatacacagg aacctacaac gcttacagaa   540
```

```
tcatcgccac caccgagggc ctgactgggc tgtggaaggg cactacccca aacctgatgc    600
ggagtgtgat cattaattgt actgagctgg tgacctatga tctgatgaag gaggcctttg    660
tgaagaacaa catcctggcc gacgacgtgc cttgtcacct ggtgagcgcc ctgatcgccg    720
gcttctgcgc cacagccatg agctcccccg tggacgtggt gaagacaaga ttcatcaata    780
gcccacctgg ccagtataaa tccgtgccta attgcgccat gaaggtgttc accaatgagg    840
ggcccaccgc ctttttcaag gggctggtgc cctccttcct gaggctgggc agttggaacg    900
tgatcatgtt cgtgtgtttc gaacagctga aaagagagct gtccaagtct agacagacca    960
tggactgcgc cacatgatga cccgggggatc caaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
agaagagctc tagagtcgac ctgcaggcat gcaagcttct cgagatgtga gcaaaaggcc   1140
agcaaaaggc caggaaccgt aaaaaggccg cgttgctggc gttttttccat aggctccgcc   1200
cccctgacga gcatcacaaa aatcgacgct caagtcagag gtggcgaaac ccgacaggac   1260
tataaagata ccaggcgttt ccccctggaa gctccctcgt gcgctctcct gttccgaccc   1320
tgccgcttac cggataccctg tccgcctttc tcccttcgag aagcgtggcg ctttctcata   1380
gctcacgctg taggtatctc agttcggtgt aggtcgttcg ctccaagctg ggctgtgtgc   1440
acgaaccccc cgttcagccc gaccgctgcg ccttatccgg taactatcgt cttgagtcca   1500
acccggtaag acacgactta tcgccactgg cagcagccac tggtaacagg attagcagag   1560
cgaggtatgt aggcggtgct acagagttct tgaagtggtg gcctaactac ggctacacta   1620
gaagaacagt atttggtatc tgcgctctgc tgaagccagt taccttcgga aaaagagttg   1680
gtagctcttg atccggcaaa caaaccaccg ctggtagcgg tggtttttttt gtttgcaagc   1740
agcagattac gcgcagaaaa aaaggatctc aagaagatcc tttgatcttt tctacggggt   1800
ctgacgctca gtggaacgaa aactcacgtt aagggatttt ggtcatgagc ctaggcgcg    1860
tcccgtcaag tcagcgtaat gctctgccag tgttacaacc aattaaccaa ttctgattag   1920
aaaaactcat cgagcatcaa atgaaactgc aatttattca tatcaggatt atcaatacca   1980
tatttttgaa aaagccgttt ctgtaatgaa ggagaaaact caccgaggca gttccatagg   2040
atggcaagat cctggtatcg gtctgcgatt ccgactcgtc caacatcaat acaacctatt   2100
aatttcccct cgtcaaaaat aaggttatca agtgagaaat caccatgagt gacgactgaa   2160
tccggtgaga atggcaaaag cttatgcatt tctttccaga cttgttcaac aggccagcca   2220
ttacgctcgt catcaaaatc actcgcatca accaaaccgt tattcattcg tgattgcgcc   2280
tgagcgagac gaaatacgcg atcgctgtta aaaggacaat tacaaacagg aatcgaatgc   2340
aaccggcgca ggaacactgc cagcgcatca acaatatttt cacctgaatc aggatattct   2400
tctaataccct ggaatgctgt ttttccgggg atcgcagtgg tgagtaacca tgcatcatca   2460
ggagtacgga taaaatgctt gatggtcgga gaggcataa attccgtcag ccagtttagt   2520
ctgaccatct catctgtaac atcattggca acgctacctt tgccatgttt cagaaacaac   2580
tctggcgcat cgggcttccc ataaagtcga tagattgtcg cacctgattg cccgacatta   2640
tcgcgagccc atttataccc atataaatca gcatccatgt tggaatttaa tcgcggcctt   2700
gagcaagacg tttcccgttg aatatggctc ataacacccc ttgtattact gtttatgtaa   2760
gcagacagtt ttattgttca tgatgatata ttttttatctt gtgcaatgta acatcagaga   2820
ttttgagaca caacgtg                                                   2837
```

```
SEQ ID NO: 2            moltype = RNA   length = 928
FEATURE                 Location/Qualifiers
source                  1..928
                        mol_type = other RNA
                        organism = synthetic construct
SEQUENCE: 2
atgggcgggc tgacagccag cgacgtgcac ccaaccctgg gagtgcagct gttttccgcc    60
ggcattgctg cctgtctggc tgatgtgatc actttcccac tggacacagc taaagtgcgg   120
ctgcaggtgc agggcgagtg cccaacaagc tctgtgatca ggtacaaggg cgtgctgggg   180
accatcaccg ccgtggtgaa gaccgagggc agaatgaaac tgtatagtgg tcttcccgcc   240
ggcctgcaga gacagatttc tagcgcctca ctgcgcattg gcctgtatga tacagtgcag   300
gagtttctga ctgccggcaa ggaaactgct ccatccctgg gcagcaaaat cctggccgga   360
ctcacaactg gcgcgcgtgc cgtcttcatc gggcagccca ctgaggtggt gaaggtgcgc   420
ctgcaggccc agagccactt gcatgggatc aaacccagat acacaggaac ctacaacgct   480
tacagaatca tcgccaccac cgagggcctg actgggctgt ggaagggctg taccccaaac   540
ctgatgcgga gtgtgatcat taattgtact gagctggtga cctatgatct gatgaaggag   600
gcctttgtga agaacaacat cctggccgac gacgtgcctt gtcacctggt gagcgccctg   660
atcgccggct ctgcgccac agccatgagc tcccccgtgg acgtggtgaa gacaagattc   720
atcaatagcc cacctggcca gtataaatcc gtgcctaatt gcgccatgaa ggtgttcacc   780
aatgaggggc ccaccgcctt tttcaagggg ctggtgccct ccttcctgag gctgggcagt   840
tggaacgtga tcatgttcgt gtgtttcgaa cagctgaaaa gagagctgtc caagtctaga   900
cagaccatgg actgcgccac atgatgac                                       928
```

```
SEQ ID NO: 3            moltype = RNA   length = 932
FEATURE                 Location/Qualifiers
source                  1..932
                        mol_type = other RNA
                        organism = synthetic construct
SEQUENCE: 3
cgccatgggc gggctgacag ccagcgacgt gcacccaacc ctgggagtgc agctgttttc    60
cgccggcatt gctgcctgtc tggctgatgt gatcactttc ccactggaca cagctaaagt   120
gcggctgcag gtgcagggcg agtgcccaac aagctctgtg atcaggtaca agggcgtgct   180
ggggaccatc accgccgtgg tgaagaccga gggcagaatg aaactgtata gtggtcttcc   240
cgccggcctg cagagacaga tttctagcgc ctcactgcgc attggcctgt atgatacagt   300
gcaggagttt ctgactgccg gcaaggaaac tgctccatcc ctgggcagca aaatcctggc   360
cggactcaca actggcggcg tggccgtctt catcgggcag cccactgagg tggtgaaggt   420
gcgcctgcag gcccagagcc acttgcatgg gatcaaaccc agatacacag gaacctacaa   480
cgcttacaga atcatcgcca ccaccgaggg cctgactggg ctgtggaagg gcactacccc   540
aaacctgatg cggagtgtga tcattaattg tactgagctg gtgacctatg atctgatgaa   600
```

```
ggaggccttt gtgaagaaca acatcctggc cgacgacgtg ccttgtcacc tggtgagcgc   660
cctgatcgcc ggcttctgcg ccacagccat gagctccccc gtggacgtgg tgaagacaag   720
attcatcaat agcccacctg gccagtataa atccgtgcct aattgcgcca tgaaggtgtt   780
caccaatgag gggcccaccg cctttttcaa ggggctggtg ccctccttcc tgaggctggg   840
cagttggaac gtgatcatgt tcgtgtgttt cgaacagctg aaaagagagc tgtccaagtc   900
tagacagacc atggactgcg ccacatgatg ac                                 932
```

SEQ ID NO: 4            moltype = RNA   length = 932
FEATURE                 Location/Qualifiers
source                  1..932
                        mol_type = other RNA
                        organism = synthetic construct
SEQUENCE: 4

```
caagatgggc gggctgacag ccagcgacgt gcacccaacc ctgggagtgc agctgttttc   60
cgccggcatt gctgcctgtc tggctgatgt gatcactttc ccactggaca cagctaaagt   120
gcggctgcag gtgcagggcg agtgcccaac aagctctgtg atcaggtaca agggcgtgct   180
ggggaccatc accgccgtgg tgaagaccga gggcagaatg aaactgtata gtggtcttca   240
cgccggcctg cagagacaga tttctagcgc ctcactgcgc attggcctgt atgatacagt   300
gcaggagttt ctgactgccg gcaaggaaac tgctccatcc ctgggcagca aaatcctggc   360
cggactcaca actggcggcg tggccgtctt catcgggcag cccactgagg tggtgaaggt   420
gcgcctgcag gcccagagcc acttgcatgg gatcaaaccc agatacacag gaacctacaa   480
cgcttacaga atcatcgcca ccaccgaggg cctgactggg ctgtggaagg gcactacccc   540
aaacctgatg cggagtgtga tcattaattg tactgagctg gtgacctatg atctgatgaa   600
ggaggccttt gtgaagaaca acatcctggc cgacgacgtg ccttgtcacc tggtgagcgc   660
cctgatcgcc ggcttctgcg ccacagccat gagctccccc gtggacgtgg tgaagacaag   720
attcatcaat agcccacctg gccagtataa atccgtgcct aattgcgcca tgaaggtgtt   780
caccaatgag gggcccaccg cctttttcaa ggggctggtg ccctccttcc tgaggctggg   840
cagttggaac gtgatcatgt tcgtgtgttt cgaacagctg aaaagagagc tgtccaagtc   900
tagacagacc atggactgcg ccacatgatg ac                                 932
```

SEQ ID NO: 5            moltype = RNA   length = 1160
FEATURE                 Location/Qualifiers
source                  1..1160
                        mol_type = other RNA
                        organism = synthetic construct
SEQUENCE: 5

```
agagggtcct gctggcgcga gggtgggtag gaggggacgc ggggactcgg cccccaacac   60
cgcgctccgt ctgcagccgc cgcctctgca ccgccgctgc ccggcggtcg gttcaaaaaa   120
cagaaatcgt gtttgctgcc cggcggacag gcgtgaagag caaggggaaag gaacttcctc   180
caccttcggg gctggagccc ttttcctctg catctccagt ctctgagtga agatgggcgg   240
gctgacagcc agcgacgtgc acccaaccct gggagtgcag ctgttttccg ccggcattgc   300
tgcctgtctg gctgatgtga tcactttccc actggacaca gctaaagtgc ggctgcaggt   360
gcagggcgag tgcccaacaa gctctgtgat caggtacaag ggcgtgctgg ggaccatcac   420
cgccgtggtg aagaccgagg gcagaatgaa actgtatagt ggtcttcccg ccggcctgca   480
gagacagatt tctagcgcct cactgcgcat tggcctgtat gatacagtgc aggagtttct   540
gactgccggc aaggaaactg ctccatccct gggcagcaaa atcctggccg gactcacaac   600
tggcggcgtg gccgtcttca tcgggcagcc cactgaggtg gtgaaggtgc gcctgcaggc   660
ccagagccac ttgcatggga tcaaacccag atacacagga acctacaacg cttacagaat   720
catcgccacc accgagggcc tgactgggct gtggaagggc actacccaa acctgatgcg   780
gagtgtgatc attaattgta ctgagctggt gacctatgat ctgatgaagg aggcctttgt   840
gaagaacaac atcctggccg acgacgtgcc ttgtcacctg gtgagcgcc tgatcgcgcc   900
cttctgcgcc acagccatga gctcccccgt ggacgtggtg aagacaagat tcatcaatag   960
cccacctggc cagtataaat ccgtgcctaa ttgcgccatg aaggtgttca ccaatgaggg   1020
gcccaccgc tttttcaagg ggctggtgcc ctccttcctg aggctgggca gttggaacgt   1080
gatcatgttc gtgtgtttcg aacagctgaa aagagagctg tccaagtcta gacagaccat   1140
ggactgcgcc acatgatgac                                               1160
```

SEQ ID NO: 6            moltype = RNA   length = 994
FEATURE                 Location/Qualifiers
source                  1..994
                        mol_type = other RNA
                        organism = synthetic construct
SEQUENCE: 6

```
acagcaccct cctgaaaact gcagcttcct tctcaccttg aagaataatc ctagaaaact   60
cacaaatgg gcgggctgac agccagcgac gtgcacccaa ccctgggagt gcagctgttt   120
tccgccggca ttgctgcctg tctggctgat gtgatcactt tcccactgga cacagctaaa   180
gtgcggctgc aggtgcaggg cgagtgccca acaagctctg tgatcaggta caagggcgtg   240
ctggggacca tcaccgccgt ggtgaagacc gagggcagaa tgaaactgta tagtggtctt   300
cccgccggcc tgcagagaca gatttctagc gcctcactgc gcattggcct gtatgataca   360
gtgcaggagt ttctgactgc cggcaaggaa actgctccat ccctgggcag caaaatcctg   420
gccggactca caactggcgg cgtggccgtc ttcatcgggc agcccactga ggtggtgaag   480
gtgcgcctgc aggcccagag ccacttgcat gggatcaaac ccagatacac aggaacctac   540
aacgcttaca gaatcatcgc caccaccgag ggcctgactg ggctgtggaa gggcactacc   600
ccaaacctga tgcggagtgt gatcattaat tgtactgagc tggtgaccta tgatctgatg   660
aaggaggcct ttgtgaagaa caacatcctg gccgacgacg tgccttgtca cctggtgagc   720
gccctgatcg ccggcttctg cgccacagcc atgagctccc ccgtggacgt ggtgaagaca   780
agattcatca atagcccacc tggccagtat aaatccgtgc ctaattgcgc catgaaggtg   840
ttcaccaatg aggggcccac cgccttttc aaggggctgg tgcctccctt cctgaggctg   900
ggcagttgga acgtgatcat gttcgtgtgt ttcgaacagc tgaaaagaga gctgtccaag   960
```

```
tctagacaga ccatggactg cgccacatga tgac                               994

SEQ ID NO: 7        moltype = RNA  length = 1393
FEATURE             Location/Qualifiers
source              1..1393
                    mol_type = other RNA
                    organism = synthetic construct
SEQUENCE: 7
atgggcgggc tgacagccag cgacgtgcac ccaaccctgg gagtgcagct gttttccgcc   60
ggcattggctg cctgtctggc tgatgtgatc actttcccac tggacacagc taaagtgcgg  120
ctgcaggtgc agggcgagtg cccaacaagc tctgtgatca ggtacaaggg cgtgctgggg   180
accatcaccg ccgtggtgaa gaccgagggc agaatgaaac tgtatagtgg tcttcccgcc   240
ggcctgcaga gacagatttc tagcgcctca ctgcgcattg gcctgtatga tacagtgcag   300
gagtttctga ctgcccggca ggaaactgct ccatccgtgc cagcaaaat cctggccgga    360
ctcacaactg cgcggcgtggc cgtcttcatc gggcagccca ctgaggtggt gaaggtgcgc   420
ctgcaggccc agagccactt gcatgggatc aaacccagat acacaggaac ctacaacgct   480
tacagaatca tcgccaccac cgagggcctg actgggctgt ggaagggcac taccccaaac   540
ctgatgcgga gtgtgatcat taattgtact gagctggtga cctatgatct gatgaaggag   600
gcctttgtga agaacaacat cctggccgac gacgtgcctt gtcacctggt gagcgccctg   660
atcgccggct tctgcgccac agccatgagc tcccccgtgg acgtggtgaa gacaagattc   720
atcaatagcc cacctggcca gtataaatcc gtgcctaatt gcgccatgaa ggtgttcacc   780
aatgagggc ccaccgcctt tttcaagggg ctggtgaccc ccttcctgag gctgggcagt    840
tggaacgtga tcatgttcgt gtgtttcgaa cagctgaaaa gagagctgtc caagtctaga   900
cagaccatgg actgcgccac atgatgactc agcttcaaga aaatgatgta acataccagt   960
gggaatcttg ctgactggat cataaaaaca aacaaaactt attcacttat tttaacctaa  1020
aaagataaag gaatttttggc agagaatttt ggacttttttt atataaaaaa gaggaaaatt 1080
aatgcctatt tcatataact ttttttttttt ctcagtgtct taagaagggg aaagcaaaac  1140
attcagcata taccctggca aatgtaatgc agataagcta ctgcatttga ccatttctgg   1200
agtgcaattg tgtgaatgaa tgtgaagaac tttaacatgt tttaattaca attccaactg   1260
gtggaaaaga aactgagtga aatgcagttt atatttataa atacttaaaa atgaagttat   1320
taaaaatatt agtttttatt aaccacagtt gtcagttaat atattcaata aagtattgct   1380
aataccctttt aaa                                                    1393

SEQ ID NO: 8        moltype = RNA  length = 1397
FEATURE             Location/Qualifiers
source              1..1397
                    mol_type = other RNA
                    organism = synthetic construct
SEQUENCE: 8
cgccatgggc gggctgacag ccagcgacgt gcacccaacc ctgggagtgc agctgttttc   60
cgccggcatt gctgcctgtc tggctgatgt gatcactttc ccactggaca cagctaaagt   120
gcggctgcag gtgcagggcg agtgcccaac aagctctgtg atcaggtaca agggcgtgct   180
ggggaccatc accgccgtgg tgaagaccga gggcagaaat gaaactgtata gtggtcttcc   240
cgccggcctg cagagacaga tttctagcgc ctcactgcgc attggcctgt atgatacagt   300
gcaggagttt ctgactgccg gcaaggaaac tgctccatcc ctgggcagca aaatcctggc   360
cggactcaca actggcggcg tggccgtctt catcgggcag cccactgagg tggtgaaggt   420
gcgcctgcag gcccagagcc acttgcatgg gatcaaaccc agatacacag gaacctacaa   480
cgcttacaga atcatcgcca ccaccgaggg cctgactggg ctgtggaagg gcactacccc   540
aaacctgatg cggagtgtga tcattaattg tactgagctg gtgacctatg atctgatgaa   600
ggaggccttt gtgaagaaca acatcctggc cgacgacgtg ccttgtcacc tggtgagcgc   660
cctgatcgcc ggcttctgcg ccacagccat gagctccccc gtggacgtgg tgaagacaag   720
attcatcaat agcccacctg gccagtataa atccgtgcct aattgcgcca tgaaggtgtt   780
caccaatgag gggcccaccg cctttttcaa ggggctggtg ccctccttcc tgaggctggg   840
cagttggaac gtgatcatgt tcgtgtgttt cgaacagctg aaaagagagc tgtccaagtc   900
tagacagacc atggactgcg ccacatgatg actcagcttc aagaaaatga tgtaacatac   960
cagtgggaat cttgctgact ggatcataaa aacaaacaaa acttattcac ttattttaac  1020
ctaaaaagat aaaggaattt ggcagagaa ttttggactt ttttatataa aaagaggaa   1080
aattaatgcc tatttcatat aacttttttt ttttctcagt gtcttaagaa ggggaaagca  1140
aaacattcag catataccct ggcaaatgta atgcagata ttgaccattt              1200
ctggagtgca attgtgtgaa tgaatgtgaa gaactttaac atgtttaat tacaattcca   1260
actggtggaa aagaaactga gtgaaatgca gtttatattt ataaatactt aaaaatgaag  1320
ttattaaaaa tattagtttt tattaaccac agttgtcagt taatatattc aataaagtat  1380
tgctaatacc ttttaaa                                                 1397

SEQ ID NO: 9        moltype = RNA  length = 1397
FEATURE             Location/Qualifiers
source              1..1397
                    mol_type = other RNA
                    organism = synthetic construct
SEQUENCE: 9
caagatgggc gggctgacag ccagcgacgt gcacccaacc ctgggagtgc agctgttttc   60
cgccggcatt gctgcctgtc tggctgatgt gatcactttc ccactggaca cagctaaagt   120
gcggctgcag gtgcagggcg agtgcccaac aagctctgtg atcaggtaca agggcgtgct   180
ggggaccatc accgccgtgg tgaagaccga gggcagaaat gaaactgtata gtggtcttcc   240
cgccggcctg cagagacaga tttctagcgc ctcactgcgc attggcctgt atgatacagt   300
gcaggagttt ctgactgccg gcaaggaaac tgctccatcc ctgggcagca aaatcctggc   360
cggactcaca actggcggcg tggccgtctt catcgggcag cccactgagg tggtgaaggt   420
gcgcctgcag gcccagagcc acttgcatgg gatcaaaccc agatacacag gaacctacaa   480
cgcttacaga atcatcgcca ccaccgaggg cctgactggg ctgtggaagg gcactacccc   540
```

-continued

```
aaacctgatg cggagtgtga tcattaattg tactgagctg gtgacctatg atctgatgaa    600
ggaggccttt gtgaagaaca acatcctggc cgacgacgtg ccttgtcacc tggtgagcgc    660
cctgatcgcc ggcttctgcg ccacagccat gagctccccc gtggacgtgg tgaagacaag    720
attcatcaat agcccacctg gccagtataa atccgtgcct aattgcgcca tgaaggtgtt    780
caccaatgag gggcccaccg cctttttcaa ggggctggtg ccctcctcc tgaggctggg      840
cagttggaac gtgatcatgt tcgtgtgtt cgaacagctg aaaagagagc tgtccaagtc      900
tagacagacc atggactgcg ccacatgatg actcagcttc aagaaaatga tgtaacatac    960
cagtgggaat cttgctgact ggatcataaa aacaaacaaa acttattcac ttattttaac    1020
ctaaaaagat aaaggaattt tggcagagaa ttttggactt ttttatataa aaaagaggaa    1080
aattaatgcc tatttcatat aactttttt ttttctcagt gtcttaagaa ggggaaagca    1140
aaacattcag catataccct ggcaaatgta atgcagataa gctactgcat ttgaccattt    1200
ctggagtgca attgtgtgaa tgaatgtgaa gaactttaac atgtttaat tacaattcca    1260
actggtggaa aagaaactga gtgaaatgca gtttatattt ataaatactt aaaaatgaag    1320
ttattaaaaa tattagtttt tattaaccac agttgtcagt taatatattc aataaagtat    1380
tgctaataac tttaaa                                                      1397

SEQ ID NO: 10       moltype = RNA  length = 1625
FEATURE             Location/Qualifiers
source              1..1625
                    mol_type = other RNA
                    organism = synthetic construct
SEQUENCE: 10
agagggtcct gctggcgcga gggtgggtag gaggggacgc ggggactcgg cccccaacac       60
cgcgctccgt ctgcagccgc cgcctctgca ccgccgctgc ccggcggtcg gttcaaaaaa      120
cagaaatcgg gtttgctgcc cggcggacag gcgtgaagag caagggaaag gaacttcctc      180
caccttcggg gctggagccc ttttcctctg catctccagt ctctgagtga agatgggcgg      240
gctgacagcc agcgacgtgc acccaaccct gggagtgcag ctgttttccg ccggcattgc      300
tgcctgtctg gctgatgtga tcactttccc actggacaca gctaaagtgc ggctgcaggt      360
gcagggcgag tgcccaacaa gctctgtgat caggtacaag ggcgtgctgg ggaccatcac      420
cgccgtggtg aagaccgagg gcagaatgaa actgtatagt ggtcttcccg ccggcctgca      480
gagacagatt tctagcgcct cactgcgcat tggcctgtat gatacagtgc aggagtttct      540
gactgccggc aaggaaactg ctccatccct gggcagcaaa atcctggccg gactcacaac     600
tggcggcgtg gccgtcttca tcgggcagcc cactgaggtg gtgaaggtgc gcctgcaggc      660
ccagagccac ttgcatggga tcaaacccag atacacagga acctacaacg cttacagaat      720
catcgccacc accgagggcc tgactgggct gtggaagggc actacccaa acctgatgcg       780
gagtgtgatc attaattgta ctgagctggt gacctatgat ctgatgaagg aggcctttgt      840
gaagaacaac atcctggccg acgacgtgcc ttgtcacctg gtgagcgccc tgatcgccgg      900
cttctgcgcc acagccatga gctcccccgt ggacgtggtg aagacaagat tcatcaatag      960
cccacctggc cagtataaat ccgtgcctaa ttgcgccatg aaggtgttca ccaatgatgg     1020
gcccaccgcc ttttttcaagg ggctggtgcc ctccttcctg aggctgggca gttggaacgt     1080
gatcatgttc gtgtgtttcg aacagctgaa aagagagctg tccaagtcta gacagaccat     1140
ggactgcgcc acatgatgac tcagcttcaa gaaaatgatg taacatacca gtgggaatct     1200
tgctgactgg atcataaaaa caaacaaaac ttattcactt atttttaacct aaaaagatct     1260
aggaattttg gcagagaatt ttggactttt ttatataaaa aagaggaaaa ttaatgccta     1320
tttcatataa cttttttt ttctcagtgt cttaagaagg ggaaagcaaa acattcagca     1380
tataccctgg caaatgtaat gcagataagc tactgcattt gaccatttct ggagtgcaat     1440
tgtgtgaaga actttaacat gttttaatta caattccaa acctgatgcg tggtggaaaa     1500
gaaactgagt gaaatgcagt ttatatttat aaatacttaa aaatgaagtt attaaaaata     1560
ttagttttta ttaaccacag ttgtcagtta atatattcaa taaagtattg ctaataacctt     1620
ttaaa                                                                   1625

SEQ ID NO: 11       moltype = RNA  length = 1459
FEATURE             Location/Qualifiers
source              1..1459
                    mol_type = other RNA
                    organism = synthetic construct
SEQUENCE: 11
acagcaccct cctgaaaact gcagcttcct tctcaccttg aagaataatc ctagaaaact       60
cacaaaatgg gcgggctgac agccagcgac gtgcacccaa ccctgggagt gcagctgttt      120
tccgccggca ttgctgcctg tctggctgat gtgatcactt tcccactgga cacagctaaa      180
gtgcggctgc aggtgcaggg cgagtgccca acaagctctg tgatcaggta caagggcgtg      240
ctgggggacca tcaccgccgt ggtgaagacc gagggcagaa tgaaactgta tagtggtctt      300
cccgccggcc tgcagagaca gatttctagc gcctcactgc gcattggcct gtatgataca      360
gtgcaggagt ttctgactgc cggcaaggaa actgctccat ccctgggcag caaaatcctg      420
gccggactca caactggcgg cgtggccgtc ttcatcgggc agcccactga ggtggtgaag      480
gtgcgcctgc aggcccagag ccacttgcat gggatcaaac ccagatacac aggaacctac      540
aacgcttaca gaatcatcgc caccaccgag ggcctgactg gctgtggaa gggcactacc      600
ccaaacctga tgcggagtgt gatcattaat tgtactgagc tggtgaccta tgatctgatg     660
aaggaggcct ttgtgaagaa caacatcctg gccgacgacg tgccttgtca cctggtgagc      720
gccctgatcg ccggcttctg cgccacagcc atgagctccc ccgtggacgt ggtgaagaca      780
agattcatca atagcccacc tggccagtat aaatccgtgc ctaattgcgc catgaaggtg      840
ttcaccaatg aggggcccac cgccttttt caaggggctg gtgcctcctt cctgaggctg       900
ggcagttgga acgtgatcat gttcgtgtgt ttcgaacagc tgaaaagaga gctgtccaag      960
tctagacagac catggactgc gccacatgat gactcagct tcaagaaaat gatgtaacat     1020
accagtggga atcttgctga ctggatcata aaaacaaaca aaacttattc acttatttta     1080
acctaaaaag ataaaggaat tttggcagag aattttggac tttttatat aaaaaagagg     1140
aaaattaatg cctatttcat ataactttt tttttctca gtgtcttaag aaggggaaag     1200
caaaacattc agcatatacc ctggcaaatg taatgcagat aagctactgc atttgaccat     1260
ttctggagtg caattgtgtg aatgaatgtg aagaacttta acatgtttta attacaattc     1320
```

-continued

```
caactggtgg aaaagaaact gagtgaaatg cagtttatat ttataaatac ttaaaaatga   1380
agttattaaa aatattagtt tttattaacc acagttgtca gttaatatat tcaataaagt   1440
attgctaata ccttttaaa                                                1459

SEQ ID NO: 12             moltype = RNA   length = 1223
FEATURE                   Location/Qualifiers
source                    1..1223
                          mol_type = other RNA
                          organism = synthetic construct
SEQUENCE: 12
atgggcgggc tgacagccag cgacgtgcac ccaaccctgg gagtgcagct gttttccgcc   60
ggcattgctg cctgtctggc tgatgtgatc actttcccac tggacacagc taaagtgcgg   120
ctgcaggtgc agggcgagtg cccaacaagc tctgtgatca ggtacaaggg cgtgctgggg   180
accatcaccg ccgtggtgaa gaccgagggc agaatgaaac tgtatagtgg tcttcccgcc   240
ggcctgcaga gacagatttc tagcgcctca ctgcgcattg gcctgtatga tacagtgcag   300
gagtttctga ctgccggcaa ggaaactgct ccatccctgg gcagcaaaat cctgccgga   360
ctcacaactg cggcgtggc cgtcttcatc gggcagccca ctgaggtggt gaaggtgcgc   420
ctgcaggccc agagccactt gcatgggatc aaacccagat acacaggaac ctacaacgct   480
tacagaatca tcgccaccac cgagggcctg actgggctgt ggaagggcac taccccaaac   540
ctgatgcgga gtgtgatcat taattgtact gagctggtga cctatgatct gatgaaggag   600
gcctttgtga agaacaacat cctggccgac gacgtgcctt gtcacctggt gagcgccctg   660
atcgccggct tctgcgccac agccatgagc tcccccgtgg acgtggtgaa gacaagattc   720
atcaatagcc cacctggcca gtataaatcc gtgcctaatt gcgccatgaa ggtgttcacc   780
aatgaggggc ccaccgcctt tttcaagggg ctggtgccct ccttcctgag gctgggcagt   840
tggaacgtga tcatgttcgt gtgtttcgaa cagctgaaaa gagagctgtc caagtctaga   900
cagaccatgg actgcgccac atgatgacct cgagctggtg ctgcatgcac gcaatgctag   960
ctgcccttt cccgtcctgg gtaccccgag tctcccccga cctcgggtcc caggtatgct   1020
cccacctcca cctgccccac tcaccacctg tgctagttcc agacacctcc caagcacgca   1080
gcaatgcagc tcaaaacgct tagcctagcc acacccccac gggaaacagc agtgattaac   1140
ctttagcaat aaacgaaagt ttaactaagc tatactaacc ccagggttgg tcaatttcgt   1200
gccagccaca ccctggagct agc                                          1223

SEQ ID NO: 13             moltype = RNA   length = 1227
FEATURE                   Location/Qualifiers
source                    1..1227
                          mol_type = other RNA
                          organism = synthetic construct
SEQUENCE: 13
cgccatgggc gggctgacag ccagcgacgt gcacccaacc ctgggagtgc agctgttttc   60
cgccggcatt gctgcctgtc tggctgatgt gatcactttc ccactggaca cagctaaagt   120
gcggctgcag gtgcagggcg agtgcccaac aagctctgtg atcaggtaca agggcgtgct   180
ggggaccatc accgccgtgg tgaagaccga gggcagaatg aaactgtata gtggtcttcc   240
cgccggcctg cagagacaga tttctagcgc ctcactgcgc attggcctgt atgatacagt   300
gcaggagttt ctgactgccg gcaaggaaac tgctccatcc ctgggcagca aaatcctggc   360
cggactcaca actggcggcg tggccgtctt catcgggcag cccactgagg tggtgaaggt   420
gcgcctgcag gcccagagcc acttgcatgg gatcaaaccc agatacacag gaacctacaa   480
cgcttacaga atcatcgcca ccaccgaggg cctgactggg ctgtggaagg gcactacccc   540
aaacctgatg cggagtgtga tcattaattg tactgagctg gtgacctatg atctgatgaa   600
ggaggccttt gtgaagaaca acatcctggc cgacgacgtg ccttgtcacc tggtgagcgc   660
cctgatcgcc ggcttctgcg ccacagccat gagctccccc gtggacgtgg tgaagacaag   720
attcatcaat agcccacctg gccagtataa atccgtgcct aattgcgcca tgaaggtgtt   780
caccaatgag gggcccaccg cctttttcaa ggggctggtg ccctccttcc tgaggctggg   840
cagttggaac gtgatcatgt tcgtgtgttt cgaacagctg aaaagagagc tgtccaagtc   900
tagacagacc atggactgcg ccacatgatg acctcgagct ggtactgcat gcacgcaatg   960
ctagcccgcc ctttcccgtc ctgggtaccc cgagtctccc ccgacctcgg gtcccaggta   1020
tgctcccacc tccacctgcc ccactcacca cctctgctag ttccagacac ctcccaagca   1080
cgcagcaatg cagctcaaaa cgcttagcct agccacaccc cacgggaaa cagcagtgat   1140
taacctttag caataaacga aagtttaact aagctatact aaccccaggg ttggtcaatt   1200
tcgtgccagc cacaccctgg agctagc                                      1227

SEQ ID NO: 14             moltype = RNA   length = 1227
FEATURE                   Location/Qualifiers
source                    1..1227
                          mol_type = other RNA
                          organism = synthetic construct
SEQUENCE: 14
caagatgggc gggctgacag ccagcgacgt gcacccaacc ctgggagtgc agctgttttc   60
cgccggcatt gctgcctgtc tggctgatgt gatcactttc ccactggaca cagctaaagt   120
gcggctgcag gtgcagggcg agtgcccaac aagctctgtg atcaggtaca agggcgtgct   180
ggggaccatc accgccgtgg tgaagaccga gggcagaatg aaactgtata gtggtcttcc   240
cgccggcctg cagagacaga tttctagcgc ctcactgcgc attggcctgt atgatacagt   300
gcaggagttt ctgactgccg gcaaggaaac tgctccatcc ctgggcagca aaatcctggc   360
cggactcaca actggcggcg tggccgtctt catcgggcag cccactgagg tggtgaaggt   420
gcgcctgcag gcccagagcc acttgcatgg gatcaaaccc agatacacag gaacctacaa   480
cgcttacaga atcatcgcca ccaccgaggg cctgactggg ctgtggaagg gcactacccc   540
aaacctgatg cggagtgtga tcattaattg tactgagctg gtgacctatg atctgatgaa   600
ggaggccttt gtgaagaaca acatcctggc cgacgacgtg ccttgtcacc tggtgagcgc   660
cctgatcgcc ggcttctgcg ccacagccat gagctccccc gtggacgtgg tgaagacaag   720
attcatcaat agcccacctg gccagtataa atccgtgcct aattgcgcca tgaaggtgtt   780
```

```
caccaatgag gggcccaccg ccttttccaa ggggctggtg ccctccttcc tgaggctggg   840
cagttggaac gtgatcatgt tcgtgtgttt cgaacagctg aaaagagagc tgtccaagtc   900
tagacagacc atggactgcg ccacatgatg acctcgagct ggtactgcat gcacgcaatg   960
ctagctgccc ctttcccgtc ctgggtaccc cgagtctccc ccgacctcgg gtcccaggta  1020
tgctcccacc tccacctgcc ccactcacca cctctgctag ttccagacac ctcccaagca  1080
cgcagcaatg cagctcaaaa cgcttagcct agccacaccc ccacgggaaa cagcagtgat  1140
taacctttag caataaacga aagtttaact aagctatact aaccccaggg ttggtcaatt  1200
tcgtgccagc cacaccctgg agctagc                                     1227

SEQ ID NO: 15          moltype = RNA  length = 1455
FEATURE                Location/Qualifiers
source                 1..1455
                       mol_type = other RNA
                       organism = synthetic construct
SEQUENCE: 15
agagggtcct gctggcgcga gggtgggtag gaggggacgc ggggactcgg cccccaacac    60
cgcgctccgt ctgcagccgc cgcctctgca ccgccgctgc ccggcggtcg gttcaaaaaa   120
cagaaatcgg gtttgctgcc cggcggacag gcgtgaagag caagggaaag gaacttcctc   180
caccttcggg gctggagccc tttccctctg catctccagt ctctgagtga agatgggcgg   240
gctgacagcc agcgacgtgc acccaaccct gggagtgcag ctgttttccg ccggcattgc   300
tgcctgtctg gctgatgtga tcactttccc actggacaca gctaaagtgc ggctgcaggt   360
gcagggcgag tgcccaacaa gctctgtgat caggtacaag ggcgtgctgg ggaccatcac   420
cgccgtggtg aagaccgagg gcagaatgaa actgtatagt ggtcttcccg ccggcctgca   480
gagacagatt tctagcgcct cactgcgcat tggcctgtat gatacagtgc aggagtttct   540
gactgccggc aaggaaactg ctccatccct gggcagcaaa atcctggccg gactcacaac   600
tggcggcgtg gccgtcttca tcgggcagcc cactgaggtg gtgaaggtgc gcctgcaggc   660
ccagagccac ttgcatggga tcaaacccag atacacagga acctacaacg cttacagaat   720
catcgccacc accgagggcc tgactgggct gtggaagggc actaccccaa acctgatgcg   780
gagtgtgatc attaattgta ctgagctggt gacctatgat ctgatgaagg aggcctttgt   840
gaagaacaac atcctggccg acgacgtgcc ttgtcaccga gtgagcgccc tgatcgccgg   900
cttctgcgcc acagccatga gctccccgt ggacgtggtg aagacaagat tcatcaatag   960
cccacctggc cagtataaat ccgtgcctaa ttgcgccatg aaggtgttca ccaatgaggg  1020
gcccaccgcc ttttcaagg ggctggtgcc ctccttcctg aggctgggca gttggaacgt  1080
gatcatgttc gtgtgtttcg aacagctgaa aagagagtc tccaagtcta gacagaccat  1140
ggactgcgcc acatgatgac ctcgagctgg tactgcatgc acgcaatgct agctgccct  1200
ttcccgtcct gggtacccg agtctccccc gacctcgggt cccaggtatg ctcccacctc  1260
cacctgcccc actcaccacc tctgctagtt ccagacacct cccaagcacg cagcaatgca  1320
gctcaaaacg cttagcctag ccacaccccc acgggaaaca gcagtgatta accttagca  1380
ataaacgaaa gtttaactaa gctatactaa ccccagggt ggtcaattc gtgccagcca  1440
caccctggag ctagc                                                 1455

SEQ ID NO: 16          moltype = RNA  length = 1289
FEATURE                Location/Qualifiers
source                 1..1289
                       mol_type = other RNA
                       organism = synthetic construct
SEQUENCE: 16
acagcaccct cctgaaaact gcagcttcct tctcaccttg aagaataatc ctagaaaact    60
cacaaaatgg gcgggctgac agccagcgac gtgcacccaa ccctgggagt gcagctgttt   120
tccgccggca ttgctgcctg tctggctgat gtgatcactt tcccactgga cacagctaaa   180
gtgcggctgc aggtgcaggg cgagtgccca acaagctctg tgatcaggta caagggcgtg   240
ctggggacca tcaccgccgt ggtgaagacc gagggcagaa tgaaactgta tagtggtctt   300
cccgccggcc tgcagagaca gatttctagc gcctcactgc gcattggcct gtatgataca   360
gtgcaggagt ttctgactgc cggcaaggaa actgctccat ccctgggcag caaaatcctg   420
gccggactca caactggcgg cgtggccgtc ttcatcgggc agcccactga ggtggtgaag   480
gtgcgcctgc aggcccagag ccacttgcat gggatcaaac ccagatacac aggaacctac   540
aacgcttaca gaatcatcgc caccaccgag ggcctgactg ggctgtggaa gggcactacc   600
ccaaacctga tgcggagtgt gatcattaat tgtactgagc tggtgaccta tgatctgatg   660
aaggaggcct ttgtgaagaa caacatcctg gccgacgacg tgccttgtca cctggtgagc   720
gccctgatcg ccggcttctg cgccacagcc atgagctccc ccgtggacgt ggtgaagaca   780
agattcatca atagcccacc tggccagtat aaatccgtgc ctaattgcgc catgaaggtg   840
ttcaccaatg aggggcccac cgccttttc aaggggctgg tgcctccctt cctgaggctg   900
ggcagttgga acgtgatcat gttcgtgtgt ttcgaacagc tgaaaagaga gctgtccaag   960
tctagacaga ccatggactg cgccacatga tgacctgagc tggtactgca tgcacgcaa  1020
tgctagctgc ccctttcccg tcctgggtac cccgagtctc ccccgacctc gggtcccagg  1080
tatgctccca cctccacctg ccccactcac cacctctgct agttccagac acctcccaag  1140
cacgcagcaa tgcagctcaa aacgcttagc ctagccacac cccacgggga aacagcagtg  1200
attaaccttt agcaataaac gaaagtttaa ctaagctata ctaaccccag ggttggtcaa  1260
tttcgtgcca gccacaccct ggagctagc                                  1289

SEQ ID NO: 17          moltype = RNA  length = 1142
FEATURE                Location/Qualifiers
source                 1..1142
                       mol_type = other RNA
                       organism = synthetic construct
SEQUENCE: 17
atgggcgggc tgacagccag cgacgtgcac ccaaccctgg gagtgcagct gttttccgcc    60
ggcattgctg cctgtctggc tgatgtgatc actttcccac tggacacagc taaagtgcgg   120
ctgcaggtgc agggcgagtg cccaacaagc tctgtgatca ggtacaaggg cgtgctgggg   180
```

```
accatcaccg ccgtggtgaa gaccgagggc agaatgaaac tgtatagtgg tcttcccgcc    240
ggcctgcaga gacagatttc tagcgcctca ctgcgcattg gcctgtatga tacagtgcag    300
gagtttctga ctgccggcaa ggaaactgct ccatccctgg gcagcaaaat cctggccgga    360
ctcacaactg gcgcgtggc cgtcttcatc gggcagccca ctgaggtggt gaaggtgcgc    420
ctgcaggccc agagccactt gcatgggatc aaacccagat acacaggaac ctacaacgct    480
tacagaatca tcgccaccac cgagggcctg actgggctgt ggaagggcac taccccaaac    540
ctgatgcgca gtgtgatcat taattgtact gagctggtga cctatgatct gatgaaggag    600
gcctttgtga agaacaacat cctggccgac gacgtgcctt gtcacctggt gagcgccctg    660
atcgccggct tctgcgccac agccatgagc tcccccgtgg acgtggtgaa gacaagattc    720
atcaatagcc cacctggcca gtataaatcc gtgcctaatt gcgccatgaa ggtgttcacc    780
aatgaggggc ccaccgcctt tttcaagggg ctggtgccct ccttcctgag gctgggcagt    840
tggaacgtga tcatgttcgt gtgtttcgaa cagctgaaaa gagagctgtc caagtctaga    900
cagaccatgg actgcgccac atgatgacgc tcgctttctt gctgtccaat ttctattaaa    960
ggttcctttg ttccctaagt ccaactacta aactggggga tattgaag ggccttgagc   1020
atctggattc tgcctgctcg ctttcttgct gtccaatttc tattaaaggt tcctttgttc   1080
cctaagtcca actactaaac tgggggatat tatgaagggc cttgagcatc tggattctgc   1140
ct                                                                  1142

SEQ ID NO: 18         moltype = RNA   length = 1146
FEATURE               Location/Qualifiers
source                1..1146
                      mol_type = other RNA
                      organism = synthetic construct
SEQUENCE: 18
cgccatgggc gggctgacag ccagcgacgt gcacccaacc ctgggagtgc agctgttttc     60
cgccggcatt gctgcctgtc tggctgatgt gatcactttc ccactggaca cagctaaagt    120
gcggctgcag gtgcagggcg agtgcccaac aagctctgtg atcaggtaca agggcgtgct    180
ggggaccatc accgccgtgg tgaagaccga gggcagaatg aaactgtata gtggtcttcc    240
cgccggcctg cagagacaga tttctagcgc ctcactgcgc attggcctgt atgatacagt    300
gcaggagttt ctgactgccg gcaaggaaac tgctccatcc ctgggcagca aaatcctggc    360
cggactcaca actggcggcg tggccgtctt catcgggcag cccactgagg tggtgaaggt    420
gcgcctgcag gcccagagcc acttgcatgg gatcaaaccc agatacacag gaacctacaa    480
cgcttacaga atcatcgcca ccaccgaggg cctgactggg ctgtggaagg gcactacccc    540
aaacctgatg cggagtgtga tcattaattg tactgagctg gtgacctatg atctgatgaa    600
ggaggccttt gtgaagaaca acatcctggc cgacgacgtg ccttgtcacc tggtgagcgc    660
cctgatcgcc ggcttctgcg ccacagccat gagctccccc gtggacgtgg tgaagacaag    720
attcatcaat agcccacctg gccagtataa atccgtgcct aattgcgcca tgaaggtgtt    780
caccaatgag gggcccaccg ccttttttcaa ggggctggtg ccctccttcc tgaggctggg    840
cagttggaac gtgatcatgt tcgtgtgttt cgaacagctg aaaagagagc tgtccaagtc    900
tagacagacc atggactgcg ccacatgatg acgctcgctt tcttgctgtc caatttctat    960
taaaggttcc tttgttccct aagtccaact actaaactgg gggatattat gaagggcctt   1020
gagcatctgg attctgcctg ctcgctttct tgctgtccaa tttctattaa aggttccttt   1080
gttccctaag tccaactact aaactggggg atattatgaa gggccttgag catctggatt   1140
ctgcct                                                              1146

SEQ ID NO: 19         moltype = RNA   length = 1146
FEATURE               Location/Qualifiers
source                1..1146
                      mol_type = other RNA
                      organism = synthetic construct
SEQUENCE: 19
caagatgggc gggctgacag ccagcgacgt gcacccaacc ctgggagtgc agctgttttc     60
cgccggcatt gctgcctgtc tggctgatgt gatcactttc ccactggaca cagctaaagt    120
gcggctgcag gtgcagggcg agtgcccaac aagctctgtg atcaggtaca agggcgtgct    180
ggggaccatc accgccgtgg tgaagaccga gggcagaatg aaactgtata gtggtcttcc    240
cgccggcctg cagagacaga tttctagcgc ctcactgcgc attggcctgt atgatacagt    300
gcaggagttt ctgactgccg gcaaggaaac tgctccatcc ctgggcagca aaatcctggc    360
cggactcaca actggcggcg tggccgtctt catcgggcag cccactgagg tggtgaaggt    420
gcgcctgcag gcccagagcc acttgcatgg gatcaaaccc agatacacag gaacctacaa    480
cgcttacaga atcatcgcca ccaccgaggg cctgactggg ctgtggaagg gcactacccc    540
aaacctgatg cggagtgtga tcattaattg tactgagctg gtgacctatg atctgatgaa    600
ggaggccttt gtgaagaaca acatcctggc cgacgacgtg ccttgtcacc tggtgagcgc    660
cctgatcgcc ggcttctgcg ccacagccat gagctccccc gtggacgtgg tgaagacaag    720
attcatcaat agcccacctg gccagtataa atccgtgcct aattgcgcca tgaaggtgtt    780
caccaatgag gggcccaccg ccttttttcaa ggggctggtg ccctccttcc tgaggctggg    840
cagttggaac gtgatcatgt tcgtgtgttt cgaacagctg aaaagagagc tgtccaagtc    900
tagacagacc atggactgcg ccacatgatg acgctcgctt tcttgctgtc caatttctat    960
taaaggttcc tttgttccct aagtccaact actaaactgg gggatattat gaagggcctt   1020
gagcatctgg attctgcctg ctcgctttct tgctgtccaa tttctattaa aggttccttt   1080
gttccctaag tccaactact aaactggggg atattatgaa gggccttgag catctggatt   1140
ctgcct                                                              1146

SEQ ID NO: 20         moltype = RNA   length = 1373
FEATURE               Location/Qualifiers
source                1..1373
                      mol_type = other RNA
                      organism = synthetic construct
SEQUENCE: 20
agagggtcct gctggcgcga gggtgggtag gaggggacgc ggggactcgg cccccaacac     60
```

```
cgcgctccgt ctgcagccgc cgcctctgca ccgccgctgc ccggcggtcg gttcaaaaaa   120
cagaaatcgg gtttgctgcc cggcggacag gcgtgaagag caaggggaaag gaacttcctc   180
caccttcggg gctggagccc ttttcctctg catctccagt ctctgagtga agatgggcgg   240
gctgacagcc agcgacgtgc acccaaccct gggagtgcag ctgtttttccg ccggcattgc   300
tgcctgtctg gctgatgtga tcactttccc actggacaca gctaaagtgc ggctgcaggt   360
gcagggcgag tgcccaacaa gctctgtgat caggtacaag ggcgtgctgg ggaccatcac   420
cgccgtggtg aagaccgagg gcagaatgaa actgtatagt ggtcttcccg ccggcctgca   480
gagacagatt tctagcgcct cactgcgcat tggcctgtat gatacagtgc aggagtttct   540
gactgccggc aaggaaactg ctccatccct gggcagcaaa atcctggccg gactcacaac   600
tggcggcgtg gccgtcttca tcgggcagcc cactgaggtg gtgaaggtgc gcctgcaggc   660
ccagagccac ttgcatggga tcaaacccag atacacagga acctacaacg cttacagaat   720
catcgccacc accgagggcc tgactgggct gtggaagggc actaccccaa acctgatgcg   780
gagtgtgatc attaattgta ctgagctggt gacctatgat ctgatgaagg aggcctttgt   840
gaagaacaac atcctggccg acgacgtgcc ttgtcacctg gtgagcgccc tgatcgccgg   900
cttctgcgcc acagccatga gctccccgt ggacgtggtg aagacaagat tcatcaatag   960
cccacctggc cagtataaat ccgtgcctaa ttgcgccatg aaggtgttca ccaatgaggg   1020
gcccaccgcc tttttcaagg ggctggtgcc ctccttcctg aggctgggca gttggaacgt   1080
gatcatgttc gtgtgtttcg aacagctgaa aagagagctg tccaagtcta cagacaccat   1140
ggactgcgcc acatgatgac gctcgctttc ttgctgtcca atttctatta aaggttcctt   1200
tgttccctaa gtccaactac taaactgggg gatattatga agggccttga gcatctggat   1260
tctgcctgct cgctttcttg ctgtccaatt tctattaaag gttcctttgt tccctaagtc   1320
caactactaa actgggggat attatgaagg gccttgagca tctggattct gcc           1373
```

SEQ ID NO: 21              moltype = RNA    length = 1208
FEATURE                    Location/Qualifiers
source                     1..1208
                           mol_type = other RNA
                           organism = synthetic construct
SEQUENCE: 21

```
acagcaccct cctgaaaact gcagcttcct tctcaccttg aagaataatc ctagaaaact   60
cacaaaatgg gcgggctgac agccagcgac gtgcacccaa ccctgggagt gcagctgttt   120
tccgccggca ttgctgcctg tctggctgat gtgatcactt tcccactgga cacagctaaa   180
gtgcggctgc aggtgcaggg cgagtgccca acaagctctg tgatcaggta caagggcgtg   240
ctggggacca tcaccgccgt ggtgaagacc gagggcagaa tgaaactgta tagtggtctt   300
cccgccggcc tgcagagaca gatttctagc gcctcactgc gcattggcct gtatgataca   360
gtgcaggagt ttctgactgc cggcaaggaa actgctccat ccctgggcag caaaatcctg   420
gccggactca caactggcgg cgtggccgtc ttcatcgggc agcccactga ggtggtgaag   480
gtgcgcctgc aggcccagag ccacttgcat gggatcaaac ccagatacac aggaacctac   540
aacgcttaca gaatcatcgc caccaccgag ggcctgactg ggctgtggaa gggcactacc   600
ccaaacctga tgcggagtgt gatcattaat tgtactgagc tggtgaccta tgatctgatg   660
aaggaggcct ttgtgaagaa caacatcctg gccgacgacg tgccttgtca cctggtgagc   720
gccctgatcg ccggcttctg cgccacagcc atgagctccc ccgtggacgt ggtgaagaca   780
agattcatca atagcccacc tggccagtat aaatccgtta caattgcgcc atgaaggtg   840
ttcaccaatg aggggcccac cgccttttc aaggggctgg tgcctcctt cctgaggctg   900
ggcagttgga acgtgatcat gttcgtgtgt ttcgaacagc tgaaaagaga gctgtccaag   960
tctagacaga ccatggactg cgccacatga tgacgctcgc tttcttgctg tccaatttct   1020
attaaaggtt cctttgttcc ctaagtccaa ctactaaact ggggggatatt atgaagggcc   1080
ttgagcatct ggattctgcc tgctcgcttt cttgctgtcc aatttctatt aaaggttcct   1140
ttgttcccta agtccaacta ctaaactggg ggatattatg aagggccttg agcatctgga   1200
ttctgcct                                                              1208
```

SEQ ID NO: 22              moltype = RNA    length = 924
FEATURE                    Location/Qualifiers
source                     1..924
                           mol_type = other RNA
                           organism = synthetic construct
SEQUENCE: 22

```
atgggcggcc tgactgccag cgacgtgcac cccaccctcg gcgtgcagct gtttagcgcc   60
ggaatcgcg cctgtctggc tgatgtgatt accttccctc tggacaccgc caaggtgcgg   120
ctgcaggtgc aaggcgagtg ccctaccagc agcgtgatta gatacaagg agttctggga   180
accatcacag ctgtggtgaa gacagaaggc agaatgaaac tgtacagcgg cctgccagcc   240
ggcctgcaga gacagatctc tagcgccagc ctgaggatcg gcctgtatga taccgtgcag   300
gagttcctga gcgccggaaa ggaaaccgct cctagcctgg gctctaagat cctggctggt   360
ctgaccacag gcggagtggc cgtgttcatc ggcgagccta cagaggtggt caaagtccgg   420
ctgcaagccc agtctcacct gcatggcatc aagcccagat acaccggcac ctacaacgcc   480
tacagaatca tcgccaccac cgagggcttg acaggcctgt ggaagggcac aacacctaat   540
ctgatgcgga gcgtgatcat caactgcacc gaactggtga cctacgacct gatgaaagag   600
gccttcgtga aaaacaacat cctggctgat gacgtgccct gccacctggt gtccgctctg   660
atcgccggct tctgcgccac agccatgagc tctcctgtgg acgtcgtgaa gaccagattc   720
atcaatagcc ctcctggaca gtacaagtcc gtgcccaact gtgccatgaa ggtgttcacc   780
aacgagggac ctacagcatt tttcaagggc ctggtgccat cattcctgag actgggctcc   840
tggaacgtga tcatgtttgt gtgcttcgag cagctgaagc gggaactgag caagagcaga   900
cagaccatga ctgcgccac ctga                                             924
```

SEQ ID NO: 23              moltype = RNA    length = 924
FEATURE                    Location/Qualifiers
source                     1..924
                           mol_type = other RNA
                           organism = synthetic construct

```
SEQUENCE: 23
atgggcggcc tgaccgcatc tgatgtgcat ccaacactgg gcgttcaact gttcagcgcc   60
ggaatcgccg cctgcctggc tgatgtgatc acattccccc tggacaccgc caaggtgcgg  120
ctgcaggtgc agggcgagtg ccctacaagc agcgtgatca gatacaaggg cgtgctggga  180
acaatcaccg ccgtggtcaa gaccgaaggg agaatgaagc tgtacagcgg cctgcctgcc  240
ggactccaga gacagattag ctccgcttct ctgcggatcg gcctgtacga taccgtgcag  300
gagttcctga ccgctggcaa ggagacagcc ccttctctgg gaagcaagat cctggccggc  360
ctcacaaccg gcggagtcgc cgtgttcatc ggccagccta ccgaggtggt gaaggtgcgc  420
ctgcaggccc agagccacct gcacggcatc aagcctagat atacaggcac ctacaacgcc  480
tacaggatca tcgctaccac cgagggcctg actggactgt ggaagggcac aacccctaat  540
ctgatgcgga gcgtgattat caactgcacc gaactggtga cctacgacct gatgaaagaa  600
gctttttgtga agaacaacat cctggccgac gacgtccect gtcacctggt gtccgccctg  660
atcgccggct tctgcgccac cgccatgagc agccccgtgg acgtggtgaa aacaagattc  720
atcaacagcc ctcctggcca atacaagtcc gtgcccaact gtgccatgaa agtgttcacc  780
aacgagggcc ctaccgcctt ttttaagggc ctggttccaa gcttcctgag actgggcagc  840
tggaatgtga tcatgttcgt gtgcttcgag cagctgaagc gggaactttc taagagcaga  900
cagaccatgg actgcgccac ctga                                         924

SEQ ID NO: 24          moltype = RNA   length = 924
FEATURE                Location/Qualifiers
source                 1..924
                       mol_type = other RNA
                       organism = synthetic construct
SEQUENCE: 24
atgggcggac tgaccgcttc tgatgttcat cctacattgg gcgtgcagct gttcagcgcc   60
ggcatcgccg cttgtctggc tgatgtgatc acattccct tggacaccgc aaaggtgcgg  120
ctgcaagtgc aaggcgagtg ccccaccagc tccgtgatcc ggtacaaggg agtcctgggt  180
acaatcaccg ccgtggtgaa aaccgaaggc agaatgaagc tgtacagcgg cctgccagcc  240
ggcctgcaga gacagatcag cagcgccagc ctgcggatcg gcctgtacga taccgtgcag  300
gagttcctga ccgctggcaa ggaaaaccgcc ccttctctgg gatctaaaat cctggccggg  360
ctgacaaccg gcggcgtggc cgtgtttatc ggccagccta cagaggtggt caaggtgcga  420
ctgcaggccc agagccacct gcacggcatt aagcccagat acaccggcac ctacaacgcc  480
tatagaatca tcgccaccac agaaggcctg acaggcctgt ggaagggcac aaccccctaat  540
ctgatgagat ctgtgatcat taactgcacc gagctggtga cctacgacct gatgaaagaa  600
gcctttgtga agaacaacat cctggccgac gacgtgcctt gccacctggt gtccgccctg  660
atcgccggct tctgcgccac agccatgagc agccctgtgg acgtggtgaa gaccagattc  720
atcaacagcc cacctggaca gtacaagtcc gtgcccaatt gtgccatgaa agtgttcacc  780
aacgagggcc ctaccgcttt tttcaaggga ctcgtcccca gcttcctgag gctcggcagc  840
tggaacgtga tcatgttcgt gtgcttcgag cagctgaaga gagagctgag caagagcaga  900
cagaccatgg actgcgccac atga                                         924

SEQ ID NO: 25          moltype = RNA   length = 924
FEATURE                Location/Qualifiers
source                 1..924
                       mol_type = other RNA
                       organism = synthetic construct
SEQUENCE: 25
atgggcggac tgaccgcctc tgatgtgcat cctaccctgg gcgtccagct gttcagcgcc   60
ggaatcgccg cttgtctggc tgatgtgatc accttccccc tggacacagc gaaggtcaga  120
ctgcaggtgc agggcgagtg tcctaccagc agcgtgatta gatacaaggg cgtgctggga  180
acaatcacag ctgtggtgaa gacagagggc agaatgaaac tgtacagcgg cctgcctgcc  240
ggcctgcaaa gacagatcag ctccgccagc ctgcggatcg gcctgtacga caccgtgcag  300
gagttcctga ccgccggcaa ggaaaaccgcc cctagcctgg gctccaagat cctggccggc  360
ttgaccaccg gaggcgtggc cgtgttcatc ggccagccta cagaagtggt gaaagtgcgg  420
ctgcaggccc agagccacct gcacggcatc aagcctagat acaccggcac ctacaacgcc  480
taccggatca tcgccacaac agaaggcctg acaggcctgt ggaagggcac aaccccctaat  540
ctgatgagaa gcgtgatcat caactgcacc gagctcgtga cctatgatct gatgaaagag  600
gccttcgtga agaacaacat cctggccgac gacgtgccat gccacctggt gtccgccctg  660
attgccggct tctgcgccac cgccatgagc tctcctgtgg acgttgtgaa aacccgcttt  720
atcaacagcc ccccggcca atacaagagc gtgcccaatt gcgccatgaa ggtctttacc  780
aacgagggtc ctacagcttt cttcaaggga ctggttccat cttttctgag actcggcagc  840
tggaacgtga tcatgttcgt gtgcttcgag cagctgaagc gggaactgag caagtctaga  900
cagaccatgg actgcgctac ctga                                         924

SEQ ID NO: 26          moltype = RNA   length = 924
FEATURE                Location/Qualifiers
source                 1..924
                       mol_type = other RNA
                       organism = synthetic construct
SEQUENCE: 26
atgggcggac tgaccgcttc tgatgtgcat cccaccctgg gcgttcaact gttcagcgcc   60
ggcatcgccg cttgtctggc agatgtgatc acctttccac tggacacagc caaggtgcgg  120
ctgcaggtgc agggcgagtg ccccacctcc tccgtgatta gatacaaggg cgttctcgga  180
accatcacag ccgtggtgaa gaccgaaggc agaatgaagc tgtacagcgg cctgcctgcc  240
ggactgcaga gacagatcag cagcgcctct ctgcggatcg gcctgtatga tacagtgcag  300
gagttcctga cagccggtaa ggaaaaccgcc cctagcctgg gatctaagat cctggccgga  360
ctgaccacag cgcgcgtcgc cgtgttcatc ggccagccta cagaggtggt gaaggtgcgg  420
cttcaagccc agagccacct gcacggcatc aagcctagat acaccggcac atacaacgcc  480
tacagaatca tcgctaccac cgagggcctg acaggccgt ggaagggcac caccccctaat  540
```

-continued

```
ctgatgagaa gcgtgatcat caactgtaca gaactggtga cctacgacct gatgaaagag   600
gcctttgtga aaaacaacat cctcgctgac gacgtgccct gccacctggt cagcgccctg   660
atcgccggct tctgcgccac cgccatgagc tctcctgtgg acgtggtcaa aaccagattc   720
atcaatagcc ccctggaca gtacaagagc gtgcctaact cgccatgaa agtgttcacc     780
aacgagggcc ctacagcttt tttcaagggc ctggtgccaa gcttcctgag actgggcagc   840
tggaacgtga ttatgttcgt gtgcttcgag cagctgaagc gggaactgag caagtcccgc   900
cagaccatgg actgcgccac ctga                                          924
```

SEQ ID NO: 27          moltype = RNA  length = 924
FEATURE                Location/Qualifiers
source                1..924
                      mol_type = other RNA
                      organism = synthetic construct
SEQUENCE: 27

```
atgggcggcc tgaccgccag cgacgtgcac cccacactgg gcgtgcagct gttcagcgcc   60
ggcatcgccg cctgcctggc tgatgtgatt acattccctc tggatacagc caaggtgcgg   120
ctgcaggtgc agggcgagtg ccctaccagc agcgtgatcc ggtacaaggg cgtgctgggc   180
accatcaccg cagtggtcaa gaccgagggc agaatgaagc tgtacagcgg cctcccccgc   240
ggactgcaaa gacagatcag ctctgcttct ctgagaatcg gactctatga taccgtgcag   300
gagttcctga ccgctggcaa ggaaaccgcc ccttccctgg gatctaagat cctggccggc   360
ctgacaaccg gcggagtggc cgtgttcatc ggccagccta ccgaagtggt gaaggtcagg   420
ctgcaggccc agagccatct gcacggcatc aaacccagat acaccggcac ctacaacgcc   480
tacagaatca tcgccaccac cgaaggcctg acaggcctgt ggaagggcac cacacctaat   540
ctgatgagaa gcgtgatcat caactgcacc gagctggtta catacgacct gatgaaagag   600
gcctttgtga agaacaacat cctggccgac gacgtgccct gtcacctggt gtccgccctg   660
atcgccggct tctgcgccac agccatgagc tctcctgtgg acgtggtgaa aaccagattc   720
atcaacagcc ctcctggcca gtacaagtcc gtgcccaatt gtgccatgaa agtttttcacc   780
aacgagggac ctacagcttt tttcaaggga ctggtcccaa gcttcctgcg gctgggcagc   840
tggaacgtga tcatgttcgt gtgctttgag cagctgaagc gggaactgag caagagcaga   900
caaacaatgg actgcgccac ctga                                          924
```

SEQ ID NO: 28          moltype = RNA  length = 924
FEATURE                Location/Qualifiers
source                1..924
                      mol_type = other RNA
                      organism = synthetic construct
SEQUENCE: 28

```
atgggcggac tgaccgctag cgacgtgcac cccacactgg gagtgcagct gttcagcgcc   60
ggcatcgccg cctgcctggc tgatgtgatc acattccccc tggacaccgc caaggtgcgg   120
ctgcaagtgc agggcgagtg ccctaccagc tccgtgatca gatacaaggg cgtgctgggc   180
accatcaccg ctgtggtcaa gaccgaaggc agaatgaaac tgtacagcgg cctgcctgcc   240
ggcctgcaga gacagatcag ctccgccagc ctgcggatcg gcctgtatga taccgttcag   300
gagttcctca ccgccggaaa agagacagcc ccttctctgg gctctaagat cctggccgga   360
ctcaccacag gcggcgtggc cgtgttcatc ggacagccta cagaagtggt gaaggtgcgg   420
cttcaggccc agagccatct gcacggcatc aagcctagat acaccggcac atacaacgcc   480
tacagaatca tcgccaccac cgaggcctg acaggcctgt ggaagggcac caccctaat   540
ctgatgagaa gcgtgattat caactgcacc gagctggtgta cctacgacct gatgaaggaa   600
gcttttgtga aaaacaacat cctggccgat gacgtcccat gtcacctggt cagcgccctg   660
atcgccggct tctgcgccac agctatgagc tctccagtgg acgtggtgaa gaccagattc   720
atcaacagcc ctcctggcca gtacaagtcc gtgcccaatt gtgccatgaa agtgtttacc   780
aacgagggtc ctactgcctt cttcaaggga ctggtgccca gctttctgag actgggcagc   840
tggaacgtga tcatgttcgt gtgcttcgag cagctgaagc gggaactgag caagtctagg   900
caaacaatgg actgcgccac atga                                          924
```

SEQ ID NO: 29          moltype = RNA  length = 861
FEATURE                Location/Qualifiers
source                1..861
                      mol_type = other RNA
                      organism = synthetic construct
SEQUENCE: 29

```
atcgccgctt gtctggctga tgtcatcacc ttccctctgg acaccgccaa ggtgcggctg   60
caggtgcagg gcgagtgccc caccagctct gtgattcggt acaagggcgt cctgggcacc   120
atcacagctg ttgtgaagac cgagggcaga atgaaactgt acagcggcct gcctgccgga   180
ctgcaaagac agatctcttc tgcttccctg agaatcggct tgtatgatac cgtgcaggag   240
ttcctcacag ccggcaagga gacagcccct agcctgggcc ccaagatcct ggccggcctg   300
accacaggcg gcgtcgccgt gttcatcggc cagcctaccg aggtggtgaa ggtgcggctg   360
caggcccaga gccatctgca cggcattaag cctagataca ccggcacata caacgcctac   420
agaatcatcg ccacaacaga aggcctgaca ggcctgtgga agggcaccac cctaacctg   480
atgagaagcg tgatcatcaa ttgcaccgaa ctggtgacct acgacctgat gaaggaagcc   540
tttgtgaaga caacatcct ggccgacgac gttccatgtc acctggtgtc tgccctgatc   600
gccgatttt gcgccacagc catgagctcc cccgtggacg tggtgaaaac cagattcatc   660
aacagccctc aggccagta caaaagcgtg cctaattgcg ccatgaaagt gttcaccaac   720
gagggaccta ccgcttttt caagggcctt gtgcccagct cctgaggct gggcagctgg   780
aacgtgatca tgttcgtgtg cttcgagcag ctgaagcggg aactgagcaa gagcagacag   840
accatggact gcgccacctg a                                              861
```

SEQ ID NO: 30          moltype = RNA  length = 924
FEATURE                Location/Qualifiers
source                1..924

-continued

```
                         mol_type = other RNA
                         organism = synthetic construct
SEQUENCE: 30
atgggcggcc tgactgcttc tgatgtgcac cccacactgg gcgtccaact gttcagcgcc    60
ggcatcgccg cctgcttggc tgacgtgatc acctttcctc tggacaccgc aaaggtgcgg   120
ctgcaggtgc agggcgagtg ccctacaagc tctgtgatcc ggtacaaggg cgttctggga   180
accatcacag ctgtggtcaa gaccgaggga agaatgaaac tgtacagcgg cctgcctgcc   240
ggcctgcaaa gacagatcag ctccgccagc ctgcggatcg gcctttatga taccgtgcag   300
gagttcctga ccgccggcaa ggaaaccgcc cctagcctgg gcagcaagat cctggccggc   360
ctgacaacag gaggcgtggc cgtgttcatc ggacagccta ccgaagtggt gaaggtgcgc   420
ctgcaggccc agagccacct gcacggcatc aagcctagat acacaggcac atacaacgct   480
tacagaatca tcgccaccac agagggcctg accggcctgt ggaagggcac cacccctaat   540
ctgatgagaa gcgtgattat caactgcacc gaactggtga cctacgacct gatgaaagag   600
gcctttgtga agaacaacat cctggccgac gacgtgccat gtcatctggt gtccgccctg   660
atcgccggat tctgcgctac cgccatgagc tccctgtgg acgtggtgaa aaccagattc   720
atcaacagcc cccccggcca gtacaagagc gtgcccaatt gcgccatgaa agtgttcacc   780
aacgagggc ctaccgcctt cttcaagggc ctcgttccaa gcttcctgag actgggatct   840
tggaacgtga ttatgttcgt gtgtttgag cagctgaagc gggaactgtc taagtcaaga   900
cagacaatgg attgcgccac atga                                           924

SEQ ID NO: 31       moltype = RNA  length = 924
FEATURE             Location/Qualifiers
source              1..924
                    mol_type = other RNA
                    organism = synthetic construct
SEQUENCE: 31
atgggcggcc tgaccgctag cgacgtgcat cctacactgg gcgtgcagct gttcagcgct    60
ggcatcgccg cctgcctggc cgatgttatc accttccccc tggataccgc caaggtcaga   120
ctgcaagtgc agggcgaatg tcctacaagc agcgtgatca gatacaaggg cgtgctggga   180
accatcacag ccgtggtgaa aacagagggc agaatgaaac tgtacagcgg cttgcctgcc   240
ggacttcaaa gacagatcag ctctgcttct ctgcggatcg gactgtacga tacagtgcag   300
gagttcctga ccgccggcaa ggaaaccgcc cctagcctgg gctccaagat cctggctgga   360
ctgacaactg gaggagtggc cgtgttcatc ggccagccta ccgaggtggt gaaggtgcgc   420
ctgcaggccc agagccacct gcacggcatc aagcccagat atacaggcac ctacaacgcc   480
taccggatta tcgccaccac cgaaggcctg accggcctgt ggaagggcac cacacctaat   540
ctgatgaggt ccgtgattat caattgcacc gagctggtga cctacgacct gatgaaagag   600
gcctttgtga agaacaacat cctggctgac gacgtgcctt gccacctggt gtccgccctg   660
atcgccggct tctgcgccac agccatgagc tctccagtgg acgttgtgaa gacaagattc   720
atcaacagcc cccccggcca gtacaaaagc gtgcctaact gtgccatgaa agtctttacc   780
aacgagggcc ctaccgcctt ctttaagggc ctcgtgccaa gcttcctgag actgggcagc   840
tggaacgtga tcatgttcgt gtgcttcgag cagctgaagc gggaactgtc taagagcaga   900
cagaccatgg actgcgccac ctga                                           924

SEQ ID NO: 32       moltype = RNA  length = 924
FEATURE             Location/Qualifiers
source              1..924
                    mol_type = other RNA
                    organism = synthetic construct
SEQUENCE: 32
atgggcggcc tgacagccag cgacgtccac cccaccctgg gcgtgcagct gttcagcgcc    60
ggcatcgctg cttgtctggc tgatgtgatc acttttccac tggataccgc aaaggtgccg   120
ctgcaggtgc agggcgagtg ccctaccagc tctgtgatca gatacaaggg cgtgctggga   180
acaatcaccg ccgttgttaa gacagaaggc agaatgaagc tgtacagcgg cctgcctgct   240
ggccttcaga gacagatcag cagcgcctct ctgcggatcg gcctgtacga caccgtgcag   300
gagttcctga ccgccggcaa ggaaaccgcc cctagcctgg gatctaagat cctggccggc   360
ctgacaaccg gaggagtcgc cgtgttcatc ggccagccta ccgaggtggt gaaagtgcgc   420
ctgcaggccc agagccacct gcacggcatc aagcctagat atacaggcac atacaacgcc   480
tacaggatca tcgccaccac cgagggcctg accggactct ggaagggcac cacccctaac   540
ctgatgaggt ccgtgattat caattgtacc gagctggtga cctacgacct gatgaaggaa   600
gccttcgtga aaacaacat cctggccgac gacgtgccct gccatctggt gtccgccctg   660
atcgccggct tctgcgccac agccatgagc tctccagtgg atgtggtgaa aaccagattc   720
atcaacagcc cccccggaca atacaagtcc gtgcctaatt gcgccatgaa agtgttcacc   780
aacgagggcc ctacagcttt tttcaagggc ctggtcccta gctttctgag actgggcagc   840
tggaacgtga ttatgttcgt gtgcttcgag cagctgaagc gggaactgag caagagcaga   900
caaacaatgg actgcgccac atga                                           924

SEQ ID NO: 33       moltype = RNA  length = 924
FEATURE             Location/Qualifiers
source              1..924
                    mol_type = other RNA
                    organism = synthetic construct
SEQUENCE: 33
atgggaggcc tgacagcttc tgatgtgcac cccaccctgg gcgtgcaact gttcagcgcc    60
ggcatcgccg cttgcctggc cgacgtgatc acattcccgg tggacaccgc caaggtgcgg   120
cttcaggtgc agggagaatg tcctaccagc agcgtgatca gatacaaggg cgtgctgggc   180
acaatcacag ctgtggtcaa gaccgaaggc agaatgaaac tgtacagcgg cctgcctgcc   240
ggcctgcaga gacagatcag ctccgccagc ctgaggatcg gcctgtacga caccgtgcag   300
gagttcctga ccgcaggcaa ggagacagcc cctagcctgg gcagcaagat cctggccggc   360
ctcacaaccg gaggagtggc cgtgttcatc ggccagccta ccgaggtggt gaaggtcaga   420
```

```
ctgcaggccc agtcccacct gcacggcatt aagcctagat acaccggcac ctataatgcc      480
taccggatca tcgccaccac cgagggactg accggcctct ggaagggcac aacacctaac      540
ctgatgcgga gcgtgatcat caactgcacc gagctggtta catacgacct gatgaaggaa      600
gcctttgtga aaaacaacat cctggctgat gatgttccat gtcatctggt gtccgccctg      660
atcgccggct tctgcgccac tgccatgagc tctcctgtgg acgtggtgaa aaccagattc      720
attaacagcc ctccaggcca atacaagagc gtgcccaatt gcgccatgaa ggtttttcacc     780
aacgagggcc ccaccgcttt tttcaaaggc ctggtgcctt cttttctgag actgggatct      840
tggaacgtga tcatgttcgt gtgcttcgag cagctgaagc gggaactgtc taagagcaga      900
cagaccatgg actgcgccac atga                                            924
```

```
SEQ ID NO: 34                  moltype = RNA  length = 924
FEATURE                        Location/Qualifiers
source                         1..924
                               mol_type = other RNA
                               organism = synthetic construct
SEQUENCE: 34
atgggcggac ttacagccag tgatgtgcat cctaccctgg gcgttcaact gttcagcgcc      60
ggaatcgccg cttgtctggc tgatgtgatc accttccccc tggacaccgc caaggtgcgg      120
ctgcaggtgc agggcgagtg ccctacaagc agcgtgatta gatacaaggg cgtgctgggc      180
accatcacag ccgtggtgaa aaccgaaggt agaatgaagc tgtacagcgg cctgcctgcc      240
ggcctgcaaa ggcagatcag ctctgcctct ctgcggatcg gcctctatga tacagtgcag      300
gagttcctga ccgctggcaa ggaaaccgct ccttctctgg gcagcaagat cctggccgga      360
ctgacaaccg gcggcgtggc cgtgtttatc ggacagccaa cagaagtggt caaagtgcgg      420
ctgcaggccc agagccacct gcacggcatc aagcctagat acaccggcac atacaacgcc      480
tacagaatca tcgccaccac tgagggcctc accggcctgt ggaagggcac cacacctaat      540
ctgatgagaa gcgtgattat caactgtacc gagctggtca cctacgacct gatgaaagag      600
gcctttgtga agaacaacat cctggccgac gacgtcccct gccacctggt gtccgccctg      660
atcgccggct tctgcgccac agctatgagc tcccctgtgg acgtggtgaa gaccagattc      720
atcaatagcc cccccggcca gtacaagagc gtgcctaact gcgccatgaa agtgttcacc      780
aacgagggcc ctaccgcttt tttcaaaggc ctggttccaa gcttcctgag actgggatct      840
tggaacgtga tcatgttcgt gtgcttcgag cagctgaagc gggaactgag caagtccaga      900
cagaccatgg actgcgccac atga                                            924
```

```
SEQ ID NO: 35                  moltype = RNA  length = 924
FEATURE                        Location/Qualifiers
source                         1..924
                               mol_type = other RNA
                               organism = synthetic construct
SEQUENCE: 35
atgggtggcc tgacagcctc cgacgtgcat cctaccctgg gagtgcaact gttcagcgcc      60
ggcatcgccg cttgtctggc tgatgtgatt accttccccc tggacacagc caaggtgaga      120
ctgcaagtgc agggcgagtg ccccacaagc agcgtgatcc ggtacaaggg cgtgctgggc      180
accatcaccg ctgtggttaa gacagaaggc agaatgaagc tgtacagcgg cctgcctgcc      240
ggcctgcaga gacagatcag ctctgcctct ctgcggatcg gcctctatga taccgtgcag      300
gagttcctga ccgccggaaa ggagacagcc ccttctctgg gaagcaagat cctggccggc      360
ctgacaaccg gcgagtggc cgtcttcatc ggccagccta cagaagtggt gaaggtgcgg       420
ctgcaggccc agagccacct gcacggcatc aagcccagat acaccggaac ctacaacgcc      480
tacagaatca tcgccaccac cgagggcctc acaggcctgt ggaaaggcac caccccctaat     540
ctgatgaggt ccgtgatcat caactgcacc gaactggtga cctacgacct gatgaaagag      600
gcctttgtga aaaacaacat cctggccgac gatgtgccat gccacctggt cagcgccctg      660
atcgctggct tttgcgcaac cgccatgagc tccccagtgg acgtggtgaa gacaagattc      720
attaacagcc ctcctggcca gtacaagagc gtccccaatt gcgccatgaa agtgttcacc      780
aacgagggac ctacagcttt cttcaagggc ctggtgccta gcttcctgag actgggcagc      840
tggaacgtga tcatgttcgt ttgttttgag cagctgaagc gggaactgag caagtctaga      900
cagaccatgg actgcgccac ctga                                            924
```

```
SEQ ID NO: 36                  moltype = RNA  length = 924
FEATURE                        Location/Qualifiers
source                         1..924
                               mol_type = other RNA
                               organism = synthetic construct
SEQUENCE: 36
atgggcggac tgaccgcctc tgatgtgcac cccaccctgg gagtgcagct gttcagcgcc      60
ggtatcgccg cttgtctggc cgacgtgatt acattccccg tggacaccgc gaaggtgcgg      120
ctgcaagtgc agggcgagtg ccctacaagc tctgttatta gatataaggg cgtgctgggc      180
accatcaccg ccgtggtgaa aaccgagggc agaatgaagc tgtacagcgg cctgcctgcc      240
ggactgcaga gacagatcag cagcgccagc ctgaggatcg gcctctacga taccgtgcag      300
gagttcctga ccgccggcaa ggagacagcc cctagcctgg gctccaagat cctgccggc       360
ctgaccacag gcggcgtcgc cgtgttcatc ggccaaccta ccgaagtgat caaagtgcgg      420
ctgcaggccc agagccacct gcacggcatc aagcccagat acaccggaac ctacaacgcc      480
tacagaatca tcgccacaac agaaggcctg acaggcctgt ggaagggcac cacacctaac      540
ctgatgcgga gcgtgatcat caattgcact gagctggtta catacgacct gatgaaggaa      600
gccttcgtga aaaacaacat cctggctgat gacgtgcctt gtcatctggt gtccgccctg      660
atcgccggat tttgcgccac cgctatgagc tctccagtgg acgtggtcaa gaccagattc      720
atcaattctc ctcctggcca gtacaagtcc gtgccaaact gcgctatgaa agtgtttacc      780
aacgagggac ctaccgcttt tttcaagggc ctggtgccca gcttcctgag actgggcagc      840
tggaacgtga tcatgttcgt gtgcttcgag cagctgaagc gggaactgag caagagcaga      900
cagaccatgg actgcgccac ctga                                            924
```

```
SEQ ID NO: 37          moltype = RNA   length = 924
FEATURE                Location/Qualifiers
source                 1..924
                       mol_type = other RNA
                       organism = synthetic construct
SEQUENCE: 37
atgggcggcc tgaccgctag cgacgtgcac cccacactgg gcgttcagct gttcagcgcc    60
ggcatcgccg cctgtctggc tgatgtgatt accttccccc tggacacagc caaggtgcgg   120
ctgcaagtgc agggcgagtg ccctaccagc agcgtgatca gatataaggg cgtgctgggc   180
accatcaccg ccgtggtgaa gaccgaaggc agaatgaagc tgtacagcgg cctgcctgcc   240
ggacttcaaa gacagatcag ctccgcttct ctgcggattg gactctacga caccgtgcag   300
gagttcctga ccgccggaaa agagacagcc ccttctctgg gatctaagat cctggccggc   360
ctgacaaccg gaggcgtggc cgtgtttatc ggacagccta cagaagtggt gaaggtgagg   420
ctgcaggccc agagccatct gcacggcatc aagcccagat acaccggcac atacaacgcc   480
taccggatca tcgccaccac cgagggcctc acaggcctgt ggaagggcac caccccctaat  540
ctgatgagat ctgtgatcat caattgcacc gagctggtca cctacgatct gatgaaagaa   600
gccttcgtca agaacaacat cctggcggat gacgttccat gtcacctggt gtccgccctg   660
atcgccggct tctgcgccac agccatgagc tccctgtgg acgtcgtgaa aacgagattc    720
atcaacagcc ctccaggcca gtacaagagc gtgcctaact gcgccatgaa agtgttcacc   780
aacgagggtc ctaccgcttt tttcaagggc ctggtgccca gctttctgag actgggcagc   840
tggaacgtga tcatgttcgt gtgcttcgag cagctgaagc gggaactgag caagtctaga   900
cagaccatgg actgcgctac atga                                          924

SEQ ID NO: 38          moltype = RNA   length = 924
FEATURE                Location/Qualifiers
source                 1..924
                       mol_type = other RNA
                       organism = synthetic construct
SEQUENCE: 38
atgggcggac tgaccgcctc tgatgtccat cctaccctgg gcgttcagct ctttagcgcc    60
ggaatcgccg cttgtctggc cgatgtcatc accttccccc tggacaccgc caaggtgcgg   120
ctgcaagtgc agggcgagtg tcctaccagc agcgtgatcc ggtacaaggg cgtgctgggc   180
actatcacag ctgtggtgaa gaccgagggc agaatgaaac tgtacagcgg cctgccagcc   240
ggcctgcaga gacagatttc cagcgctagc ctgagaatcg gcctgtatga taccgtgcag   300
gagttcctga ccgcaggcaa ggaaaaccgc cctagcctgg gcagcaagat cctggccggc   360
ctgacaaccg gcggcgtggc cgtgtttatt ggacagccta cagaggtggt gaaggtgagg   420
ctgcaggccc agagccacct gcacggcatc aagcccagat acaccggcac ctacaacgcc   480
tacagaatca tcgccacaac cgaaggcctg acaggactgt ggaagggcac cacacctaat   540
ctgatgagaa gcgtgatcat caattgcacc gagctggtga cctacgacct gatgaaggaa   600
gcctttgtga agaacaacat cctggccgac gacgtgccct gccacctggt gtccgccctg   660
atcgctggct tctgcgccac agccatgagc tctcctgtgg acgtggtcaa aaccagattc    720
atcaacagcc ctcccggcca gtacaaaagc gtcccaaact gcgccatgaa agtgttcacc   780
aacgagggac ctacagcttt cttcaaggga cttgtgcctt ccttcctgcg gctgggcagc   840
tggaacgtga tcatgttcgt gtgcttcgag cagctgaagc gggaactgtc taagtctaga   900
caaacaatgg actgcgccac ctga                                          924

SEQ ID NO: 39          moltype = RNA   length = 924
FEATURE                Location/Qualifiers
source                 1..924
                       mol_type = other RNA
                       organism = synthetic construct
SEQUENCE: 39
atgggcgggc tcacagcttc tgatgtgcat cctacactgg gcgtccagct gttcagcgcc    60
ggaatcgccg cttgtctggc cgatgtgatc accttccccc tggacaccgc caaggtgcgg   120
ctgcaagtgc agggcgagtg ccctaccagc tctgtgatca gctacaaggg cgtgctgggc   180
accatcacag ctgtggtgaa gaccgaaggc agaatgaaac tgtacagcgg cctgcctgcc   240
ggcctgcaaa gacaaatcag cagcgccagc ctgagaatcg gactgtatga tacagtgcag   300
gagttcctga ctgctggcaa ggagacagcc cctagcctgg gaagcaagat ccttgccgga   360
ctgaccaccg gcgcgtggc cgtgtttatc ggccagccta ccgaagtggt taaggtgcgg    420
ctgcaggccc agagccacct gcacggcatc aagcctagat acaccggcac ctacaacgcc   480
tacagaatta tcgccacaac cgaaggtctg acaggactgt ggaagggcac caccccctaac  540
ctgatgcgga gcgtcatcat taactgcacc gagctggtta catacgacct gatgaaagag   600
gcctttgtga agaacaacat cctggccgac gacgtcccat gtcacctggt gtccgccctg   660
atcgccggct tctgcgccac agccatgagc tccctgtgg acgtggtgaa gacaagattc    720
atcaacagcc cccccggcca gtacaagtct gtgcccaatt gcgccatgaa agtgttcacc   780
aacgagggcc ctaccgcttt tttcaagggc ctggtgccct cttctctcag actgggcagc   840
tggaatgtga tcatgttcgt gtgcttcgag cagctgaagc gggaactgag caaatccaga   900
cagaccatgg actgcgccac ctga                                          924

SEQ ID NO: 40          moltype = RNA   length = 924
FEATURE                Location/Qualifiers
source                 1..924
                       mol_type = other RNA
                       organism = synthetic construct
SEQUENCE: 40
atgggcggcc tgaccgccag cgacgtgcat cctacactag gcgtgcagct gttcagcgcc    60
ggcatcgccg cctgcctggc tgatgtgatt accttccccc tggacaccgc caaggtgcgg   120
ctgcaagtgc agggcgagtg tcctaccagc agcgtgatca gatacaaggg agtgctggga   180
acaatcaccg ccgtggtgaa aaccgaggga agaatgaagc tgtacagcgg cctccccgcc   240
```

```
ggcctgcaga gacagatcag ctctgcttct ctgcggatcg gcctgtatga taccgtgcag  300
gagttcctga cagctggcaa ggagacagcc cctagcctgg gcagcaagat cctggccgga  360
ctcacaaccg gcggagtggc cgtgtttatt ggccagccta cagaagtggt caaagtgcgg  420
ctgcaggccc agagccacct gcacggcatc aagcccagat acaccggcac ctacaacgcc  480
tacagaatca tcgccacaac agaaggcctg accggactgt ggaagggcac cacccctaat  540
ctgatgaggt ccgtgatcat caactgcacc gaactggtca cctacgacct gatgaaaag  600
gcctttgtca agaacaacat cctggccgat gacgtgcctt gtcacctggt gtccgccctg  660
atcgccggct tctgcgccac agctatgagc tctcctgtgg acgtggttaa gaccagattc  720
atcaacagcc ctccaggcca atacaagtcc gtgccaaatt gcgccatgaa ggtgttcacc  780
aacgagggtc ctaccgcttt tttcaagggc ctggtgccca gcttcctgag actgggctct  840
tggaacgtga tcatgttcgt gtgcttcgag cagctgaagc gggaactgag caaaagcaga  900
cagaccatgg actgcgctac atga                                        924

SEQ ID NO: 41          moltype = RNA  length = 924
FEATURE                Location/Qualifiers
source                 1..924
                       mol_type = other RNA
                       organism = synthetic construct
SEQUENCE: 41
atgggcggcc tgaccgcttc cgatgtgcac cccaccctgg gcgtgcagct gttcagcgcc  60
ggcatcgccg cttgtctggc cgacgtgatc acttttccac tggacacagc caaggtgcgg  120
ctgcaagtgc agggcgagtg ccccaccagc tccgtgatcc ggtacaaagg cgtgctgggc  180
accatcaccg ccgtggtgaa gacagaaggc agaatgaaac tgtacagcgg cctgcctgcc  240
ggcctgcaga ggcagatcag cagcgcctct ctgcggatcg gactgtacga caccgtgcag  300
gagttcctga cggccggaaa agagacagcc cctagcctcg gcagcaagat cctggccggc  360
ctcaccaccg gcggtgtggc cgtgttcatt ggacaaccta ccgaagtggt gaaggtcaga  420
ctgcaggccc agagccacct gcatggcatc aagcctagat acaccggaac atacaacgcc  480
tacagaatca ttgccaccac cgagggactg acaggcctgt ggaagggcac cacacctaat  540
ctgatgagaa gcgtgatcat caattgtacc gagctggtta catatgacct gatgaaggaa  600
gccttcgtga aaaacaacat ccttgctgat gatgtgcctt gccacctggt gtccgccctg  660
atcgccggct tctgcgccac cgcaatgagc agccctgtgg acgtcgtgaa gaccagattc  720
atcaacagcc cccctggcca gtacaagagc gtgcctaact gcgccatgaa ggtgttcacc  780
aacgagggcc ctacagcttt tttcaagggc ctggtcccat cttttctgag actgggatct  840
tggaacgtga tcatgttcgt gtgcttcgag cagctgaagc gggaactgag caagtctaga  900
cagaccatgg actgcgctac atga                                        924

SEQ ID NO: 42          moltype = RNA  length = 924
FEATURE                Location/Qualifiers
source                 1..924
                       mol_type = other RNA
                       organism = synthetic construct
SEQUENCE: 42
atgggcggcc tgaccgctag cgacgtgcat cctaccctgg gagtgcagct gttcagtgcc  60
ggcatcgctg cttgtctggc tgatgtgatc accttccccc tggacaccgc aaaggtgcgg  120
ctgcaagtgc agggagaatg tcctacaagc tccgtgatta gatataaggg cgtgctgggt  180
accattacag ccgtggtcaa aaccgaaggc agaatgaaac tgtacagcgg cctccctgcc  240
ggcctgcagc gccagatcag cagcgccagc ctgcggatcg gactgtacga taccgtgcag  300
gagttcctga ccgccggcaa ggaaaccgcc cctagcctgg gctccaagat cctggccggc  360
ctgacaacag gcggagtggc cgtctttatc ggccagccta cagaggtggt gaaggttaga  420
ctgcaggccc agagccacct gcacggaatc aagcccagat acaccggcac ctacaacgcc  480
tacagaatca tcgccaccac cgagggcctg acaggcctgt ggaagggcac cacccctaat  540
ctgatgcgca gcgtgatcat caactgcacc gagctggtga cctacgatct gatgaaaag  600
gcctttgtga agaacaacat cctggccgac gacgtgccgt gccacctggt gtctgccctg  660
atcgccggct tctgcgccac cgccatgagc tctccagtgg acgtggtgaa aaccagattc  720
atcaacagcc ctccaggcca atacaagtcc gtgcccaatt gcgccatgaa ggtgttcacc  780
aacgagggcc ctacagcttt tttcaagggc ctggtcccca gcttcctgag actgggatct  840
tggaacgtga tcatgttcgt gtgcttcgag cagctcaagc gggaactgtc taagagcaga  900
cagaccatgg actgcgccac atga                                        924

SEQ ID NO: 43          moltype = RNA  length = 924
FEATURE                Location/Qualifiers
source                 1..924
                       mol_type = other RNA
                       organism = synthetic construct
SEQUENCE: 43
atgggaggcc tgaccgcatc tgatgtgcac cctacactgg gagtgcagct gttcagcgcc  60
ggaatcgccg cttgtctggc cgatgtgatt accttccccc tggacaccgc caaggtgcgc  120
ctgcaggtgc agggcgagtg ccctaccagc tctgtgatca gatacaaagg cgtgctgggc  180
accatcaccg ctgtggtcaa gacagagggc agaatgaaac tgtacagcgg cctccccgcc  240
ggcctgcaaa gacagatcag cagcgccagc ctgagaatcg gcctgtatga caccgtgcag  300
gagttcctga cagctggcaa ggaaaccgcc cctagcctgg gcagcaagat cctggccggt  360
cttacaaccg gcgcgcgtgg ccgtgttcatc ggccaaccta cagaagtggt gaaggtgcgg  420
ctgcaggccc agagccacct gcatggcatc aagcctagat acactggaac atacaacgcc  480
taccggatca tcgccaccac cgagggcctg acaggccctgt ggaagggcac caccccctaat  540
ctgatgagat ccgtgatcat caactgcacc gagctggtca cctacgacct gatgaaagaa  600
gcctttgtga agaacaacat cctgctgat gacgttccat gccacctggt gtctgccctg  660
atcgccggct tctgcgccac agccatgagc tccctgtgg acgtggtgaa gaccagattc  720
atcaatagcc ctccaggaca gtacaagtcc gtccctaact gcgccatgaa agtgttcacc  780
aacgagggcc ccacagcttt tttcaagggc ctggtgccca gcttcctgcg gctgggatct  840
```

-continued

```
tggaacgtga ttatgttcgt ttgtttgag cagctgaagc gggaactgag caagagcaga   900
cagaccatgg actgcgccac ctga                                          924

SEQ ID NO: 44           moltype = RNA  length = 924
FEATURE                 Location/Qualifiers
source                  1..924
                        mol_type = other RNA
                        organism = synthetic construct
SEQUENCE: 44
atgggcggac tgaccgcttc tgatgtgcat cccacactgg gcgtgcaact gttcagcgcc   60
ggaatcgccg catgcctggc tgatgttatt accttccctc tggataccgc caaggtgcgg   120
ctgcaagtgc agggcgagtg tcctaccagc agcgtgatca gatacaaggg cgtgctggga   180
accatcaccg ccgtggtgaa gacagagggc agaatgaaac tgtattctgg cctgcctgcc   240
ggcctgcaga gacagatctc cagcgccagc ctgcggatcg gcctgtacga caccgtgcag   300
gagttcctga cagctggcaa ggaaaccgcc cctagcctgg gctctaagat cctggctggc   360
ctgaccacag gcgcgtggc cgttttatt ggccagccta ccgaggtggt gaaggtgcgc   420
ctccaggccc agagccacct gcacggcatc aagcccagat acaccggcac atacaacgcc   480
tacagaatca tcgccacaac agagggcctg accggacctg ggaagggaac aacccctaac   540
ctgatgcgga gcgtgatcat caattgcacc gaactggtga cctacgacct gatgaaagaa   600
gccttcgtga aaaacaacat cctggccgac gacgtgccat gccacctggt gtccgccctg   660
atcgccggct tctgcgccac agccatgagc agccctgtgg acgtggtcaa gaccagattc   720
atcaacagcc ccccggcca gtacaagtcc gtgcctaatt gtgccatgaa agtgttcacc   780
aacgagggtc ctacagcttt tttcaagggc cttgtgccat cttttctgag actgggcagc   840
tggaacgtga tcatgttcgt ctgcttcgag cagctgaagc gggaactgag caagagcaga   900
cagaccatgg actgcgccac ctga                                          924

SEQ ID NO: 45           moltype = RNA  length = 924
FEATURE                 Location/Qualifiers
source                  1..924
                        mol_type = other RNA
                        organism = synthetic construct
SEQUENCE: 45
atgggaggcc tgaccgcttc tgatgtgcat cccaccctgg gcgtccagct gttcagcgcc   60
ggcatcgccg cttgtctggc tgatgtgatt acattccccc tggacaccgc caaggtgcgg   120
ctgcaagtgc agggcgagtg ccccaccagc agcgtgatca gatataaggg cgttctgggc   180
accatcaccg ccgtggtcaa gaccgaaggc agaatgaaac tgtacagcgg cctgcctgcc   240
ggcctgcaaa gacagatcag cagcgccagc ctcaggatcg gcctgtacga cacagtgcag   300
gagttcctga cagctggcaa ggaaaccgcc ccttctctgg gcagcaagat cctggccgga   360
ctgaccacag gcggcgtggc cgtctttatc ggacagccta cagaagtggt gaaggtgcag   420
ctgcaggccc agagccacct gcacggcatt aagcctagat acaccggcac atacaacgcc   480
tacagaatca tcgccaccac agagggcctg acaggcctgt ggaagggcac caccccctaat   540
ctgatgcgga gcgtgatcat caattgtacc gagctggtga cctacgatct gatgaaagag   600
gccttcgtga aaaacaacat cctggccgac gacgtgccat gccacctcgt gtccgccctg   660
atcgccggct tctgcgccac agccatgagc tctcctgtgg acgtcgtgaa gaccagattc   720
atcaacagcc ctcctggaca gtacaagtcc gtgccaaact gcgccatgaa agtgttcacc   780
aacgagggtc ctaccgcttt tttcaagggc ctggtgccat cttttctgag actgggatcc   840
tggaacgtga tcatgttcgt gtgcttcgag cagctcaagc gggaactgag caagagcaga   900
caaacaatgg actgcgctac atga                                          924

SEQ ID NO: 46           moltype = RNA  length = 924
FEATURE                 Location/Qualifiers
source                  1..924
                        mol_type = other RNA
                        organism = synthetic construct
SEQUENCE: 46
atgggcggcc ttacagctag cgacgtgcac cctaccctgg gagtgcagct gttcagcgcc   60
ggaatcgccg cctgcctggc tgatgtgatc acattccccc tggacaccgc caaggtgcgg   120
ctgcaagtgc agggcgagtg ccccaccagc agcgtgatcc ggtacaaagg cgtgctggga   180
accatcaccg ccgtggtgaa gacagaagga agaatgaaac tgtactcagg cctgcctgcc   240
ggcctgcaac gccagatcag ctctgcttct ctgagaatcg gactgtatga taccgtgcag   300
gagttcctga ccgctggcaa ggaaaccgcc cctagcctgg gcagcaagat cctggccggc   360
ctgacaacag gtgccgtcgc cgtgttcatc ggccagccta ctgaggtggt gaaggttaga   420
ctgcaggccc agagccatct gcacggcatc aagcccagat acaccggcac ctacaacgcc   480
tacagaatca tcgccacaac cgagggcctg accggcctct ggaagggcac aacccctaat   540
ctgatgagaa gcgtgatcat caactgcacc gagctggtga cctacgatct gatgaaggaa   600
gcctttgtga agaacaacat cctggccgac gacgtgcctt gccacctcgt gtccgccctg   660
attgccggct tctgcgccac cgccatgagc agccctgtgg acgtggtgaa aaccagattc   720
atcaacagcc cacctggcca gtacaagtcc gtgcccaact gcgccatgaa ggtgttcacc   780
aatgagggac ctacagcatt cttcaagggc ctggtcccat cttttctgcg gctgggctcc   840
tggaacgtga tcatgttcgt ttgtttgag cagctgaaac gggaactgag caagtctaga   900
cagaccatgg actgtgctac atga                                          924

SEQ ID NO: 47           moltype = RNA  length = 924
FEATURE                 Location/Qualifiers
source                  1..924
                        mol_type = other RNA
                        organism = synthetic construct
SEQUENCE: 47
atgggcggcc tgaccgcttc tgatgtgcac cccacactgg gagtccagct gttcagcgcc   60
```

```
ggcatcgccg cttgtctggc cgatgtgatt acttttccac tggacaccgc caaggtgcgg    120
ctgcaggtgc aaggcgagtg ccctaccagc agcgtgatca gatacaaggg cgtgctgggc    180
accatcaccg ctgttgtgaa gaccgaaggc agaatgaaac tgtacagcgg cctgcctgcc    240
ggactgcaaa gacagatcag ctccgccagc ctgcgcatcg gactgtacga taccgtgcag    300
gagttcctga cagccggcaa ggagacagcc cctagcctgg gctctaagat cctggctggc    360
ctgaccacag gcggagtggc cgtcttcatc ggccagccta ccgaggtggt caaagtgcgg    420
ctgcaggccc agagccacct gcatggcatc aagccccggt atacaggcac ctacaacgcc    480
tacagaatca ttgccacaac agagggcctg accggcctgt ggaagggaac cacccccaat    540
ctgatgagaa gcgtgatcat caactgcacc gaactggtga cctacgacct gatgaaggaa    600
gccttcgtga aaaacaacat cctcgccgac gacgtgcctt gtcacctggt gtccgccctg    660
atcgccggct tctgcgccac cgccatgagc tcccctgtgg acgtggtgaa gacaagattc    720
atcaacagcc ctcctggcca gtacaagagc gtgccaaatt gcgccatgaa ggtgtttacc    780
aacgagggcc ctacagcttt tttcaagggc cttgtgccca gcttcctgag actcggatct    840
tggaacgtga tcatgttcgt ctgcttcgag cagctgaagc gggaactgtc taaaagcaga    900
cagaccatgg actgcgcaac atga    924
```

SEQ ID NO: 48          moltype = RNA   length = 924
FEATURE                Location/Qualifiers
source                 1..924
                       mol_type = other RNA
                       organism = synthetic construct
SEQUENCE: 48

```
atgggcggac tcaccgccag cgacgtgcac ccaaccctgg gcgtgcagct gttcagcgcc    60
ggaatcgccg cttgtctggc cgacgtgatt accttccctc tggatacagc caaggtgcgg    120
ctgcaggtgc agggcgagtg ccccaccagc agcgtcatcc ggtataaggg cgttctgggc    180
accatcacag ctgtggtgaa gaccgaaggt agaatgaaac tgtacagcgg cctccctgcc    240
ggcctgcaaa gacagatcag ctctgcttct ctgcggatcg gactgtacga caccgtccag    300
gagttcctga cagctggcaa ggagacagcc ccttctctgg gatccaagat cctggccggc    360
ctgacaacag gcggcgtggc cgtctttatt ggccagccta ccgaagtggt gaaggtgaga    420
ctgcaggccc agtcccacct gcatggcatc aagcctagat acaccggcac ttacaacgcc    480
tacagaatca tcgcaaccac cgaaggcctg accggcctgt ggaagggaac aacccctaac    540
ctgatgagaa gcgtgatcat caattgcacc gagctggtga cctacgacct gatgaaagag    600
gcctttgtga aaaacaacat cctggctgat gatgtgccct gccaccttgt gtccgccctg    660
atcgccggat tttgtgccac cgccatgagc tctcctgtgg acgtggtgaa aaccagattc    720
atcaacagcc cccccggcca gtacaagagc gtgcctaact gcgccatgaa agtgttcacc    780
aacgagggcc ctacagcctt cttcaagggc ctggtgccaa gcttcctgag gctgggcagc    840
tggaatgtga tcatgttcgt gtgcttcgag cagctgaagc gggaactgag caagtcaaga    900
caaacaatgg actgcgccac ctga    924
```

SEQ ID NO: 49          moltype = RNA   length = 924
FEATURE                Location/Qualifiers
source                 1..924
                       mol_type = other RNA
                       organism = synthetic construct
SEQUENCE: 49

```
atgggcggcc tcaccgcctc tgatgtgcac cctacactgg gcgtgcagct gttcagcgcc    60
ggaatcgccg cttgtctggc tgatgtgatt accttccccc tggacacagc aaaggtgcgg    120
ctgcaagtgc aaggcgagtg ccctaccagc tccgtgatca gatacaaagg cgtcctgggc    180
accatcaccg ctgtggtcaa gaccgaaggc agaatgaagc tgtacagcgg cctgcctgct    240
ggcctgcaga gacagatcag cagcgccagc ctgagaatcg gcctgtatga taccgtgcag    300
gagttcctga ccgccggcaa ggaaaccgcc ccttctctgg gaagcaagat cctggccgga    360
ctgacaaccg gcggagtggc cgtgtttatc ggacagccta cagaagtggt gaaagtgcgg    420
ctgcaggccc agagccacct gcacggcatc aagcccagat acaccggcac ctacaacgcc    480
tacagaatca tcgccaccac agagggcctg accggcctgt ggaaggggac aacccctaat    540
ctgatgcgga gcgtgatcat caactgcact gagctggtca catacgacct gatgaaagag    600
gcctttgtga agaacaacat cctggccgac gacgtgccat gtcatctcgt gtccgccctg    660
attgccggct tctgcgccac cgccatgagc agccctgtgg acgtcgtgaa gacaagattc    720
atcaacagcc cccccggcca gtacaagtcc gtgccaaatt gcgccatgaa agtgttcacc    780
aacgagggcc ctacagcttt tttcaagggc ctggttccta gcttcctgag gctgggatct    840
tggaacgtga tcatgttcgt gtgcttcgag cagctgaagc gggaactgtc taagtcaaga    900
cagaccatgg actgcgccac atga    924
```

SEQ ID NO: 50          moltype = RNA   length = 924
FEATURE                Location/Qualifiers
source                 1..924
                       mol_type = other RNA
                       organism = synthetic construct
SEQUENCE: 50

```
atgggcggct tgacagctag cgacgtgcac ccaaccctgg gcgtccagct gttcagcgct    60
ggaatcgccg cttgtctggc cgacgtgatc acatttcctc tggacaccgc caaggttaga    120
ctgcaagtgc agggcgagtg ccctaccagc tccgtgatca gatacaaggg cgtgctggga    180
accatcaccg ccgtggtcaa gaccgaaggt agaatgaagc tgtacagcgg cctgcctgcc    240
ggccttcagc ggcagatcag ctctgcctct ctgcgcatcg gcctgtacga taccgtgcag    300
gagtttctga ccgcaggcaa ggaaaacagc cctagcctgg gctgcaagat tctggccgga    360
ctgactacag gcggagtggc cgtgttcatc gggcagccca cagaggtggt gaaggtgcgg    420
ctgcaggccc agagccacct gcatggcatc aagcccagat acacaggcac atacaacgcc    480
tacagaatca ttgctacaac cgagggcctg accggcctgt ggaagggcac cacacctaat    540
ctgatgcggt ccgtgatcat caactgcacc gaactggtga cctatgatct gatgaaagag    600
gcctttgtga agaacaacat cctcgccgat gacgtccctt gccacctggt gtccgccctg    660
```

```
atcgccggct tctgcgccac cgccatgagc agccctgtgg acgtggtgaa aaccagattc   720
atcaatagcc cccccggcca atacaaaagc gtgcctaact gtgccatgaa agtgttcacc   780
aacgagggcc ctaccgcttt cttcaagggc ctggtgccaa gtttcctgag actgggatct   840
tggaacgtga tcatgttcgt gtgcttcgag cagctgaagc gggaactgag caagtctaga   900
cagaccatgg actgcgccac atga                                         924

SEQ ID NO: 51         moltype = RNA   length = 924
FEATURE               Location/Qualifiers
source                1..924
                      mol_type = other RNA
                      organism = synthetic construct
SEQUENCE: 51
atgggcggac tgacagcctc tgatgtgcac cccacactgg gcgtccagct gttcagcgcc   60
ggcatcgccg cttgtctggc cgacgtgatc accttcccac tggacaccgc aaaggtgcgg   120
ctgcaggtgc aaggcgagtg tcctaccagc agcgtgatcc gctacaaggg cgtgctgggc   180
accatcaccg ccgttgtgaa gaccgaaggc agaatgaagc tgtacagcgg ccttcctgcc   240
ggactgcaaa gacagatcag ctccgcttct ctgcggatcg gactgtatga tacagtgcag   300
gagttcctga cagctgggaa agagacagcc cctagcctgg gcagcaagat cctggctgga   360
ctgaccaccg gcgggcgtggc cgtgtttatc ggccagccta ccgaggtggt gaaggtgaga   420
ctgcaggccc agagccacct gcacggcatc aagcctagat acaccggcac atacaacgcc   480
tacagaatca tcgccacaac agaaggcctg accggcctgt ggaagggcac cacacctaat   540
ctgatgcgga gcgtgattat caattgcacc gagctggtga cctacgacct gatgaaagaa   600
gccttcgtga agaacaacat cctggccgat gacgttccat gccatctggt gtccgccctg   660
atcgccggct tctgcgccac cgccatgtcc agccccgtgg acgtggtgaa aaccagattc   720
atcaacagcc ctcctggaca gtacaagtcc gtgcctaact cgccatgaa ggtgttcacc    780
aacgagggcc ccaccgcttt ttttaagggc ctggtcccca gcttcctgag actcggatct   840
tggaacgtga ttatgttcgt gtgcttcgag cagctgaagc gggaattgtc taaaagcaga   900
cagaccatgg actgcgccac atga                                         924

SEQ ID NO: 52         moltype = RNA   length = 924
FEATURE               Location/Qualifiers
source                1..924
                      mol_type = other RNA
                      organism = synthetic construct
SEQUENCE: 52
atgggaggcc tgaccgctag cgacgtgcac cccacactgg gcgttcagct gttcagcgcc   60
ggcatcgccg cttgtctggc tgatgttatt accttccccc tggacaccgc caaggtgaga   120
ctgcaagtgc agggcgaatg tcctaccagc tctgtgatcc ggtacaaggg cgtgctgggc   180
acaatcaccg cagtggtcaa gacagaaggc agaatgaagc tgtacagcgg cctgcctgcc   240
ggcctgcaga gacaaatcag ctctgcctcc ctgagaatcg gcctgtatga taccgtgcag   300
gagttcctga ccgccggaaa agagacagcc cctagcctgg gcagcaagat cctggccgga   360
cttaccacag gcgggcgtggc cgtgttcatt ggacagccta ccgaggtggt gaaagtgcgg   420
ctgcaggccc agagccacct gcacggcatc aagcctagat acaccggaac ttacaacgcc   480
tacagaatca tcgccaccac cgaaggcctg accggcctgt ggaagggtac aacccctaat   540
ctgatgcgga gcgtgatcat caactgcacc gagctggtga cctacgatct gatgaaagag   600
gccttgtca agaacaacat cctggccgac gacgtgcctt gccatctggt gtccgccctg    660
atcgccggct tctgcgccac agctatgagc tccctgtgg acgtggtgaa gaccagattc    720
atcaacagcc cccccggcca gtacaagagc gtgcccaaat gcgccatgaa agtctttacc   780
aacgagggcc ctacagcttt tttcaaggga ctcgtgccat cattcctgcg gctgggctct   840
tggaacgtga tcatgttcgt gtgcttcgag cagctgaaga gggaactgag caagtctaga   900
cagaccatgg actgcgccac atga                                         924

SEQ ID NO: 53         moltype = RNA   length = 924
FEATURE               Location/Qualifiers
source                1..924
                      mol_type = other RNA
                      organism = synthetic construct
SEQUENCE: 53
atgggcggac tgacagctag cgacgtgcac cctaccctgg gcgtccagct gttcagcgcc   60
ggaatcgccg cttgtctggc cgatgtgatt acattccccc tggataccgc caaggtgcgg   120
ctgcaagtgc agggcgagtg ccctacctcc agcgtgatcc ggtacaaggg agtgctggga   180
acaatcaccg ccgtggtgaa gaccgaaggc agaatgaaac tgtacagcgg cctcccccgcc   240
ggccttcaaa gacagatcag ctctgccagc ctgcggatcg gcctgtacga cacagtgcag   300
gagttcctga ccgccggcaa ggaaaccgcc ccttctctgg gttctaagat cctggctgga   360
ctgaccaccg gcgggcgtggc cgtgtttatt ggacagccta ccgaggtggt gaaggtgcgg   420
ctgcaggccc agagccatct gcacggcatc aagcccagat acaccggcac ctacaacgcc   480
tacagaatca tcgctaccac cgagggcctg accggcctgt ggaagggcac aacacctaat   540
ctgatgagaa gcgtgatcat caactgtaca gaactggtga cttatgatct gatgaaagaa   600
gccttgtga agaacaacat cctggccgac gacgtgccat gccacctggt gtccgccctg     660
atcgccggct tctgcgccac cgccatgagc agccccgtgg acgtggtcaa aaccagattc   720
atcaacagcc ctcctggcca gtacaagtcc gttccaaatt gcgccatgaa agtgttcacc   780
aacgagggcc ctacagcttt tttcaagggc ctggtcccta gcttcctgag actcggatct   840
tggaacgtga tcatgttcgt gtgcttcgag cagctgaaga gggagctgag caagagcaga   900
cagaccatgg actgcgcaac atga                                         924

SEQ ID NO: 54         moltype = RNA   length = 861
FEATURE               Location/Qualifiers
source                1..861
                      mol_type = other RNA
```

```
                             organism = synthetic construct
SEQUENCE: 54
atcgctgctt gtctggccga cgtgattaca ttccctctgg acaccgccaa ggtgcggctc    60
caggtgcaag gcgaatgtcc taccagctcc gtgatccggt acaaaggcgt cctgggaacc   120
atcaccgccg tggtgaaaac cgagggcaga atgaaactgt acagcggcct gcctgccgga   180
ctgcaaagac agatcagcag cgccagcctg cggatcggcc tttatgatac cgtcagga    240
ttcctgaccg ccggcaagga gactgcccct agcctgggct ctaagatcct ggctggcctg   300
acaaccggcg gcgtcgccgt gttcatcgga cagcctaccg aggtggtgaa ggttagactg   360
caggcccaga gccacctgca cggcatcaag ccaagataca aggcaccta caacgcctac   420
agaatcatcg ccacaaccga gggcctcaca gggctgtgga agggcaccac acctaatctg   480
atgagaagcg tgatcatcaa ttgcaccgaa ctggttacat acgacctgat gaaggaagcc   540
tttgtgaaga acaacatcct ggcggatgac gtgccctgcc atctggtgtc cgccctgatc   600
gccggcttct cgcgccacagc tatgagctcc cctgtggacg tggtgaagac cagattcatt   660
aacagcccc ccggccagta caagagcgtg ccaaactgcg ccatgaaagt gttcaccaac   720
gagggtccta cagctttttt caagggcctg gtgcctagct ttctgaggct gggctcttgg   780
aacgtgatca tgttcgtctg cttcgagcag ctgaagcggg aactgagcaa gtctagacag   840
accatggact gcgccacatg a                                             861

SEQ ID NO: 55          moltype = RNA   length = 924
FEATURE                Location/Qualifiers
source                 1..924
                       mol_type = other RNA
                       organism = synthetic construct
SEQUENCE: 55
atgggcggac tgacagccag cgacgtgcac cccaccctgg gagtgcagct gttcagcgcc    60
ggcatcgccg cttgcctggc tgatgtgatc acttttccac tggacaccgc aaaggtgaga   120
ctgcaggtgc agggcgaatg tcctacaagc agcgtgatta gatacaaggg cgtgctgggc   180
acaatcacgg ctgtggtcaa gaccgagggc agaatgaagc tgtacagcgg cttgcctgcc   240
ggcctccaga ggcagatcag ctccgcctct ctgcggatcg gcctctacga caccgtgcag   300
gagttcctga cagccgggaa ggagacagcc ccttctctgg cgagcaagat cctggccgga   360
ctgaccaccg cgggcgtggc cgtgttcatt ggacagccca ccgaagtggt gaaagttcgg   420
ctgcaagccc agagccatct gcacggcatc aagcccagat acaccggcac ctacaacgcc   480
tacagaatca tcgccacaac agaaggcctg accggcctgt ggaagggcac cacccctaac   540
ctgatgcggt ccgtgatcat caattgcacc gagctggtca cctatgatct gatgaaagag   600
gccttcgtga agaacaacat cctggccgac gacgtcccat gccacctggt gtccgccctg   660
atcgccggct tctgcgctac agccatgagc tctcctgttg atgtggtgaa aaccagattc   720
atcaacagcc ctcctggcca gtacaaaagc gtgcctaatt gtgccatgaa ggtgttcacc   780
aacgagggac ctaccgcctt tttcaagggc ctggtgccca gctttctgag actgggatct   840
tggaacgtga tcatgttcgt gtgcttcgag cagctgaagc gggaactgag caagagcaga   900
caaacaatgg actgcgctac ctga                                           924

SEQ ID NO: 56          moltype = RNA   length = 924
FEATURE                Location/Qualifiers
source                 1..924
                       mol_type = other RNA
                       organism = synthetic construct
SEQUENCE: 56
atgggcggac tgaccgcctc tgatgtgcac cctaccctgg gcgtgcaact gttcagcgcc    60
ggcatcgccg cttgtctggc cgacgtgatt acattccctc tggacaccgc caaggtgcgg   120
ctgcaagtgc agggcgaatg ccctacctcc agcgttatcc ggtacaaggg agttctgggc   180
accatcacag ctgtggtgaa aaccgagggc agaatgaagc tgtacagcgg cctccccgcc   240
ggactgcaga gacagatcag cagcgcctct ctgaggatcg gcctatatga caccgtgcag   300
gagttcctga cagccggcaa ggaaacagcc cctagcctgg gcagcaagat cctggccggc   360
ctgaccaccg cgcgcgtggc cgtctttatc ggccagccta cagaggtggt gaaagtgcgg   420
ctgcaggccc agagccacct gcacggcatt aagcctagat acaccggcac ctacaacgcc   480
tacagaatca tcgccacaac cgaaggcctg acaggcctgt ggaagggcac aaacacctaac   540
ctgatgcgga gcgtgatcat caattgcacc gaactggtca cctacgacct gatgaaagag   600
gcctttgtga agaacaacat cctggctgat gatgtgccat gtcatctggt ctccgccctg   660
atcgccggtt tctgcgccac cgctatgagc tcccctgtgg acgtggtgaa gaccagattc   720
atcaacagcc ccccggcca gtacaagtct gtgccaaatt gcgctatgaa agtgttcacc   780
aacgagggac ctacagcttt tttcaagggc ctggtgccca gcttcctcag actgggatct   840
tggaacgtga tcatgttcgt gtgcttcgag cagctgaaga gagagctgag caagagcaga   900
cagaccatgg actgcgccac ctga                                           924

SEQ ID NO: 57          moltype = RNA   length = 924
FEATURE                Location/Qualifiers
source                 1..924
                       mol_type = other RNA
                       organism = synthetic construct
SEQUENCE: 57
atgggaggac tgaccgccag cgacgtgcac cctaccctgg gagtgcagct gttcagcgcc    60
ggaatcgccg cctgcctggc cgatgtcatc accttccccc tggatacagc taaggtgcgg   120
ctgcaggtgc agggcgagtg ccccacaagc agcgtgatta gatacaaggg cgtgctgggc   180
acaatcacag ctgtggtgaa gaccgagggc agaatgaaac tgtacagcgg cctgcctgcc   240
ggcctgcaaa gacagatcag cagcgcctct ctgcggatcg gcctctacga caccgtgcag   300
gagttcctga ccgccggcaa ggaaaccgcc cctagcctgg ctccaagat cctggctgga   360
ctgaccaccg cgcgcgtggc cgtgttcatc ggccaaccta cagaggtggt caaagtgcgg   420
ctgcaggccc agagccacct gcatggcatc aagcctagat acaccggcac ctacaacgcc   480
tacagaatca tcgccaccac agaaggcctg accggcctgt ggaagggcac gactcctaat   540
```

```
ctgatgcgga gcgtgatcat caactgcacc gaactggtga cctatgacct gatgaaagag  600
gcctttgtga aaaacaacat ccttgctgat gacgttccat gtcacctggt gtccgccctg  660
atcgccggct tctgcgccac agccatgtct tctcctgtgg acgtggtgaa gacaagattt  720
atcaacagcc ctccaggcca gtacaagagc gtgcccaatt cgccatgaa ggtgttcacc  780
aacgaaggcc ctaccgcttt tttcaaggga ctggtcccca gcttcctgag actgggttct  840
tggaacgtga ttatgttcgt gtgcttcgag cagctgaagc gcgagctgag caagtccaga  900
cagaccatgg actgtgccac atga                                         924
```

SEQ ID NO: 58                   moltype = RNA   length = 924
FEATURE                         Location/Qualifiers
source                          1..924
                                mol_type = other RNA
                                organism = synthetic construct
SEQUENCE: 58

```
atgggcggac tgaccgcttc tgatgtgcac cctaccctgg gcgtgcagct gttctccgcc  60
ggcatcgccg cttgtctggc cgacgtgatt acttttccac tggacaccgc aaaggtcaga  120
ctgcaggtgc agggcgagtg ccccacaagc agcgtgatca gatataaggg cgtgctggga  180
accatcaccg ccgtggtgaa gaccgagggc agaatgaagc tgtacagcgg cctccccgcc  240
ggcctgcaga gacagatcag ctctgccagc ctgcggatcg gactctacga tacagtgcag  300
gagttcctga ccgctggcaa ggaaaccgcc cctagcctgg gttctaagat cctggccgga  360
ctgaccaccg gaggagtggc cgtgttcatc ggccaaccta ccgaggtggt caaggtgcgg  420
ctgcaagccc agagccatct gcacggcatc aagcctgaac acaccggcac atacaacgcc  480
tacagaatta tcgccaccac agaaggcctg acaggcctgt ggaagggcac caccccctaat  540
ctgatgcgga gcgttatcat caactgcacc gaactggtga cctacgacct gatgaaagag  600
gccttcgtga agaacaacat cctggctgat gacgtgccct gccacctggt gtccgccctg  660
atcgccggct tctgcgccac agccatgagc agccctgtgg acgtggtgaa aacaagattc  720
atcaacagcc ctcctggcca gtacaagagc gtgcccaaact gtgccatgaa agtctttacc  780
aacgagggcc ctacagcttt tttcaaggc ctagtgccct ccttcctgag gctgggctct  840
tggaatgtga tcatgttcgt gtgcttcgag cagctgaagc gggaactgag caaaagcaga  900
cagacaatgg actgcgccac atga                                         924
```

SEQ ID NO: 59                   moltype = RNA   length = 924
FEATURE                         Location/Qualifiers
source                          1..924
                                mol_type = other RNA
                                organism = synthetic construct
SEQUENCE: 59

```
atgggcggcc tgaccgccag tgatgtgcac cccaccctgg gtgttcaact gttctctgcc  60
ggaatcgccg cctgcctggc cgacgtgatc acctttccac tggacaccgc caaggtgagg  120
ctgcaggtgc agggcgagtg tcctacaagc agcgtgatca gatacaaggg cgtgctgggc  180
accatcaccg ctgtggtcaa gacagagggc agaatgaaac tgtacagcgg cctgcctgcc  240
ggcctccagc ggcagatcag ctccgcctct cttcggatcg gcctctacga caccgtgcag  300
gagttcctga cagctggcaa ggaaaccgcc ccttctctgg gatctaagat cctggctggc  360
ctgaccacag gaggagtggc cgtgtttatc ggccagccta ccgaagtggt gaaggtgcgg  420
ctgcaggccc agagccatct gcacggcatc aagcctagat atacaggcac ctacaacgcc  480
tacagaatca tcgcgacaac cgaggccctg accggcctgt ggaagggcac aacacctaat  540
ctgatgagaa gcgtgattat taactgcacc gagctggtta catcgatct gatgaaagaa  600
gccttcgtga agaacaacat cctggccgat gacgtgcctt gtcacctggt gtccgctctg  660
atcgccggct tctgcgccac ggccatgagc tccctgtgg acgtggtcaa aaccagattc  720
atcaacagcc ccccggcca gtacaagagc gtgcccaatt cgccatgaa agtctttacc  780
aacgagggac ctaccgcttt cttcaaggc ctggtgccaa gcttcctgag actgggcagc  840
tggaacgtga tcatgttcgt gtgcttcgag cagctgaagc gggaactgag caagagcaga  900
caaacaatgg actcgccac ctga                                          924
```

SEQ ID NO: 60                   moltype = RNA   length = 924
FEATURE                         Location/Qualifiers
source                          1..924
                                mol_type = other RNA
                                organism = synthetic construct
SEQUENCE: 60

```
atgggcggcc tgacagccag tgatgtgcac cccaccctgg gcgtgcaact gttcagcgcc  60
ggcatcgcag cctgcctggc cgacgtgatc acatttccat tggacacagc caaggtgaga  120
ctgcaggtgc agggcgagtg ccccacaagc agcgtgattc ggtacaaggg cgtgctgggc  180
accatcaccg ccgtggtcaa gaccgaaggc aggatgaaac tgtacagcgg cctgcctgcc  240
ggcctgcaga gacagatcag ctctgctagc ctgagaatcg gactctacga caccgtccag  300
gagttcctga ctgctggcaa ggaaaccgcc ccttctctgg gaagcaagat cctggccgga  360
ctcactaccg gcgagtggc cgtgttcatc ggccagccta cagaggtggt gaaagtgcgg  420
ctgcaagccc agagccatct gcacggcatc aagcctagat acaccggcac ctacaacgcc  480
tacagaatca tcgccaccac agaaggcctg accggcctgt ggaagggcac aaccccctaat  540
ctgatgcggt ctgtgatcat caattgcaca gagctggtga cctatgacct gatgaaagaa  600
gccttcgtga agaacaacat cctggctgat gatgtgccct gtcacctggt ctccgccctg  660
atcgccggct tctgcgccac cgccatgtcc agccctgtgg acgtggtgaa gacaagattc  720
atcaacagcc cacctggcca gtacaagtct gttcccaact gtgctatgaa agtgtttacc  780
aacgagggac ctaccgcttt tttcaaggga ctggtgccta gcttcctgcg gctgggctcc  840
tggaacgtga tcatgttcgt gtgcttcgag cagctgaaga gagagctgag caagagcaga  900
cagaccatgg actgcgccac atga                                         924
```

SEQ ID NO: 61                   moltype = RNA   length = 924
FEATURE                         Location/Qualifiers

```
source              1..924
                    mol_type = other RNA
                    organism = synthetic construct
SEQUENCE: 61
atgggcggcc tgaccgcctc tgatgtgcac cctaccctgg gcgtgcagct gttcagcgcc    60
ggaatcgccg cctgtctggc cgacgtgatc acctttccac tggacaccgc taaagtgcgg   120
ctgcaggtgc aaggcgagtg ccctacaagc tctgtgatca gatacaaggg agtgctgggc   180
accatcacac ccgtggtgaa gaccgaaggc agaatgaaac tgtacagcgg cctgcctgct   240
ggactgcaaa gacagatcag ctctgctagc ctgaggcacg gactttatga taccgtgcag   300
gagttcctga cagccggcaa agagacagcc cctagcctgg gctccaagat cctggccggc   360
ctgaccacag gaggcgtcgc cgtgttcatc ggccagccta cagaagtggt caaggtgcgg   420
ctacaggccc agagccacct gcacggcatc aagcccagat acaccggcac ctacaacgcc   480
taccggatca tcgccacaac cgagggcctg accggcctct ggaagggcac aaccccctaac  540
ctgatgcgca gcgtgatcat caattgcacc gaactggtca cctacgacct gatgaaagaa   600
gccttcgtga agaacaacat cctggctgat gacgtgccct gccatctggt gtccgccctg   660
atcgccggct tctgcgccac cgccatgagc agccccgtgg acgtggttaa gacaagattc   720
attaactccc ctccaggcca gtacaagagc gtgcctaatt gcgccatgaa ggtgttcacc   780
aacgagggac ctacagcttt tttcaagggc ctggtgccca gcttcctgag actgggcagc   840
tggaacgtga ttatgttcgt gtgttttgag cagctgaagc gggagctgtc taagtccaga   900
cagaccatgg actgcgcaac atga                                          924

SEQ ID NO: 62          moltype = RNA   length = 924
FEATURE                Location/Qualifiers
source                 1..924
                       mol_type = other RNA
                       organism = synthetic construct
SEQUENCE: 62
atgggcggac tgacagccag tgatgtgcac cccaccctgg gagttcagct gttcagcgct    60
ggaatcgccg cctgcctggc cgacgtgatt acatttcctc tggacaccgc caaggtgcgg   120
ctgcaagtgc agggcgagtg tcctacaagc agcgtgatcc ggtacaaggg cgtgctggga   180
accatcacag ctgtggtgaa aaccgaggga agaatgaagc tgtacagcgg cctgcctgct   240
ggcctgcaga gacagatcag ctccgcttct ctgcggatcg gcctttatga taccgtgcag   300
gagttcctga cagctggcaa ggaaaccgcc cctagcctgg gctctaaaat cctggctggc   360
ctgaccaccg gtggcgtggc cgtgttcatc ggccagccta cagaagtggt caaggtgcgg   420
ctgcaggccc agagccacct gcacggcatc aagcccagat acaccggcac atacaacgcc   480
tacagaatca tcgccaccac cgagggccta accggcctgt ggaagggcac cacccctaat   540
ctgatgagaa gcgtgatcat caactgcacc gaactggtga cctacgacct catgaaggaa   600
gcctttgtga agaacaacat cctggccgat gacgtgccct gccatctggt ctccgccctg   660
atcgccggct tctgcgccac agccatgagc agccccgtgg acgtggtgaa gacaagattc   720
atcaacagcc ctcctggcca gtacaagagc gtgcccaatt gtgccatgaa agtgtttacc   780
aacgagggcc ctaccgcctt cttcaaggga ctggttccat ccttcctgag gctgggcagc   840
tggaacgtga tcatgttcgt gtgcttcgag cagctgaaga gagagctgtc taaatctaga   900
caaacaatgg actgcgccac ctga                                          924

SEQ ID NO: 63          moltype = RNA   length = 924
FEATURE                Location/Qualifiers
source                 1..924
                       mol_type = other RNA
                       organism = synthetic construct
SEQUENCE: 63
atgggaggcc tgaccgctag cgacgtgcac cctacactgg gcgtgcagct gttcagcgcc    60
ggcatcgccg catgcctggc tgatgtgatc accttccccc tggataccgc caaggtgcgg   120
ctgcaagtgc agggcgagtg ccctacaagc tccgtgatca gatacaaggg agtgctgggc   180
acaatcacag ctgtggtgaa aaccgagggc agaatgaagc tgtacagcgg cctgcctgcc   240
ggacttcaga gacagattag cagtgcctct ctgagaatcg gcctgtatga tacagtgcag   300
gagttcctga cagccggcaa agagacagct ccttccctgg gcagcaagat cctggccggc   360
ctgaccaccg gcgcgcgtggc cgtgttcatc ggacagccta ccgaagtggt caaagtgcgg   420
ctgcaggccc agagccacct gcatggcatc aagcctcggt acaccggcac ctacaacgcc   480
tacagaatca tcgccaccac agaaggcctg accggactgt ggaagggaac cacccctaac   540
ctgatgagaa gcgtgatcat caattgcact gagctggtga cctacgacct gatgaaggaa   600
gccttcgtta agaacaacat cctgccgac gacgtcccct gtcacctggt cagcgccctg   660
atcgccggct tctgcgccac cgccatgagc tctccagtgg acgtggtgaa gaccagattc   720
atcaacagcc ccccggcca gtacaaaagc gtgcctaatt gcgccatgaa ggtgtttacc   780
aacgagggcc ctacagcttt tttcaagggc ctggtgccat ctttcctgcg cctcggaagc   840
tggaacgtga ttatgttcgt ttgttttgag cagctgaagc gggaactgtc taagtccaga   900
caaacaatgg actgcgccac ctga                                          924

SEQ ID NO: 64          moltype = RNA   length = 924
FEATURE                Location/Qualifiers
source                 1..924
                       mol_type = other RNA
                       organism = synthetic construct
SEQUENCE: 64
atgggcggcc tgacagcctc tgatgtgcac cctaccctgg gagtgcagct gttcagcgcc    60
ggcatcgccg cttgtctggc cgatgtgatc accttttcctc tggacaccgc taaggtgcgc   120
ctgcaggtgc agggcgagtg tcctaccagc agcgtgatca gatacaaggg cgtgctgggc   180
accatcacag cagtggtcaa aaccgagggc agaatgaaac tgtacagcgg cctccccgcc   240
ggcctgcaaa gacaaatcag ctctgccagc ctgcggattg gcctgtatga caccgtacag   300
gagttcctga cagccggaaa ggaaaccgcc ccttctctgg gatccaagat cctggccggc   360
```

```
ctgaccactg gcggagtggc cgtgttcatc ggccagccta ccgaggtggt gaaggtgcgg   420
ctgcaggccc agagccacct gcatggcatc aagcctagat acacaggcac gtacaacgcc   480
tacagaatca tcgccaccac cgaaggactg accggcctgt ggaagggcac aacccctaac   540
ctgatgagaa gcgtcatcat caactgcacc gaactggtca catacgacct gatgaaagag   600
gcctttgtga agaacaatat cctggccgac gatgtgccat gccacctggt gtccgccctc   660
atcgccggct tctgcgctac cgctatgagc tccctgtgg acgtggtgaa gacccggttc   720
atcaacagcc cccccggcca gtacaaaagc gtgccaaatt gcgccatgaa ggtgttcaca   780
aacgagggac ctacagcttt tttcaagggc ctggttccca gcttcctgag actgggctct   840
tggaacgtga tcatgttcgt gtgcttcgag cagctgaagc gggaactgag caagagcaga   900
cagaccatgg actgcgccac atga                                         924
```

SEQ ID NO: 65          moltype = RNA  length = 924
FEATURE                Location/Qualifiers
source                 1..924
                       mol_type = other RNA
                       organism = synthetic construct
SEQUENCE: 65

```
atgggcggac tgaccgcttc tgatgtgcac cctacactgg gcgtccaact gttctctgcc   60
ggcatcgccg cttgtctggc tgatgtgatc acattccccc tggacaccgc caaggtgcgc   120
ctgcaggtgc agggcgagtg ccctacctct agcgtgattc ggtacaaggg cgtgctgggc   180
accatcacag ccgttgtgaa gaccgaaggc agaatgaaac tgtactccgg cctccctgcc   240
ggcctgcaaa gacagatcag cagcgccagc ctcagaattg gcctgtatga taccgtgcag   300
gagttcctga ccgccggcaa ggagacagcc cctagcctgg gcagcaagat cctggccggc   360
ctgacaaccg gcgggagtcgc cgtgtttatc ggacagccta ccgaggtggt gaaagtgcgg   420
ctgcaggccc agagccacct gcacggcatc aagcccagat acaccggcac ctacaacgcc   480
taccggatca tcgccaccac cgaaggcctg accggcaat ggaagggcac aaccccctaa   540
ctgatgcgga gcgtgatcat caactgcaca gaactggtca cctacgacct gatgaaggaa   600
gccttcgtga agaacaacat cctggccgac gacgttccat gtcatctggt gtccgccctg   660
atcgccggct tctgcgcgac cgctatgagc agccctgtgg acgtggtgaa gacaagattc   720
atcaacagcc cccccggcca gtacaagtcc gtgcctaatt gcgccatgaa agtgttcacc   780
aacgagggcc ctacagcttt tttcaaggga ctggtgccat cttttctgag actgggaagc   840
tggaacgtga tcatgttcgt gtgcttcgag cagctgaaga gagagctgag caaaagcaga   900
cagacgatgg actgcgccac atga                                         924
```

SEQ ID NO: 66          moltype = RNA  length = 924
FEATURE                Location/Qualifiers
source                 1..924
                       mol_type = other RNA
                       organism = synthetic construct
SEQUENCE: 66

```
atgggcggac tgaccgcttc tgatgtgcat cccaccctgg gagtgcagct gttcagcgcc   60
ggcatcgctg cttgtctggc cgacgtgatc accttccccc tggacaccgc caaggtgcgc   120
ctgcaagtgc agggcgagtg ccctaccagc agcgtgatca gatacaaggg cgtgctgggc   180
acaatcaccg ccgtggtgaa gaccgagggc agaatgaaac tgtatagtgg cctgcctgcc   240
ggtctccagc ggcagattag ctctgccagc ctgcggatcg gcctgtacga caccgtgcag   300
gagtttctga cagcaggcaa agagacagcc ccttctctcg gaagcaagat cctggccggc   360
ctgaccaccg gcgggcgtggc cgtgtttatc ggacaaccta cagaagtggt gaaagtgcgg   420
ctgcaggccc agagccacct gcacggcatc aagcctagat acaccggaac atacaacgcc   480
tacagaatca tcgccaccac cgaaggcctg accggcttat ggaagggcac cacacctaat   540
ctgatgagaa gcgtgattat caactgtaca gagctggtga cctacgacct gatgaaggaa   600
gccttcgtga agaacaacat cctggctgat gatgtgccat gccacctggt gtccgccctg   660
atcgccggct tctgcgccac cgccatgagc agccctgtcg acgtcgtgaa gacaagattc   720
atcaacagcc cccccggcca gtacaagtcc gtgccaaatt gcgccatgaa agttttcacc   780
aacgagggcc ctacagcttt tttcaaggga ctggtcccta gcttcctgag actgggctcc   840
tggaacgtga tcatgttcgt gtgcttcgag cagctgaagc gggaactgtc taagagcaga   900
cagaccatgg actgcgccac gtga                                         924
```

SEQ ID NO: 67          moltype = RNA  length = 924
FEATURE                Location/Qualifiers
source                 1..924
                       mol_type = other RNA
                       organism = synthetic construct
SEQUENCE: 67

```
atgggcggac tgacagcctc tgatgtgcac cccaccctgg gagtgcagct gttcagcgcc   60
ggcatcgccg cttgtctggc cgacgtgatt accttccctc tggacaccgc aaaggtgagg   120
ctgcaggttc agggcgagtg ccctaccagc agtgtgatcc ggtacaaggg cgtactgggc   180
accatcaccg ctgtggtgaa gacagaaggc agaatgaaac tgtacagcgg ccttcccgcc   240
ggcctgcaaa gacagatcag cagcgcctct ctgcggatcg gcctgtatga tacagtgcag   300
gagttcctga cagccggcaa ggaaaccgcc cctagcctgg gatctaagat cctggctgga   360
ctgaccaccg gcgggcgtggc cgtgttcatc ggccaaccta ccgaggtggt caaggtgcgg   420
ctgcaggccc agagccacct gcatggcatc aagcctagat acaccggcac atacaacgcc   480
tacagaatca tcgccaccac cgagggcctc accggcctgt ggaagggaac aaccctaat   540
ctgatgagaa gcgtgatcat caattgcacg gagctggtga cctacgacct gatgaaggaa   600
gccttttgtga aaacaacat cctggccgat gacgtgccat gtcacctggt gtccgccctg   660
atcgccggct tttgcgccac cgctatgagc tctcctgtgg acgtggtgaa aacaagattc   720
atcaacagcc ctccaggcca gtacaagtcc gtccccaact gcgccatgaa agtgttcacc   780
aacgagggcc ctacagcttt tttcaaggga ctggtcccca gcttcctgag actgggcagc   840
tggaacgtga ttatgttcgt gtgcttcgag cagctgaagc gggaactgag caagtccaga   900
cagaccatgg actgcgccac atga                                         924
```

-continued

```
SEQ ID NO: 68            moltype = RNA  length = 924
FEATURE                  Location/Qualifiers
source                   1..924
                         mol_type = other RNA
                         organism = synthetic construct
SEQUENCE: 68
atgggaggac tgacagcctc tgatgtgcat cccaccctgg gcgtgcagct gttcagcgcc    60
ggcatcgccg cttgtctggc cgatgtgatt accttccccc tggacaccgc caaggtgcgg   120
ctgcaggttc agggcgagtg ccccacaagc agcgtgatca gatacaaggg cgtgctgggc   180
accatcaccg cagtggtgaa gacagaaggc agaatgaaac tgtacagcgg cctgcctgcc   240
ggcctgcaaa gacagatcag ctccgccagc ctgagaatcg gcctgtatga taccgtgcag   300
gagttcctca cagccggcaa ggaaaccgcc ccttctctgg ggtccaagat cctggctggc   360
ctgaccacag gaggcgtcgc cgtgtttatc ggacagccta cagaggtggt gaaggtgcgg   420
ctgcaggccc agagccacct gcacggcatc aagcctagat acaccggcac ctacaacgcc   480
tacagaatca tcgccaccac cgaaggcctg accggcctct ggaagggaac caccctaat    540
ctgatgcgga gcgtgatcat caactgcacc gagctggtga cctacgacct gatgaaagag   600
gcctttgtga agaacaacat cctggccgac gacgtgcctt gtcacctggt cagcgccctg   660
atcgccggct tctgcgctac agctatgagc tctcctgtgg acgtggtgaa gaccagattc   720
attaacagcc cacctggcca gtacaagtcc gtgccaaatt gcgccatgaa agtcttcacc   780
aacgagggac ctacagcttt tttcaagggc ctggtgccca gcttcctgag gctgggctct   840
tggaacgtga tcatgttcgt gtgcttcgag cagctgaagc gggaactgtc taaaagcaga   900
caaacaatgg actgcgccac atga                                          924

SEQ ID NO: 69            moltype = RNA  length = 924
FEATURE                  Location/Qualifiers
source                   1..924
                         mol_type = other RNA
                         organism = synthetic construct
SEQUENCE: 69
atgggcggac tcacagccag cgacgtacat cctacactgg gcgtgcagct gttcagcgcc    60
ggcatcgctg cctgcctggc tgatgtgatc accttccccc tggatacagc aaaggttaga   120
ctgcaagtgc agggcgagtg ccccacaagc agcgtgatcc ggtacaaagg cgtgctggga   180
accattacag ctgtggtgaa gacagagggc agaatgaagc tgtattctgg cctgcctgcc   240
ggcctgcaga gacagatcag ctctgctagc ctgcggatcg gcctgtacga caccgtgcag   300
gagttcctca cagccggaaa ggaaaccgcc ccttctctgg gcagcaagat cctggccggc   360
ctgaccacag gcggcgtggc cgtgtttatt ggacaaccta cagaggtggt caaggtcaga   420
ctgcaggccc agagccacct gcacggcatc aaacctagat acaccggcac ctacaacgcc   480
tacagaatca tcgccaccac cgagggcctg accggccttt ggaagggaac caccctaat    540
ctgatgcgca gcgtgatcat caattgtacc gaactggtga catacgacct gatgaaagaa   600
gcctttgtga aaaacaacat cctggccgac gatgtgccat gccacctggt gtccgccctg   660
atcgccggct tctgcgccac cgctatgagc tccctgtgg acgtggtgaa gaccagattc   720
atcaacagcc cccccggcca gtacaagtcc gtgcccaact gccatgaa ggtcttcact   780
aacgagggtc ctaccgcctt tttcaaggga ctggttccaa gcttcctgag gctgggctct   840
tggaacgtga tcatgttcgt gtgcttcgag cagctgaagc gggaactgag caagagccgg   900
cagaccatgg actgcgccac ctga                                          924

SEQ ID NO: 70            moltype = RNA  length = 924
FEATURE                  Location/Qualifiers
source                   1..924
                         mol_type = other RNA
                         organism = synthetic construct
SEQUENCE: 70
atgggaggtc tcacagccag cgacgtacac cccacattag gggttcagct ctttagtgca    60
ggcatagccg cttgcctcgc tgatgttatt acttttcccc tcgacactgc taaggtgcga   120
ctgcaagtac agggcgaatg ccctacttca tcagtgattc gatacaaggg cgtgattgggc   180
actattactg ccgtcgtgaa aacagaaggc cgtatgaagc tgtatagtgg gctgccagcg   240
ggattgcaga ggcagatcag ctctgcatct ctgcgaatcg gactgtacga caccgttcaa   300
gagttcctta ccgcaggaaa ggagacagca cctagcctag ggtccaaaat cttggcaggt   360
ctcactacag ggggcgtagc tgttttcatc ggacaaccca cagaagttgt aaaggtccga   420
ctccaagcac agagccatct tcacgggatc aaacctcgct acactggcac gtacaacgct   480
tacaggatca tcgccactac agagggttta acagggcttt ggaaggggac aacacctaat   540
ctgatgcgat ccgtgattat taactgcacc gaattggtga cttacgatct catgaaggag   600
gccttcgtga agaacaacat cttggcggac gacgtgcctt gtcatttagt ctctgcacta   660
atagccggat tctgtgccac cgccatgtcg agcctgttg acgtcgtgaa gacgcggattt   720
atcaattctc ctcctggtca atataagagt gtccctaatt gtgccatgaa ggtcttcaca   780
aacgagggcc ctacagcctt tttcaaggga ctcgtcccat cctttctacg gctcggttct   840
tggaacgtca tcatgttcgt gtgtttcgaa caactgaaac gagagctgtc caaaagtagg   900
cagaccatgg actgcgctac ttga                                          924

SEQ ID NO: 71            moltype = RNA  length = 924
FEATURE                  Location/Qualifiers
source                   1..924
                         mol_type = other RNA
                         organism = synthetic construct
SEQUENCE: 71
atgggcggtc taacggcctc tgacgtccat cccacacttg gggtgcagct cttcagtgcg    60
gggatcgccg cctgcttggc cgatgtcatt acttttcctc tggacacagc aaaggtgcga   120
ttgcaggttc aaggagaatg ccccacctcc tccgtcattc gatataaagg cgttttgggg   180
```

-continued

```
acgatcactg ccgtggtgaa gacggagggc cgtatgaaat tgtacagcgg gctgccagca   240
ggcctgcaga ggcagataag ctccgcatca ttgcgaatcg gcctgtacga cacagtgcaa   300
gaatttctta ctgccggaaa ggagacagca cccagtttgg ggagcaaaat cctcgccggg   360
ctgaccacag gcggcgtcgc tgtatttatt ggacagccta ctgaagtggt aaaggtacga   420
ctccaggccc agtctcatct gcacggaatc aagcctagat acactgggac atataacgct   480
tacaggatca tcgctacaac agaaggcctc actggacttt ggaagggcac aactcctaat   540
ttaatgcgat cagtcatcat caattgcacc gagttggtca catacgacct aatgaaggag   600
gccttcgtga aaaacaatat actcgcagat gacgttcctt gtcacttagt gtctgcgctg   660
atcgccggat tttgtgccac cgccatgtct agccctgttg atgtcgtgaa gacaaggttt   720
atcaattcac cacctggcca gtataaatct gttcctaatt gtgcaatgaa ggtgttcacg   780
aatgaaggtc caacagcatt cttcaagggg cttgtccctt catttctgcg actgggatca   840
tggaacgtga tcatgtttgt gtgttttgaa caactgaaaa gagagctgtc gaagtccagg   900
cagacaatgg actgcgccac ctga                                          924
```

SEQ ID NO: 72           moltype = RNA  length = 924
FEATURE                Location/Qualifiers
source                 1..924
                         mol_type = other RNA
                         organism = synthetic construct SEQUENCE: 72
```
atgggcggac tgaccgcttc cgacgtacac cctaccttag gagtgcagct cttcagtgca   60
ggaatcgccg cttgccttgc tgatgtcatt acttttccat tagacaccgc caaggtgcgg   120
ctacaggttc agggcgaatg tcccacttct tccgtcattc ggtacaaagg cgttctggga   180
acgatcacag ctgtcgtgaa aaccgaaggc cgtatgaagc tgtacagcgg gcttccagca   240
ggacttcaga ggcagatcag ctcggcgtcc ttacgcatcg gactctacga cacagtccaa   300
gaattcctca cagctggaaa ggaaactcct cctagcctgg ggagcaaaat actggccggg   360
ctcacaacag gcggcgttgc tgtgtttatt ggacagccca ctgaggttgt caaggtccgc   420
ctgcaagccc aaagccacct tcacgggatt aagcctcgct acactggaac atacaatgca   480
tatagaatca tcgccaccac cgaaggccta actggactgt ggaaagggac aacacctaac   540
ttaatgcggt cagttattat taactgcact gagttagtga cttacgatct catgaaggaa   600
gcattcgtga agaacaacat tttggcagat gacgttcctt gtcatttggt ttccgcatta   660
atagccgggt tttgtgctac cgccatgtct ccccagtcg acgtcgtgaa gacaaggttt   720
ataaattccc cacctggcca gtataaaagt gtccctaact gtgcaatgaa agtcttcaca   780
aacgagggcc ctaccgcctt cttcaagggg cttgttccct cttttctgcg actcggctca   840
tggaacgtca tcatgtttgt ctgtttttgaa cagctgaaaa gggagctatc aaagtcaaga   900
cagaccatgg actgcgccac ctga                                          924
```

SEQ ID NO: 73           moltype = RNA  length = 924
FEATURE                Location/Qualifiers
source                 1..924
                         mol_type = other RNA
                         organism = synthetic construct SEQUENCE: 73
```
atgggcggcc tgaccgcttc agacgttcac ccgacgttgg gagtgcagct attcagcgca   60
ggaatagccg cttgcttagc agatgtgatt actttccctc tcgatactgc taaggtccgc   120
cttcaagttc agggcgaatg ccctacttct tccgtgattc gctataaggg cgtactggga   180
actattacag ctgtcgtgaa aacagaaggc cgcatgaagc tacagagcgg actccctgcc   240
gggttacaaa gacaaatcag ctcagcttcc ctgcggatcg gcttgtacga caccgttcag   300
gaattcctca cagccggaaa ggagactgca cctagtttag gaagcaaaat tctcgcaggg   360
cttaccacag gtgtggcgtcg cgttttcatt ggacaaccaa ccgaagtagt taaggtccga   420
ctccaagctc aatctcacct cacacggaatt aagcctcgct acactggcac gtataacgct   480
tataggatta tcgctacaac agaaggatta acgggcctgt ggaagggcac cacccccaat   540
ttaatgcgat cagtcatcat caactgcacc gagttggtaa catacgatct catgaaggaa   600
gccttttgtga aaaacaacat actggcagac gacgtccctt gtcatttggt ttctgcgctc   660
atcgcagggt tttgtgctac cgccatgtct agccctgttg acgttgtcaa gacacgattt   720
ataaactctc caccaggcca gtataaatct gtccctaatt gtgccatgaa ggtcttcaca   780
aacgagggtc ccactgcttt cttcaagggg cttgttccct cgtttctgcg gcttggatcc   840
tggaatgtta tcatgtttgt gtgctttgaa cagttgaaaa gagagttgtc caaatccagg   900
cagactatgg actgcgccac atag                                          924
```

SEQ ID NO: 74           moltype = RNA  length = 924
FEATURE                Location/Qualifiers
source                 1..924
                         mol_type = other RNA
                         organism = synthetic construct SEQUENCE: 74
```
atgggagggc tcagcagcaag cgacgtgcat ccaaccttag gagtacagct cttcagtgca  60
ggaatcgccg cttgcctagc cgatgtcatt acctttccac tggacaccgc taaggttcgc  120
ctgcaagttc agggcgagtg tcctacctct tctgtaattc gatataaagg cgtgttgggg  180
acaatcacag ctgtcgtgaa aacagaaggc cgcatgaagc tctacagcgg actgccagca  240
ggtttgcaac ggcagataag ctcagcatcc ctccgtatcg ggctgtacga cacagttcag  300
gaattcctca ctgccgggaa agagacagcc cctagcttgg ggagcaaaat tttggccggg  360
ctcactacag gtgtggcgtcg tgtgttcatt ggacaaccca ctgaggtggt gaaggtacga  420
ctccaggctc aaagccattt cacacgggatt aaaccacgct acactggaac ttacaacgca  480
tacagaatca tcgctaccac agaaggtttg acgggactttt ggaaagggac aacacctaat  540
ttaatgcgat ctgtcatcat caattgcact gaattggtga cttatgacct gatgaaagaa  600
gcatttgtta aaaataacat cctggcggat gatgtccctt gtcatttggt atcagcactc  660
attgcagggt tttgtgccac cgccatgtct ccccagttga tgttgtaaa gacacggttc  720
ataaactcac ctccaggcca gtataagagt gtccccaatt gtgcaatgaa agtgttcaca  780
```

```
aacgaaggtc caactgcatt cttcaagggg cttgttccct ctttccttcg tctcggatcc   840
tggaacgtga taatgtttgt gtgttttgaa caacttaaac gagagctttc taaaagtagg   900
cagactatgg actgtgcaac gtag                                          924

SEQ ID NO: 75          moltype = RNA  length = 924
FEATURE                Location/Qualifiers
source                 1..924
                       mol_type = other RNA
                       organism = synthetic construct
SEQUENCE: 75
atgggcggcc tcaccgcatc agacgtccat ccaacattgg gggtgcagct cttcagtgcc   60
ggcatcgctg cctgtctcgc cgacgtcatt acctttccgt tagatactgc aaaggtccgc   120
ctgcaggttc aaggcgagtg cccaacttcc tccgttattc gctacaaggg cgtgctggga   180
acaatcaccg cagtggtgaa aacagagggc cgaatgaagc tctactccgg gctaccagca   240
ggcttgcaga ggcaaatcag ttctgcatcc ctgcgcatcg gtctatacga cactgttcag   300
gagttcctca ccgccgggaa ggagacagcc cctagtttgg gcagcaaaat actgcccggg   360
ctcacaacag gtggcgttgc cgtttttcatc ggacaaccaa ccgaggtcgt gaaggtgcga   420
ctgcaagcac aaagccatct ccacgggatc aagcctagat acactggaac ttacaacgcc   480
tacaggatca tcgctacaac cgaaggctta actggactct ggaaagggac aacccctaac   540
ttaatgcgaa gcgtcataat caactgtaca gaactagtca catacgatct catgaaagaa   600
gcctttgtga aaaataatat cctggcagat gacgttcctt gtcacctggt ctcagcactg   660
atcgccggat tttgcgctac tgcaatgtct tctcctgttg atgttgtgaa aacacggttc   720
ataaattctc ctccaggtca gtataagagt gttcctaatt gtgccatgaa agtcttcact   780
aacgaaggtc ctacagcatt ctttaaggga ctcgttccct cttttctccg tcttggctca   840
tggaacgtta tcatgtttgt gtgttttgaa cagctgaaga gggagctgtc caaatcaaga   900
caaaccatgg actgcgccac atga                                          924

SEQ ID NO: 76          moltype = RNA  length = 924
FEATURE                Location/Qualifiers
source                 1..924
                       mol_type = other RNA
                       organism = synthetic construct
SEQUENCE: 76
atgggagggc ttactgctag tgacgtccac cctaccctcg gagttcagct cttcagtgcc   60
ggaatcgccg cgtgcctcgc cgacgtgatt acctttccac tagacaccgc taaggtgcgg   120
ctgcaagtcc aggcgagtg tcctacatcc tccgtcattc gctataaagg cgttttgggc   180
accatcacgc ctgtagtcaa aacagagggc cgtatgaagc tctacagcgg gctgcccgcc   240
gggttgcaga gacaaataag ctctgcttct ctgcggatcg gtctgtacga cactgttcag   300
gagttcctca ctgctggtaa ggagacagca cctagcttgg gtagtaaaat tctcgcaggg   360
ctcactacag gcgcgctcgc cgtattcatt ggacagccca ccgaagttgt gaaggtacga   420
ctgcaagctc agtcccatct gcacgggata aaacctcgtt acactggcac ttacaatgct   480
tacaggataa tagctacaac agaaggctta acgggactct ggaaggggac aacacccaaat   540
ttaatgtcat ctgttatcat caactgcact gaactcgtga cctatgatct gatgaaggaa   600
gcctttgtga aaaacaacat cctggccgac gacgttccct gtcacttagt gtctgcactc   660
atcgccggct tctgtgccac cgctatgtcc tccctgtgg acgttgtgaa gacacgcttc   720
ataaattccc ctcctggcca atacaaaagc gtgcctaact gtgccatgaa ggtttttcaca  780
aacgagggc ctactgcttt tttcaaaggc ctcgttcctt cctttcttcg gctcgggtcc   840
tggaatgtca tcatgttcgt gtgttttgag cagttaaaga gagagcttag caaatccagg   900
cagaccatgg actgcgccac ctga                                          924

SEQ ID NO: 77          moltype = RNA  length = 924
FEATURE                Location/Qualifiers
source                 1..924
                       mol_type = other RNA
                       organism = synthetic construct
SEQUENCE: 77
atggggggac tgaccgccag cgacgtgcac cctactctgg gagtccagct cttcagtgcc   60
ggtatcgccg cctgtcttgc cgatgttata acatttcccc tggacacagc taaggtccga   120
cttcaagttc aaggcgaatg tcccacttct tctgtcatcc ggtacaaagg cgtactggga   180
accatcacag cagtggtgaa aaccgaaggc cgtatgaagc tttacagcgg actcccagca   240
ggactgcaga ggcaaataag ctcggcatca ctgcggatcg gcctctacga taccgtccag   300
gagtttctga ccgccggaaa agaaacagct cctagtttgg gcagtaaaat actgcccggg   360
ctcactacag gtggcgttgc cgtttttcata ggacaaccaa cagaagtggt caaggtcaga   420
ctacaggctc aaagtcacct tcacgggatt aaacctcgat ataccgaaat ttataacgct   480
tataggatca tagccacgac agaaggcttg actgggctct ggaaggggac aacacctaac   540
ttaatgcgat ccgtgatcat aaattgtact gagctcgtga cttacgatct catgaaagag   600
gcgttcgtaa aaaataacat attggcagat gatgttccct gtcacttagt ttccgcactg   660
atcgccgggt tttgtgcaac agctatgtct tctcctgtcg acgttgtcaa aacacggttc   720
ataaattctc ctccgggcca atataaaagt gtccctaact gtgccatgaa agtcttcacg   780
aatgaggggc ctacagcctt ctttaaggga ctggtccct cgtttcttcg cctcggttca   840
tggaatgtta tcatgttcgt gtgttttgag cagttaaagc gggagctgag caagagtaga   900
caaacaatgg actgcgccac ctga                                          924

SEQ ID NO: 78          moltype = RNA  length = 924
FEATURE                Location/Qualifiers
source                 1..924
                       mol_type = other RNA
                       organism = synthetic construct
SEQUENCE: 78
```

```
atgggcggat tgaccgccag cgatgtgcat cccacgttag gtgtgcagct ctttagcgca    60
ggtattgccg cgtgcttagc ggatgtgatt acgtttcccc tcgacacggc taaggtacgg   120
cttcaagtcc agggcgagtg cccaacttct tccgtaattc gctacaaagg cgttctcgga   180
accatcacag ccgtggtgaa gacagaaggc cgcatgaaac tttacagcgg actgccagcc   240
ggcttgcaga ggcagataag ctcggcctct ctccgcactg gtttgtacga cacggttcag   300
gagttcctta ctgctggaaa ggagacagca cccagtctgg ggagcaaaat cctagccggg   360
cttacaacag gtggtgtggc tgtcttcatt ggacagccca ctgaggttgt taaggtacgg   420
ctgcaggctc aaagccacct ccacggcatc aaaccacgct atactggtac atataacgcc   480
tacaggatca ttgcgactac agaaggactc acaggactgt ggaaggggac gactcctaat   540
ttaatgcggt ctgtgatcat caactgcacc gaactggtca cttacgatct aatgaaagag   600
gctttcgtga aaaataatat cttggccgat gacgtgcctt gtcacctcgt ttctgcgctc   660
atcgccggat tctgtgcaac cgccatgtct tctccggttg acgttgtcaa aacacgattt   720
ataaactcac caccaggcca atacaaaagc gtccccaact gtgcaatgaa agtcttcaca   780
aacgaaggcc cgacagcgtt ctttaagggg ctcgtcccct cctttcttcg gctcggttcc   840
tggaatgtta taatgtttgt gtgttttgaa cagctaaaaa gggagctgtc aaaatccagg   900
caaacaatgg actgtgcaac atga                                         924
```

SEQ ID NO: 79          moltype = RNA   length = 924
FEATURE                Location/Qualifiers
source                 1..924
                       mol_type = other RNA
                       organism = synthetic construct
SEQUENCE: 79

```
atggggggac tgacagccag tgatgtgcat cccactctgg gtgttcagct tttcagcgcc    60
gggattgccg catgtctcgc tgatgtaatt acttttcctc tcgacacagc taaagtccgc   120
ctgcaggttc agggagagtg tccaacgtcc tccgtgattc ggtataaagg agtttttagga  180
acaatcacag cagtggtgaa gaccgagggc cggatgaagc tctacagcgg gctccccggca 240
ggattgcaga ggcaaatcag ttctgcctct ctccgtatcg gcctgtacga tactgtacaa   300
gaattcctca ccgccggaaa ggagacagca cccagtttgg ggagtaaaat tctggcaggg   360
ctgaccacag gcggcgtggc tgttttcatt ggacagccta ccgaggtggt caaggtccga   420
ttgcaggctc aatctcatct tcacggcata aaacctagat atactgggac atacaacgct   480
tacaggatca tcgcaaccac agaaggcctg actggactat ggaaagggac aacacccaat   540
ttaatgcgat cagtcattat caactgcact gaattggtaa catacgatct catgaaggaa   600
gctttcgtga agaataacat cctcgcagat gacgttcctt gtcaccttgt gtctgcactg   660
atcgccggat tttgtgccac cgcgatgtct tccccggtcg atgttgtgaa gacacgattc   720
ataaattctc caccaggcca atacaaaagc gttcccaact gtgccatgaa agtatttaca   780
aacgaaggcc cgacagcttt ctttaagggg ctcgtccct catttcttcg actcggttcc    840
tggaatgtaa tcatgtttgt gtgtttcgaa caattaaaaa gggagctgag taaaagtaga   900
caaaccatgg actgcgccac ctag                                         924
```

SEQ ID NO: 80          moltype = RNA   length = 924
FEATURE                Location/Qualifiers
source                 1..924
                       mol_type = other RNA
                       organism = synthetic construct
SEQUENCE: 80

```
atgggtggtc tcacagccag tgacgttcat cccactctgg gggttcagct tttcagtgca    60
ggaatcgccg cctgcctcgc cgacgtgatc acctttccgt tggacactgc caaagtacgc   120
ctacaggtcc agggcgagtg tcctacttct tccgtgattc ggtataaggg tgtgctagga   180
accatcactg ccgtggtgaa aacagagggc cgtatgaaac tctacagcgg gttgcctgcc   240
gggctacaga ggcagatcag ctcagcttcc ttgagaatcg gtctctacga cacggtccag   300
gaatttctta ctgccgggaa ggagactgca cctagtctgg gcagcaaaat tttagcgggg   360
ctcacaacag gcggcgtggc tgtattcatt ggacaaccca cagaggttgt gaaggtccga   420
ctgcaggctc aaagccatct gcacggcatt aaacctcgct cacactggca cttacaatgct 480
taccgaatca ttgctacaac tgagggcctt actggactct ggaaaaggcac aactcccaat  540
ttaatgcgat ccgtaatcat caattgcact gaactcgtga cttacgacct catgaaggaa   600
gcttttgtga aaaataacat cctggcagat gacgtcccct gtcacttggt ttctgctctt   660
atcgcaggat tctgcgcaac cgccatgtca tctccagtgg acgttgtgaa gacaaggttc   720
ataaattccc ctcccggtca atataaaagt gtccccaatt gtgccatgaa ggtgttcaca   780
aacgaaggcc caaccgcctt ttttaagggg cttgttccat cttttctgcg tctcggatcc   840
tggaacgtca tcatgttcgt gtgttttgaa caattgaaaa gggagttgtc gaagtccagg   900
caaacaatgg attgtgcaac gtaa                                         924
```

SEQ ID NO: 81          moltype = RNA   length = 924
FEATURE                Location/Qualifiers
source                 1..924
                       mol_type = other RNA
                       organism = synthetic construct
SEQUENCE: 81

```
atgggcggac tcacggcttc cgacgtccat cccaccctgg gggtgcagct cttcagcgca    60
ggcattgccg cgtgtctcgc cgatgttatt acttttccac ttgacaccgc taaggtgcga   120
ttacaggtcc agggcgaatg cccaacatct tccgtgatcc ggtataaagg tgtcctggga   180
accattaccg cggtggtgaa gacagaaggc cgcatgaaac tgtacagcgg gctgcccgca   240
gggctgcaga gacaaataag ctccgcatcc ctccgcactg gactatacga cacagttcag   300
gaattcctca cggccgggaa ggagacagcc cctagtctgg gaagcaagat tcttgctggg   360
ctcactacag gcggcgtcgc tgtcttcatt ggacaaccta ctgaggtggt gaaggtccga   420
ctgcaagccc aatcccacct tcatggaatc aagcctcgct cactgggac atataacgcc   480
tatagaatca ttgctactac agaaggcttg actggccttt ggaaagggac aactcccaat   540
ttaatgcgaa gcgtgattat caattgcact gaactcgtga cttacgatct catgaaggaa   600
```

```
gcatttgtga aaaacaacat cctggctgat gacgttccat gtcatctggt atctgcactg   660
atcgccggat tttgcgctac tgccatgtct agccctgtag atgtcgtcaa gacacggttc   720
attaattctc ctccaggcca atacaaaagt gtccccaatt gtgctatgaa agtgttcaca   780
aatgagggcc ccacagcctt ctttaagggg ctcgtcccct cttttctgcg cctcggttcc   840
tggaatgtca tcatgtttgt gtgcttcgag caattgaagc gagagttgtc aaagtcccgg   900
cagactatgg attgtgccac gtaa                                          924

SEQ ID NO: 82          moltype = RNA  length = 924
FEATURE                Location/Qualifiers
source                 1..924
                       mol_type = other RNA
                       organism = synthetic construct
SEQUENCE: 82
atgggaggcc tcaccgctag tgacgtgcac cctactctgg gtgtacagct cttcagtgca   60
ggaatcgccg cgtgcttggc cgatgttatt acttttcccc tggacacagc taaggtgcgc   120
ctgcaggttc aggggagtg tcccacctcc tccgtcatca gatacaaagg cgtttagga    180
accatcacag ccgtggtaaa aactgagggc cgcatgaagc tctacagcgg tctcccggca   240
ggacttcaga ggcagatcag ctctgcatca ctccgtatcg ggctctacga caccgttcaa   300
gagtttctta cagcaggaaa ggagactgca cccagtttgg gaagcaaaat tctggcaggt   360
cttacaaccg gcggcgtggc tgtgttcatc ggacagccca ctgaggtggt caaggtgcgg   420
ctccaggctc aatctcactt gcacggcatc aagcctcgct cacactggca gtacaatgct   480
tacagaatca ttgcaactac agaaggcctg acaggacttt ggaagggaac aactcctaac   540
cttatgcgat ccgttatcat taactgcaca gagctcgtca catatgacct catgaaggaa   600
gcgttcgtga aaaataacat ccttgcagat gacgttcctt gccacttggt gtccgcgctg   660
atcgccggat tctgtgctac cgctatgtca agccctgtcg acgtcgtgaa gacaaggttc   720
atcaattccc ctccaggaca atataagagt gttcctaacc gtgcaatgaa agtattcaca   780
aacgaaggcc ccaccgcctt cttcaaggga ctggttcctc cttttcttcg actcggttcc   840
tggaacgtta tcatgttcgt gtgttttgag caattaaaaa gggagctgtc aaagtcccgg   900
cagacaatgg actgtgccac atga                                          924

SEQ ID NO: 83          moltype = RNA  length = 924
FEATURE                Location/Qualifiers
source                 1..924
                       mol_type = other RNA
                       organism = synthetic construct
SEQUENCE: 83
atgggtggtt taaccgcaag cgacgtccac cccaccctag gggtgcagct cttcagtgca   60
ggaatcgccg catgtctcgc cgacgtcatt acatttccct tagacaccgc taaggtgcgc   120
ctccaggtcc agggcgaatg tcccacatct tctgtaatcc gctataaagg cgtacttgga   180
acaatcacag ctgtagtgaa aaccgagggc cggatgaaac tgtacagtgg gctgcccgca   240
ggactgcaga ggcagatcag ctccgcatca ctgcgaatcg ggctttacga caccgtgcag   300
gaatttctca ctgccggaaa agagactgct cccagtctgg gtagcaaaat tctggccgga   360
ctcacaacag gcggcgtagc tgtcttcatt ggccagccca ccgaggtggt taaggtccgg   420
ctgcaagccc aatcccacct tcacggtatc aagccgcgtt acactggaac ttacaacgct   480
tacagaatta tcgctaccac cgaaggctta acgggactct ggaaggggac aactcccaat   540
ttaatgcgat ccgttatcat caactgcacc gaactagtga cctatgacct catgaaggaa   600
gccttcgtga aaaacaacat cctggcagac gacgtgcct gtcacctggt ctctgcactc    660
atcgctggat tctgtgctac agcaatgtca tctcctgtcg acgttgtgaa gacacgattc   720
atcaactctc cacctggtca gtataaaagt gtccctaact gtgccatgaa ggtcttcaca   780
aatgaaggcc ctaccgcatt cttcaagggg ctcgtcccct cctttttacg cctcggctcc   840
tggaacgtta ttatgtttgt atgttttgag caactcaaaa gggagctgtc aaaatccaga   900
cagactatgg actgcgccac atga                                          924

SEQ ID NO: 84          moltype = RNA  length = 924
FEATURE                Location/Qualifiers
source                 1..924
                       mol_type = other RNA
                       organism = synthetic construct
SEQUENCE: 84
atgggtgggc tgaccgccag cgatgttcat ccgactttag gtgtgcaact cttcagtgcc   60
ggcatcgccg cctgcctcgc tgatgtgatt acctttcctc ttgataccgc taaggtacgg   120
ctgcaggtcc aaggcgaatg ccccacctct tccgtcattc ggtacaaagg cgtgttggga   180
acaattacgg cagtcgtgaa gactgaaggc cgaatgaaac tctacagtgg gctgcctgct   240
ggtttgcaga gacagataag ctcagcgtct ctgcgaatcg gctctatga cacggttcag    300
gagttcctca ccgctgggaa ggagacagct cctagtctgg gaagcaaaat actcgccgga   360
ctaacaaccg gtggcgttgc tgtattcatc ggacagccta ccgaagtcgt taaggtcaga   420
ctccaggctc agagccacct gcatggcatt aagcctcgct cacactggtac ctacaacgct  480
tacaggatta tcgctaccac agaaggcctg actggactgg ggaaagggac aactcctaat   540
ttaatgcgct ctgttatcat caactgcacc gaattggtca cttacgatct catgaaggaa   600
gcgtttgtga aaaacaacat cttggctgat gacgttcctt gtcacctagt ttcggcactc   660
atcgctgggt tttgtgccac cgccatgtct tctcctgtcg acgttgtcaa acaaggttt    720
ataaactcac caccaggtca gtataaaagt gtccctaact gtgccatgaa agtcttcacc   780
aacgaagggc ccacagcttt cttcaagggg cttgtccctt cgtttctacg actcggatct   840
tggaacgtga tcatgtttgt ctgtttcgag caattgaagc gagagctgtc taagtctagg   900
cagacaatgg actgcgcaac ctga                                          924

SEQ ID NO: 85          moltype = RNA  length = 924
FEATURE                Location/Qualifiers
source                 1..924
```

-continued

```
                         mol_type = other RNA
                         organism = synthetic construct
SEQUENCE: 85
atggggggggc tgacagcttc tgacgtacat cctactctgg gggtccaact cttcagtgcc     60
ggaatcgccg cttgcctcgc tgacgttatc accttccctt tagacacagc taaagtccga    120
ctgcaagttc aaggcgagtg ccctacttct tccgtgatca gatacaaggg cgtgctgggt    180
acaattactg cggtggtgaa aactgaaggc cgcatgaagc tctatagcgg gctgcctgca    240
ggcttgcaga ggcagataag ctcagcctcc ctgcggattg gtctgtacga tactgttcag    300
gagttcctta ccgctggaaa ggagacagct cccagtttag ggagcaaaat cctggccgga    360
ctcactacag gcggcgtcgc tgtcttcatt ggacagccca cagaggttgt aaaggtaagg    420
ctgcaagccc aaagccacct ccacggcatc aaacctcgct atactgggac ttacaacgct    480
taccgaatca tagctacaac cgaaggctta actggactgt ggaagggcac aacaccaaac    540
ttaatgcgat cagttattat caactgcacc gaactggtta cttatgatct catgaaagaa    600
gcttttgtga aaaataacat cctcgctgat gacgtccctt gtcatttggt gtctgcatta    660
atcgccggat tttgtgcgac cgctatgtcg agtcctgtcg acgttgtgaa aacacgattc    720
ataaattcac ctcccgggca gtataaaagc gttcccaatt gtgccatgaa ggtattcacc    780
aacgaaggtc ctacggcatt cttcaagggg ctggttcctt cctttcttcg gctcggttcc    840
tggaatgtta tcatgtttgt ctgtttttgaa cagctgaaaa gggagctatc aaagtccagg    900
cagaccatgg actgcgctac ttga                                            924

SEQ ID NO: 86            moltype = RNA  length = 924
FEATURE                  Location/Qualifiers
source                   1..924
                         mol_type = other RNA
                         organism = synthetic construct
SEQUENCE: 86
atgggcggac tcacagcctc ggacgtgcac cccacactgg gagttcagct tttcagcgca     60
ggcatagccg cctgcctcgc agatgtgatt acctttcctc tagacactgc taaggtccgc    120
ttgcaagtcc agggcgagtg cccaacttct agtgtgatcc gatataaggg cgtgttgggg    180
accattacgg cggtcgttaa aacagagggc cgcatgaagc tatatgtggg gctgccagcc    240
ggcctgcaga ggcagatcag ctctgcctcc ctacgtatcg gcctgtatga caccgttcag    300
gagttcctta ctgcaggaaa agaaactgct cctagcttgg gcagcaaaat tctcgccggg    360
ctcactacag gcggcgtggc tgtgttcatt ggacagccta ctgaagtggt caaggtccga    420
ctgcaggctc aaagccacct ccatggcatc aaacctcgct acactggcac atataacgct    480
tacagaatca tagccacaac tgaagggctc acaggacttt ggaagggggac aacacctaac    540
ttaatgcgat ctgttatcat aaactgcacc gaactcgtaa cgtatgatct catgaaggag    600
gccttcgtga aaaacaacat cctggccgac gacgttccat gtcatttggt ttccgctctc    660
atcgccgggt tttgtgctac tgctatgtca agccctgtcg atgttgttaa gacacgattt    720
ataaactccc cacctggcca gtataagagc gtccccaact gcgccatgaa ggtgttcaca    780
aacgaagggc ccacagcgtt ctttaagggg ctggtcccct cttttctacg gctcggatcc    840
tggaacgtta tcatgttcgt gtgtttcgaa caattaaaaa gggagctctc caagtcacgg    900
caaacaatgg actgcgctac atag                                            924

SEQ ID NO: 87            moltype = RNA  length = 924
FEATURE                  Location/Qualifiers
source                   1..924
                         mol_type = other RNA
                         organism = synthetic construct
SEQUENCE: 87
atgggcggtc ttactgctag tgacgtgcac ccaacgctgg gggtgcaact cttcagtgct     60
ggcatcgccg cttgccttgc cgacgttatt acttttccct tagataccgc taaggtccga    120
ttgcaggtcc aaggcgaatg ccctacatca tcagttattc gatataaagg tgttctaggt    180
accattaccg ccgtggtgaa aaccgagggc cgcatgaagc tttacagcgg gcttcctgcc    240
ggcctacagc gccagataag ctcagcatct ctacggatcg gactgtacga caccgtgcag    300
gagttcctta cagccggaaa ggaaacagct cctagtctgg gcagcaaaat cctcgccggg    360
ctcaccacag gcggtgtcgc tgtattcatt ggtcaaccca ctgaggtcgt aaaggtccga    420
ctgcaggctc aaagtcacct gcacggtata aaaccgcggt acactggtac ttacaacgcc    480
tataggatca tcgctacaac ggagggctta actggattgt ggaaggggac gactcctaac    540
ttaatgcgct ctgtcatcat aaattgcacc gaactggtta cttacgacct catgaaggaa    600
gccttcgtga aaaacaacat cctggcagat gacgttccat gccacctcgt gtctgcactc    660
atcgcaggat tctgtgctac cgctatgtct agtccagtcg atgttgtcaa gacacggttt    720
atcaattcac caccaggaca atataaaagt gtcccaaact gtgccatgaa agtcttcaca    780
aacgaggggc ctacagcatt cttcaagggg ctcgtcccct cttttctgcg gctcgggtct    840
tggaacgtta tcatgtttgt gtgtttcgaa cagctaaaaa gggaactgtc caagtcaagg    900
caaacaatgg actgcgccac ctaa                                            924

SEQ ID NO: 88            moltype = RNA  length = 924
FEATURE                  Location/Qualifiers
source                   1..924
                         mol_type = other RNA
                         organism = synthetic construct
SEQUENCE: 88
atggggggtc tgaccgcgag cgacgtccat cctaccctgg gtgttcagct cttcagtgcg     60
ggcatcgccg cgtgcctggc cgacgttatt accttccct tagacacagc aaaggtacga     120
ctacaggtac aaggcgaatg tcctacttct tccgttattc gctataaggg cgtcttggga    180
accattactg ctgtggtaaa aacggaaggc cgcatgaagc tgtatagcgg gctgcccgcg    240
ggccttcaga ggcagatcag ctcggcctcc ctgcgtattg gattgtacga cacagtccaa    300
gaattcctta ccgccgggaa agaaacagca cctagcctgg gcagcaaaat actcgccgga    360
ctcactacag gcggcgtggc cgtgtttatt ggacagccta ctgaggtggt caaggtccga    420
```

```
ctgcaggccc agagtcactt gcacggcatc aaaccacggt atactggcac gtacaacgct     480
tacaggatca tcgcaaccac cgaaggctta acaggactct ggaagggtac aacgcctaat     540
ttaatgcgct ccgtcatcat aaaattgcacc gagctcgtga cttatgatct catgaaggaa    600
gcctttgtga agaataacat cctggcagac gacgttccct gtcacctagt atctgcactc     660
atcgcaggat tctgcgccac cgctatgtct tctcccgtag atgtcgttaa gacgcggttt     720
attaattcgc cacccggtca atataaaagt gtccctaatt gtgccatgaa ggtctttaca     780
aacgaaggcc ctaccgcctt tttttaagggg ctggttcctt cttttttacg gctcgggtcg    840
tggaacgtca tcatgttcgt gtgtttgaa cagctgaaac gggaactttc caaatccagg       900
cagacaatgg actgcgctac ttga                                            924
```

SEQ ID NO: 89          moltype = RNA   length = 924
FEATURE               Location/Qualifiers
source                1..924
                      mol_type = other RNA
                      organism = synthetic construct
SEQUENCE: 89

```
atgggtggtc tgaccgcaag tgacgtgcat cctacactgg gagtgcagct cttcagtgcg      60
ggcattgccg cttgccttgc cgatgtaatt acctttccat tagacacagc caaggtgcgc     120
ctgcaggttc agggagaatg tccaacgtct tccgtgattc ggtataaggg cgttctgggc     180
accattacgc ctgtggtgaa aacagaaggc cgtatgaaac tttacagcgg actccctgca     240
gggctacagc gacagatcag ctctgcttct ctgcgtatcg gtttgtatga cacagtacag     300
gagttcctca ctgccggaaa ggagactgca cccagtttag gcagcaaaat ccttgcaggg    360
ctcacaacag gtggcgttgc cgtttttatc ggacagccca cagaagtggt gaaggtacga     420
ctgcaagctc agagtcacct gcacgggatc aagcctcgct atactggaac ttataacgct     480
tatagaatca ttgctactac agaaggtcta actggactct ggaaagggac aacacctaat     540
ttaatgcgat ctgttatcat caactgcaca gaactggtga cttatgacct catgaaggaa    600
gcttttgtga aaaacaacat cctcgcagac gacgttcctt gtcacctggt gtctgcactc     660
attgcagggt tttgtgcaac cgccatgtct tctcctgttg acgttgtcaa aacacgtttt    720
ataaactcac ctcctggaca gtacaagagt gtccccaatt gtgccatgaa ggtattcaca     780
aacgaaggc ccaccgcatt ctttaagggg ctggttccct cttttctgcg cctcggttct      840
tggaacgtga taatgtttgt gtgctttgaa cagttaaaaa gagaactatc caaatcaagg     900
cagacaatgg actgtgccac atga                                            924
```

SEQ ID NO: 90          moltype = RNA   length = 924
FEATURE               Location/Qualifiers
source                1..924
                      mol_type = other RNA
                      organism = synthetic construct
SEQUENCE: 90

```
atgggaggac tgacagccag cgacgttcac cctacactgg gggttcagct cttcagcgcg      60
ggaatcgctg cttgcctcgc tgatgtcatt acttttcctc ttgatacagc taaggtccga     120
ctgcaagttc agggcgaatg ccctacttct tccgtcatcc gctacaaggg cgtgctgggc     180
accatcacag ctgtcgtaaa aacagagggc cgcatgaaac tatatgcgg cttgcccgca      240
gggctgcaaa ggcagatcag ctctgcgtcc ctccggatcg gactgtacga cacagtgcag     300
gaatttctta cggccggaaa ggagactgct cctagcttgg gtagcaaaat tctcgccggg    360
ctgaccacag gcggtgtggc tgtgttcatc gggcagccta ccgaggttgt taaggtgcga     420
ctgcaggctc aaagtcacct gcatggaatc aagcctcgct acactggtac atataacgct     480
tatcggatta ttgcaaccac tgaaggcctc acaggcctct ggaagggcac cactcctaat     540
ttaatgcgat cagtcatcat aaaattgcacc gaactcgtga cttatgatct catgaaggaa    600
gcttttgtaa aaaacaacat tctggctgac gacgttccct gccatctggt gtcggctctc     660
atcgcaggat tttgtgcaac cgccatgtct tctcctgtcg acgttgtgaa aacaaggttt     720
ataaactcac cacctggcca atataagtct gttcccaatt gtgccatgaa ggtgttcaca     780
aatgaaggtc ccacagcatt cttcaaaggg cttgttccct cctttcttcg gctcgggtcc     840
tggaacgtca tcatgttcgt gtgctttgaa cagttaaaaa gggaactgag taagtccagg     900
cagacaatgg actgtgctac atga                                            924
```

SEQ ID NO: 91          moltype = RNA   length = 924
FEATURE               Location/Qualifiers
source                1..924
                      mol_type = other RNA
                      organism = synthetic construct
SEQUENCE: 91

```
atgggtggcc taactgccag tgacgttcat cccactttgg gagtgcagct tttcagcgca      60
ggaattgctg cttgccttgc tgacgttatt acctttccat tagataccgc gaaggtccgc     120
ttgcaagtcc aaggcgagtg cccaacttca tccgtcattc gctacaaagg cgttctgggt     180
accatcacag ccgtcgtgaa gaccgaaggc cgcatgaaac tctatagcgg gctgcccgcg     240
ggcctccaga ggcaaatcag ctcagcttcc ttgcgcatcg gattatacga cactgttcaa     300
gagtttctta cagccggaaa ggagacagcg cctagtctgg ggagtaaaat cttggccggg    360
ctcacaacag gcggcgttcgc cgtattcatc ggacagccca ccgaagtagt caaggtccga     420
ctgcaggctc aatctcatct acatggtatc aagccccgct acactggcac atataacgct     480
tatagaatta ttgctacaac agaaggctta actggactat ggaagggcac tacacctaat     540
ttgatgcggt ccgtcatcat caattgcacc gagctcgtaa cttacgatct aatgaaggag    600
gccttcgtga aaaacaacat tctggccgat gatgtccctt gtcacttggt ctctgcactg     660
atcgccggat tctgtgccac cgccatgtct agccctgtcg acgtcgtgaa aacgcgattc     720
atcaattctc cccccggtca gtataaatct gttcccaatt gtgctatgaa ggtgttcaca     780
aacgaaggcc caactgcatt ctttaaaggg ctagtaccct ctttctgcg gcttggctcc       840
tggaatgtca tcatgttcgt gtgtttcgaa caactgaaaa gggagctgtc caaatccagg     900
cagactatgg actgcgccac ctga                                            924
```

-continued

```
SEQ ID NO: 92          moltype = RNA   length = 924
FEATURE                Location/Qualifiers
source                 1..924
                       mol_type = other RNA
                       organism = synthetic construct
SEQUENCE: 92
atgggtggac tcacagcttc agacgtccat ccaaccctgg gagtgcagct cttcagtgcc    60
ggaatcgccg catgcctggc agacgtcatt acctttcccc tggatacagc caaggtgcga   120
ctacaggttc aggggaatg ccctacatcc tctgtgatcc ggtataaggg cgtgctgggg    180
accattacag ccgtggtaaa gaccgagggc cgcatgaagc tttatagcgg gctccccgcc   240
ggcttgcaga ggcagatcag ctccgcatca ctgcgaatcg ggttgtacga cacagtgcag   300
gaatttctta ctgctggaaa agagactgcc cctagtctgg gcagcaaaat cctgccgggg   360
ctgactacag gtggcgttgc tgtctttatt ggacagccca ctgaggttgt aaaggtgcga   420
ctgcaagctc aatcccacct ccacggaatt aagccacgct atactggaac gtataacgcc   480
tataggatca ttgctacaac agaaggtttg actgggcttt ggaagggtac aacacccaat   540
ttaatgcgat ccgtcattat caactgcacc gaactagtga catacgatct catgaaggaa   600
gcatttgtga aaaataacat cctggctgac gacgttcctg tcacttagt atctgcactg    660
atcgctgggt tttgtgcaac cgcaatgtct tcccccgtcg atgtcgtcaa aacaagattt    720
ataaattctc cacctggaca atataaaagt gttcccaact gcgctatgaa ggtcttcaca   780
aacgaaggcc caaccgcatt ctttaagggg ctagttcctt cttttcttcg gcttggttct   840
tggaacgtca tcatgttcgt gtgtttcgaa cagttgaagc gggagctgtc aaaatcgagg   900
cagaccatgg actgcgctac gtaa                                          924

SEQ ID NO: 93          moltype = RNA   length = 924
FEATURE                Location/Qualifiers
source                 1..924
                       mol_type = other RNA
                       organism = synthetic construct
SEQUENCE: 93
atggggggac tgactgcctc ggacgtccat ccgacactgg gtgtgcagct cttcagtgca    60
gggatcgctg cttgtctcgc cgacgttata acctttcccc tagacacggc caaggtacgt   120
ctacaggttc agggcgaatg ccctacttct tctgtcattc gttacaaagg tgtgttaggg   180
accataacag cggtagtgaa gaccgaaggc cgcatgaaac tctacagcgg gcttcctgcc   240
ggactgcaac ggcagattag ctctgcatcc ctgcgcattg ggctgtacga cactgtgcag   300
gaattcctca cagcaggaaa ggagacagcg cctagtctgg ggagtaaaat cctcgcagga   360
ctaacgacag gtggcgtcgc tgtgttcatt ggacagccta ccgaggttgt gaaggtaagg   420
ctgcaagccc aatcacacct gcacggaatt aagcctcgct acactggaac ttacaacgcc   480
tacaggatta ttgccacaac cgagggcctt actggactat ggaaggggac aacacctaat   540
cttatgcgat cagttattat caactgcact gagttggtaa cctacgatct catgaaggaa   600
gcgttcgtga aaaacaatat cctggccgac gacgtgccct gccatttggt gtctgcactg   660
atcgcaggat tttgtgctac cgcaatgtct tctcctgtcg atgttgtgaa gacacggttt    720
atcaattccc caccgggcca gtataaaagt gttcctaact gtgccatgaa agtattcaca   780
aacgaaggcc ccacagcctt cttcaagggg ctagttccct cattccttcg gctcgggtcc   840
tggaatgtca tcatgtttgt gtgttttgaa cagttaaaac gagagctctc gaagtccagg   900
cagacaatgg actgtgccac gtga                                          924

SEQ ID NO: 94          moltype = RNA   length = 924
FEATURE                Location/Qualifiers
source                 1..924
                       mol_type = other RNA
                       organism = synthetic construct
SEQUENCE: 94
atgggcggtc tcacggcctc agacgttcat ccaacgctgg gcgtgcagct cttcagtgca    60
ggaatcgccg cttgcctggc tgatgtcatt acctttcctc ttgacactgc caaggtgcgg   120
ttgcaggtcc agggtgaatg cccaacttct tctgttattc gctacaaagg cgttttggga   180
accatcaccg ctgtggtgaa aacagagggg cgcatgaagc tgtacagcgg gctgccagcg   240
ggactacagc gacagataag ctcagcatca cttcggattg gtctgtatga cacagttcag   300
gagttcctca ctgctggaaa gggagacagc cctagtctgg gtagcaaaat cctggctggg   360
ctaacaacag gcggcgtagc tgtatttatt ggacaaccca ctgaggtgt caaggtccga   420
ctgcaggccc aatctcacct gcatggcatc aagcctcgct acactggtac ttacaacgct   480
tacaggatca tagctacaac cgaaggccta actgggctgt ggaagggcac gacacccaat   540
ttaatgcgat ccgtcatcat aaactgcacc gaactcgtta catatgatct tatgaaggaa   600
gcatttgtga aaaataacat cctggcagat gacgttcctt gtcatctggt ttctgcactc   660
atcgcgggat tttgtgctac cgctatgtca gtcccgtcg acgtcgtgaa gacacggttc    720
ataaattccc caccgggcca gtacaaaagt gtccccaact gtgcaatgaa agtcttcaca   780
aacgaaggcc ccacagcatt cttcaaggga ctagttccct cctttctacg cctcggctct   840
tggaacgtaa tcatgttcgt gtgttttgaa caattaaaaa gggagctgtc taaatcacgt   900
caaactatgg actgcgccac atga                                          924

SEQ ID NO: 95          moltype = RNA   length = 924
FEATURE                Location/Qualifiers
source                 1..924
                       mol_type = other RNA
                       organism = synthetic construct
SEQUENCE: 95
atgggaggcc taacagcttc tgatgtccac cccaccttg gagtgcagct cttcagtgca     60
ggtatcgctg cttgcctggc cgatgttata acctttcctc tggatacagc caaggtgcga   120
ttgcaggtcc agggcgagtg cccgacctca agcgtgatcc gatataaagg cgtgttggga   180
actatcacag ccgtcgtgaa gaccgaaggc cgaatgaagc tttacagcgg acttcctgcc   240
```

-continued

```
ggcctgcaga ggcagataag ctctgcatct ctccggatcg gactgtacga cacagtccaa   300
gagttcctta ctgcaggaaa ggagactgca cctagtttag ggagcaagat cttggccgga   360
ctcacaacag gtggcgttgc tgtttttata ggacagccta ctgaagtggt gaaggtgaga   420
ctgcaggctc aaagccatct gcacggcatc aaacctcgct atactggaac atataatgct   480
tataggatca ttgcgaccac agagggcctc acagggctgt ggaaagggac aacccctaat   540
ttgatgcggt cagtcatcat caactgcact gagctagtta cttatgatct catgaaagaa   600
gcatttgtca aaaataacat tctggcagat gatgtgcctt gtcacctggt gtctgcatta   660
atcgcaggat tctgcgccac cgctatgtca tctcctgtcg atgttgtgaa gacacgattc   720
ataaactccc ctcctggtca atataagagc gttcccaact gcgctatgaa agtcttcacc   780
aacgagggcc caacagcttt cttcaagggg ctcgtgccct cctttctccg actgggatcc   840
tggaatgtga tcatgtttgt ctgctttgag cagttgaaac gggaattgtc taaatcgagg   900
caaactatgg actgcgccac atga   924
```

SEQ ID NO: 96            moltype = RNA   length = 924
FEATURE                  Location/Qualifiers
source                   1..924
                         mol_type = other RNA
                         organism = synthetic construct
SEQUENCE: 96

```
atgggcggcc tgacagcctc agacgttcat cccacattgg gtgttcagct cttcagtgca   60
ggtattgccg cctgtctcgc cgatgtaata acctttccac tcgacaccgc taaggtccgc   120
cttcaggttc agggcgagtg ccccaccagt tccgttatca gatacaaagg tgtcctaggg   180
accattacag cggtggtgaa gaccgagggc cgtatgaagc tctatagcgg gctgccagca   240
ggcctccagc gccagataag ctctgcctcc ctgcggatcg gcctctatga cacagtccaa   300
gaattcctca cagctggaaa ggagactgcg cctagtctgg gtagcaagat ccttgccgga   360
ctcaccacag gcgcgcttgc tgtattcatt ggacagccta ctgaagtagt caaggttcga   420
ctgcaggccc aaagtcacct ccacggcatt aagcctcgct acactggtac gtataacgct   480
tatagaataa tagccacaac agaaggctta acgggactct ggaaggggac tacacctaat   540
ttaatgcgat ccgtcatcat caactgcact gagcttgtaa cttacgacct catgaaggaa   600
gccttcgtga aaaataacat tttggctgat gacgttccgt gtcacctggt gtctgcactc   660
attgcagggt tctgtgccac cgccatgtct tctccggtcg acgttgtgaa gacgcgattc   720
atcaattccc ctcccggtca atataaatct gtccccaatt gtgccatgaa agtattcact   780
aacgagggcc caacagcctt tttcaagggg cttgttcctt cctttttgcg gctcggatct   840
tggaacgtta tcatgttcgt gtgttttgaa caattgaaac gggagttgtc taagtcccgc   900
caaacgatgg actgcgctac ctga   924
```

SEQ ID NO: 97            moltype = RNA   length = 924
FEATURE                  Location/Qualifiers
source                   1..924
                         mol_type = other RNA
                         organism = synthetic construct
SEQUENCE: 97

```
atgggtgggc tgaccgcaag tgacgtgcac cccacgttag gggtgcaact cttcagtgcc   60
ggaattgccg cctgcctcgc tgatgttatt acttttcctc tggacaccgc gaaggtacgg   120
ttgcaagtcc aaggcgaatg tccaacctct tccgtcattc ggtataaagg cgtccttggg   180
accatcactg ctgtcgtgaa aacggagggc cgtatgaaac tctacagcgg gcttcctgca   240
ggcctgcaaa ggcagatcag ttcagcttcc ctgcggatcg ggctgtatga caccgtgcag   300
gaattcctta ctgcaggtaa ggagaccgca cccagtttgg ggtccaaaat cttggcagga   360
ctcacaacag gaggcgttgc tgtattcatc ggacagccca ccgaagtggt aaaggtaaga   420
ctgcaggccc agtctcacct gcacggcatc aagcctcgct acactggaac ctacaacgcc   480
tacaggatca ttgccaccac tgaaggtctc actggattat ggaagggac cactcccaat   540
ttaatgcgat cagtcatcat aaaattgcacc gaattggtta cttacgatct catgaaagaa   600
gcgtttgtga aaaataatat ccttgcagac gacgttcctt gtcacctggt atctgcgctc   660
atcgccggat tttgcgcgac cgccatgtct tctcctgtcg atgttgtcaa aacacggttt   720
atcaactctc ctcctggtca atataaaagt gttcccaatt gtgccatgaa ggtcttcacc   780
aacgaaggcc ctacagcatt ctttaagggg cttgttccct cctttctgcg ccttggttct   840
tggaatgtca tcatgtttgt ctgtttcgaa caactaaaaa gggagctgag caagagtaga   900
caaaccatgg actgtgcaac atga   924
```

SEQ ID NO: 98            moltype = RNA   length = 924
FEATURE                  Location/Qualifiers
source                   1..924
                         mol_type = other RNA
                         organism = synthetic construct
SEQUENCE: 98

```
atgggtggcc ttaccgcttc ggacgttcat cccaccctgg gcgttcagct gtttagcgcc   60
ggaatagccg catgtctcgc cgatgtaatc acctttcctc tggataccgc caaggtgcgc   120
ctacaagtcc aaggcgaatg cccgacctct tctgttattc ggtataaagg tgtcttggga   180
accatcactg cagtcgtaaa aacagaaggc cgtatgaaac tctacagcgg acttcctgct   240
gggctccaga ggcagataag ctctgcctcc ttgaggattg tctgtacga caccgttcag   300
gagttcctta cagcgggaaa ggagacagct cccagcttag gcagcaaaat acttgccggg   360
cttacaacag gtgcgtggc ggtgttcatt ggacagccta ccgaggtggt aaaggtgcga   420
ctgcaggccc agtctcattt gcatgggatc aagccgcgct acactgggac ttataacgcc   480
tatagaataa ttgctacgac ggaagggctta actggactt ggaaggggac aacacctaat   540
ttgatgcggt cggtcataat caattgcacc gaactggtga cttatgacct catgaaagag   600
gctttTgtga agaacaacat cctgctgac gacgttcctt gtcatcttgt atcagcactt   660
atcgcaggat tctgtgcaac agcaatgtcc agcctgtcg atgttgtcaa aacacggttc   720
ataaattctc cacctggcca atataaaagc gtccccaatt gtgccatgaa agtattcaca   780
aacgaaggc caaccgcctt cttcaaggga ctcgtcccct cctttctccg tctcggatcc   840
```

```
tggaatgtta tcatgttcgt gtgctttgag caattaaagc gagagctctc caagtcaagg    900
caaacaatgg actgcgctac atag                                           924

SEQ ID NO: 99         moltype = RNA  length = 924
FEATURE               Location/Qualifiers
source                1..924
                      mol_type = other RNA
                      organism = synthetic construct
SEQUENCE: 99
atgggaggtc tcaccgcatc tgatgtgcat ccaacactgg gggttcagct cttcagtgcg    60
ggaatagccg cctgtctggc tgatgttatt acctttcccc tggacaccgc aaaggtacga    120
ctccaagtcc agggcgaatg tccgacctca tcggtgatta gatacaaagg cgtgttgggg    180
accatcaccg cagtcgtgaa aacagaaggc aggatgaaac tttacagtgg gctgcccgca    240
ggcctgcaga ggcagatcag ctctgcatct ctacgcatcg gcttgtacga taccgtccga    300
gaattcctga cagcaggcaa agaaaccgcc cccagtctgg gtagtaagat tttggcaggg    360
ctgactacag gtggtgtcgc tgtcttcatc gggcaaccca ctgaagtggt gaaggtgcga    420
ctgcaagctc agagtcacct gcacggaata aaacctcgct atactggtac ctacaacgct    480
tatagaatta tcgcgaccac cgaaggcctc actggactct ggaaagggac gacacctaac    540
ttgatgcgat ccgtaatcat caattgcact gagctagtta catacgatct catgaaggag    600
gcattcgtga aaaacaatat cctggccgat gacgtccctt gtcacttggt ttccgcgctc    660
atcgcaggat tctgtgctac cgccatgtca tcccccgtcg atgtcgttaa aactcggttc    720
attaactcac cccctggcca gtacaaaagt gttcctaact gtgccatgaa ggtgttcaca    780
aatgagggcc ccacagcatt cttcaaggga ctagtccctt cttttcttcg gctcggcagc    840
tggaatgtca tcatgttcgt gtgcttcgaa cagctaaaac gagagctgtc caagtcaagg    900
caaaccatgg actgtgccac atag                                           924

SEQ ID NO: 100        moltype = RNA  length = 924
FEATURE               Location/Qualifiers
source                1..924
                      mol_type = other RNA
                      organism = synthetic construct
SEQUENCE: 100
atggggggggc tcaccgcctc cgatgtgcac cccacccttg gagttcagct cttcagtgca    60
ggaatcgccg cttgcctcgc cgatgttatt actttccct tagacacagc gaaggtacgc     120
ctgcaggttc aaggcgaatg tccaacttca agcgtgattc gatacaaagg cgtgctcgga    180
acaatcacag ctgtggtgaa gacagagggc cgaatgaagc tgtactctgg tctcccagca    240
ggcctccaga ggcagatcag ctccgcatcc ttgcgtatcg gactgtacga cacagtccaa    300
gaatttctta cagctggaaa ggaaacagct cctagtctgg gaagcaaaat ccttgcaggt    360
cttaccacag gcggcgtcgc cgtgttcatt ggacagccta ctgaggttgt gaaggtccga    420
ctgcaggctc aatcccatct gcatggtatt aagccacgct acactggaac atataacgct    480
tacagaatca tcgcaaccac agagggcttg acaggactct ggaaaggcac gacgcccaat    540
ttaatgcgat ccgtcatcat caactgcaca gaactggtaa cgtatgatct catgaaagaa    600
gcttttgtga agaataacat cttggcagac gacgttccat gtcacctggt ttctgcattg    660
atcgccggat tctgtgctac tgctatgtca tcgcctgttg acgtcgtaaa gacacgcttt    720
ataaactccc cacctggtca atataaaagt gtccccaact gtgcaatgaa agtcttcaca    780
aacgaaggcc ctacagcatt ttttaaggga ctggttcct cctttcttcg tctcggatcc     840
tggaatgtca ttatgtttgt atgctttgaa cagctgaaaa gagagctgtc caaatccaga    900
caaacaatgg actgtgcaac ctga                                           924

SEQ ID NO: 101        moltype = RNA  length = 924
FEATURE               Location/Qualifiers
source                1..924
                      mol_type = other RNA
                      organism = synthetic construct
SEQUENCE: 101
atgggcggtc tgacagccag cgacgtgcat cccacactgg gtgtgcagct cttcagtgca    60
ggaattgccg cttgcctcgc tgatgttatt acatttcctc tagatactgc caaggtacga    120
ttgcaggttc aaggcgaatg cccaacaagt agcgttatcc gatataaagg cgtgttggga    180
accatcaccg ctgtagtgaa aaccgaaggc aggatgaagc tctacagcgg gctcccagcc    240
ggcctacaaa ggcagataag ctccgcctcc ctgcgtatcg gattgtacga cacggtccaa    300
gagttcctta cagcgggaaa agagacagcg cctagcttgg ggtccaaaat tctgcccgga    360
ctcacaacag gaggtgtggc tgtgttcatt ggacagccta cagaagttgt caaggtgcga    420
ctacaggctc aatctcacct gcatgggata aaacctcgct acactgggac ttacaacgct    480
tacaggatta ttgccacaac agaaggcctg acgggacttt ggaaaggtac aacacctaat    540
ttaatgcgtt ccgttatcat caattgcact gagctggtca cttacgatct catgaaggaa    600
gcattcgtga aaaataacat cttggcagat gacgttcct gtcacttggt gtccgcactg     660
atcgcaggat tctgtgccac tgcaatgtca agccctgtcg atgtcgtgaa aacaaggttt    720
atcaattccc cacctggtca gtataaatct gttcctaatt gtgccatgaa ggtattcacc    780
aacgaaggcc ccacagcctt ctttaaggga ctggttcct cttttctccg gcttggatcc     840
tggaacgtca taatgttcgt atgttttgag cagttaaaaa gagagctgtc taaatccagg    900
cagacaatgg actgtgctac atag                                           924

SEQ ID NO: 102        moltype = RNA  length = 924
FEATURE               Location/Qualifiers
source                1..924
                      mol_type = other RNA
                      organism = synthetic construct
SEQUENCE: 102
atgggcggac ttacagcatc tgacgtgcac cctacattag gtgttcagct cttcagtgca    60
```

-continued

```
ggcatcgctg cttgcctcgc cgatgtcatt acctttcctc tggataccgc taaggtacgc   120
ctccaggttc agggcgaatg cccaacttcc tccgtgattc gatataaggg agttttggga   180
accattacgg ctgtggtgaa gactgagggc cgaatgaaac tttacagcgg gctgcctgcg   240
ggactgcagc ggcagatcag ctcagcttcg ttgcggatcg ggctatatga caccgttcag   300
gaattcctta cggccggaaa ggaaaccgca cctagtctgg gtagtaaaat tcttgccggg   360
cttacgacag gcggcgtcgc tgtgttcatt ggccaaccca ctgaggtggt aaaggtccgg   420
cttcaggctc aaagccacct gcacggaatc aagcctcgct acactggaac atacaacgct   480
tacaggatca tagccactac agaaggcctg acagggcttt ggaagggcac gacacccaat   540
ttaatgcggt ctgtgatcat caattgcact gaactggtga cttacgacct catgaaggaa   600
gctttcgtga aaaacaacat actggccgat gacgtcccat gtcatctggt gtccgcattg   660
atcgccggat tttgtgctac agctatgtct tcccctgtcg acgtcgttaa gacacgattt   720
ataaactctc caccaggaca atacaagagt gtccccaatt gcgccatgaa agtcttcaca   780
aacgaaggcc ctacagcctt ctttaagggg ctcgttccct cctttcttcg gctcggctct   840
tggaacgtca tcatgttcgt gtgcttcgag caactgaaac gggagttatc caaaagtaga   900
cagaccatgg actgcgctac ttga                                          924
```

SEQ ID NO: 103          moltype = RNA  length = 924
FEATURE                 Location/Qualifiers
source                  1..924
                        mol_type = other RNA
                        organism = synthetic construct
SEQUENCE: 103
```
atgggcggat taactgccag tgacgtccac cccactctgg gggtacaact cttcagtgcc   60
ggaatcgccg cttgtctcgc cgatgttatt acctttccct tagacaccgc taaggtcgcgc   120
ctgcaagttc aaggcgaatg cccaacatca agcgttatac gatataaggg cgttctcggg   180
accatcacag ctgttgtaaa aacagaaggc cgtatgaaac tctacagcgg actgcctgcc   240
ggcctgcaga ggcagatcag ttcggcgtcc ctgcgcatcg gtttgtacga taccgtgcaa   300
gaattcctga ccgccggaaa agagacagct cccagtttgg gtagtaaaat tctggcgggg   360
ctcacaacag gtggcgttgc tgtgttcatc ggacagccta cagaggtagt caaggtccga   420
ctccaggctc aatcacacct gcacggaatc aaacctcgct acactgggac atacaacgct   480
tacaggatta tcgccaccac agaaggcttg actgggttgt ggaagggcac aacacctaat   540
ttaatgcgat ctgtcataat caattgcacg gaactagtaa cgtacgatct catgaaagaa   600
gcttttgtga aaaataacat tctggcagat gacgtcccct gtcacttggt gtctgcactc   660
atagctggat tttgtgcaac tgctatgtca tcccccgtcg atgtcgtgaa aacacggttt   720
atcaattcac caccaggcca atacaaatct gtacctaatt gtgccatgaa ggtgttcacg   780
aacgaagggc caacagcctt cttcaagggg cttgttccat cctttctccg actcgggtca   840
tggaatgtga tcatgttcgt gtgtttcgag caactgaaaa gagagttgtc aaagagtaga   900
caaacgatgg actgcgccac atga                                          924
```

SEQ ID NO: 104          moltype = RNA  length = 924
FEATURE                 Location/Qualifiers
source                  1..924
                        mol_type = other RNA
                        organism = synthetic construct
SEQUENCE: 104
```
atgggtggat tgactgcctc cgatgtccat cctacattgg gggttcagct cttcagtgcg   60
ggcatcgccg cttgccttgc cgatgtcatt acctttccat tagacacagc taaggtacgt   120
ctacaagtcc aaggagaatg cccccacctct tctgtgatta gatacaaggg cgtactggga   180
accatcacag ctgtcgtgaa gaccgaggga cgcatgaagc tttacagcgg gctgccagca   240
ggactgcaga ggcagataag ctcagcatcc ctgcgaatcg gactatacga cacagtccag   300
gaatttctta ctgcgggaaa agagacagct cccagtttag ggagtaaaat actcgccggg   360
ctgacaacag gcggcgttgc cgtttttcata ggacagccga ctgaagtggt taaggtgcga   420
ctccaagctc agtctcacct gcatggtatc aaacctcgct atactggtac atataacgcc   480
tacaggatta tagcaacaac agaaggtttg actggactct ggaaggggac aacacccaat   540
ttgatgcgat ccgtcattat taactgcacc gagctcgtaa cctatgatct catgaaggag   600
gcctttgtaa aaaacaacat cctggcagac gacgttcctt gccacttggt ttcagcactc   660
atcgccgggt tctgtgctac cgctatgtct agccctgtgg atgttgtcaa aacacgattc   720
atcaattcac caccgggcca atataaatct gtccccaatt gcgccatgaa ggtcttcaca   780
aatgaaggcc cgactgcctt cttcaagggg ctcgttcctt cttttctccg gctcgggtcc   840
tggaatgtga taatgttcgt gtgtttcgaa cagctgaaaa gggagctgtc aaaatcaagg   900
caaaccatgg actgcgccac ctga                                          924
```

SEQ ID NO: 105          moltype = RNA  length = 924
FEATURE                 Location/Qualifiers
source                  1..924
                        mol_type = other RNA
                        organism = synthetic construct
SEQUENCE: 105
```
atggggaggtc tgacagcttc agacgtacac cccacattag gcgtgcaact cttcagtgcc   60
ggcatagccg cttgcctcgc cgatgttatt acctttcctc tggacaccgc taaggtgcga   120
cttcaggttc agggcgagtg tccaacctca tccgttattc gatacaaagg cgtgctagga   180
accataaccg ccgtggtcaa gacggaaggc cgtatgaaac tttacagcgg actcccagcg   240
ggactccaga gacaaataag ctctgcatct cttcgaatcg gactgtacga taccgtccag   300
gagtttctaa cagctttgaa ggagacagca cctagtttgg tcagcaaaat tcttgccgga   360
gagttttctaa cagctttgaa ggagacagca cctagtttgg tcagcaaaat tcttgccgga   360
ctcactacag gaggcgtcgc cgtgtttatt ggacagccca cagaggtagt gaaggtgcga   420
ctgcaggccc aatctcatct gcacggaatt aaaccgcgct acaccggtac atataacgcc   480
tacagaatca tcgctaccac agaaggtctg actgggttgt ggaaggggac aacccccaat   540
ttaatgcgat ctgtgatcat caactgcact gagctggtca cttacgatct catgaaagaa   600
gcattcgtga aaaacaacat tttggctgac gacgtcccat gtcatttagt ttctgcgctc   660
```

```
atcgctgggt tttgtgctac agcaatgtct tctcccgttg atgtcgtcaa aacacgattc   720
ataaactctc cacctggcca atacaaaagt gttcctaact gtgccatgaa agtcttcacg   780
aacgaaggcc ccacagcctt cttcaagggg ctggttccct cctttcttcg gctcggatcc   840
tggaatgtaa tcatgtttgt gtgcttcgaa cagttaaaaa gagagctctc aaaatcaagg   900
cagacaatgg attgtgccac ttga                                          924

SEQ ID NO: 106          moltype = RNA  length = 924
FEATURE                 Location/Qualifiers
source                  1..924
                        mol_type = other RNA
                        organism = synthetic construct
SEQUENCE: 106
atgggtggac tgacagctag cgatgtgcac cccacactgg gcgtgcaact cttcagtgct   60
ggtattgccg cttgcctcgc cgacgtcata acgtttccct tagacactgc taaagtccgg   120
cttcaggtcc agggtgaatg cccaacctct tcagtcatcc gttataaagg cgtgctggga   180
accatcacag cggtggtaaa aacagagggc cgcatgaagc tgtatagcgg gctccccgca   240
ggcctccaga ggcagataag ctctgcttct ctgcggatcg gtttgtatga cactgttcaa   300
gaattcctta ccgccggcaa agaaaccgca cctagtctgg gtagtaaaat cctcgccggg   360
ctcactacag gcggtgtcgc cgtattcatc ggacaaccta ccgaggtggt caaggtaaga   420
ctgcaggccc aaagccacct gcacggcatc aaacctcgct acaccggcac ttacaacgcc   480
tacaggatta tagctaccac cgaaggcttg acgggactgt ggaaaggcac aaccccaaat   540
ttaatgcggt ccgttattat caactgcacc gagctggtaa cttatgatct catgaaggaa   600
gcatttgtga aaaataacat cttggcagac gacgttccat gtcacttggt ttcggcgcta   660
atcgccggat tttgtgctac agccatgtca tccctgtcg atgtcgtgaa gacaaggttc     720
atcaattcac caccaggtca gtacaaaagt gtccccaatt gcgcaatgaa agtattcaca   780
aacgaaggcc caaccgcgtt ttttaagggg cttgttccct cctttctgcg cctcggttct   840
tggaatgtca tcatgtttgt atgcttcgag cagctgaaac gggagctgtc caagtccaga   900
cagactatgg actgtgcgac atga                                          924

SEQ ID NO: 107          moltype = RNA  length = 924
FEATURE                 Location/Qualifiers
source                  1..924
                        mol_type = other RNA
                        organism = synthetic construct
SEQUENCE: 107
atggggggggc tgacagcttc agacgttcac cccaccctgg gagttcaact ctttagtgct   60
ggaatcgccg cctgcctcgc agatgtcatc acctttcctc tggatacagc aaaggtgcgg   120
cttcaggttc agggcgaatg tccaacttct tcagtgatcc gctataaagg cgtcttggga   180
accatcaccg cagtcgtgaa gaccgaaggc cgaatgaagc tttacagcgg gctgccagcc   240
gggctgcaac gacagataag ctcagcatcc ctgcgtatg gcctatacga caccgtccaa    300
gagtttctca ctgccggaaa ggagacagct cccagtctgg gaagcaagat cttagccgga   360
ctcaccacag gcggcgtggc cgtgttcatt ggacaaccta ccgaggttgt taaggtgcga   420
ctacagctc agagccatct gcatgggatt aaaccacgct atactggaac ttacaacgct    480
tataggatta tcgccaccac tgaaggatta actggacttt ggaagggcac aacacccaac   540
ttgatgcgat cagtgatcat aaaattgcacc gaactggtga cctacgatct catgaaggag  600
gctttcgtga agaacaacat acttgccgac gacgttcctt gtcacctcgt ctctgcgttg   660
atcgccgggt tctgcgctac tgctatgtca tctcccgtcg atgttgtgaa aacaaggttt   720
atcaattcgc ctccaggcca gtataaaagt gtccctaact gtgccatgaa agtgttcaca   780
aatgaaggcc ccacagcatt tttcaaggga ctcgttcctt cctttcttcg tctcggatcc   840
tggaatgtca tcatgtttgt gtgcttcgag caattgaaac gagagctgtc gaagtcacga   900
caaaccatgg actgcgcaac ctga                                          924

SEQ ID NO: 108          moltype = RNA  length = 924
FEATURE                 Location/Qualifiers
source                  1..924
                        mol_type = other RNA
                        organism = synthetic construct
SEQUENCE: 108
atgggtggtc tcactgcaag cgacgtgcat ccaacactgg gggttcagct cttcagcgcc   60
ggaatcgccg cttgccttgc cgacgtcata acttttcctt tagataccgc taaggtacgc   120
ctgcaagtcc agggcgagtg ccccacatca agtgtgattc gctacaaagg cgttttgggg   180
accatcacag cagtggtgaa gacggaaggc cgaatgaaac tttatagcgg actgccagca   240
ggactgcagc gccaaataag ctctgcttca ctgcgtatcg tctatatga taccgtgcag   300
gaatttctta ctgcaggaaa ggagacggca cccagtttgg ggagcaaaat cttggccgga   360
ctgactacag gcggtgtcgc tgtattcatt ggacagccaa ctgaagtggt gaaggtgcga   420
ctccaggctc aatctcacct gcacggtatc aaaccccgct acactggcac atataacgct   480
tacaggatta tcgctacgac agaaggctta acgggcctct ggaaaggcac caccctaat    540
ttaatgcgat ctgtcatcat caattgcact gaactgtaa cgtatgatct catgaaagaa    600
gcgtttgtga aaataatat cctggcggac gacgtccctt gtcacctggt gtctgcactt    660
atcgccggat tttgtgccac cgccatgtcc agtcctgttg acgttgtcaa aacaaggttc   720
atcaattcac ctcctggtca atataaaagt gttcccaact gtgccatgaa agtcttcaca   780
aatgaaggtc ccacagcttt ttttaaagga ctagttcctt ccttcctgcg gcttggatcc   840
tggaatgtca tcatgtttgt gtgttttgaa cagctgaaac gggaacttag taaatccaga   900
cagaccatgg actgtgccac ctga                                          924

SEQ ID NO: 109          moltype = RNA  length = 924
FEATURE                 Location/Qualifiers
source                  1..924
                        mol_type = other RNA
```

-continued

```
                      organism = synthetic construct
SEQUENCE: 109
atgggtggtc taaccgcttc agacgtgcat cctactctgg gagtgcagct cttcagtgca   60
ggtatcgccg cttgccttgc cgacgtgatc acctttcccc tggacaccgc taaggtgcgc  120
ctgcagaccc agggcgaatg tcctacatca agcgtgatcc ggtataaagg cgtattggga  180
accatcactg ctgtggtaaa gactgaagga agaatgaagc tatacagcgg gcttccagct  240
ggacttcaga ggcagatcag ctccgcttct ttgcgtatcg gcctgtacga caccgttcag  300
gaatttctca ctgcaggaaa ggagacagca cccagcctgg gcagcaaaat tctagccggg  360
ctcaccacag gtggcgttgc tgtatttata gggcaaccaa cagaggtggt caaggtgagg  420
ctgcaagctc aatcccactt acacggtatt aagccacgct atactggaac ttacaacgcc  480
tacaggatta ttgctacaac agaaggtctt actggacttt ggaaggggac aacacctaat  540
ttaatgcggt ccgtgatcat taactgcacc gaattggtta cctacgatct catgaaagaa  600
gcctttgtga agaataacat cttggccgat gacgttcctt gtcacctcgt gtctgcacta  660
atagccggat tctgtgctac agctatgtca tctcctgtcg atgttgtcaa aacgaggttt  720
atcaattctc ctccgggtca gtataaaagt gtccctaatt gtgccatgaa agtattcacg  780
aacgaaggac ccaccgcctt cttcaaggga cttgttcctt cttttctccg tctcggttcc  840
tggaatgtca tcatgttcgt gtgttttgaa cagctgaaaa gggaacttag caaatcaaga  900
caaactatgg actgtgctac gtga                                          924

SEQ ID NO: 110          moltype = RNA  length = 924
FEATURE                 Location/Qualifiers
source                  1..924
                        mol_type = other RNA
                        organism = synthetic construct
SEQUENCE: 110
atgggggtc tgactgcctc agacgttcat ccgacactgg gggtgcagct cttcagtgcc    60
ggcattgccg cttgcctcgc cgatgtcatt acttttcctc tggacaccgc gaaggtccgc  120
ctgcaagttc agggcgagtg tcctacatct tccgtcatcc ggtataaagg cgttctggga  180
accatcacag ccgtcgtgaa gaccgagggc cgaatgaagc tttacagcgg gctgcctgct  240
gggctgcagc gacagataag ctccgcttct cttcggacag ggctgtacga cacagtacag  300
gagtttctca cagctggaaa ggagactgca cccagtttgg gtagtaaaat tctcgcgggg  360
ctcaccactg gcggtgtcgc tgtgtttatt ggtcagccta ctgaggtcgt caaggtcagg  420
ctgcaggctc agagccatct gcatgggatc aaacctcgct cacactggcac atataatgcc  480
tacaggataa ttgcaacaac agaaggcctg actggactgt ggaaagggac aacacccaat  540
ttaatgcgat ccgtcatcat taattgcacc gagctcgtaa catacgatct catgaaggag  600
gcatttgtga aaaataacat tttagcagat gatgttccat gtcacctggt atcagcactc  660
atcgcaggat tctgtgctac tgctatgtct tctccagtgg acgtggtgaa gactcggttt  720
atcaattctc cacctggcca atacaaaagt gtccctaact gtgccatgaa ggtattcact  780
aacgaaggcc cgactgcctt ctttaaggga ctcgtccctt cttttctgcg gcttggctcg  840
tggaacgtga ttatgtttgt gtgttttgaa cagctgaaaa gggagctaag taagagcagg  900
caaacaatgg actgtgccac ttga                                          924

SEQ ID NO: 111          moltype = RNA  length = 924
FEATURE                 Location/Qualifiers
source                  1..924
                        mol_type = other RNA
                        organism = synthetic construct
SEQUENCE: 111
atgggtgggc tcaccgcatc agacgttcac cccacactgg gagttcaact cttcagtgcg    60
ggcatcgccg cctgcctggc tgacgttatt acttttcctc tggacacagc taaggtacgt  120
ttacaggttc aaggagaatg tcccacttct tccgtgattc ggtataaagg cgttttgggg  180
actatcacag ccgtagtgaa gacagaaggc cgcatgaagc tctacagtgg tctgccagca  240
ggcctgcagc gacaaatcag ctctgcttca ctgcgtatcg gtttgtacga cactgtgcaa  300
gaattcctca ccgcaggaaa ggagaccgca cccagcttag ggagcaaaat ccttgccggg  360
ctcacaacag gcggcgtcgc tgtgttcatc ggacagccta cagaggtggt taaggtaaga  420
cttcaggccc agtcacacct tcatggtata aaacctcgct atactggaac gtacaatgct  480
tacaggatca tcgccaccac agaaggcctc acagggctgt ggaaaggtac aaccectaat  540
ttgatgcgat cagtcatcat caattgcact gagctggtga cttacgatct catgaaggaa  600
gcttttgtca aaaacaacat actggccgat gacgtcccat gccacctggt ttccgcactc  660
atcgcaggat tctgtgccac cgcaatgtct tctcctgtcg atgtcgtgaa gacacgattt  720
atcaattcac ctcctggaca gtacaaatct gtccccaatt gtgccatgaa agtgttcaca  780
aacgaagggc caacagcctt ttttaagggg ctcgtgccct cctttcttcg actcggatct  840
tggaacgtca ttatgtttgt gtgttttgaa cagttaaaaa gagagctctc caaatctagg  900
cagacaatgg attgcgccac ttag                                          924

SEQ ID NO: 112          moltype = RNA  length = 924
FEATURE                 Location/Qualifiers
source                  1..924
                        mol_type = other RNA
                        organism = synthetic construct
SEQUENCE: 112
atgggcggtc tcacagctag cgatgtgcat cccacgctgg gggtgcaact tttcagcgcg    60
ggcatcgccg cttgcttagc tgatgtcatt accttttccct tagatacggc taaggtccgc  120
cttcaggtcc agggcgaatg tcccacctca tccgtgattc gctataaggg cgtattaggg  180
acaatcacag ccgtcgtgaa gaccgagggc cgtatgaaac tctatagcgg gctgcccgcc  240
ggattgcagc gacagatcag ctctgcatcc ctgcgaattg gcctgtatga cactgtgcag  300
gaattcctca ccgccgggaa agagacgcg cccagtctgg gcagcaagat actggccgga  360
ctcactacag gtggcgtggc ggtgttcatt ggacagccta cagaggtggt taaggttaga  420
ctgcaggctc aatcccatct gcacgggatc aaacctcgct atactggcac ttataatgct  480
```

```
tacaggatca ttgccacgac agagggcctc actggacttt ggaaagggac aacacccaat   540
ttaatgcgaa gcgttatcat caactgcacc gagctcgtga cctatgatct gatgaaggaa   600
gcctttgtaa aaaacaacat cctggcagat gacgtcccat gtcacttggt atctgcactc   660
atagctggct tttgtgctac cgccatgtct tccctgtgg atgtggtaaa gacacgattc    720
atcaattctc cacctggtca atataaaagt gttcctaatt gtgcaatgaa agtattcact   780
aacgaaggcc caacagcgtt cttcaagggg ctcgtgccat cttttctgcg gctcgggtcc   840
tggaatgtca tcatgtttgt gtgcttcgaa cagttaaaaa gggaactgtc aaaatcaagg   900
cagacaatgg attgcgctac ttga                                          924

SEQ ID NO: 113            moltype = RNA  length = 924
FEATURE                   Location/Qualifiers
source                    1..924
                          mol_type = other RNA
                          organism = synthetic construct
SEQUENCE: 113
atgggcggtc tgaccgcatc tgacgtacat cctacccttg gggtgcagct ctttagtgct   60
ggaatcgccg cttgccttgc ggacgttatt acttttccct tagatactgc taaggtgcgc   120
ctccaggtcc agggcgagtg tcctacatca tccgttattc gctacaaggg cgtattaggc   180
actattacag ccgtggtgaa aaccgaaggc cgcatgaaat tgtatagcgg gctccctgct   240
ggtttgcaaa ggcagatcag ctccgcttct ctgcggatcg gtttatacga caccgttcag   300
gagtttctta ccgcaggaaa ggagacggca cctagtttag ggagcaaaat tctcgccggg   360
ctcactacag gtggcgtcgc cgtattcatc ggacagccta cagaggtggt aaaggtacgc   420
ctgcaagctc agtctcatct gcacggcatt aaacctcgct cacactgggac atataacgct   480
tataggatta tcgccacaac agaaggccta acgggactat ggaaaggcac aaccccaac    540
ttaatgcggt ctgtcattat caactgcact gaactcgtga cttacgatct tatgaaagaa   600
gctttcgtga agaacaacat cctggccgat gatgttcatt gtcacttggt gtccgcactt   660
atcgctggat tctgtgctac cgctatgtca tcccctgtcg acgtcgttaa aaacacgcttc  720
ataaattctc cacctggtca atataaaagt gttcccaatt gtgccatgaa ggtgtttaca   780
aatgagggac ccacagcctt tttcaagggc ctggttccat cgtttctacg gctcggatcc   840
tggaacgtca tcatgttcgt ctgttttgag caactgaaac gggagctttc caaatccaga   900
cagacgatgg actgtgctac ttga                                          924

SEQ ID NO: 114            moltype = RNA  length = 924
FEATURE                   Location/Qualifiers
source                    1..924
                          mol_type = other RNA
                          organism = synthetic construct
SEQUENCE: 114
atggggggtt taaccgcttc agatgtgcat ccaacgctgg gggtgcaact tttcagtgca   60
gggattgccg cttgcctcgc agacgtcatt acttttccat tggacaccgc aaaggtgcgc   120
ctgcaggtcc agggcgaatg cccaacttca tcgttatca gatataaggg cgtcttggga   180
accatcacag ccgtggtgaa gactgaaggc aggatgaaac tctacagcgg gctcccagcc   240
ggcctacagc ggcaaatcag ctccgcatcc ctgagaatcg gctgtatga caccgttcaa    300
gaattcctaa ccgcaggaaa gggagacagca cccagtctgg gaagtaaaat tctcgctggg   360
ctgactactg gcggcgtggc cgtattcatc ggacaaccta ctgaagtggt taaggtacgg   420
ctacaagctc aaagccacct gcacggcatt aaaccacgct atactggcac ttacaatgct   480
tataggataa ttgcaacaac agaaggcctc actggacttt ggaagggac aacacctaat   540
ctgatgcgat ctgttattat taattgcact gagctcgtga cttacgatct catgaaagag   600
gcctttgtga agaataatat cctggcagac gacgttcctt gccaccttgt gtccgcacta   660
atcgcgggat tctgtgccac cgcaatgtct agccctgtgg atgttgtcaa aacacggttt   720
ataaactccc ctcccggcca gtataaaagt gtccccaatt gtgcaatgaa ggtcttcact   780
aatgaaggcc ccacagcatt tttcaaaggg ctggtgccct cctttcttcg gctcggatcc   840
tggaacgtga tcatgttcgt gtgtttcgaa cagctgaaaa gggagttgtc aaagagcaga   900
caaaccatgg actgtgctac ctga                                          924

SEQ ID NO: 115            moltype = RNA  length = 924
FEATURE                   Location/Qualifiers
source                    1..924
                          mol_type = other RNA
                          organism = synthetic construct
SEQUENCE: 115
atgggaggtt taactgccag cgacgttcat ccaactctgg gggtgcagct cttcagtgca   60
ggcatcgccg catgcctcgc tgacgtgatt acgtttcctt tagacaccgc taaggtccgt   120
cttcaagtcc aaggcgaatg tcctacttct tccgtcattc gttacaaggg cgtgttgggg   180
accatcacag ccgtggtgaa gactgaaggc aggatgaaac tttatagcgg gctccctgct   240
ggcttacaga ggcaaatcag ctctgcttca ctccggattg ggctctacga cactgtccag   300
gaatttctta ccgccggaaa gggagacagc cccagcttgg ggagtaaaat cctcgcggga   360
ctcactacag gcggcgtcgc cgtcttcatt gggcaaccca ctgaggtggt gaaggtccgg   420
ttgcaggctc aatcccacct tcacggcatt agcctcgct acacaggcac atacaacgcc    480
tacagaatca ttgccaccac agaagggtta accggacttt ggaaggggac aacacccaac   540
ttaatgcgat ctgtcatcat caattgcact gaactcgtga cttacgacct catgaaggaa   600
gcctttgtga agaataacat cttggccgac gacgttcctt gtcacctggt ttctgcatta   660
attgctggtt tttgtgctac tgccatgtca tctcctgttg atgtcgtcaa aacacggttc   720
atcaactccc ctcccgggca gtacaaatct gtccccaatt gtgccatgaa agtcttcaca   780
aacgagggtc caaccgcctt cttcaaaggg cttgttccct cttttcttcg tctcggctcc   840
tggaacgtga tcatgttcgt gtgcttcgaa cagctgaaga gggaactgtc aaaatccagg   900
caaacgatgg attgtgccac atga                                          924

SEQ ID NO: 116            moltype = RNA  length = 924
```

```
FEATURE            Location/Qualifiers
source             1..924
                   mol_type = other RNA
                   organism = synthetic construct
SEQUENCE: 116
atgggcggtt taacggcaag cgacgtgcat cccacgctgg gcgtgcagct tttcagtgcc   60
ggaatcgctg cttgcttagc agacgttata acttttcccc ttgacacggc caaggtccgc  120
ctgcaagtcc aaggcgaatg tccaacctca tcggttatcc gctataaagg cgttttggga  180
actattacag ccgtcgtgaa gaccgagggc aggatgaaac tttacagcgg gctccctgct  240
ggtttgcaga ggcagataag ctcagcatcc cttcgaattg gtctgtacga caccgttcag  300
gagttcctta ctgcgggaaa ggaaacagcc cctagtttgg gcagcaaaat tctggccggg  360
ctgactacag gtggtgtcgc cgtatttatt ggacaaccca cagaagtagt aaaggttcga  420
ctgcaggccc agagccattt gcatggaatc aagccgcgct acactggtac ttacaacgcc  480
tatagaatca tcgccaccac agagggatta actggacttt ggaagggac aacccctaat  540
ttaatgcgat cagttatcat caattgcacc gagctagtga cgtacgatct catgaaagaa  600
gcatttgtca aaaacaacat tttggcagat gacgttccat gtcacttggt ctctgcgtta  660
atcgccggat tttgtgcaac cgctatgtct tctcctgtcg acgttgtgaa gacaaggttc  720
ataaactctc cacctggcca atataaaagt gtccctaatt gtgccatgaa agtctttact  780
aatgaagggc ctaccgcatt ttttaagggg ctcgttccgt cctttctgcg gctcggatcc  840
tggaacgtga tcatgttcgt gtgttttgag cagttgaaaa gggagctgtc taagtcaagg  900
caaacgatgg attgtgccac ctga                                          924
```

```
SEQ ID NO: 117     moltype = RNA   length = 924
FEATURE            Location/Qualifiers
source             1..924
                   mol_type = other RNA
                   organism = synthetic construct
SEQUENCE: 117
atggggggtc ttactgcatc agacgttcat cccacactgg gggtgcagct cttcagtgcg   60
ggcatcgccg cgtgcctcgc agatgtcatt acgtttcccc tggatacagc taaggtgcgc  120
ctgcaggtcc agggcgaatg cccaacttcc tccgtaatcc gttacaaagg cgtgttgggc  180
accatcacag ccgtcgtgaa gaccgaggga cgtatgaaac tttacagcgg gctccctgcc  240
gggctgcaac ggcagatcag ctccgcttcc ctccgtatcg gactatacga cacagtgcag  300
gaattcctta cggctggaaa agagacggca cctagcttgg gcagcaaaat cttggcaggg  360
ctcactacag gtggcgttgc tgtctttatc ggacagccta ctgaggtagt gaaggtccgt  420
ctccaagctc aatcccacct gcacggcatc aaacctcgat acaccggcac ttataacgcc  480
tacaggatta tcgctactac agaaggcctt actgggctgt ggaaggggac aacacctaat  540
ttaatgcggt cggttatcat caattgcact gagctcgtga cctacgatct catgaaggaa  600
gcgtttgtga aaaacaacat tctggcagat gacgtcccat gtcacttggt gtctgctctc  660
atcgccggat tttgtgccac cgccatgtct tccctgttg acgttgtgaa aacaagattt  720
atcaattctc ctccaggtca atataaaagt gtccccaatt gtgccatgaa ggtgttcaca  780
aatgagggcc aacggcatt cttcaagggg ctcgtccctt cctttcttcg actggggtcg  840
tggaacgtca tcatgtttgt atgctttgaa caattgaaac gggagctgtc caagtcccgg  900
cagacaatgg actgtgccac ttag                                          924
```

```
SEQ ID NO: 118     moltype = RNA   length = 924
FEATURE            Location/Qualifiers
source             1..924
                   mol_type = other RNA
                   organism = synthetic construct
SEQUENCE: 118
atgggcggcc tgacagcttc tgatgtgcat cctacactgg gtgtgcaact tttcagtgcg   60
ggaatcgctg cttgcctcgc cgacgtcatt acctttccct tagacacagc aaaggtccgc  120
ctgcaggtcc aaggcgagtg tcctacttcc tccgtcattc gatacaaggg tgtgctggga  180
accatcaccg ctgttgtaaa aacagaaggc cgtatgaaac tttacagcgg actgccagcc  240
ggtttacaga ggcagatcag ctctgcgtcg ctgcgtatcg ggctctatga caccgtccaa  300
gagttcctaa cagcagggaa ggagacacgc cccagcctgg ggagtaaaat cctcgcagga  360
ctcacaacag gtggtgtcgc cgtgttcatt ggacagccaa ctgaggtggt gaaggtccga  420
ctgcaggccc agtcccacct ccacgggatc aaacctcgct acacgcggac gtacaacgct  480
tatagaatca tcgccaccac agaagggctc acaggactct ggaaggggac aacacctaat  540
ttgatgcgat ctgttattat taattgtact gaactcgtga cttatgatct catgaaggag  600
gcctttgtga aaaacaacat cctggccgac gacgtcccat gtcacctggt atctgcactg  660
atcgccggat tctgtgcaac cgccatgtca tctcctgttg acgttgtcaa gacacgcttc  720
ataaactctc ctccgggtca gtataaaagt gtccccaatt gtgccatgaa agtatttacc  780
aacgaaggcc caaccgcatt ctttaagggg cttgtgccat cttttctgcg gctgggctcc  840
tggaatgtca tcatgttcgt gtgtttcgaa caattaaaaa gagagctgtc gaagtcccgg  900
cagacgatgg actgcgccac ttag                                          924
```

```
SEQ ID NO: 119     moltype = RNA   length = 924
FEATURE            Location/Qualifiers
source             1..924
                   mol_type = other RNA
                   organism = synthetic construct
SEQUENCE: 119
atggggggtc tcacagctag tgacgttcat cctacactcg gagtgcagct cttcagtgca   60
ggaatcgccg cttgccttgc agacgttatc acctttcctc ttgacaccgc taaggtccga  120
ctgcaggtcc aaggcgagtg tcccacctcc tccgtaatca gatacaaggg tgtcctgggg  180
acaatcaccg cagtcgtaaa gacagagggc cgtatgaaac tttacagcgg gctccccggca  240
ggattgcagc gccagatcag ctccgcatct ctgagaattg gtctctacga cactgttcaa  300
```

```
gaattcctaa cagccggaaa ggagactgca cccagtctgg gaagtaaaat actagccggg   360
ctcaccacag gcggcgttgc tgtattcata ggacagccta ccgaagtagt caaggtcaga   420
cttcaggctc agtctcatct gcacggaatc aagccccgtt ataccggaac ttataatgct   480
tacaggatca tcgccaccac agaaggctta actggacttt ggaaggggac cacacctaat   540
ttaatgcgtt ccgttataat caactgcacc gagctagtga cttacgacct catgaaggag   600
gcatttgtga aaaacaacat cctggcagat gacgttcctt gtcacttagt gtctgcactc   660
atcgccggat tttgtgcaac cgccatgtcc agtcccgtcg atgtcgttaa gactcggttc   720
attaactccc ctccgggcca atacaaatct gtccctaact gtgccatgaa agtatttaca   780
aacgagggtc ctacagcctt ctttaagggg ctcgtcccgt cttttctccg gctaggctcg   840
tggaacgtta tcatgtttgt gtgtttcgaa caactaaaaa gagagctttc caaatccagg   900
caaaccatgg attgcgcaac ttga                                          924
```

```
SEQ ID NO: 120          moltype = RNA  length = 924
FEATURE                 Location/Qualifiers
source                  1..924
                        mol_type = other RNA
                        organism = synthetic construct
SEQUENCE: 120
atgggggggcc tgacagcttc cgacgtccac cccacattgg gagttcagct cttcagtgca   60
ggaatcgccg cttgccttgc cgatgtcatt acttttcctt tggataccgc taaggtgcgc   120
ctgcaagtcc agggcgagtg tcctacttct tctgtgattc gatacaaggg cgtcttagga   180
actattacag ccgtcgtgaa aaccgaaggt cgtatgaagc tcacagtgg gtgccagcc   240
ggactgcagc ggcagataag ctcagcttct ctccgaatcg gactgtacga caccgttcag   300
gagtttctta ctgccgggaa ggaaaccgca cccagtctgg ggagcaaaat tcttgccggg   360
ctcaccacag gcggcgtcgc cgtcttcatc ggacagccta ccgaagtcgt gaaggtgcga   420
ctgcaagccc agtcacacct gcatggcatc aagccacgtt atactggaac ttacaacgct   480
tacaggatta tcgccaccac tgaaggcctt actggactct ggaagggggac aactcctaat   540
ttaatgcgat cagttatcat taactgcaca gagctcgtta cttatgacct tatgaaggaa   600
gcattcgtga aaaacaacat cttagcagac gacgtcccct gtcacctggt atctgcacta   660
atcgccggat tttgtgctac cgccatgtca tcccctgtgg acgtcgtaaa gacgcgattc   720
ataaattctc ctcccggtca atacaaatcg gtccccaatt gtgccatgaa agtgttcaca   780
aacgaggggc caaccgcctt tttcaaaggg cttgtgccct cttttctgcg actcggctcc   840
tggaatgtca tcatgttcgt gtgcttcgaa cagctaaaaa gggagctgtc taaatccagg   900
caaacaatgg actgtgctac ttaa                                          924
```

```
SEQ ID NO: 121          moltype = RNA  length = 924
FEATURE                 Location/Qualifiers
source                  1..924
                        mol_type = other RNA
                        organism = synthetic construct
SEQUENCE: 121
atgggcggtc ttacagcaag cgacgttcat cccacactcg gggtgcagct ctttagtgcg   60
ggaatcgccg cttgcctcgc cgacgtgata acctttccgt tggacacagc caaagtacgc   120
cttcaagtcc agggcgagtg cccaacttct tccgtgattc gatataaagg cgtgttggga   180
accattactg ccgtcgtgaa gaccgaaggc cgcatgaagt tatacagcgg gctgcccgct   240
gggttgcaga ggcagataag ctctgcctcc ctgcgtatcg gcttgtatga cacggttcaa   300
gaattcctca ctgccgggaa ggagaccgcc cccagcttgg gcagcaaaat cctggccggg   360
ctcactacag gcggcgtggc tgtatttatt ggacaaccta ccgaagttgt taaggtacga   420
cttcaagctc aatctcacct gcacggaatt aaaccgcgct cactggaac ttacaacgct   480
tatcgaatta ttgccactac agaaggctta acaggacttt ggaagggggac gacccctaat   540
ttaatgcggt cggttatcat caattgcacc gaattggtga catcgatct tatgaaagag   600
gctttcgtga aaaacaacat cttggcagat gacgttcctt gtcacttagt atccgcatta   660
atcgccggat tctgtgctac tgccatgtcc tcccctgttg atgttgtcaa gacaaggttc   720
ataaattcgc ctcctggcca atataaaagt gtccccaatt gtgccatgaa agtcttcacc   780
aacgaggggc ctacgccctt ctttaagggg ctcgtcccgt cttttctgcg tctggggtcc   840
tggaacgtga tcatgtttgt gtgttttgag caattgaaaa gagagctgtc gaagtccaga   900
cagacgatgg actgtgctac atga                                          924
```

```
SEQ ID NO: 122          moltype = RNA  length = 924
FEATURE                 Location/Qualifiers
source                  1..924
                        mol_type = other RNA
                        organism = synthetic construct
SEQUENCE: 122
atgggtggac tgaccgcttc ggacgttcac cctaccctgg gagtgcagct cttcagtgca   60
ggaatcgccg cgtgcctcgc cgatgtcatt acttttcctt tagatacagc taaagtgcgg   120
ctgcaagtcc aaggagaatg ccccacatcc tcagtcattc gatacaaagg cgttttgggg   180
accatcactg ccgtcggtgaa aacagagggc cgaatgaagt tctacagcgg gctgccagcc   240
ggattgcaga ggcagatcag ctccgcatct ctgcgaatcg ggttgtacga cacagttcag   300
gagtttctga ctgccgggaaa ggagaccgca cctagtttgg gcagtaaaat cctggccgga   360
ctcactacag gtggcgtcgc cgtatttatc gggcagccca ccgaagttgt gaaggtccgg   420
ctgcaggctc agtctcacct acacgggatt aagccacgct acactgggac atacaacgct   480
tataggatca tcgccaccac tgaaggtctt acgggacttt ggaaaggcac aacacccaac   540
ctaatgcgat ctgttatcat caattgtact gagctcgtcg cttacgatct gatgaaagaa   600
gcgtttgtga aaaacaacat tctcgcagat gacgttccat gtcatctagt gtccgcactc   660
atcgccgggt tctgtgcaac cgccatgtcc agcctgttg acgtcgttaa gacaagatt   720
attaattctc caccaggcca atacaaaagc gtccctaact gtgccatgaa agtgttcaca   780
aacgaggggc ctactgcctt ctttaagggg ctggttcccc ctttctgcg actcggatcc   840
tggaatgtca tcatgttcgt atgctttgag caattgaaaa gagagttgtc taagtcaaga   900
```

```
caaaccatgg actgcgccac atga                                          924

SEQ ID NO: 123          moltype = RNA  length = 924
FEATURE                 Location/Qualifiers
source                  1..924
                        mol_type = other RNA
                        organism = synthetic construct
SEQUENCE: 123
atgggcggcc taaccgcgag tgacgttcac cctactttag gggtgcagct tttcagcgca   60
ggcatcgcag cctgcctcgc tgacgtcatt acatttcccc tcgacaccgc caaggtccgc   120
ctgcaagttc agggtgaatg tccgacttcc tccgtcattc gttataaagg cgtgctcggg   180
accattaccg ctgtggtgaa gaccgaaggc cgcatgaaac tgtatagcgg gctgcctgcg   240
ggtctccaga gacaaatcag ctcagcctct ctccgtatcg gcctatacga tacagttcaa   300
gaattcttaa cggccgggaa agaaaccgca ccttctctgg gaagcaaaat tctcgccggg   360
ctcactacag gcggcgtcgc cgtcttcatc ggccaaccaa ctgaagttgt taaggtacga   420
ctgcaagctc aaagtcacct tcacggcatc aagcctcgct cacctggcac ttacaatgct   480
tacaggatta tcgctacaac cgaaggccta actggactct ggaaggggac aacacccaat   540
ttgatgcggt ctgttattat caactgcaca gaactcgtga catacgatct catgaaggaa   600
gctttcgtga agaataacat cctggctgat gatgtccctt gccacctcgt atctgctctg   660
atcgcaggat tttgtgctac cgctatgtca agccctgtcg acgtcgtaaa aacacggttt   720
ataaactccc ccctggcca gtacaagtct gtccctaatt gtgccatgaa agtcttcacc   780
aatgaaggcc ccactgcctt tttcaagggg ctcgtgccct cctttctgcg gctcgggtcc   840
tggaatgtca tcatgtttgt gtgttttgag caactgaaaa gggagttaag taaatccagg   900
cagaccatgg actgcgccac atga                                          924

SEQ ID NO: 124          moltype = RNA  length = 924
FEATURE                 Location/Qualifiers
source                  1..924
                        mol_type = other RNA
                        organism = synthetic construct
SEQUENCE: 124
atgggcggtc tgacagcatc cgacgtgcat cctactctgg gggtgcagct cttcagcgcc   60
gggattgccg cgtgcctcgc tgatgttata acttttcccc tggacaccgc taaggtccgt   120
ctgcaagttc agggcgagtg ccccacctct tctgtaattc gctataaagg cgtccttgga   180
accataactg ctgttgtgaa gactgaaggc cgtatgaagc tctatagcgg gctgcctgcg   240
ggcctgcaga ggcagatcag ctccgcctcc ctccgtatcg gcctgtacga cactgtccaa   300
gaattcctca ctgctggaaa agaaactgca cccagtctgg ggagtaagat cctcgccggg   360
cttactacag gtggcgtcgc tgtctttatt ggacagccaa cagaggtcgt gaaggtgcga   420
ctgcaggctc aaagccacct gcatggaatt aaacctcgct cacctggaac ctataacgcc   480
tataggatta tcgcaaccac cgaaggttta actgggctct ggaagggaac aactcctaat   540
ctaatgcgat cagttattat caattgcact gaactcgtta cttatgatct catgaaggaa   600
gcctttgtga aaaataatat attggcggac gacgtccctt gtcacctggt atccgcactt   660
atcgccggat tttgtgctac cgctatgtcc agccctgtcg atgttgttaa aacaagattt   720
ataaactctc ccctggtca atataaaagt gttcctaact gtgccatgaa ggtcttcact   780
aacgaaggcc ccacagcttt ttttaagggg cttgttccct cctttttgcg gctgggttct   840
tggaatgtga tcatgttcgt ctgttttgaa cagctgaaaa gggagctatc caaatccaga   900
cagacgatgg actgtgccac ctga                                          924

SEQ ID NO: 125          moltype = RNA  length = 924
FEATURE                 Location/Qualifiers
source                  1..924
                        mol_type = other RNA
                        organism = synthetic construct
SEQUENCE: 125
atgggtggtc tgactgctag tgatgtgcat ccaacactgg gggtgcaact tttcagtgct   60
gggatcgccg cctgcctcgc cgacgttata acttttccgc tggataccgc caaggtgcgc   120
ctacaggttc agggcgagtg tcctacctct tcagtgattc gatataaagg cgtcttgggt   180
accatcactg ctgtggtgaa gactgaaggc cgcatgaagc tctacagcgg cctgccagcg   240
ggcttacaga ggcagatcag ctccgcttcc ctgcgcatcg gcctgtacga cacagtccaa   300
gaatttctta ctgccgggaa ggaaaccgct ccaagtttgg ggtccaaaat tctcgccggg   360
ctcaccacag gtggtgtcgc tgtctttatt ggccagccta ccgaagtggt gaaggtccga   420
ctccaagctc agtcccatct ccacggaatt aagcctcggt acaccgggac ttacaatgct   480
tatagaatca tcgctaccac agaaggatta actggacttt ggaagggcac gacacccaat   540
ttgatgcggt cagtcattat caactgcaca gagttgtta cctatgatct catgaaggaa   600
gcctttgtga aaaataacat tctggcagac gacgttccat gtcacctggt ttctgcatta   660
atcgctgggt tttgtgctac cgccatgtca tctcctgtcg acgttgtgaa aacccggttt   720
ataaattcac cacctggcca gtataaaagc gttcccaatt gtgccatgaa ggtgttcaca   780
aatgagggcc ctaccgcatt cttcaaaggg ctcgtcccat ccttctccg tctaggatcc   840
tggaatgtca taatgttcgt ctgttttgaa cagttaaaaa gggaactgag taaatccagg   900
caaacaatgg actgcgctac ctga                                          924

SEQ ID NO: 126          moltype = RNA  length = 924
FEATURE                 Location/Qualifiers
source                  1..924
                        mol_type = other RNA
                        organism = synthetic construct
SEQUENCE: 126
atgggaggtc tgactgcaag cgacgtacac ccaactctag gagtgcagct ctttagtgca   60
ggaattgccg cttgtctcgc tgatgtcatt acttttccct tggataccgc taaggtccgt   120
```

-continued

```
ctgcaggtcc agggcgagtg tcctacttca tctgtcattc gttataaagg cgtattggga   180
accattacag cagtcgtgaa aactgagggc cgcatgaagc tctacagtgg gcttccagct   240
ggcctgcagc gacagatcag ctcggcgtcc ctgcgtattg gcctatacga cacagtccaa   300
gagttcctca cagctgggaa ggagaccgcg ccaagtttgg gcagcaaaat actcgccggt   360
ctcacaacag gcggcgttgc cgtattcatt ggacagccca ctgaggtcgt taaggtacga   420
ctacaggctc agtctcatct ccatgggata aaacctcgct atactggcac atacaatgct   480
tatcgaatca tcgcaacaac cgaaggcctc acagggctgt ggaaagggac gacacctaac   540
ttaatgcggt cagtgatcat caactgcact gaactggtga cctacgatct gatgaaggaa   600
gctttcgtaa agaataacat tctggcagac gacgtcccat gtcatctagt atccgcgtta   660
atcgccggat tttgtgccac tgctatgtct tccccctgtcg atgttgtgaa gacacgattc   720
ataaactctc ctcccggcca atacaaatct gtccctaatt gtgccatgaa ggtcttcaca   780
aacgagggtc caacagcctt ttttaagggg ctcgttcctt cgtttcttcg gcttgggtcc   840
tggaatgtga tcatgtttgt gtgtttgaa caattgaaga gagagctctc taagtccagg   900
cagacaatgg attgtgccac ctag                                          924
```

SEQ ID NO: 127          moltype = RNA  length = 924
FEATURE                 Location/Qualifiers
source                  1..924
                        mol_type = other RNA
                        organism = synthetic construct
SEQUENCE: 127
```
atgggtggac tgacagccag cgatgtgcac cctacgctcg gagttcagct ctttagcgcc   60
ggcatcgccg cctgccttgc cgatgtcatt acatttcctc tagacactgc taaggtacgc   120
ctgcaggtcc aaggagaatg tccaacatca tccgtaattc ggtacaaagg tgtattgggg   180
accatcaccg ctgtcgtgaa gactgagggc cgcatgaaac tttacagcgg gctgccagcg   240
ggcctgcaga ggcaaataag ctctgcatcc ctgcgcacg gcctgtacga cacagttcag   300
gaatttctta ctgccggaaa ggagactgca cccagtctgg ggagcaaaat tctcgccggc   360
ctcactacag gcggcgtagc cgtattcata ggacaaccta ccgaagtcgt caaggtaaga   420
ctgcaggccc aatcacatct gcatgggatc aagccacgct acaccgggac atacaatgcc   480
tataggatta tcgccacaac cgaaggctta actgggctct ggaaggggac aacccctaat   540
ttaatgcgat cagttatcat taattgtacg gaactggtga catacgacct catgaaggaa   600
gcttttgtaa aaaataacat cctggcagac gacgtcccat gtcatttggt ctctgcatta   660
atcgccggat tttgtgccac cgctatgtca agccctgtcg atgttgtcaa gacgcggttc   720
ataaattccc ctcccggcca gtacaaaagt gttcctaact gtgccatgaa ggtgttcacc   780
aacgaaggcc ccactgcatt cttcaagggg ttggttcctt cctttctgcg gctcggatcc   840
tggaatgtca tcatgtttgt gtgtttcgag cagctgaaaa gagagctctc taagtctaga   900
caaacaatgg actgcgcaac ctga                                          924
```

SEQ ID NO: 128          moltype = RNA  length = 924
FEATURE                 Location/Qualifiers
source                  1..924
                        mol_type = other RNA
                        organism = synthetic construct
SEQUENCE: 128
```
atgggggggtc tcacagcttc tgacgttcat ccaacactgg gagtgcagct ctttagcgca   60
ggaattgccg cttgtctcgc cgacgtcata acttttccct tagacaccgc taaggtccgc   120
ctgcaggtcc agggcgaatg tcctacatct tcagtgatcc gctataaagg cgtcttggga   180
accatcactg cagtcgtgaa gaccgaaggc cgtatgaagc tgtacagcgg actgccggca   240
gggctccaga ggcaaataag ttccgcatca ctgcgaattg gtctgtatga caccgttcag   300
gaattcctga cagccggaaa agaaacagca cctagcttgg gtagcaaaat tctggccggt   360
ctcaccacag gcggcgttgc tgtttttcata ggacagccca ccgaggtagt aaaggtgcga   420
cttcaggcac agagtcatct gcacggcatc aaaccgcgct acacgggcac ttacaacgct   480
tataggatca tcgccactac agaaggccta actggtctgt ggaagggcac aacacctaat   540
ttaatgcgat ctgttattat caattgtact gaactcgtaa catatgacct catgaaggaa   600
gcctttgtaa aaaacaacat cctcgcagat gacgtcccat gccatttggt ttcagctcta   660
atagcaggat tttgtgctac tgccatgtct tctcccgtcg acgttgtaaa gacacgattc   720
attaattctc cacctggtca gtataaatct gtccctaatt gtgcaatgaa agtcttcaca   780
aacgaaggcc caaccgcatt cttcaaaggg cttgtgcctt cctttctgcg actcggctcc   840
tggaacgtta tcatgttcgt gtgcttcgaa caactgaagc gggagctgtc aaaatccagg   900
cagacaatgg actgtgccac atga                                          924
```

SEQ ID NO: 129          moltype = RNA  length = 924
FEATURE                 Location/Qualifiers
source                  1..924
                        mol_type = other RNA
                        organism = synthetic construct
SEQUENCE: 129
```
atgggcgggc tcacagcaag cgacgtccat cctacactgg gtgtgcagct cttcagtgca   60
ggaatagccg cctgtctcgc cgatgttatt acttttccct tagatacggc aaaggtccgc   120
cttcaagtcc agggcgagtg cccaacatca tctgtcatac gttataaggg cgtattgggc   180
accatcacag ccgtggtgaa aaccgaagga cggatgaagc tctatagcgg actgccagca   240
gggctacaaa ggcagatcag ctcagcctct ctacggatcg gattgtacga cactgtccaa   300
gaattcctca ctgcggggaa ggaaacagca cccagtttgg ggagtaaaat cctggccggt   360
ctcaccacag gcggcgtcgc cgtcttcatt ggacagccta caggtgtggt gaaggttcga   420
ctgcaagccc aaagtcacct gcacggaatc aagccacgct acactggaac ttataacgct   480
tacaggatta tcgccaccac cgaagggctc actgggctgt ggaaggggac aactcctaac   540
ttgatgcggt ctgtcattat caactgcacc gaattggtga cttacgatct catgaaagaa   600
gctttttgtga aaaacaacat ccttgcagac gacgttcctt gtcacctggt gtccgcactc   660
atcgccggat tctgtgccac cgctatgtct agccctgtcg acgttgtcaa aacacgtttt   720
```

-continued

```
ataaactctc cgcccggcca gtacaaaagc gtccccaact gtgccatgaa ggtgttcacc  780
aacgagggtc ccactgcctt cttcaagggt ctggttcctt cttttctgcg gctcggatct  840
tggaatgtga tcatgttcgt ctgctttgaa caattaaaac gggagctgtc caagagtaga  900
caaacgatgg actgcgccac gtga                                         924

SEQ ID NO: 130         moltype = RNA   length = 1134
FEATURE                Location/Qualifiers
source                 1..1134
                       mol_type = other RNA
                       organism = synthetic construct
SEQUENCE: 130
gagacccaag ctggctagcg gaattcgtcg actggatccg gtaccgagga gatctgccgc  60
cgcgatcgcc atgggcgggc tgacagccag cgacgtgcac ccaaccctgg gagtgcagct  120
gttttccgcc ggcattgctg cctgtctggc tgatgtgatc actttcccac tggacacagc  180
taaagtgcgg ctgcaggtgc agggcgagtg cccaacaagc tctgtgatca ggtacaaggg  240
cgtgctgggg accatcaccg ccgtggtgaa gaccgagggc agaatgaaac tgtatagtgg  300
tcttcccgcc ggcctgcaga gacagatttc tagcgcctca ctgcgcattg gcctgtatga  360
tacagtgcag gagtttctga ctgccggcaa ggaaactgct ccatccctgg gcagcaaaat  420
cctggccgga ctcacaactg gcggcgtggc cgtcttcatc gggcagccca ctgaggtggt  480
gaaggtgcgc ctgcaggccc agagccactt gcatgggatc aaacccagat acacaggaac  540
ctacaacgct tacagaatca tcgccaccac cgagggcctg actgggctgt ggaagggcac  600
taccccaaac ctgatgcgga gtgtgatcat taattgtact gagctggtga cctatgatct  660
gatgaaggag gcctttgtga agaacaacat cctggccgac gacgtgcctt gtcacctggt  720
gagcgccctg atcgccggct tctgcgccac agccatgagc tcccccgtgg acgtggtgaa  780
gacaagattc atcaatagcc cacctggcca gtataaatcc gtgcctaatt gcgccatgaa  840
ggtgttcacc aatgagggc ccaccgcctt tttcaaggg ctggtgccct ccttcctgag  900
gctgggcagt tggaacgtga tcatgttcgt gtgtttcgaa cagctgaaaa gagagctgtc  960
caagtctaga cagaccatgg actgcgccac atgatgaccc gggagggccc gcggccgctc  1020
gagtctagag ggcccgttta aacgtctgag tgggcggcga attcaaaaaa aaaaaaaaaa  1080
aaaaaaaaaa aaaaaaaaaa aaaaaaaaaa aaaaaaaaaa aaaaaaaaaa aaaa        1134
```

LIPID NANOPARTICLES WITH RNA FOR COSMETIC TREATMENT

SEQUENCE LISTING

The instant application contains a Sequence Listing which has been submitted electronically in XML file format and is hereby incorporated by reference in its entirety. Said XML copy, created on Dec. 23, 2025, is named 12447_012652-US3_SL.xml and is 241,154 bytes in size.

BACKGROUND

Traditionally, adipose tissue is categorized into two main types with distinct functions: white adipose tissue (WAT) and brown adipose tissue (BAT). WAT, composed primarily of large, unilocular adipocytes, serves as the body's principal site for storing energy in the form of triglycerides. Conversely, BAT is specialized for energy expenditure through non-shivering thermogenesis, a process driven by the unique mitochondrial protein, Uncoupling Protein 1 (UCP1). Dysfunction within these adipose depots, particularly the excessive expansion and inflammation of WAT characteristic of overweight/obesity, is intimately linked to the development of metabolic disorders and diseases, including impaired glucose tolerance, metabolic syndrome, type 2 diabetes, cardiovascular disease, non-alcoholic fatty liver disease, and at least thirteen different types of cancer. Therefore, understanding and manipulating adipose tissue function represents a significant frontier in treating human disease.

A paradigm shift in adipose tissue biology occurred with the confirmation of metabolically active BAT in adult humans. That paradigm shift was further expanded by the discovery of inducible "browning" or "beigeing" of WAT. Beige adipose tissue (BeAT) is defined by the emergence or development of cells, in WAT, that express UCP1. The "beigeing" process can be activated by specific stimuli such as chronic cold exposure or treatment with β-adrenergic agonists. Like classical brown adipocytes, beige cells possess multilocular lipid droplets, abundant mitochondria, and express UCP1, enabling them to consume caloric fuel via heat production. This process increases the body's thermogenic capacity.

UCP1, also known historically as thermogenin, is an inner mitochondrial membrane protein, primarily found in brown and beige adipocytes. UCP1 provides an alternative pathway for proton re-entry into the mitochondrial matrix, effectively bypassing ATP synthase. This regulated "proton leak" dissipates the energy stored in the proton motive force (PMF) directly as heat, rather than converting it into chemical energy in the form of ATP. This conversion of the PMF to heat is the core mechanism of non-shivering thermogenesis mediated by brown and beige fat.

There is an unmet need in the art for an agent to induce UCP1 expression in WAT and other tissues, thereby bypassing natural upstream controls. This strategy offers the potential advantage of inducing thermogenesis independent of external stimuli like cold, while also circumventing the body's inherent negative controls on upregulating heat production. An ideal agent would thus increase local energy expenditure by generating heat and thereby reduce the size of adipose tissue deposits.

SUMMARY

To address the above-mentioned unmet needs, the present technology presents methods, compositions and systems for directing a change in the cell state of human WAT to BeAT, agents to achieve that change and systems/protocols for taking advantage of the thermogenic and calorie-expending properties of BeAT in order to achieve local reductions of adipose tissue and systemic change in the properties of adipose tissue.

The present disclosure provides an RNA molecule comprising (consisting essentially of, or consisting of) a nucleotide sequence about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleotide sequence set forth in any of SEQ ID NOs: 1 to 130, including any of SEQ ID NO: 1, SEQ ID NO:2, SEQ ID NO:3, SEQ ID NO:4, SEQ ID NO:5, SEQ ID NO:6, SEQ ID NO: 7, SEQ ID NO:8, SEQ ID NO:9, SEQ ID NO: 10, SEQ ID NO: 11, SEQ ID NO:12, SEQ ID NO: 13, SEQ ID NO:14, SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO: 30, SEQ ID NO:31, SEQ ID NO:32, SEQ ID NO:33, SEQ ID NO:34, SEQ ID NO:35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 47, SEQ ID NO:48, SEQ ID NO:49, SEQ ID NO:50, SEQ ID NO:51, SEQ ID NO:52, SEQ ID NO: 53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO: 64, SEQ ID NO:65, SEQ ID NO:66, SEQ ID NO: 67, SEQ ID NO:68, SEQ ID NO:69, SEQ ID NO: 70, SEQ ID NO:71, SEQ ID NO: 72, SEQ ID NO: 73, SEQ ID NO:74, SEQ ID NO: 75, SEQ ID NO: 76, SEQ ID NO: 77, SEQ ID NO: 78, SEQ ID NO: 79, SEQ ID NO:80, SEQ ID NO: 81, SEQ ID NO: 82, SEQ ID NO: 83, SEQ ID NO: 84, SEQ ID NO: 85, SEQ ID NO:86, SEQ ID NO: 87, SEQ ID NO: 88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO: 98, SEQ ID NO:99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, and SEQ ID NO: 130.

Also encompassed by the present disclosure is a lipid nanoparticle comprising (i) an RNA molecule encoding human uncoupling protein 1 (UCP1); and (ii) an ionizable cationic lipid (ICL), a non-cationic lipid (NCL), a sterol, and a polyethylene glycol (PEG)-modified lipid, at a molar ratio of ICL (20-80):NCL (2-40):sterol (10-70):PEG-modified lipid (0.2-10); at a molar ratio of ICL (25-75):NCL (4-35): sterol (15-65):PEG-modified lipid (0.5-8); at a molar ratio of ICL (30-70):NCL (6-30):sterol (20-60):PEG-modified lipid (0.5-6); at a molar ratio of ICL (35-65):NCL (8-25):sterol (25-55):PEG-modified lipid (1-4); at a molar ratio of ICL (35-60):NCL (10-16):sterol (30-50):PEG-modified lipid (1.5-2.5); or at a molar ratio of ICL (40-50):NCL (9-10): sterol (35-45):PEG-modified lipid (1.5-2.5).

The RNA molecule may comprise (consist essentially of, or consist of) a nucleotide sequence about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the nucleotide sequence set forth in any of SEQ ID NOs: 1 to 130.

In certain embodiments, one or more uridine nucleotides of the RNA molecule are substituted with pseudouridines. In certain embodiments, all uridine nucleotides of the RNA molecule are substituted with pseudouridines. In certain embodiments, at least or about 10%, at least or about 20%, at least or about 30%, at least or about 40%, at least or about 50%, at least or about 60%, at least or about 70%, at least or about 80%, at least or about 90%, at least or about 95%, at least or about 96%, at least or about 97%, at least or about 98%, at least or about 99%, or about 100%, uridine nucleotides of the RNA molecule are substituted with pseudouridines.

In certain embodiments, one or more uridine nucleotides of the RNA molecule are substituted with N1-Methylpseudouridines. In certain embodiments, all uridine nucleotides of the RNA molecule are substituted with N1-Methylpseudouridines. In certain embodiments, at least or about 10%, at least or about 20%, at least or about 30%, at least or about 40%, at least or about 50%, at least or about 60%, at least or about 70%, at least or about 80%, at least or about 90%, at least or about 95%, at least or about 96%, at least or about 97%, at least or about 98%, at least or about 99%, or about 100%, uridine nucleotides of the RNA molecule are substituted with N1-Methylpseudouridines.

The RNA molecule may be a messenger RNA (mRNA).

Ionizable cationic lipids (ICLs) include, but are not limited to, C14-4, SM-102, ALC-0315, DLin-MC3-DMA, LP-01, 4A3-SC8, cKK-E12, 3060; 10, C3-K2-E14, Lipid A9, OF-02, TCL053, DLin-DMA, C12-200, DLin-KC2-DMA, and mixtures thereof.

Non-cationic lipids (NCLs) include, but are not limited to, distearoylphosphatidylcholine (DSPC), dioleoylphosphandylcholine (DOPC), dipalmitoylphosphatidylcholine (DPPC), dioleoylphosphatidylglycerol (DOPG), dipalmitoylphosphatidlylglycerol (DPPG), dioleoylphosphatidylethanolamine (DOPE), palmitoyloleoylphosphatidylcholine (POPC), palmitoyloleol-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanoiamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, and mixtures thereof.

Sterols include, but are not limited to, cholesterol, fecosterol, sitosterol, ergosterol, campesterol, stigmasterol, brassicasterol, tomatidine, tomatine, ursolic acid, alpha-tocopherol, and mixtures thereof.

PEG-modified lipids include, but are not limited to, a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

Non-limiting examples of PEG-lipids include 1,2-dimyristoyl-sn-glycerol methoxypolyethylene glycol (PEG-DMG), 1,2-distearoyl-sn-glycero-3-phosphoethanolamine-N-[amino (polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

The present disclosure provides a pharmaceutical composition comprising: a synthetic mRNA comprising (consisting essentially of, or consisting of) the nucleotide sequence set forth in SEQ ID NO: 6, SEQ ID NO: 3, or SEQ ID NO: 4, wherein the synthetic mRNA is packaged in a lipid nanoparticle (LNP).

In certain embodiments, the lipid nanoparticle comprises (C14-4:NCL:cholesterol:PEG-modified lipid) at a molar ratio of (35:16:46.5:2.5), (50:10:38.5:1.5) or (56.5:10:31.8: 1.7).

In certain embodiments, the lipid nanoparticle comprises (SM-102:NCL:Cholesterol:PEG-modified lipid) at a molar ratio of (50:10:38.5:1.5), (48.3:9.1:40.5:2.1) or (46.6:10.4: 41.2:1.8).

The present disclosure further provides a pharmaceutical composition comprising the RNA molecule. The present disclosure also provides a pharmaceutical composition comprising the lipid nanoparticle.

The present disclosure provides a method of treating a condition in a subject. The method comprises administering the present RNA molecule, lipid nanoparticle, or pharmaceutical composition to the subject.

The condition may be overweight/obesity. The condition may be a metabolic disorder. The conditions include, but are not limited to, impaired glucose tolerance, metabolic syndrome, diabetes (e.g., type 2 diabetes), cardiovascular diseases, non-alcoholic fatty liver disease, lipedema, cancer (such as breast cancer, colon cancer, melanoma, and prostate cancer), hypertension (e.g., treatment-resistant hypertension), and heart failure (e.g., heart failure with preserved ejection fraction).

The present disclosure provides a method of treating a subject for targeted body fat reduction in an area of the subject. The method comprises administering the present RNA molecule, lipid nanoparticle, or pharmaceutical composition to the area of the subject.

The present disclosure provides methods and compositions for increasing the quantities and/or the ratios of brown/beige adipocytes in WAT. In various aspects, the cellular manipulations described herein are guided and/or mediated by messenger RNA (mRNA) that may be in vitro transcribed ("IVT" or "synthetic"). Proteins encoded by the mRNA can provide cellular instructions for transitioning a cell from one state to a different cellular state. In one embodiment, lipid nanoparticle (LNP)-packaged synthetic mRNA is introduced into cells that reside in WAT (WAT-cells). Examples of WAT-cells include, but are not limited to, adipocytes, mesenchymal stem cells, stromal cells, fibroblasts, vascular cells, perivascular cells, nerve cells, and immune cells.

An aspect of the present disclosure relates to a method for generating UCP1-positive WAT-cells. This converts WAT (a tissue comprised of many WAT-cells) into beige adipose tissue (BeAT) or brown adipose tissue (BAT). BeAT may include beige adipocytes or brown adipocytes. The method may comprise, contacting WAT-cells with mRNA encapsulated in an LNP, wherein the mRNA encodes UCP1, or other proteins/enzymes (e.g. Adipose Triglyceride Lipase and Hormone-Sensitive Lipase to mobilize fatty acids from triglycerides; Creatine kinase and phosphocreatine phosphatase to promote futile creatine cycling) that may induce UCP1 protein production in WAT-cells.

An aspect of the present disclosure relates to a pharmaceutical composition comprising: an mRNA encoding UCP1, said mRNA encapsulated in an LNP. The pharmaceutical composition may be introduced into WAT-cells.

An aspect of the present disclosure relates to a composition of a treatment for directing a change in state of any WAT-cells comprising: contacting said WAT-cells with a payload of mRNA, protein, plasmid DNA or oligonucleic acid encapsulated in MITO-Porter (a liposome-based carrier for delivering a payload to the mitochondria via membrane fusion) for targeting the payload to the mitochondria. The payload may effectuate a state change transition of the WAT-cells to UCP1-positive.

In one embodiment, the disclosure may be a pharmaceutical composition comprising an mRNA comprising a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in SEQ ID NO: 130. The mRNA may be packaged in a lipid nanoparticle (LNP).

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in any of SEQ ID NO: 1 to SEQ ID NO: 130.

In another embodiment, the LNP is of an LNP component molar ratio substantially similar to that of LNP ID I (Table 1).

In another embodiment, the LNP is of an LNP component molar ratio substantially similar to that of LNP ID D (Table 1).

In another embodiment, the mRNA comprises one or more modified uridine nucleotides.

In another embodiment, the modified uridine nucleotide is pseudouridine.

In another embodiment, the modified uridine nucleotide is N1-Methylpseudouridine.

In a second embodiment, the disclosure provides a method of preparing a pharmaceutical composition, the method comprising preparing a synthetic mRNA comprising a nucleotide sequence set forth in SEQ ID NO: 2, SEQ ID NO: 8, or SEQ ID NO: 18; and packaging said synthetic mRNA in a lipid nanoparticle (LNP).

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in any of SEQ ID NO: 2, SEQ ID NO: 8, or SEQ ID NO: 18.

In another embodiment, the LNP is of an LNP component molar ratio substantially similar to that of LNP ID I (Table 1).

In another embodiment, the LNP is of an LNP component molar ratio substantially similar to that of LNP ID D (Table 1).

In another embodiment, the mRNA comprises one or more modified uridine nucleotides.

In another embodiment, the modified uridine nucleotide is pseudouridine.

In another embodiment, the modified uridine nucleotide is N1-Methylpseudouridine.

In a third embodiment, the disclosure provides a method of treating a subject for targeted body fat reduction in an area of the subject. The method may comprise delivering to the area a pharmaceutical composition comprising an mRNA; wherein the mRNA comprises a nucleotide sequence at least or about 70% identical to the nucleotide sequence set forth in SEQ ID NO: 3, SEQ ID NO: 9, or SEQ ID NO: 17.

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in any of SEQ ID NO: 3, SEQ ID NO: 9, or SEQ ID NO: 17.

The method may further comprise identifying an area of the subject for targeted fat reduction.

In another embodiment, the area comprises the abdomen, the outer arms, flanks, upper back, lumbar region, calves, submental fat, dorsal cervical fat, axillary fat, lateral chest wall, outer thighs, inner thighs, or combinations thereof.

In another embodiment, the delivery is carried out in a single bolus injection.

In another embodiment, the delivery is carried out in a series of injections in the area.

In another embodiment, the delivery is carried out transdermally by a penetration enhancer.

In another embodiment, the delivery is carried out transdermally by a vesicular carrier.

In another embodiment, the delivery is carried out trans-dermally by a microneedle injection.

In another embodiment, the delivery is carried out trans-dermally by iontophoresis, sonophoresis or jet injection.

In one embodiment, the present disclosure provides a pharmaceutical composition comprising UCP1 protein (NCBI RefSeq: NP_001735.1) encapsulated in MITO-Por-ter. WO/2006/095837. U.S. Pat. No. 11,814,640. Yamada et al., Dual function MITO-Porter, a nano carrier integrating both efficient cytoplasmic delivery and mitochondrial mac-romolecule delivery, Mol Ther. 2011, 19 (8): 1449-56. Cojocaru et al., Mitochondrial Dysfunction, Oxidative Stress, and Therapeutic Strategies in Diabetes, Obesity, and Cardiovascular Disease, Antioxidants (Basel), 2023; 12 (3): 658. Norota et al., Lipid nanoparticle delivery of the CRISPR/Cas9 system directly into the mitochondria of cells carrying m. 7778G>T mutation in MtDNA (mt-Atp8), Sci-entific Reports, volume 15, Article number: 18717 (2025). Yasuzaki et al., Mitochondrial matrix delivery using MITO-Porter, a liposome-based carrier that specifies fusion with mitochondrial membranes, Biochem. Biophys. Res. Com-mun. 2010; 397 (2): 181-6. Yamada et al., MITO-Porter: A liposome-based carrier system for delivery of macromol-ecules into mitochondria via membrane fusion, Biochim. Biophys. Acta. 2008; 1778 (2): 423-32. Yamada et al., Mitochondrial drug delivery systems for macromolecule and their therapeutic application to mitochondrial diseases, Adv. Drug Deliv. Rev. 2008; 60 (13-14): 1439-62.

In another embodiment, the UCP1 protein may be opti-mized to increase its active life by including factors which inhibit the effects of mitochondrial proteases LONP1 and ClpXP.

In another embodiment, the UCP1 protein may be opti-mized to increase its binding affinity to the inner mitochon-drial matrix by optimizing the mitochondrial targeting signal (MTS) of the UCP1 protein, introduction of destabilizing elements, and/or the introduction of chaperone binding sites.

BRIEF DESCRIPTION OF THE DRAWINGS

FIG. 8: t=0; FIG. 9: t+1 day; FIG. 10: t+2 days; FIG. 11: t+3 days; FIG. 12: t+4 days; FIG. 13: t+5 days; FIG. 14: t+6 days.

FIG. 15: t=0; FIG. 16: t+1 day; FIG. 17: t+2 days; FIG. 18: t+3 days; FIG. 19: t+4 days; FIG. 20: t+5 days; FIG. 21: t+6 days.

DETAILED DESCRIPTION

Figure 1:
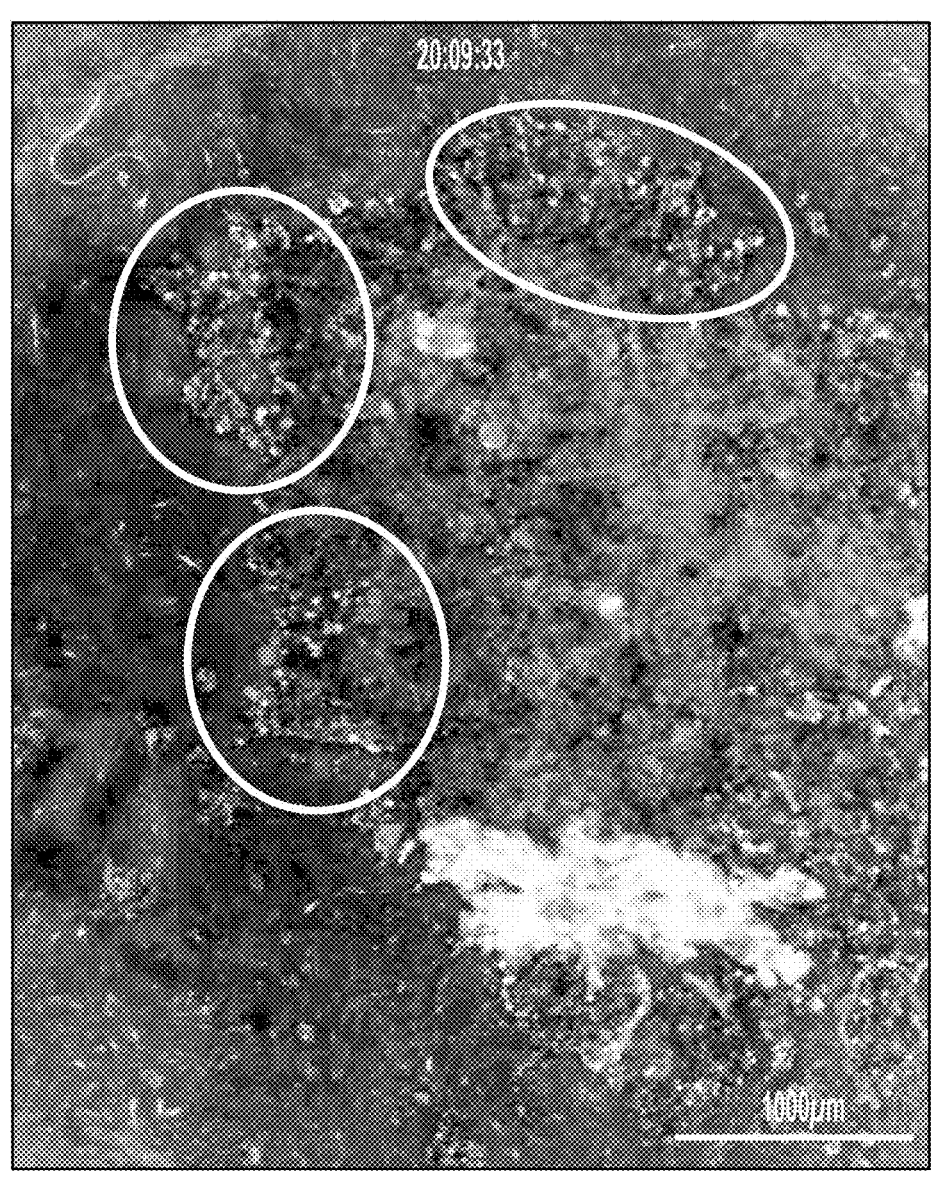
FIG. 1 is a microscope image of human adipose tissue transfected with the mRNA of SEQ ID NO: 130 encoding UCP1 encapsulated in LNPs.

Detailed descriptions of one or more embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present invention in any appropriate manner.

UCP1-positive cells, including brown and/or beige adipocytes (BAs), are able to uncouple the proton motive force from ATP generation in order to produce thermal energy. This mechanism allows mammals, through non-shivering thermogenesis, to regulate body temperature in cold environments. Because of its metabolically active nature, UCP1-positive WAT-cells represent a promising pathway for non-surgical intervention for diseases whose pathophysiology is driven by excess fat. Examples of such diseases include obesity, diabetes, lipedema, cancer (such as breast cancer, colon cancer, melanoma, and prostate cancer), hypertension (e.g., treatment-resistant hypertension), heart failure (e.g., heart failure with preserved ejection fraction), and other indications.

Provided herein are compositions, methods, formulations and devices to: 1) increase UCP1 levels in WAT-cells, thereby enhancing the metabolic activity of the treated tissue, and 2) activate the thermogenic activity of the BAs in the treated tissue so as to consume fatty acids through thermogenesis thereby reducing the volume of adipose tissue in the treated tissue.

Referring to the Sequence Listing incorporated by reference herein, SEQ ID NO: 130 is an optimized version of the mRNA encoding for human UCP1, including modifications to the 5' and 3' UTRs such as inserting a ribosome binding site, a Kozak sequence and a double stop codon. SEQ ID NOs: 2-21 were created as further optimizations of SEQ ID NO: 130 using GenScript Biotech Corporation GenSmart tool with several modifications including modifications selected from deleting the 5' UTR, incorporating Translation Initiator of 5' UTR (TISU), the genomic human UCP1 5' UTR, the consensus genomic human fatty acid binding protein 4 (FABP4) 5' UTR, the consensus genomic human UCP1 3' UTR, the Cominarty 3' UTR, and the consensus genomic human beta-globin (HBB) 3' UTR in tandem tail-to-head sequence. For example, SEQ ID NO: 2 is 928 nucleotides long which corresponds to nucleotides 54 through 981 of SEQ ID NO: 130. As another example, SEQ ID NO: 3 is 932 nucleotides long which corresponds to nucleotides 50 through 981 of SEQ ID NO: 130. As another example, SEQ ID NO: 8 is 1397 nucleotides long whose nucleotides 1 through 929 correspond to nucleotides 50 through 978 of SEQ ID NO: 130. As another example, SEQ ID NO: 17 is 1142 nucleotides long whose nucleotides 1 through 928 correspond to nucleotides 54 through 981 of SEQ ID NO: 130.

SEQ ID NOs: 22 through 129 are optimizations of SEQ ID NOs: 130 and 2 through 21 using various UTR sequences. The optimizations of the UTR regions of SEQ ID NOs: 22 through 129 are designed to prevent the formation of secondary and tertiary RNA structures that can inhibit translation. The 5' UTR sequences were selected to produce high protein expression level in human WAT.

SEQ ID NOs: 22 through 24: codon optimized human UCP1 mRNA using custom 5' and 3' UTRs. The 5' UTR: Modified genomic human FABP4 5' UTR with a Kozak sequence inserted. The 3' UTR: double stop codon.

SEQ ID NOs: 25 through 27: codon optimized human UCP1 mRNA using custom 5' and 3' UTRs. The 5' UTR: Modified genomic human LIPE 5' UTR with a Kozak sequence inserted. The 3' UTR: double stop codon.

SEQ ID NOs: 28 through 30: codon optimized human UCP1 mRNA using custom 5' and 3' UTRs. The 5' UTR: Modified genomic human PLIN1 5' UTR with a Kozak sequence inserted. The 3' UTR: double stop codon.

SEQ ID NOs: 31 through 33: codon optimized human UCP1 mRNA using custom 5' and 3' UTRs. The 5' UTR: Modified genomic human COL1A 5' UTR with a Kozak sequence inserted. The 3' UTR mRNA: double stop codon.

SEQ ID NOs: 34 through 36: codon optimized human UCP1 mRNA using custom 5' and 3' UTRs. The 5' UTR: Modified genomic human LEP 5' UTR with a Kozak sequence inserted. The 3' UTR for these CDS: double stop codon.

SEQ ID NOs: 37 through 39: codon optimized human UCP1 mRNA using custom 5' and 3' UTRs. The 5' UTR: Modified genomic human ADIPOQ 5' UTR with a Kozak sequence inserted. The 3' UTR: double stop codon.

SEQ ID NOs: 40 through 44: codon optimized human UCP1 mRNA using custom 5' and 3' UTRs. The 5' UTR: Consensus genomic human FABP4 5' UTR. The 3' UTR: double stop codon.

SEQ ID NOs: 45 through 49: codon optimized human UCP1 mRNA using custom 5' and 3' UTRs. The 5' UTR: Consensus genomic human Lipase E, Hormone Sensitive Type (LIPE) 5' UTR. The 3' UTR: double stop codon.

SEQ ID NOs: 50 through 54: codon optimized human UCP1 mRNA using custom 5' and 3' UTRs. The 5' UTR: Consensus genomic human perilipin 1 (PLIN1) 5' UTR. The 3' UTR: double stop codon.

SEQ ID NOs: 55 through 59: codon optimized human UCP1 mRNA using custom 5' and 3' UTRs. The 5' UTR: Consensus genomic human collagen 1A (COL1A) 5' UTR. The 3' UTR: double stop codon.

SEQ ID NOs: 60 through 64: codon optimized human UCP1 mRNA using custom 5' and 3' UTRs. The 5' UTR: Consensus genomic human leptin (LEP) 5' UTR. The 3' UTR: double stop codon.

SEQ ID NOs: 65 through 69: codon optimized human UCP1 mRNA using custom 5' and 3' UTRs. The 5' UTR: Consensus genomic human adiponectin (ADIPOQ) 5' UTR. The 3' UTR: double stop codon.

SEQ ID NOs: 70 through 74: codon optimized human UCP1 mRNA using custom 5' and 3' UTRs. The 5' UTR: Modified genomic human FABP4 5' UTR with a Kozak sequence inserted. The 3' UTR: double stop codon.

SEQ ID NOs: 75 through 79: codon optimized human UCP1 mRNA using custom 5' and 3' UTRs. The 5' UTR: Modified genomic human LIPE 5' UTR with a Kozak sequence inserted. The 3' UTR: double stop codon.

SEQ ID NOs: 80 through 84: codon optimized human UCP1 mRNA using custom 5' and 3' UTRs. The 5' UTR: Modified genomic human PLIN1 5' UTR with a Kozak sequence inserted. The 3' UTR: double stop codon.

SEQ ID NOs: 85 through 89: codon optimized human UCP1 mRNA using custom 5' and 3' UTRs. The 5' UTR: Modified genomic human COL1A 5' UTR with a Kozak sequence inserted. The 3' UTR: double stop codon.

SEQ ID NOs: 90 through 94: codon optimized human UCP1 mRNA using custom 5' and 3' UTRs. The 5' UTR: Modified genomic human LEP 5' UTR with a Kozak sequence inserted. The 3' UTR: double stop codon.

SEQ ID NOs: 95 through 99: codon optimized human UCP1 mRNA using custom 5' and 3' UTRs. The 5' UTR: Modified genomic human ADIPOQ 5' UTR with a Kozak sequence inserted. The 3' UTR: double stop codon.

SEQ ID NOs: 100 through 104: codon optimized human UCP1 mRNA using custom 5' and 3' UTRs. The 5' UTR: Consensus genomic human FABP4 5' UTR. The 3' UTR: double stop codon.

SEQ ID NOs: 105 through 109: codon optimized human UCP1 mRNA using custom 5' and 3' UTRs. The 5' UTR: Consensus genomic human LIPE 5' UTR. The 3' UTR: double stop codon.

SEQ ID NOs: 110 through 114: codon optimized human UCP1 mRNA using custom 5' and 3' UTRs. The 5' UTR: Consensus genomic human PLIN1 5' UTR. The 3' UTR: double stop codon.

SEQ ID NOs: 115 through 119: codon optimized human UCP1 mRNA using custom 5' and 3' UTRs. The 5' UTR: Consensus genomic human COL1A 5' UTR. The 3' UTR: double stop codon.

SEQ ID NOs: 120 through 124: codon optimized human UCP1 mRNA using custom 5' and 3' UTRs. The 5' UTR: Consensus genomic human LEP 5' UTR. The 3' UTR: double stop codon.

SEQ ID NOs: 125 through 129: codon optimized human UCP1 mRNA using custom 5' and 3' UTRs. The 5' UTR: Consensus genomic human ADIPOQ 5' UTR. The 3' UTR: double stop codon.

The genomic coding sequence of UCP1 for *Homo sapiens* is known. UCP homologs from non-human animals, such as lower primates, horses, cows, pigs, sheep, goats, and chicken can also be used with the lipid nanoparticles.

The synthetic mRNA may further comprise siRNA, circular RNA, self-replicating mRNA, or mRNA designed for gene editing, including but not limited to, CRISPR-Cas9 systems. The LNP vesicle may be tailored specifically to enhance transfection of the target adipocytes and WAT. Tailoring of the LNP may include adjusting the molar ratios of ionizable lipids, helper phospholipids, polyethylene glycol (PEG)-lipids, and sterols, as well as immunogenicity-reducing molecules including but not limited to steroids and steroid pro-drugs.

The "lipid nanoparticle" comprises one or more lipids (e.g., cationic lipids, non-cationic lipids, and/or PEG-modified lipids) which are formulated to deliver one or more mRNA to one or more target cells. Suitable lipids include, for example, phosphatidyl (e.g., phosphatidylglycerol, phosphatidylcholine, phosphatidylserine, phosphatidylethanolamine, sphingolipids, cerebrosides, and gangliosides). Various polymers may also be incorporated into the lipid nanoparticles, including, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine.

The lipid nanoparticles may range in size from about 20 nm to about 200 nm, about 50 nm to about 200 nm, about 60 nm to about 150 nm, about 50 nm to about 150 nm, about 80 nm to about 150 nm, about 60 nm to about 80 nm, about 80 nm to about 100 nm, about 100 nm to about 120 nm, or about 120 nm to about 150 nm.

The lipid nanoparticles can incorporate an ionizable cationic lipid (ICL) to encapsulate the mRNA and/or enhance the delivery of mRNA into the target cell. A "cationic lipid" refers to any lipid species that carry a net positive charge at a selected pH, such as physiological pH. Ionizable cationic lipids may contain one, two, three, or more fatty acid or fatty alkyl chains and a pH-titratable amino head group (e.g., an alkylamino or dialkylamino head group). An ionizable cationic lipid is typically protonated (i.e., positively charged) at a pH below the pKa of the amino head group and is substantially not charged at a pH above the pKa.

Ionizable cationic lipids include, but are not limited to, DLin-DMA, DLin-D-DMA, DLin-MC3-DMA, DLin-KC2-DMA, DODMA and amino alcohol lipids. The amino alcohol cationic lipid can be the lipids described in and/or made by the methods described in U.S. Patent Publication No. US20130150625. As a non-limiting example, the cationic lipid can be 2-amino-3-[(9Z,12Z)-octadeca-9,12-dien-1-yloxy]-2-{[(9Z,2Z)-octadeca-9,12-dien-1-yloxy]methyl}propan-1-ol; 2-amino-3-[(9Z)-octadec-9-en-1-yloxy]-2-{[(9Z)-octadec-9-en-1-yloxy]methyl}propan-1-ol; 2-amino-3-[(9Z,12Z)-octadeca-9,12-dien-1-yloxy]-2-[(octyloxy)methyl]propan-1-ol; and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol; or any pharmaceutically acceptable salt or stereoisomer thereof.

Non-limiting examples of ionizable lipids include 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,16SZ)—N,N-dimethyl-3-nonydocosa-13-16-dien-1-amine (L608), 2-({8-[(3B)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3B)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy) heptadecanedioate (L319), DLinDMA, (2S)-2-({8-[(3)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and mixtures thereof. In addition to these, an ionizable cationic lipid may also be a lipid including a cyclic amine group.

U.S. Pat. No. 9,738,593 is incorporated by reference in its entirety.

Non-cationic lipids (NCL) may also be used in the lipid nanoparticles. Non-cationic lipids include, but are not limited to, distearoylphosphatidylcholine (DSPC), dioleoylphosphandylcholine (DOPC), dipalmitoylphosphatidylcholine (DPPC), dioleoylphosphatidylglycerol (DOPG), dipalmitoylphosphatidlylglycerol (DPPG), dioleoylphosphatidylethanolamine (DOPE), palmitoyloleoylphosphatidylcholine (POPC), palmitoyloleol-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanoiamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof.

Such non-cationic lipids may be used alone, or may be used in combination with other excipients, for example, cationic lipids. When used in combination with a cationic lipid, the non-cationic lipid may comprise a molar percentage of 5% to about 90%, or about 10% to about 70% of the total lipid present in the lipid nanoparticle.

Polyethylene glycol (PEG)-modified lipids, such as PEG-modified phospholipids, PEG/lipid conjugates and derivatized lipids such as DMG-PEG (2000), derivatized ceramides (PEG-CER), including N-Octanoyl-Sphingosine-1-[Succinyl(Methoxy Polyethylene Glycol)-(C8 PEG-2000 ceramide), or ALC-0159 can be incorporated into the lipid nanoparticle. The PEG-modified lipids include, but are not limited to, a polyethylene glycol chain of up to 5 kDa covalently attached to a lipid with alkyl chain(s) of $C_6$-$C_{20}$ length. The PEG-modified lipids and derivatized lipids can be present at varying molar percentages, e.g., from about 0% to about 20%, about 0.5% to about 20%, about 1% to about 15%, about 4% to about 10%, or about 2% of the total lipids present in the lipid nanoparticle.

The terms "PEG-modified lipid" and "PEG-lipid" are used interchangeably and can refer to polyethylene glycol (PEG)-modified lipids. Non-limiting examples of PEG-lipids include PEG-modified phosphatidylethanolamine, PEG-modified phosphatidic acid, PEG-ceramide conjugates (e.g., PEG-CerC14 or PEG-CerC20), PEG-modified dialkylamines, and PEG-modified 1,2-diacyloxypropan-3-amines. Such lipids are also referred to as PEGylated lipids. For example, a PEG-lipid may be PEG-c-DOMG, PEG-DMG, PEG-DLPE, PEG-DMPE, PEG-DPPC, PEG-S-DSG, PEG-c-DMA, or a PEG-DSPE lipid.

PEG-modified lipids include, but are not limited to, a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the PEG-lipids include, but are not limited to, 1,2-dimyristoyl-sn-glycerol methoxypolyethylene glycol (PEG-DMG), 1,2-distearoyl-sn-glycero-3-phosphoethanolamine-N-[amino (polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

Non-limiting examples of PEG-modified lipids include, PEG-c-DOMG (R-3-[(ω-methoxy-poly(ethyleneglycol) 2000) carbamoyl)]-1,2-dimyristyloxypropyl-3-amine) (also referred to herein as PEG-DOMG), PEG-DSG (1,2-Distearoyl-sn-glycerol, methoxypolyethylene glycol), PEG-DMG (1,2-Dimyristoyl-sn-glycerol), PEG-DPG (1,2-Dipalmitoyl-sn-glycerol, methoxypolyethylene glycol), and mixtures thereof.

In one embodiment, the lipid nanoparticles described herein may comprise a PEG lipid which is a non-diffusible PEG. Non-limiting examples of non-diffusible PEGs include PEG-DSG and PEG-DSPE.

In some embodiments, the lipid moiety of the PEG-lipids includes those having lengths of from about C14 to about C22, or from about C14 to about C16. In some embodiments, a PEG moiety, for example an mPEG-NH2, has a size of about 1000, 2000, 5000, 10,000, 15,000 or 20,000 daltons. In one embodiment, the PEG-lipid is PEG2k-DMG.

U.S. Pat. Nos. 10,406,113; 8,158,601 and 10,821,175 are incorporated herein by reference in their entirety.

In some embodiments, the ratio of PEG in the lipid nanoparticle (LNP) is increased or decreased and/or the carbon chain length of the PEG lipid is modified from C14 to C18 to alter the pharmacokinetics and/or biodistribution of the LNP. As a non-limiting example, LNPs contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-modified lipid.

In certain embodiments, to package mRNA into an LNP, a lipid mixture of four components (ICL, NCL, Cholesterol, PEG/Lipid Conjugatge) is dissolved in ethanol and is rapidly mixed with an mRNA solution in an acidic aqueous buffer. As ethanol is diluted by the aqueous buffer, the change in solvent polarity drives the self-assembly of the lipids and encapsulated mRNA into a core-shell nanostructure. Subsequently, the acidic buffer is exchanged with PBS to achieve a neutral pH, neutralizing the ionizable lipid, and stabilizing the final LNP formulation. This process yields nanoparticles that protect the mRNA payload and facilitates its delivery into target cells.

To reduce immunogenicity and inflammation, active and pro-drug forms of anti-inflammatory steroids can be incorporated into the LNPs. For example, the ester prodrugs of rofleponide and/or budesonide can be incorporated into an LNP using amino lipids such as Dlin-MC3-DMA or L608.

LNPs may include the following lipids shown in Table 1.

TABLE 1

| LNP Component Molar Ratios | | | | | |
| --- | --- | --- | --- | --- | --- |
| LNP ID | ICL Molecule | ICL | NCL | Cholesterol | PEG/Lipid Conjugate |
| A | ALC-0315 | 50 | 10 | 38.5 | 1.5 |
| | | 46.3 | 9.4 | 42.7 | 1.6 |
| | | 47.2 | 9.2 | 42.2 | 1.4 |
| B | DLin-MC3-DMA | 50 | 10 | 38.5 | 1.5 |
| | | 51.2 | 10 | 37.4 | 1.4 |
| | | 49.4 | 11.2 | 37.8 | 1.6 |
| C | LP-01 | 45 | 9 | 44 | 2 |
| | | 43.5 | 10 | 44.3 | 2.2 |
| | | 46.3 | 9.4 | 42.3 | 2 |
| D | SM-102 | 50 | 10 | 38.5 | 1.5 |
| | | 48.3 | 9.1 | 40.5 | 2.1 |
| | | 46.6 | 10.4 | 41.2 | 1.8 |
| E | 4A3-SC8 | 38.5 | 30 | 30 | 1.5 |
| | | 35 | 16 | 46.5 | 2.5 |
| | | 45 | 11 | 42.5 | 1.5 |
| F | cKK-E12 | 35 | 16 | 46.5 | 2.5 |
| | | 45 | 11 | 42.5 | 1.5 |
| | | 50 | 10 | 38.5 | 1.5 |
| G | 306Oi10 | 35 | 16 | 46.5 | 2.5 |
| | | 50 | 10 | 38.5 | 1.5 |
| | | 40 | 32.5 | 25 | 2.5 |
| H | C3-K2-E14 | 50 | 10 | 38.5 | 1.5 |
| | | 56.5 | 10 | 31.8 | 1.7 |
| | | 35 | 16 | 46.5 | 2.5 |
| I | C14-4 | 35 | 16 | 46.5 | 2.5 |
| | | 50 | 10 | 38.5 | 1.5 |
| | | 56.5 | 10 | 31.8 | 1.7 |

TABLE 1-continued

| LNP Component Molar Ratios | | | | | |
|---|---|---|---|---|---|
| LNP ID | ICL Molecule | ICL | NCL | Cholesterol | PEG/Lipid Conjugate |
| J | Lipid A9 | 50 | 10 | 38.5 | 1.5 |
| | | 35 | 16 | 46.5 | 2.5 |
| | | 40 | 32.5 | 25 | 2.5 |
| K | OF-02 | 40.3 | 14.9 | 43.7 | 1.1 |
| | | 56.5 | 10 | 31.8 | 1.7 |
| | | 52.7 | 17.5 | 28.7 | 1.1 |
| L | TCL053 | 60 | 10.6 | 27.3 | 2.1 |
| | | 50 | 10 | 38.5 | 1.5 |
| | | 35 | 16 | 46.5 | 2.5 |

The above list is intended to be exemplary and LNPs of other component molar ratios as described herein may be appropriate for the specific application contemplated herein.

For example, the composition of the LNP (e.g. ICL, Cholesterol, DSPC, and DMG-PEG2000) can be combined to yield different molar ratios. In one embodiment, the molar ratio of ICL to Cholesterol to DSPC to PEG/LIPID CONJUGATE are (3 to 80):(3 to 80):(1 to 50):(0.2 to 10). In another embodiment, the molar ratio of ICL to Cholesterol to DSPC to PEG/LIPID CONJUGATE are (7 to 80):(7 to 80):(3 to 50):(1.0 to 10). In another embodiment, the molar ratio of ICL to Cholesterol to DSPC to PEG/LIPID CONJUGATE are (10 to 80):(10 to 80):(4 to 50):(1.5 to 10). In another embodiment, the molar ratio of ICL to Cholesterol to DSPC to PEG/LIPID CONJUGATE are (13 to 80):(13 to 80):(5 to 50):(2.0 to 10). In another embodiment, the molar ratio of ICL to Cholesterol to DSPC to PEG/LIPID CONJUGATE are (3 to 75):(3 to 75):(1 to 45):(0.2 to 7). In another embodiment, the molar ratio of ICL to Cholesterol to DSPC to PEG/LIPID CONJUGATE are (7 to 75):(7 to 75):(3 to 45):(1.0 to 7). In another embodiment, the molar ratio of ICL to Cholesterol to DSPC to PEG/LIPID CONJUGATE are (10 to 75):(10 to 75):(4 to 45):(1.5 to 7). In another embodiment, the molar ratio of ICL to Cholesterol to DSPC to PEG/LIPID CONJUGATE are (13 to 75):(13 to 75):(5 to 45):(2.0 to 7). In another embodiment, the molar ratio of ICL to Cholesterol to DSPC to PEG/LIPID CONJUGATE are (3 to 70):(3 to 70):(1 to 40):(0.2 to 5). In another embodiment, the molar ratio of ICL to Cholesterol to DSPC to PEG/LIPID CONJUGATE are (7 to 70):(7 to 70):(3 to 40):(1.0 to 5). In another embodiment, the molar ratio of ICL to Cholesterol to DSPC to PEG/LIPID CONJUGATE are (10 to 70):(10 to 70):(4 to 40):(1.5 to 5). In another embodiment, the molar ratio of ICL to Cholesterol to DSPC to PEG/LIPID CONJUGATE are (13 to 70):(13 to 70):(5 to 40):(2.0 to 5).

In a second embodiment, the molar ratio of ICL to Cholesterol to DSPC to PEG/LIPID CONJUGATE are (3 to 80):(3 to 70):(1 to 50):(0.2 to 10). In another embodiment, the molar ratio of ICL to Cholesterol to DSPC to PEG/LIPID CONJUGATE are (7 to 80):(7 to 70):(3 to 50):(1.0 to 10). In another embodiment, the molar ratio of ICL to Cholesterol to DSPC to PEG/LIPID CONJUGATE are (10 to 80):(10 to 70):(4 to 50):(1.5 to 10). In another embodiment, the molar ratio of ICL to Cholesterol to DSPC to PEG/LIPID CONJUGATE are (13 to 80):(13 to 70):(5 to 50):(2.0 to 10). In another embodiment, the molar ratio of ICL to Cholesterol to DSPC to PEG/LIPID CONJUGATE are (3 to 75):(3 to 80):(1 to 45):(0.2 to 7). In another embodiment, the molar ratio of ICL to Cholesterol to DSPC to PEG/LIPID CONJUGATE are (7 to 75):(7 to 80):(3 to 45):(1.0 to 7). In another embodiment, the molar ratio of ICL to Cholesterol to DSPC to PEG/LIPID CONJUGATE are (10 to 75):(10 to 80):(4 to 45):(1.5 to 7). In another embodiment, the molar ratio of ICL to Cholesterol to DSPC to PEG/LIPID CONJUGATE are (13 to 75):(13 to 80):(5 to 45):(2.0 to 7). In another embodiment, the molar ratio of ICL to Cholesterol to DSPC to PEG/LIPID CONJUGATE are (3 to 70):(3 to 75):(1 to 40):(0.2 to 5). In another embodiment, the molar ratio of ICL to Cholesterol to DSPC to PEG/LIPID CONJUGATE are (7 to 70):(7 to 75):(3 to 40):(1.0 to 5). In another embodiment, the molar ratio of ICL to Cholesterol to DSPC to PEG/LIPID CONJUGATE are (10 to 70):(10 to 75):(4 to 40):(1.5 to 5). In another embodiment, the molar ratio of ICL to Cholesterol to DSPC to PEG/LIPID CONJUGATE are (13 to 70):(13 to 75):(5 to 40):(2.0 to 5).

In a third embodiment, the molar ratio of ICL to Cholesterol to DSPC to PEG/LIPID CONJUGATE are (3 to 80):(3 to 80):(1 to 40):(0.2 to 10). In another embodiment, the molar ratio of ICL to Cholesterol to DSPC to PEG/LIPID CONJUGATE are (7 to 80):(7 to 80):(3 to 40):(1.0 to 10). In another embodiment, the molar ratio of ICL to Cholesterol to DSPC to PEG/LIPID CONJUGATE are (10 to 80):(10 to 80):(4 to 40):(1.5 to 10). In another embodiment, the molar ratio of ICL to Cholesterol to DSPC to PEG/LIPID CONJUGATE are (13 to 80):(13 to 80):(5 to 40):(2.0 to 10). In another embodiment, the molar ratio of ICL to Cholesterol to DSPC to PEG/LIPID CONJUGATE are (3 to 75):(3 to 75):(1 to 50):(0.2 to 7). In another embodiment, the molar ratio of ICL to Cholesterol to DSPC to PEG/LIPID CONJUGATE are (7 to 75):(7 to 75):(3 to 50):(1.0 to 7). In another embodiment, the molar ratio of ICL to Cholesterol to DSPC to PEG/LIPID CONJUGATE are (10 to 75):(10 to 75):(4 to 50):(1.5 to 7). In another embodiment, the molar ratio of ICL to Cholesterol to DSPC to PEG/LIPID CONJUGATE are (13 to 75):(13 to 75):(5 to 50):(2.0 to 7). In another embodiment, the molar ratio of ICL to Cholesterol to DSPC to PEG/LIPID CONJUGATE are (3 to 70):(3 to 70):(1 to 45):(0.2 to 5). In another embodiment, the molar ratio of ICL to Cholesterol to DSPC to PEG/LIPID CONJUGATE are (7 to 70):(7 to 70):(3 to 45):(1.0 to 5). In another embodiment, the molar ratio of ICL to Cholesterol to DSPC to PEG/LIPID CONJUGATE are (10 to 70):(10 to 70):(4 to 45):(1.5 to 5). In another embodiment, the molar ratio of ICL to Cholesterol to DSPC to PEG/LIPID CONJUGATE are (13 to 70):(13 to 70):(5 to 45):(2.0 to 5).

In a fourth embodiment, the molar ratio of ICL to Cholesterol to DSPC to PEG/LIPID CONJUGATE are (3 to 80):(3 to 80):(1 to 50):(0.2 to 5). In another embodiment, the molar ratio of ICL to Cholesterol to DSPC to PEG/LIPID CONJUGATE are (7 to 80):(7 to 80):(3 to 50):(1.0 to 5). In another embodiment, the molar ratio of ICL to Cholesterol to DSPC to PEG/LIPID CONJUGATE are (10 to 80):(10 to 80):(4 to 50):(1.5 to 5). In another embodiment, the molar ratio of ICL to Cholesterol to DSPC to PEG/LIPID CONJUGATE are (13 to 80):(13 to 80):(5 to 50):(2.0 to 5). In another embodiment, the molar ratio of ICL to Cholesterol to DSPC to PEG/LIPID CONJUGATE are (3 to 75):(3 to 75):(1 to 45):(0.2 to 10). In another embodiment, the molar ratio of ICL to Cholesterol to DSPC to PEG/LIPID CONJUGATE are (7 to 75):(7 to 75):(3 to 45):(1.0 to 10). In another embodiment, the molar ratio of ICL to Cholesterol to DSPC to PEG/LIPID CONJUGATE are (10 to 75):(10 to 75):(4 to 45):(1.5 to 10). In another embodiment, the molar ratio of ICL to Cholesterol to DSPC to PEG/LIPID CONJUGATE are (13 to 75):(13 to 75):(5 to 45):(2.0 to 10). In another embodiment, the molar ratio of ICL to Cholesterol to DSPC to PEG/LIPID CONJUGATE are (3 to 70):(3 to 70):(1 to 40):(0.2 to 7). In another embodiment, the molar ratio of ICL to Cholesterol to DSPC to PEG/LIPID CON-JUGATE are (7 to 70):(7 to 70):(3 to 40):(1.0 to 7). In another embodiment, the molar ratio of ICL to Cholesterol to DSPC to PEG/LIPID CONJUGATE are (10 to 70):(10 to 70):(4 to 40):(1.5 to 7). In another embodiment, the molar ratio of ICL to Cholesterol to DSPC to PEG/LIPID CON-JUGATE are (13 to 70):(13 to 70):(5 to 40):(2.0 to 7).

LNP ID A:
    ICL: ALC-0315
Formal Name: 2-hexyl-decanoic acid, 1,1'-[[(4-hydroxy-butyl)imino]di-6,1-hexanediyl]ester
Alternative Names: ((4-Hydroxybutyl) azanediyl)bis (hexane-6,1-diyl)bis(2-hexyldecanoate)
CAS Number: 2036272-55-4
Molecular Formula: $C_{48}H_{95}NO_5$ LNP ID B:
    ICL: DLin-MC3-DMA
Formal Name: 4-(dimethylamino)-butanoic acid, (10Z, 13Z)-1-(9Z,12Z)-9,12-octadecadien-1-yl-10,13-nona-decadien-1-yl ester
Alternative Names: (6Z,9Z,28Z,31Z)-heptatriaconta-6,9,28, 31-tetraen-19-yl 4-(dimethylamino) butanoate
CAS Number: 1224606-06-7
Molecular Formula: $C_{43}H_{79}NO_2$ LNP ID C:
    ICL: LP-01
Formal Name: 9Z,12Z-octadecadienoic acid, 3-[4,4-bis(oc-tyloxy)-1-oxobutoxy]-2-[[[3-(diethylamino)propoxy]car-bonyl]oxy]methyl]propyl ester
Alternative Names: CIN-16645, 9Z,12Z-octadecadienoic acid, 3-[4,4-bis(octyloxy)-1-oxobutoxy]-2-[[[3-(diethyl-amino) propoxy]carbonyl]oxy]methyl]propyl ester
    CAS Number: 1799316-64-5
    Molecular Formula: $C_{50}H_{93}NO_9$ LNP ID D:
    ICL: SM-102
Formal Name: 8-[(2-hydroxyethyl) [6-oxo-6-(undecyloxy) hexyl]amino]-octanoic acid, 1-octylnonyl ester
Alternative Names: Lipid H, Heptadecan-9-yl 8-((2-hy-droxyethyl) (6-oxo-6-(undecyloxy) hexyl)amino)-octano-ate
CAS Number: 2089251-47-6
Molecular Formula: $C_{44}H_{87}NO_5$ LNP IDE:
    ICL: 4A3-SC8
CAS Number: 1857340-78-3
Molecular Formula: $C_{75}H_{139}N_3O_{16}S_4$ LNP ID F:
    ICL: cKK-E12
Formal Name: 3,6-bis[4-[bis(2-hydroxydodecyl)amino] butyl]-2,5-piperazinedione
Alternative Names: 3,6-bis(4-(bis(2-hydroxydodecyl) amino)butyl) piperazine-2,5-dione
CAS Number: 1432494-65-9
Molecular Formula: $C_{60}H_{120}N_4O_6$ LNP ID G:
    ICL: $306O_{i10}$
Formal Name: tetrakis(8-methylnonyl) 3,3',3'',3'''-(((methyl-azanediyl)bis(propane-3,1-diyl))bis(azanetriyl))tetrapro-pionate
CAS Number: 2322290-93-5
Molecular Formula: $C_{59}H_{115}N_3O_8$ LNP ID H:
    ICL: C3-K2-E14
Formal Name: 3,3'-(propylazanediyl)bis(N-(2-(bis(2-hy-droxytetradecyl)amino)ethyl)propanamide)

CAS Number: 2933215-86-0
Molecular Formula: $C_{69}H_{141}N_5O_6$

LNP ID I:
    ICL: C14-4
Formal Name: 1,1'-[2-[2-[4-[2-[2-[2-[bis(2-hydroxytetra-decyl)amino]ethoxy]ethyl](2-hydroxytetradecyl)amino] ethyl]-1-piperazinyl]ethoxy]ethyl]imino]bis-2-tetradeca-nol
CAS Number: 2639634-80-1
Molecular Formula: $C_{84}H_{173}N_5O_7$ LNP ID J:
    ICL: Lipid A9
Formal Name: bis(2-butyloctyl) 10-(N-(3-(dimethylamino) propyl)nonanamido)nonadecanedioate
Alternative Names: 1,19-Bis(2-butyloctyl) 10-[3-(dimethyl-amino) propyl](1-oxononyl)amino]nonadecanedioate
CAS Number: 2036272-50-9
Molecular Formula: $C_{57}H_{112}N_2O_5$ LNP ID K:
    ICL: OF-02
Formal Name: 3,6-bis[4-[bis[(9Z,12Z)-2-hydroxy-9,12-oc-tadecadien-1-yl]amino]butyl]-2,5-piperazinedione
Alternative Names: 3,6-bis(4-(bis((9Z,12Z)-2-hydroxyocta-deca-9,12-dien-1-yl)amino)butyl) piperazine-2,5-dione
CAS Number: 1883431-67-1
Molecular Formula: $C_{84}H_{152}N_4O_6$ LNP ID L:
    ICL: TCL053
Formal Name: 2-(((4-(dimethylamino) butanoyl)oxy) methyl)-2-((((Z)-tetradec-9-enoyl)oxy)methyl)propane-1,3-diyl(9Z,9'Z)-bis(tetradec-9-enoate)
CAS Number: 2361162-70-9
Molecular Formula: $C_{53}H_{95}NO_8$ In another embodiment, the 5' UTR region may comprise a ribosome binding site, a Kozak sequence, a modified genomic human LIPE 5' UTR, a modified genomic human LEP 5' UTR, a modified genomic human COL1A 5' UTR, a modified genomic human ADIPOQ 5' UTR, a modified genomic human PLIN1 5' UTR, a translation initiator of short 5' UTR (TISU), a consensus genomic human LIPE 5' UTR, a consensus genomic human UCP1 5'UTR, a consen-sus genomic human PLIN1 5' UTR, a consensus genomic human COL1A 5' UTR, a consensus genomic human LEP 5' UTR, a consensus genomic human ADIPOQ 5' UTR, a consensus genomic human FABP4 5' UTR, or combinations thereof.

In another embodiment, the 3' UTR region may comprise a double stop codon, a consensus genomic human UCP1 3' UTR, a Cominarity 3' UTR, or combinations thereof. The Cominarity 3' UTR is a combination and optimization of segments from the human mitochondrial 12S rRNA (mtRNR1) and the human AES/TLE5 gene. The AES seg-ment of 136 nt with two C→Ψ mutations was added after two trinucleotides following the second stop codon. The mtRNR1 segment of 139 nt was added immediately after.

In another embodiment, the mRNA of the present disclo-sure comprises (consists essentially of, or consists of) a nucleotide sequence about 80% to about 100%, about 85% to about 100%, about 90% to about 100%, or about 95% to about 100%, identical to the amino acid sequence set forth in SEQ ID NO:130.

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth SEQ ID NO: 130.

In another embodiment, the mRNA of the present disclosure comprises (consists essentially of, or consists of) a nucleotide sequence about 80% to about 100%, about 85% to about 100%, about 90% to about 100%, or about 95% to about 100%, identical to the amino acid sequence set forth in any of SEQ ID NO:2 through SEQ ID NO: 21.

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in any of SEQ ID NO:2 through SEQ ID NO:21.

In an alternative embodiment, the mRNA of the present disclosure comprises (consists essentially of, or consists of) a nucleotide sequence about 80% to about 100%, about 85% to about 100%, about 90% to about 100%, or about 95% to about 100%, identical to the amino acid sequence set forth in any of SEQ ID NO:22 through SEQ ID NO: 129.

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in any of SEQ ID NO:22 through SEQ ID NO: 129.

In another embodiment, the sequence of the mRNA may be selected from one of SEQ ID NO: 1 to SEQ ID NO: 130, encoding for UCP1 by the ribosomes of a target cell packaged in a lipid nanoparticle (LNP) for transfection of WAs or ASCs with the packaged mRNA.

In certain embodiments, the mRNA comprises (consists essentially of, or consists of) a nucleotide sequence at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the nucleotide sequence set forth in any of SEQ ID NO: 1 through SEQ ID NO:130.

In another embodiment, cells transfected with a pharmaceutical composition comprising the present mRNA will express UCP1 and undergo a process of lipolysis through non-ATP generating respiration, generating heat and reducing the overall FFA content of the transfected and nearby cells.

In another embodiment, a physician may administer the pharmaceutical composition comprising the present mRNA packaged in an LNP to a patient seeking to accomplish spot fat reduction.

In another embodiment, a physician administering the present mRNA packaged in an LNP to a patient seeking to accomplish spot fat reduction may administer the pharmaceutical composition in a bolus injection in the targeted area.

In another embodiment, a physician administering the present mRNA packaged in an LNP to a patient seeking to accomplish spot fat reduction may administer the pharmaceutical composition in a series of injections in the targeted area.

In another embodiment, a physician administering the present mRNA packaged in an LNP to a patient seeking to accomplish spot fat reduction may administer the pharmaceutical composition transdermally. The transdermal administration may be accomplished through the use of penetration enhancers (e.g. DMSO, oleic acid, lauric acid, sodium lauryl sulfate, sodium ducosate, sodium oleate, cetyltrimethylammonium bromide, benzalkonium chloride, polysorbates, sorbitan esters, polyoxyethylene alkyl ethers, Laurocarpam, propylene glycol monolaurate, lecithin, terpenes), vesicular carriers (e.g. liposomes, ethosomes, niosomes) microneedle injection, iontophoresis, sonophoresis, jet injection or other suitable means.

Microneedle injectors utilize microscopic needles, typically ranging from 50 to 900 micrometers in length, to bypass the skin's outermost layer, the stratum corneum, and deliver therapeutic agents directly into the underlying epidermal or dermal layers. The microneedles can be disposed in an array on a patch wherein several hundred or several thousand microneedles are disposed.

Iontophoresis utilizes a low-level electrical current to facilitate the transport of ions across biological membranes, most notably the skin. The medication is disposed on a patch with an electrode that conducts electricity to drive the ions across the membrane.

Sonophoresis, also known as phonophoresis, is a noninvasive technique that utilizes ultrasound waves to temporarily increase the permeability of the skin. This enhanced permeability allows for the improved delivery of therapeutic agents, such as medications and cosmetics, across the skin barrier and into deeper tissues.

Jet injection employs a high-velocity stream of liquid that penetrates the skin to deliver the substance into the underlying tissues. A jet injector creates a very fine, high-pressure jet of liquid that is powerful enough to pierce the skin and reach the desired tissue depth-typically the intradermal, subcutaneous, or intramuscular layer. This is achieved by rapidly forcing a pre-measured dose of medication through a tiny orifice in the injector's nozzle.

In another embodiment, a physician administering the present mRNA packaged in an LNP to a patient seeking to accomplish spot fat reduction may administer the pharmaceutical composition several times over the course of periodic patient encounters.

In another embodiment, a physician administering the present mRNA packaged in an LNP to a patient seeking to accomplish spot fat reduction may administer the pharmaceutical composition in a manner prescribed by an algorithm, LLM or machine learning implementation to accomplish the desired spot fat reduction.

In another embodiment, an mRNA, comprising the nucleotide sequence set forth in one of SEQ ID NO: 2 through SEQ ID NO: 21 disclosed in the Sequence Listing incorporated by reference herein, encoding for UCP1 is packaged in a lipid nanoparticle (LNP). The packaged synthetic mRNA may be for transfection of WAs or ASCs.

In another embodiment, cells transfected with a pharmaceutical composition comprising mRNA of any of SEQ ID NO: 2 through SEQ ID NO: 21 will express UCP1 and undergo a process of lipolysis through non-ATP generating respiration, generating heat and reducing the overall FFA content of the transfected cells.

In another embodiment, a physician may administer the pharmaceutical composition comprising the mRNA of any of SEQ ID NOs: 2 through 21 packaged in an LNP to a patient seeking to accomplish spot fat reduction.

In another embodiment, the mRNA comprising the nucleotide sequence set forth in any of SEQ ID NOs: 2 through 21 packaged in an LNP is administered to a patient seeking to accomplish spot fat reduction. The packaged mRNA may be administered in a bolus injection in the targeted area.

In another embodiment, the mRNA comprising the nucleotide sequence set forth in any of SEQ ID NOs: 2 through 21 packaged in an LNP is administered to a patient seeking to accomplish spot fat reduction in a series of injections in the targeted area.

In another embodiment, the mRNA comprising the nucleotide sequence set forth in any of SEQ ID NOs: 2 through 21 packaged in an LNP is administered transdermally to a patient seeking to accomplish spot fat reduction. The transdermal administration may be accomplished through the use of penetration enhancers (e.g. DMSO, oleic acid, lauric acid, sodium lauryl sulfate, sodium ducosate, sodium oleate, cetyltrimethylammonium bromide, benzalkonium chloride, polysorbates, sorbitan esters, polyoxyethylene alkyl ethers, Laurocarpam, propylene glycol monolaurate, lecithin, terpenes), vesicular carriers (e.g. liposomes, ethosomes, niosomes) microneedle injection, iontophoresis, sonophoresis, jet injection or other suitable means.

In another embodiment, the mRNA comprising the nucleotide sequence set forth in any of SEQ ID NOs: 2 through 21 packaged in an LNP is administered to a patient seeking to accomplish spot fat reduction several times over the course of periodic patient encounters.

In another embodiment, a physician administering the mRNA comprising the nucleotide sequence set forth in any of SEQ ID NOs: 2 through 21 packaged in an LNP to a patient seeking to accomplish spot fat reduction may administer the pharmaceutical composition in a manner prescribed by an algorithm, LLM or machine learning implementation to accomplish the desired spot fat reduction.

In alternative embodiment, a synthetic mRNA, comprising the nucleotide sequence set forth in any of SEQ ID NOs: 22 through 129 disclosed in the Sequence Listing incorporated by reference herein, encoding for UCP1 is packaged in a lipid nanoparticle (LNP).

In an alternative embodiment, cells transfected with a pharmaceutical composition comprising mRNA comprising the nucleotide sequence set forth in any of SEQ ID NO: 22 through SEQ ID NO: 129 will express UCP1 and undergo a process of lipolysis through non-ATP generating respiration, generating heat and reducing the overall FFA content of the transfected cells.

In an alternative embodiment, a physician may administer the pharmaceutical composition comprising the mRNA of SEQ ID NOs: 22 through 129 packaged in an LNP to a patient seeking to accomplish spot fat reduction.

In an alternative embodiment, a physician administering the mRNA comprising the nucleotide sequence set forth in any of SEQ ID NOs: 22 through 129 packaged in an LNP to a patient seeking to accomplish spot fat reduction may administer the pharmaceutical composition in a bolus injection in the targeted area.

In an alternative embodiment, a physician administering the mRNA comprising the nucleotide sequence set forth in any of SEQ ID NOs: 22 through 129 packaged in an LNP to a patient seeking to accomplish spot fat reduction may administer the pharmaceutical composition in a series of injections in the targeted area.

In an alternative embodiment, a physician administering the mRNA comprising the nucleotide sequence set forth in any of SEQ ID NOs: 22 through 129 packaged in an LNP to a patient seeking to accomplish spot fat reduction may administer the pharmaceutical composition transdermally. The transdermal administration may be accomplished through the use of penetration enhancers (e.g. DMSO, oleic acid, lauric acid, sodium lauryl sulfate, sodium ducosate, sodium oleate, cetyltrimethylammonium bromide, benzalkonium chloride, polysorbates, sorbitan esters, polyoxyethylene alkyl ethers, Laurocarpam, propylene glycol monolaurate, lecithin, terpenes), vesicular carriers (e.g. liposomes, ethosomes, niosomes) microneedle injection, iontophoresis, sonophoresis, jet injection or other suitable means.

In an alternative embodiment, a physician administering the mRNA comprising the nucleotide sequence set forth in any of SEQ ID NOs: 22 through 129 packaged in an LNP to a patient seeking to accomplish spot fat reduction may administer the pharmaceutical composition several times over the course of periodic patient encounters.

In an alternative embodiment, a physician administering the mRNA comprising the nucleotide sequence set forth in any of SEQ ID NOs: 22 through 129 packaged in an LNP to a patient seeking to accomplish spot fat reduction may administer the pharmaceutical composition in a manner prescribed by an algorithm, LLM or machine learning implementation to accomplish the desired spot fat reduction.

In another embodiment, the synthetic mRNA may in addition to or alternatively encode for the B3 adrenoreceptor, PR/SET domain 16 (PRDM16), Peroxisome proliferator-activated receptor gamma coactivator-1 alpha (PGC-1alpha), CCAAT/enhancer binding protein beta (C/EPB-Beta), Krüppel-like Factor 11 (KLF11), and/or nuclear receptor interacting protein 1 (NRIP1). In certain embodiments, the present pharmaceutical composition may comprise a first mRNA encoding UPC1, and one or more mRNAs encoding the B3 adrenoreceptor, PR/SET domain 16 (PRDM16), Peroxisome proliferator-activated receptor gamma coactivator-1 alpha (PGC-1alpha), CCAAT/enhancer binding protein beta (C/EPB-Beta), Krüppel-like Factor 11 (KLF11), nuclear receptor interacting protein 1 (NRIP1), or combinations thereof.

In another embodiment, the synthetic mRNA may be modified with a 5' cap, a 5' untranslated region, polymorphisms in the target protein coding sequence, nucleic acid substitutions to reduce immunogenicity and/or enhance mRNA longevity within the cell, and/or a 3' untranslated region including one or more poly-A tails.

The mRNA can be chemically or biologically modified. Modifications to an mRNA include the depletion of a base (e.g., by deletion or by the substitution of one nucleotide for another) or modification of a base, chemically by covalent addition pendant groups which are not naturally found in such mRNA molecules. For example, the number of C and/or U residues in an mRNA sequence may be reduced. In another embodiment, the number of C and/or U residues is reduced by substitution of one codon encoding a particular amino acid for another codon encoding the same or a related amino acid. The mRNA nucleic acids can also incorporate pseudouridines. Substitutions and modifications to the mRNA of the present invention may be performed by methods readily known to one of ordinary skill in the art.

Modifications to the mRNA can also be made to the 3' and 5' ends of an mRNA molecule. These modifications include a poly A tail or a longer poly A tail, the alteration of the 3' UTR or the 5' UTR or complexing the mRNA with a protein or complementary nucleic acid molecule.

Exemplary mRNA sequences are provided in the Sequence Listing incorporated by reference herein.

The present mRNA or pharmaceutical composition may be delivered via local delivery directly into WAT. Dosages will range from 0.001 mg/kg to 1.0 mg/kg. The frequency of dosing into a given anatomic area may be no more than once per week, per five days, per three days, or per day. Total duration of treatment will be determined by the patient and their healthcare provider, accounting for factors including but not limited to desired treatment endpoint, tolerability of the drug's delivery, tolerability of the drug's side effects, and patient's lifestyle preferences (i.e. how often they want to get the treatment).

In another embodiment, the synthetic mRNA encoding for UCP1 packaged in an LNP is formulated for injectable delivery to a target area. This may include a dilute formulation that may be injected into a large area of subcutaneous fat using a blunt canula or other means fit for such purpose. This injectable delivery may alternatively include direct injection to a target site of adipose tissue. This formulation may include a carrier solution that protects the LNP vesicles during transport and injection and may further comprise a buffering solution fit for that purpose.

In another embodiment, the synthetic mRNA encoding for UCP1 packaged in an LNP is formulated for transdermal delivery to a target area. This formulation may include a transdermal carrier such as a nanostructured lipid carrier molecule suspended in a cream or gel to be rubbed on the skin over the target area. Transdermal delivery may be further effectuated by iontophoresis, a microneedle patch or a topical formulation to be applied after disruption of the skin barrier via methods including but not limited to microneedling, laser treatment, and chemical peels.

In another embodiment, the synthetic mRNA encoding for UCP1 packaged in an LNP is formulated for systemic delivery to multiple sites within a patient's body. This formulation may include a carrier solution that protects the LNP vesicles during transport and injection/intravenous delivery and may further comprise a buffering solution fit for that purpose.

In a second embodiment, a patient treated with a synthetic mRNA encoding for UCP1 packaged in an LNP employs an apparatus to cool the pharmaceutically generated BeAT in order to activate the thermogenic process of BeAT. This apparatus may comprise: ice packs, a cold-water tub or a system that circulates chilled water through a pad or patch positioned on the surface of the skin over a target area. This apparatus may comprise an internal cooling mechanism for precisely regulating the temperature of the cooling apparatus or of the pad or patch positioned on the surface of the skin over a target area.

In another embodiment, the cooling apparatus may be used as part of a protocol prescribed by a treating physician for activating the thermogenic properties of the BeAT for predetermined time periods in order to achieve the specific goals of the patient with regards to reduction of the appearance of adipose tissue in the target area.

In another embodiment, the BeAT may be activated by B3 agonists (e.g. mirabegron), caffeine and like molecules, ibuprofen and like molecules, 4-heptylbenzoic acid; bromododecanoic acid; dodecanoic acid; nonadecanoic acid; oleic acid; retinoic acid; tetradecylthioacetic acid; TTNPB; TUG-891.

In another embodiment, the protocol prescribed by the treating physician may include a time frame for repeat treatment of the target area with the synthetic mRNA encoding for UCP1 packaged in an LNP. The time frame may reflect the rate of turnover of UCP1 in the target cells.

In another embodiment, a state change transition of target cells from white adipocytes to beige or brown adipocytes may include contacting cells from WAT with a payload of mRNA, protein, plasmid DNA or oligonucleic acid encapsulated in MITO-Porter (a liposome-based carrier for delivering a payload to the mitochondria via membrane fusion) for targeting the payload to the mitochondria.

In another embodiment, the invention may be a pharmaceutical composition comprising UCP1 protein (NCBI RefSeq: NP_001735.1) encapsulated in MITO-Porter.

In another embodiment, the UCP1 protein may be optimized to increase its active life by including factors which inhibit the effects of mitochondrial proteases LONP1 and ClpXP.

In certain embodiments, factors which may inhibit the effects of mitochondrial proteases LONP1 and ClpXP may include but are not limited to: modifying protease cleavage sites, glycosylation, incorporation of non-natural amino acids, and/or enhancing protein structural stability.

In certain embodiments, modifying a protease cleavage site may include substitution of one or more amino acids such as lysine or arginine with threonine or glutamine to prevent protease activity at a preferred cleavage site.

In certain embodiments, modifying a protease cleavage site may include the introduction of proline next to the preferred cleavage site of the target protease.

In certain embodiments, glycosylation may include adding glycans to the protein to prevent the protease from accessing the cleavage site.

In certain embodiments, the glycans may be N-linked, and for example, attached to asparagine.

In certain embodiments, the glycans may be O-linked, and for example, attached to serine or threonine.

In certain embodiments, the incorporation of non-natural amino acids may include the inclusion of D-amino acids at the cleavage site to prevent protease recognition of the cleavage site.

In certain embodiments, the incorporation of non-natural amino acids may include the inclusion of Beta-amino acids at the cleavage site to reduce the affinity of the protease for the cleavage site.

In certain embodiments, enhancing protein structural stability may include the introduction of disulfide bonds between two or more amino acids in the protein or the introduction of salt bridges in the protein's core.

In another embodiment, the UCP1 protein may be optimized to increase its binding affinity to the inner mitochondrial matrix by optimizing the mitochondrial targeting signal (MTS) of the UCP1 protein, introduction of destabilizing elements, and/or the introduction of chaperone binding sites.

In certain embodiments, enhancing the MTS may include increasing the positive charge of the protein to improve recognition of the protein by TOM20 and TOM22.

In certain embodiments, increasing the positive charge of the protein may include substituting neutral or negatively charged amino acids with positively charged amino acids such as arginine or lysine.

In certain embodiments, enhancing the MTS may include optimizing the amphipathicity of the protein.

In certain embodiments, optimizing the amphipathicity of the protein may include improving the balance of amino acids in the amphipathic alpha helix that forms the MTS such that the positively charged side of the helix includes as many positively charged amino acids as possible and the hydrophobic side of the helix includes as many hydrophobic amino acids as possible.

In certain embodiments, enhancing the MTS may include substitution of the extant MTS with a highly efficient MTS such as that of human cytochrome c oxidase subunit 8 (COX8) or that of superoxide dismutase 2 (SOD2).

In certain embodiments, enhancing the MTS may include optimizing the length of the MTS.

In certain embodiments, the introduction of folding desta-bilizing elements may increase the proportion of unfolded protein available for import to the mitochondria.

In certain embodiments, the introduction of chaperone binding sites may include engineering binding sites for mitochondrial chaperone molecules such as Hsp70 to increase the efficiency of its import to the mitochondria.

The present invention may be better understood by reference to the following non-limiting examples, which are presented in order to more fully illustrate the preferred embodiments of the invention. They should in no way be construed to limit the broad scope of the invention.

EXAMPLES

Example 1

Synthetic mRNA expressing mCherry fluorescent protein was synthesized via in vitro transcription from a linearized DNA plasmid. Specifically, high-purity plasmid was linearized with a restriction enzyme at a site downstream of the IVT mRNA sequence that was to be transcribed. Following linearization, the resulting linear template DNA was purified with phenol/chloroform extraction using DNAse-free reagents. The final, air-dried DNA pellet was resuspended in nuclease-free water at a concentration of 0.5-1 µg/µl.

To synthesize the IVT mRNA, a reaction mix comprised of sufficient nuclease-free water to produce a total reaction volume of 20 µL, 2 µL of 10× T7 CleanCap Reagent AG Reaction Buffer (New England Biolabs), 2 µL of 60 mM ATP (final concentration 6 mM), 2 µL of 50 mM CTP (final concentration 5 mM), 2 µL of 50 mM N1-Methyl-Pseudou-ridine-5'-Triphosphate (final concentration 5 mM), 2 µL of 50 mM GTP (final concentration 5 mM), 2 µL of 40 mM AG cap analog (final concentration 4 mM), 1 µg of linearized template DNA, 1 µL of 0.1M dithiothreitol (final concen-tration 5 mM), and 2 µL of T7 RNA Polymerase Mix (New England Biolabs) was prepared. The reaction was allowed to proceed for 2-16 hours, with reaction time adjusted based on reaction yield. Following the IVT reaction, DNAse I was added to the mix to degrade the template DNA, thereby purifying the IVT mRNA transcript. The IVT mRNA was further purified with gel electrophoresis or the Monarch RNA Cleanup Kit (New England Biolabs).

A poly(A) tail was added to the transcript by preparing a reaction mix comprised of sufficient nuclease-free water to produce a total reaction volume of 20 µL, 1-10 µg of purified IVT mRNA, 2 µL of 10× E. coli Poly(A) Polymerase Reaction Buffer (New England Biolabs), 2 µL of 10 mM ATP, and 1 µL of E. coli Poly(A) Polymerase (final amount 5 units, New England Biolabs). The reaction was incubated for 30 minutes and then stopped by EDTA addition. The final IVT mRNA product was purified with phenol-chloroform extraction, column-based cleanup, or the Monarch RNA Cleanup Kit (New England Biolabs). QA/QC was per-formed via Sanger sequencing and UV Light Absorbance.

The synthetic mRNA was encapsulated into lipid nan-oparticles, yielding a reporter gene test article. Specifically, 0.3 mL of an ethanolic solution of the lipid components (see Table 1) in a syringe pump and 0.9 mL of a solution of the mRNA in RNase-free citrate buffer (100 mM, pH 3) in a syringe pump were mixed simultaneously at flow rates of 3 mL/min for the lipids and 9 mL/min for the mRNA (total flow rate of 12 mL/min) using a microfluidic chip. Follow-ing micro fluidic mixing, the resulting mCherry mRNA LNPs were dialyzed overnight against 500 sample volume of PBS (pH 7.4). Agrawal et al., Standardizing a Protocol for Streamlined Synthesis and Characterization of Lipid Nan-oparticles to Enable Preclinical Research and Education, bioRxiv, 2025, doi.org/10.1101/2025.07.31.667476

Subcutaneous fat was donated by a patient undergoing elective surgery under an IRB-approved protocol. The fat was stabilized for long-term ex vivo culture: 50 mg of fat was sandwiched between two sheets of adipose-derived stromal cells in a culture medium. The culture medium was comprised of DMEM, 10% fetal bovine serum, and antibi-otic and antifungal prophylactics. The ex vivo fat was treated with the mCherry reporter gene test article by adding the mCherry mRNA-LNP to the culture medium in doses ranging from 0.1 to 10 mg of mRNA per kg of fat. Fluo-rescence and brightfield microscopy images were captured every 4 to 6 hours using an automated system for a total of 48 hours. New red fluorescence in previously non-fluores-cent cells in FIG. 1 indicated successful transfection of ex vivo human fat. The white circles in FIG. 1 indicate cells expressing mCherry.

Example 2

Figure 2:
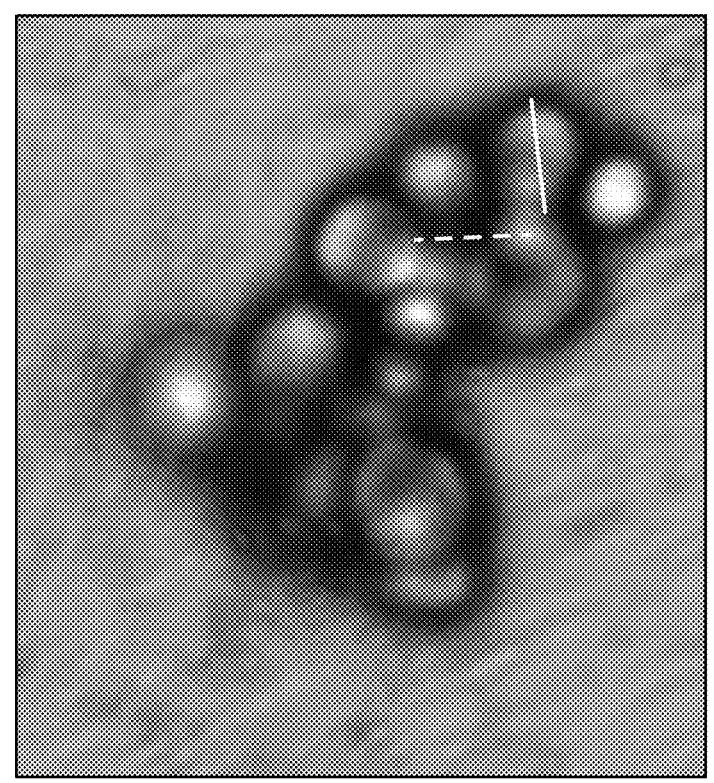
FIG. 2 is a first and a last frame of a 6-day time lapse showing a negative control study of untreated human adi-pose tissue in culture.
Figure 2:
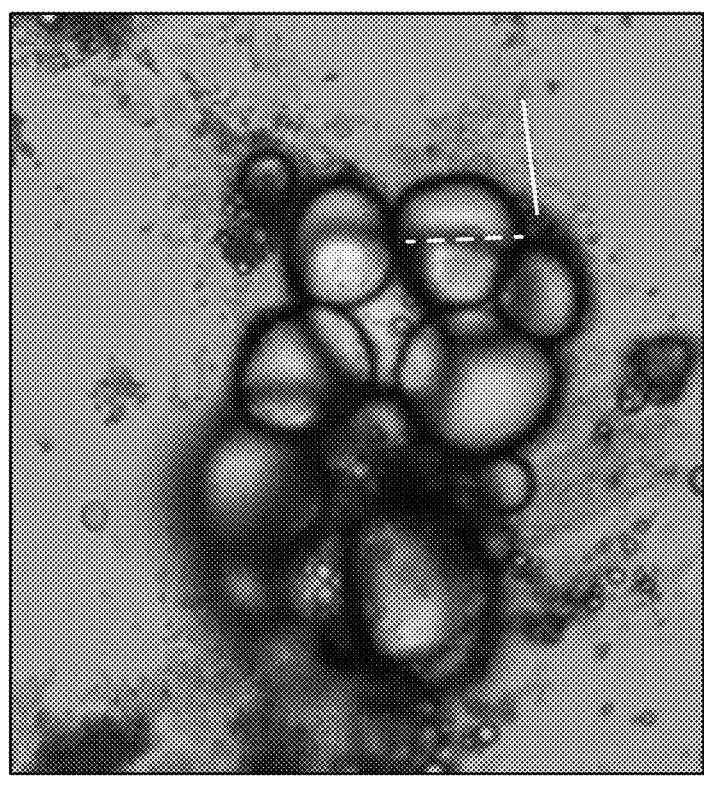

Subcutaneous fat was donated by a patient undergoing elective surgery under an IRB-approved protocol. The fat was stabilized for long-term ex vivo culture. This study served as a negative control where the ex vivo cultured fat was not treated. The culture medium was comprised of DMEM, 10% fetal bovine serum, and antibiotic and anti-fungal prophylactics. Brightfield microscopy images were captured every 4 to 6 hours using an automated system for a total of 6 days (144 hours). No significant change in the adipocytes' diameter was observed. In FIG. 2, the dashed line marked the diameter of one representative mature adipocyte within the adipose tissue cluster at the start of the experiment (hour 0). The solid line marked the diameter of the same adipocyte at the end of the experiment (hour 144).

Example 3

Synthetic mRNA of SEQ ID NO: 130 expressing UCP1 was synthesized via in vitro transcription from a linearized DNA plasmid. The synthetic mRNA was encapsulated as described above into lipid nanoparticles of composition LNP D of component molar ratio (SM-102:DSPC:Cholesterol:PEG/Lipid Conjugate) of 50:10:38.5:1.5, yielding a drug candidate test article.

Figure 3:
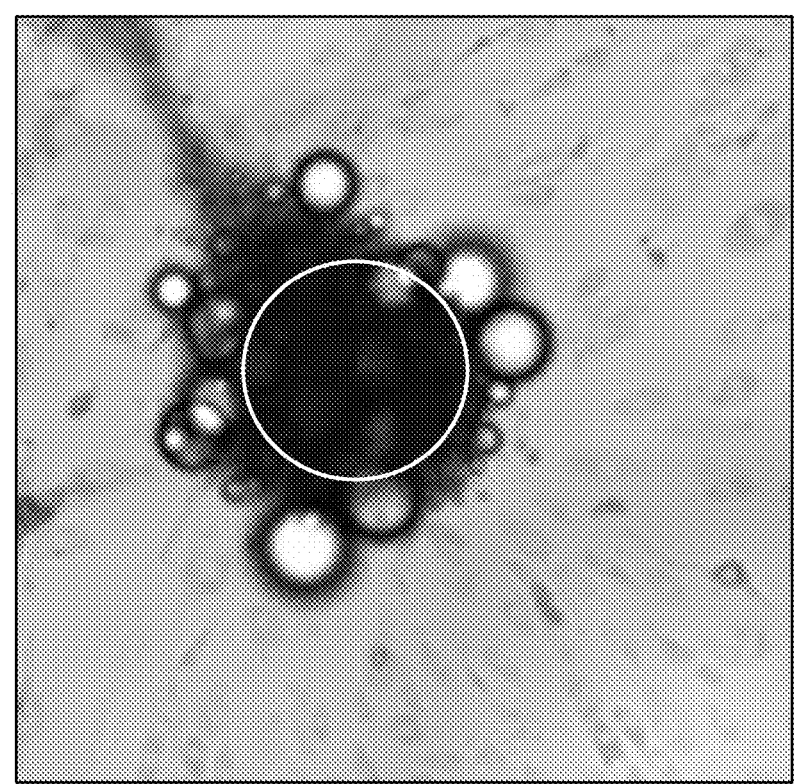
FIG. 3 is a first and a last frame of a 6-day time lapse showing a full dose study (Example 3) of human white adipose tissue transfected with an mRNA construct express-ing UCP1. The mRNA caused shrinkage of said white adipose tissue.
Figure 3:
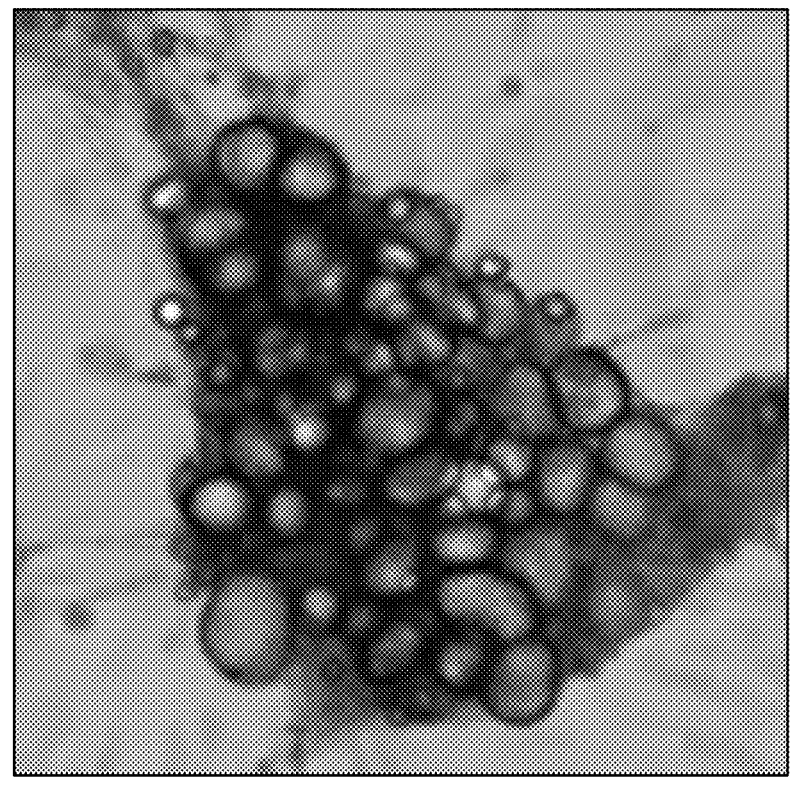

Subcutaneous fat was donated by a patient undergoing elective surgery under an IRB-approved protocol. The same donated fat was used in this study as in the negative control study (Example 2). The fat was stabilized for long-term ex vivo culture. The culture media was comprised of DMEM, 10% fetal bovine serum, and antibiotic and antifungal prophylactics. The ex vivo fat was exposed to the drug candidate test article at full dose (5 µg drug candidate per 100 mg of ex vivo fat) by adding 5 µg of mRNA to the culture media. Brightfield microscopy images were captured every 4 to 6 hours using an automated system for a total of 6 days (144 hours). FIG. 3 shows that the diameters of treated fat cells shrank by up to 65% as observed in visual microscopy, with a majority of the unilocular adipocytes shrinking to the point where they could no longer be visually identified as mature, unilocular adipocytes. The white circle in the right panel of FIG. 3 indicates cells that had shrunk to a point that they are no longer individually visually identifiable at the original level of magnification and depth of field.

Example 4

Synthetic mRNA of SEQ ID NO: 130 expressing UCP1 was synthesized via in vitro transcription from a linearized DNA plasmid. The synthetic mRNA was encapsulated into lipid nanoparticles as described above in Example 3, yielding a drug candidate test article.

Figure 4:
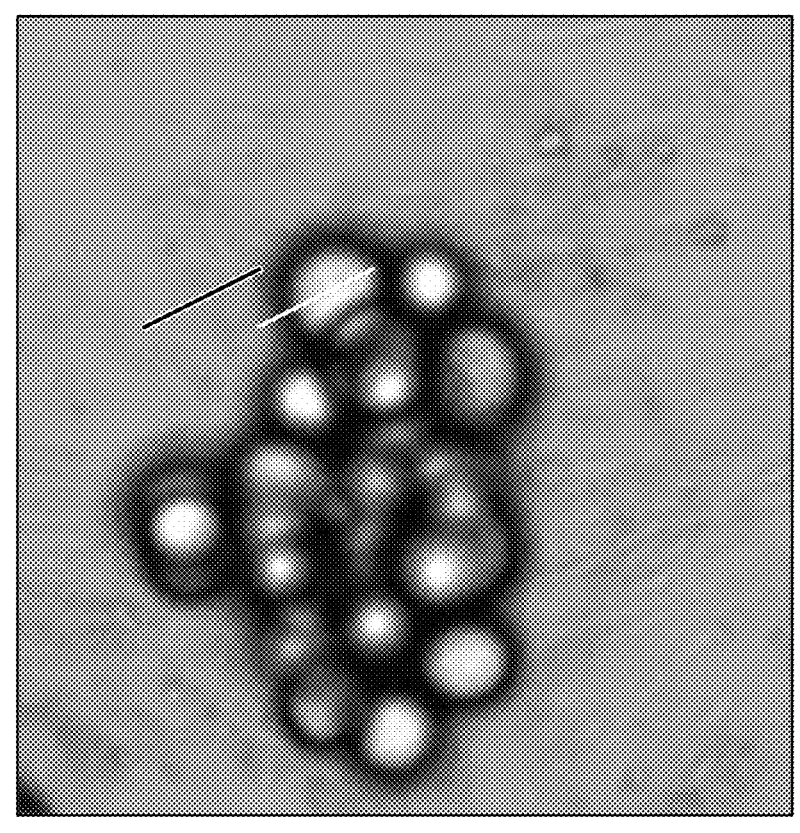
FIG. 4 is a first and a last frame of a 6-day time lapse showing a half dose study (Example 4) of human adipose tissue transfected with an mRNA construct expressing UCP1. The mRNA caused shrinkage of said white adipose tissue.
Figure 4:
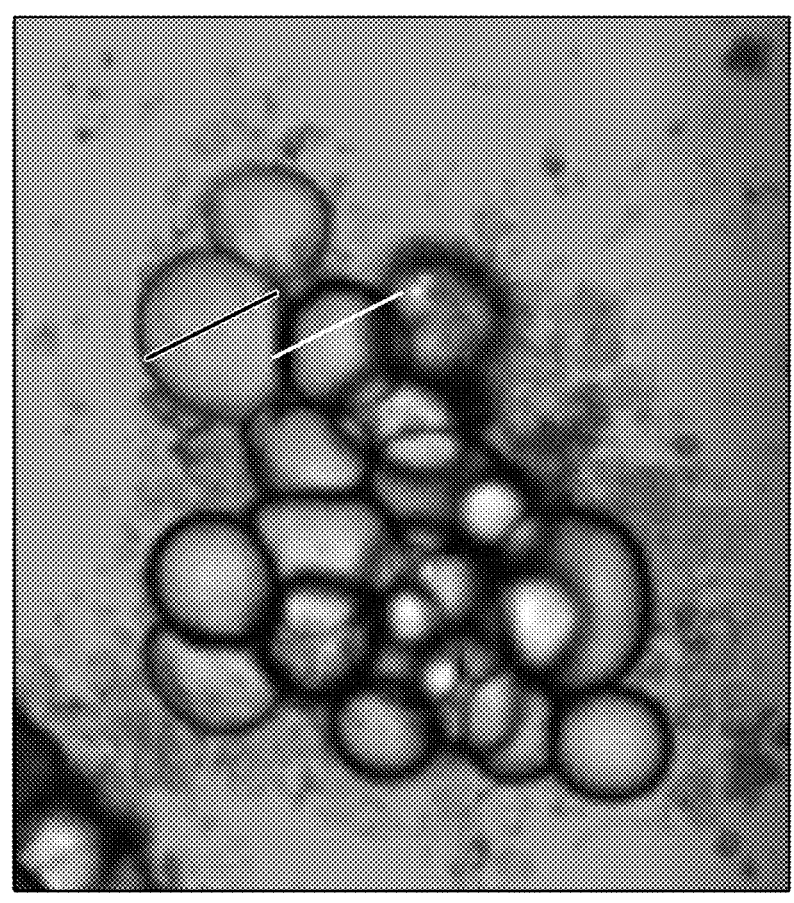

Subcutaneous fat was donated by a patient undergoing elective surgery under an IRB-approved protocol. The same donated fat was used in this study as in the negative control study (Example 2) and the full-dose study (Example 3). The fat was stabilized for long-term ex vivo culture. The culture media was comprised of DMEM, 10% fetal bovine serum, and antibiotic and antifungal prophylactics. The ex vivo fat was treated with the drug candidate test article at half dose (2.5 µg drug candidate per 100 mg of ex vivo fat) by adding 2.5 ug of mRNA to the culture media. Brightfield microscopy images were captured every 4 to 6 hours using an automated system for a total of 6 days (144 hours). FIG. 4 shows that every treated fat cluster shrank significantly, but less so than with the full-dose. The lines in FIG. 4 denote the diameter of one representative mature adipocyte within the adipose tissue cluster at the start of the experiment (hour 0) and at the end of the experiment (hour 144).

Example 5

Figure 5:
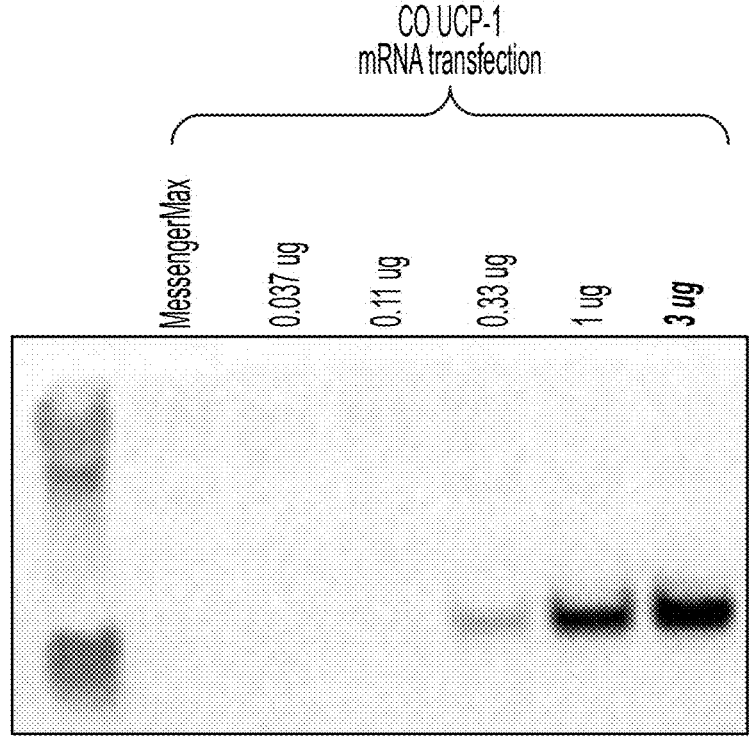
FIG. 5 is a Western Blot result showing relative protein expression levels for varying doses of an mRNA construct of SEQ ID NO: 130 expressing UCP1 in human adipose tissue.

Synthetic mRNA of SEQ ID NO: 130 expressing UCP1 was synthesized via in vitro transcription from a linearized DNA plasmid. The synthetic mRNA was encapsulated using Lipofectamine™ MessengerMAX™ Transfection Reagent. Varying doses of the synthetic mRNA (0.037 µg, 0.11 µg, 0.33 µg, 1 µg and 3 µg) were used to treat human adipose-derived stem cells (ASCs) for 48 hours. Treatment was performed by adding drug test articles to the ASC culture media (DMEM, 10% fetal bovine serum, and antibiotic and antifungal prophylactics.) After 48 hours, the ASCs were lysed, and total protein was isolated. The protein isolated were assayed via Western Blot to provide a semi-quantitative assessment of the amount of UCP1 protein (FIG. 5).

Example 6

Figure 6:
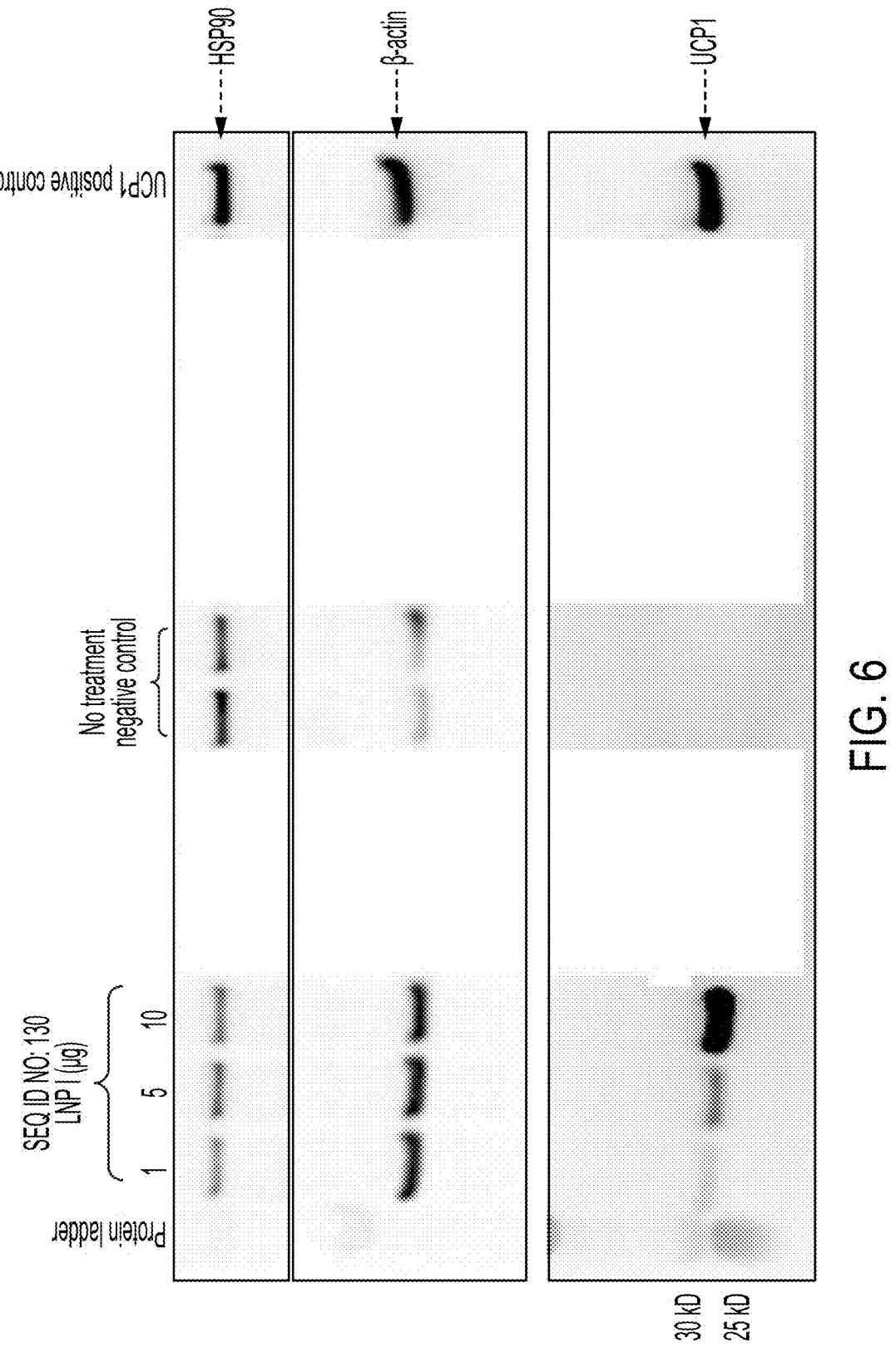
FIG. 6 is a Western Blot result showing relative protein expression levels for varying doses of an mRNA construct of SEQ ID NO: 130 expressing UCP1 encapsulated in LNP I in human adipose tissue.
Figure 7:
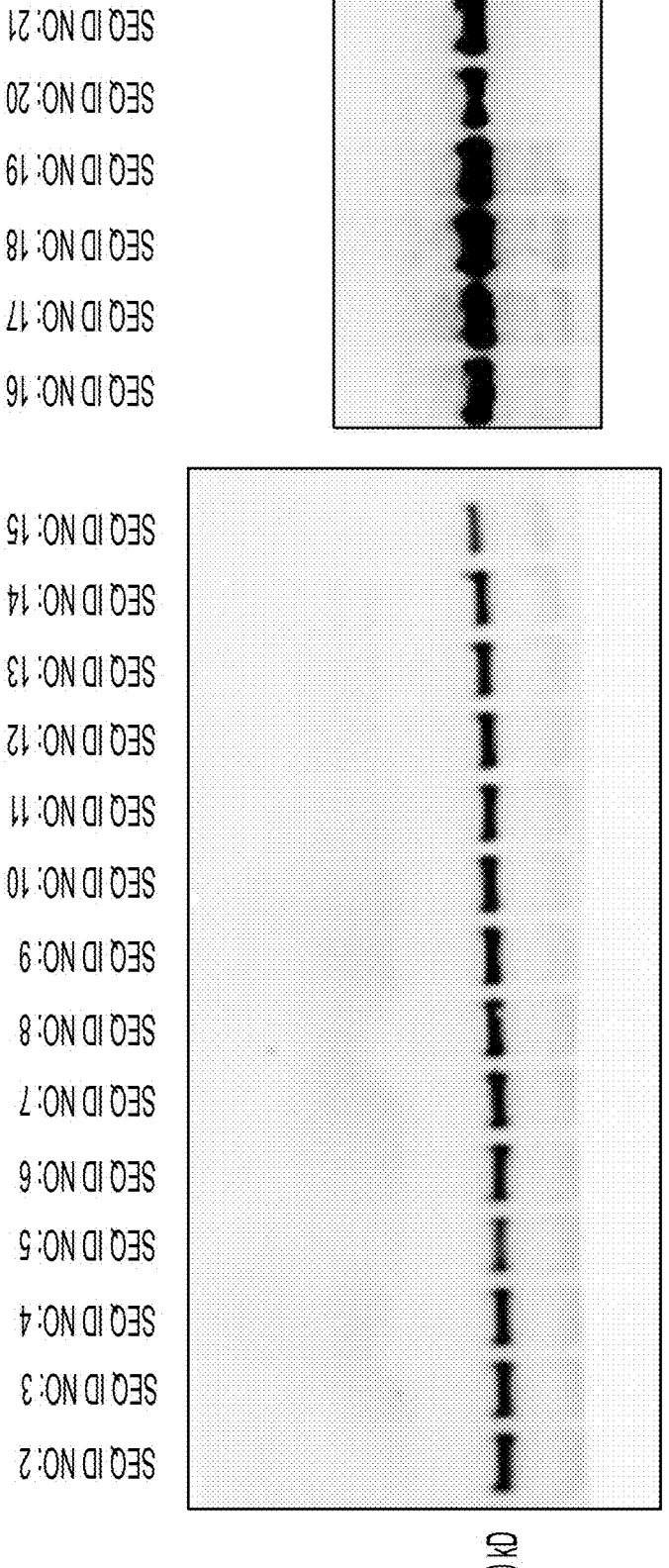
FIG. 7 is a series of Western Blot results showing protein expression by cells derived from human white adipose tissue transfected with mRNA constructs of SEQ ID NO: 2 through SEQ ID NO: 21.
Figure 8:
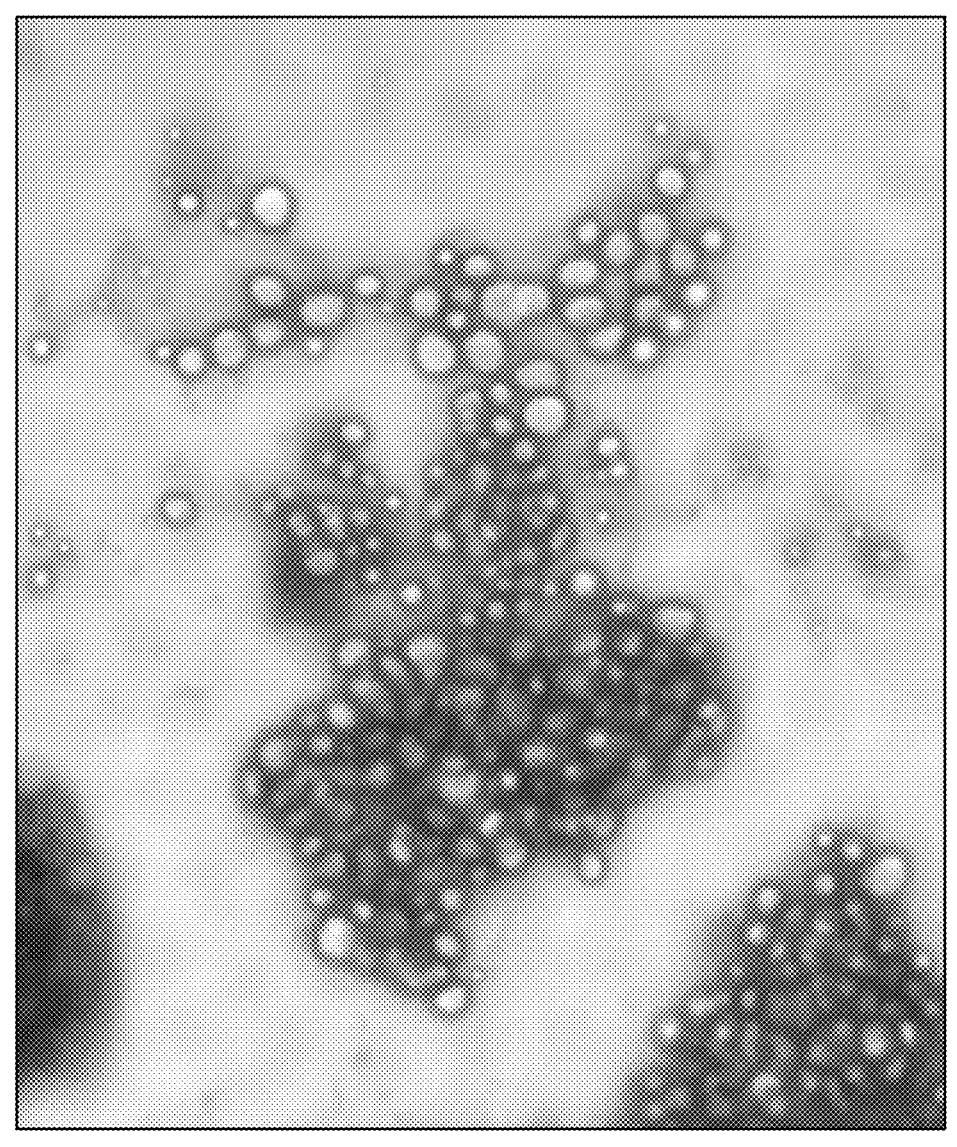
FIG. 8, FIG. 9, FIG. 10, FIG. 11, FIG. 12, FIG. 13, and FIG. 14 show shrinkage of the transfected human WAT in one day intervals from the start to the end point at t+6 days after treatment with a 1 μg dose of mRNA of SEQ ID NO: 130.
Figure 9:
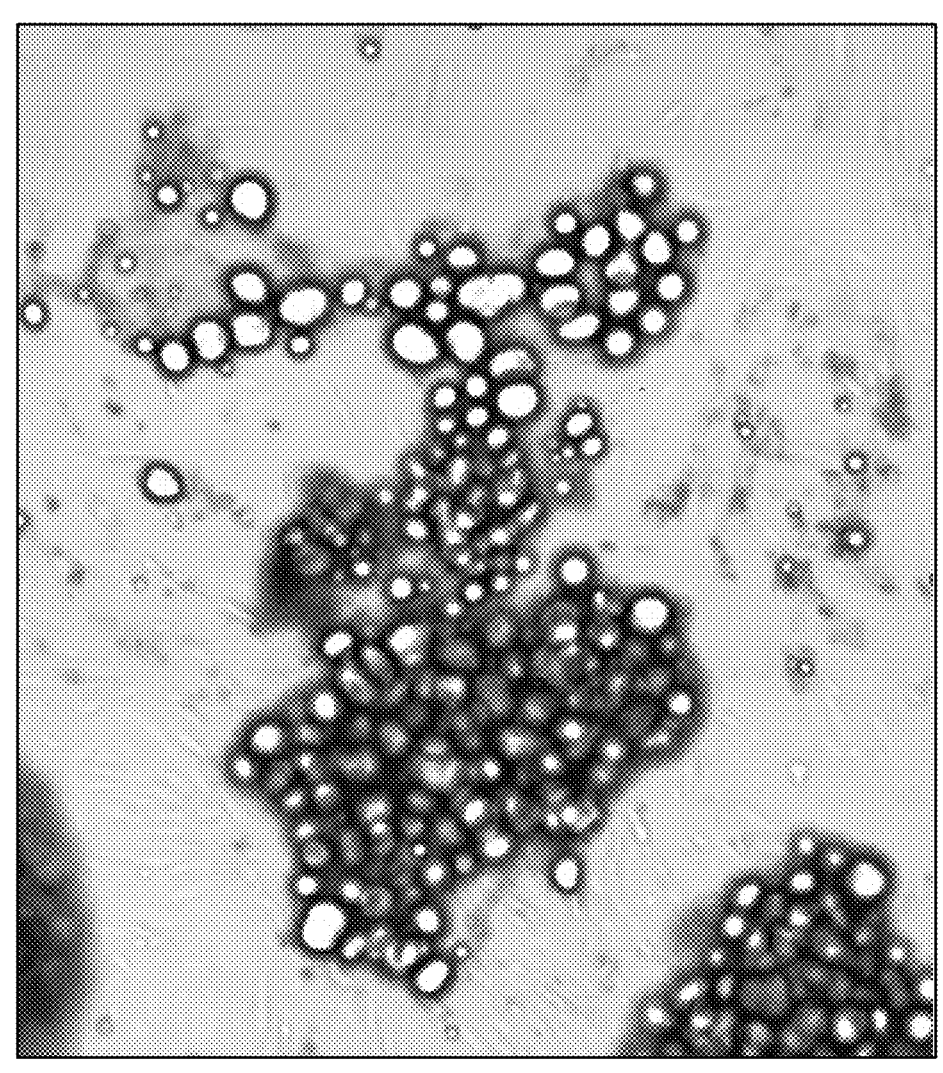
Figure 10:
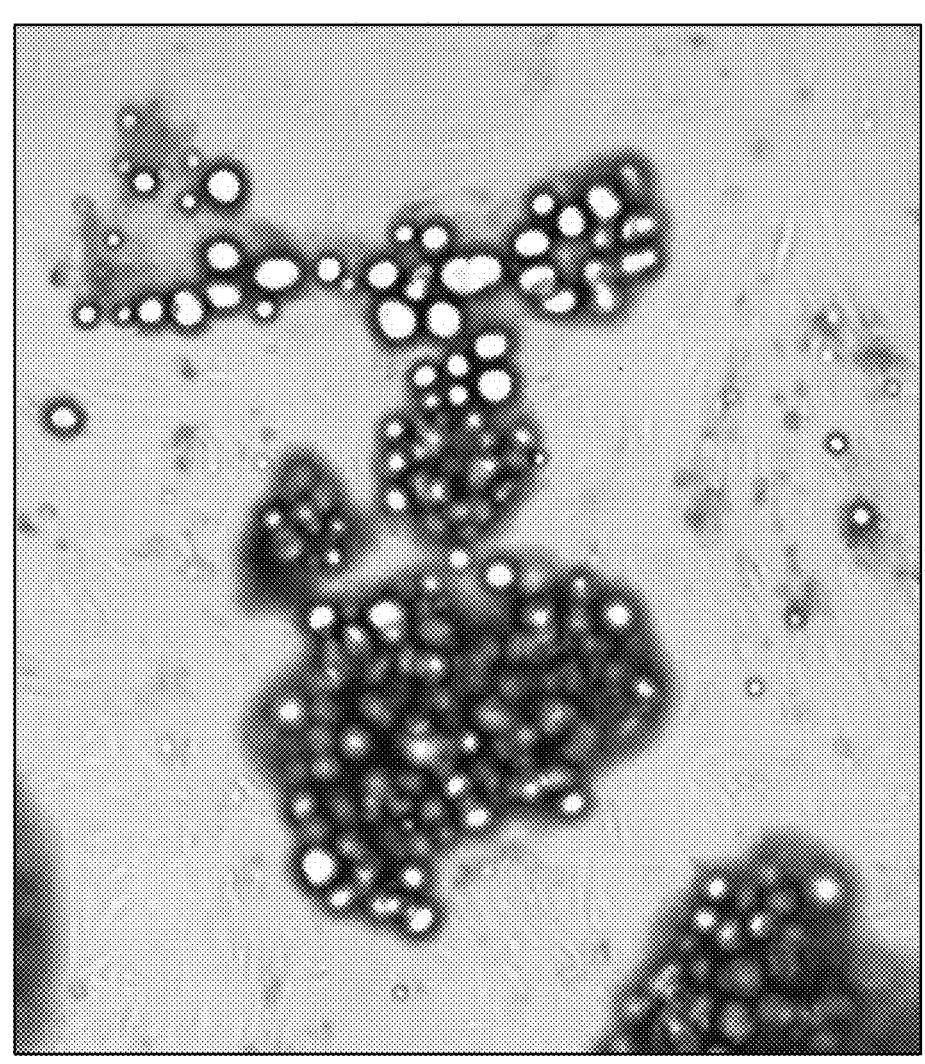
Figure 11:
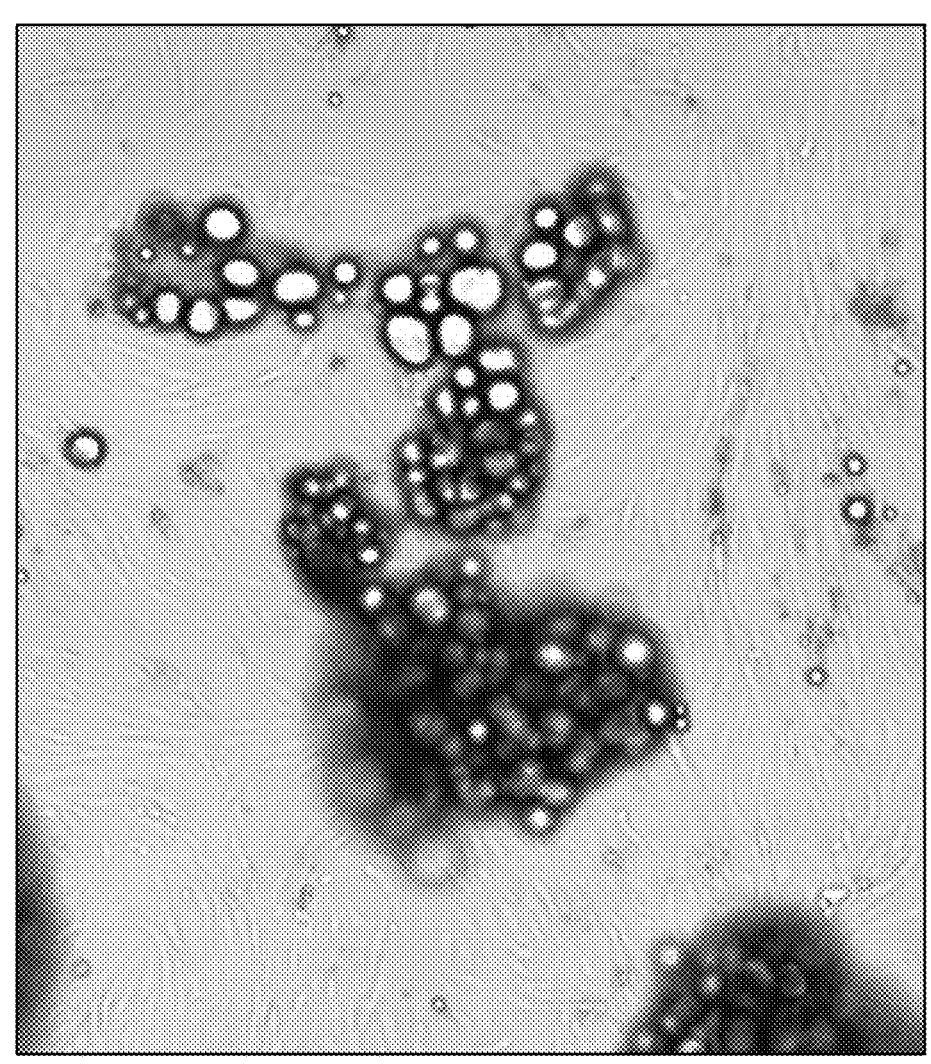
Figure 12:
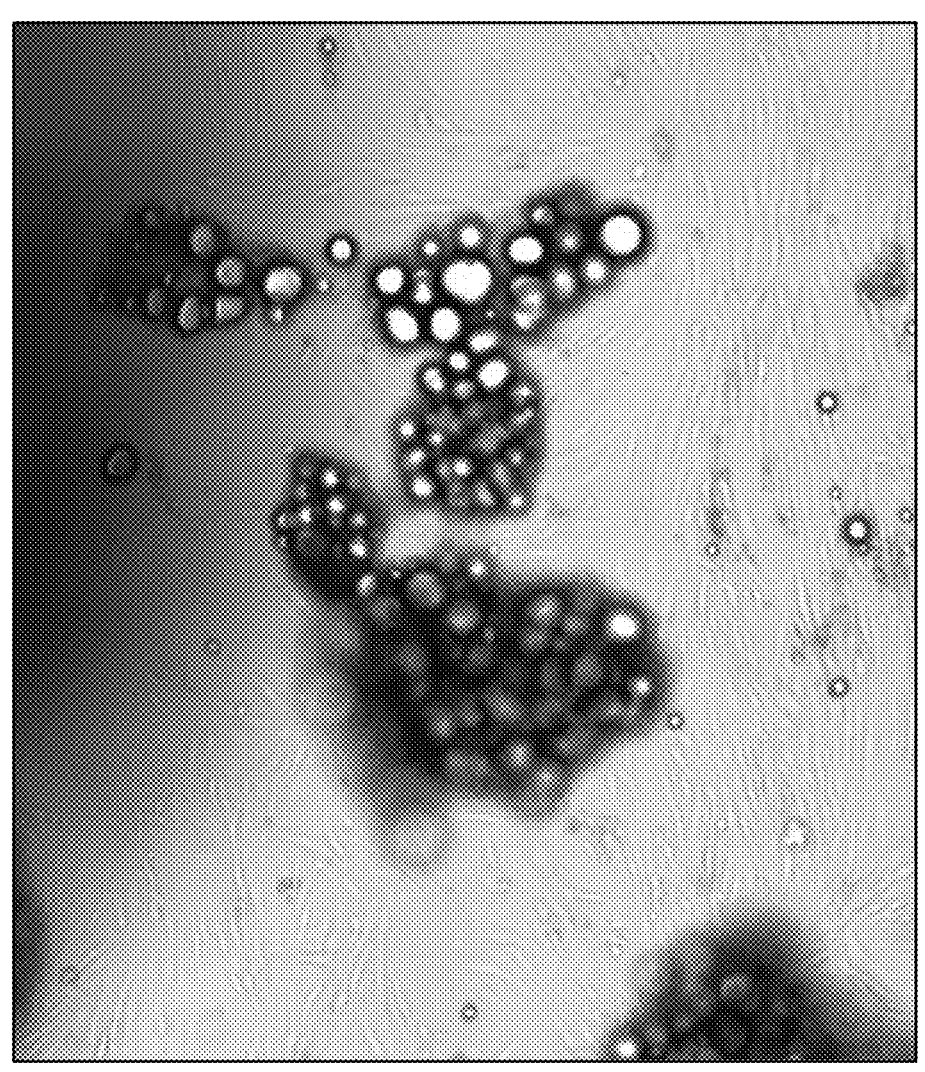
Figure 13:
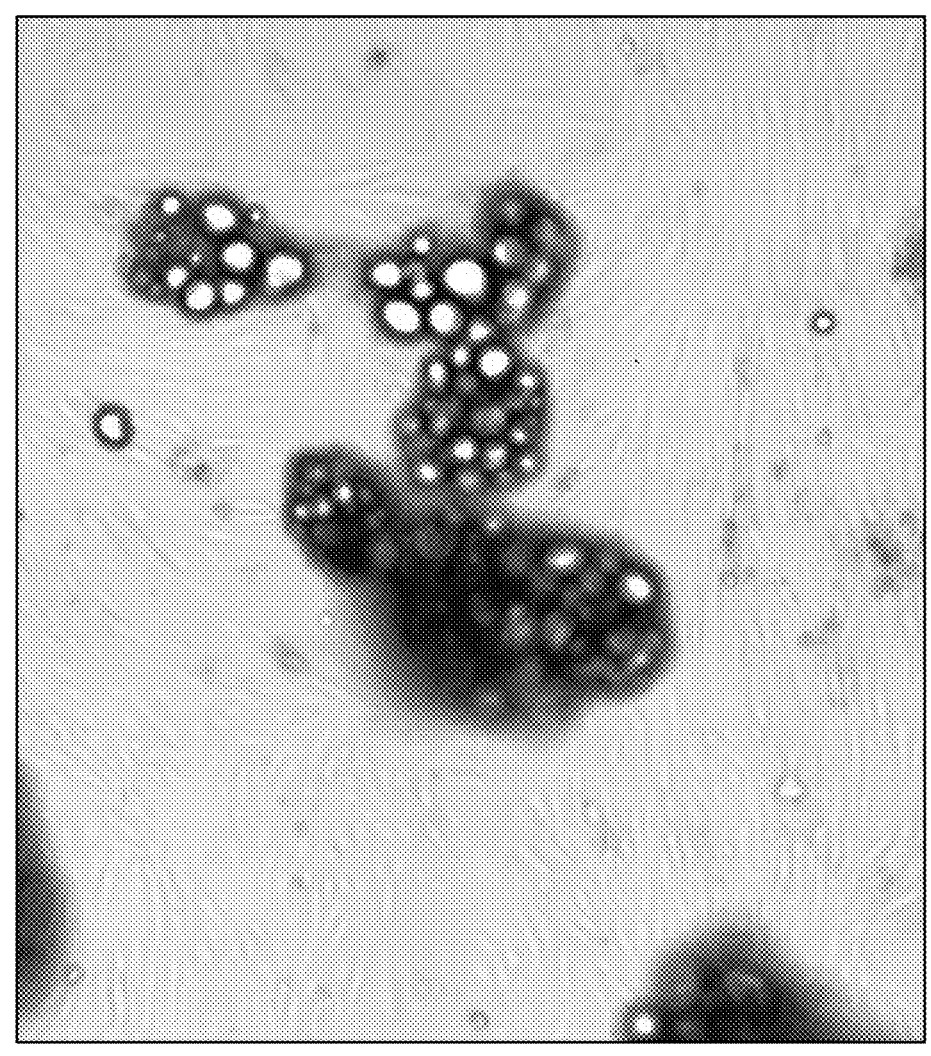
Figure 14:
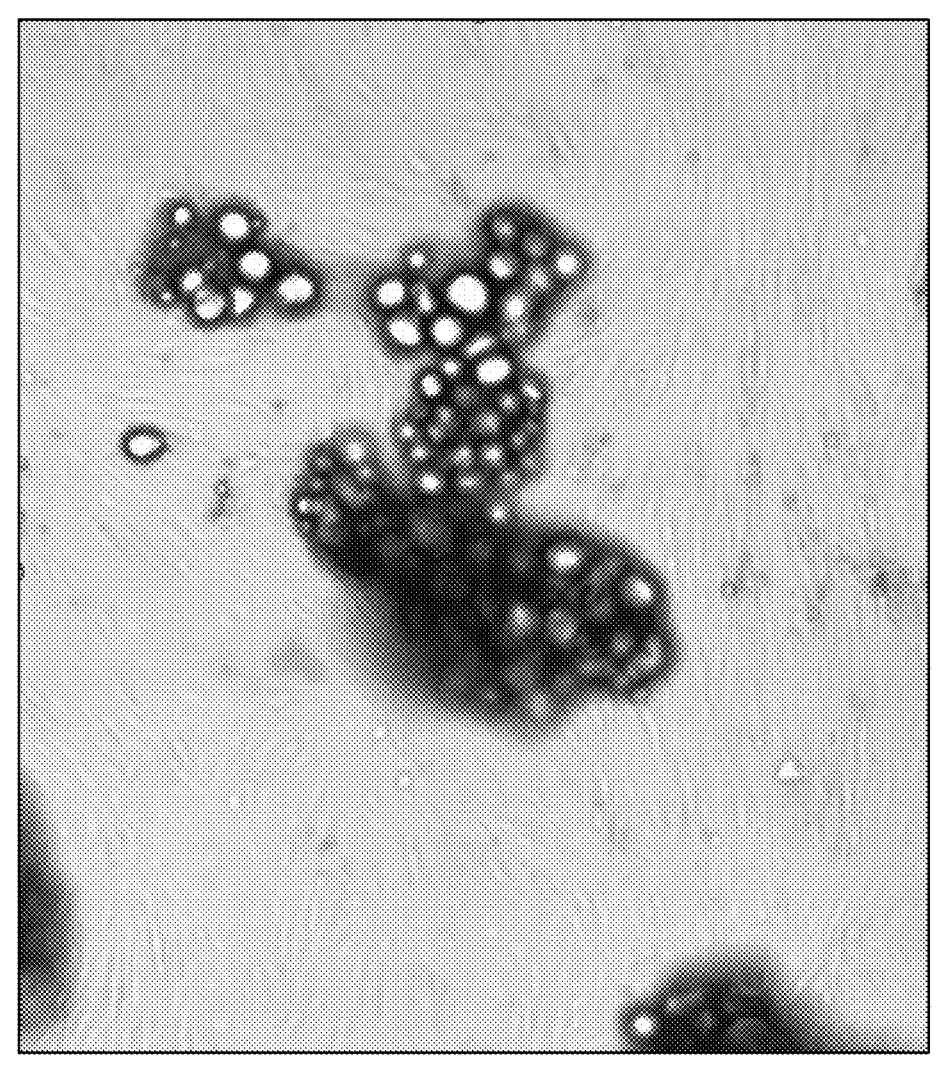

The sequence of mRNA of SEQ ID NO: 130 was created using A plasmid Editor (ApE). The coding sequence (CDS)

was optimized using the GenScript Biotech Corporation GenSmart tool. The mRNA was manufactured by GeneFab Inc. using N1-methylpseudouridine as a substitute for uridine and packaged in LNP I as described above. The packaged mRNA was used to treat cultured, ex vivo human white adipose tissue that was prepared as described above. Treatment was performed by adding our drug test articles to the ex vivo fat culture media (DMEM, 10% fetal bovine serum, and antibiotic and antifungal prophylactics.) After 24 hours, culture media was aspirated from the dish; cells were washed in chilled phosphate buffered saline (PBS) and then PBS was aspirated completely. Lysis buffer was added to the culture dish and supplemented with protease and phosphatase inhibitors. Cells and cell lysate were transferred to a pre-chilled microcentrifuge tube. The lysate was incubated on ice for 15-30 mins and then centrifuged at high speed for 20 minutes to pellet cell debris. Supernatant was loaded into a new microcentrifuge tube and protein quantified. Sodium Dodecyl Sulfate-Polyacrylamide Gel Electrophoresis (SDS-PAGE), blotting, immunodetection and imaging were performed. FIG. 6 presents the resulting images confirming the presence of UCP1 in the transfected WAT, as well as expected levels of housekeeping genes heat shock protein 90 (HSP90) and beta-actin (β-actin).

Figure 15:
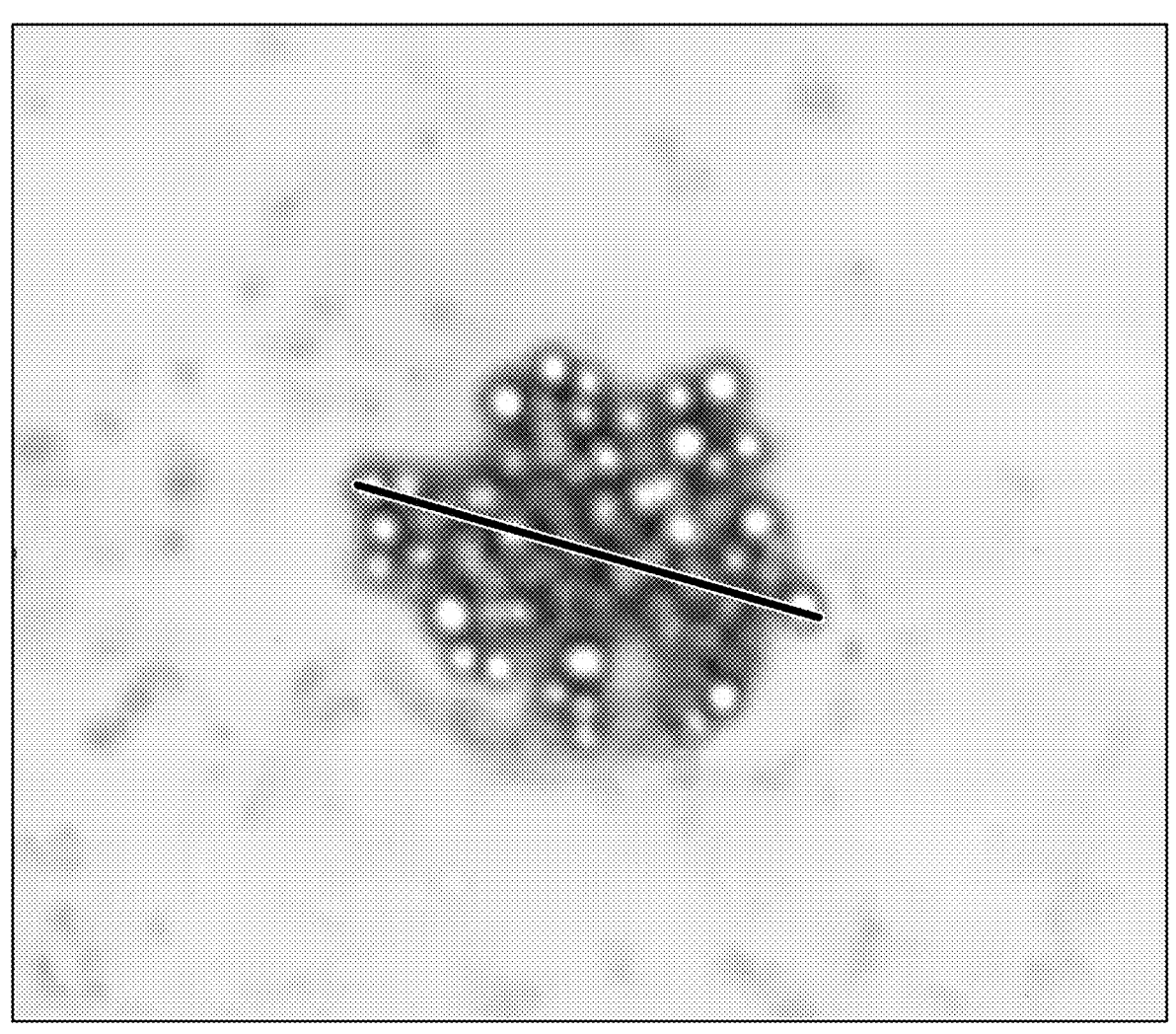
FIG. 15, FIG. 16, FIG. 17, FIG. 18, FIG. 19, FIG. 20, and FIG. 21 show shrinkage of the transfected human WAT in one day intervals from the start to the end point at t+6 days after treatment with a 5 μg dose of mRNA of SEQ ID NO: 130.
Figure 16:
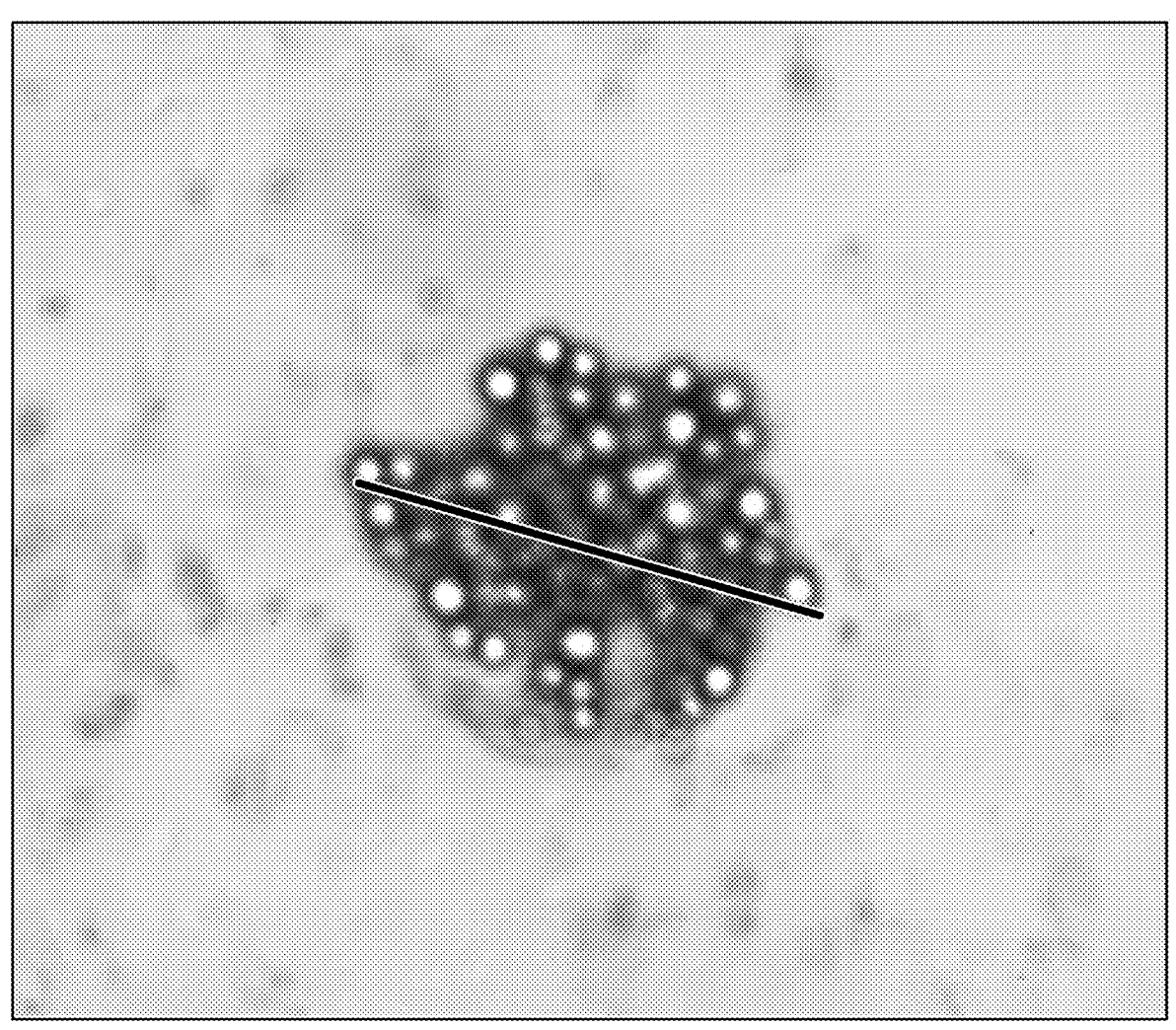
Figure 17:
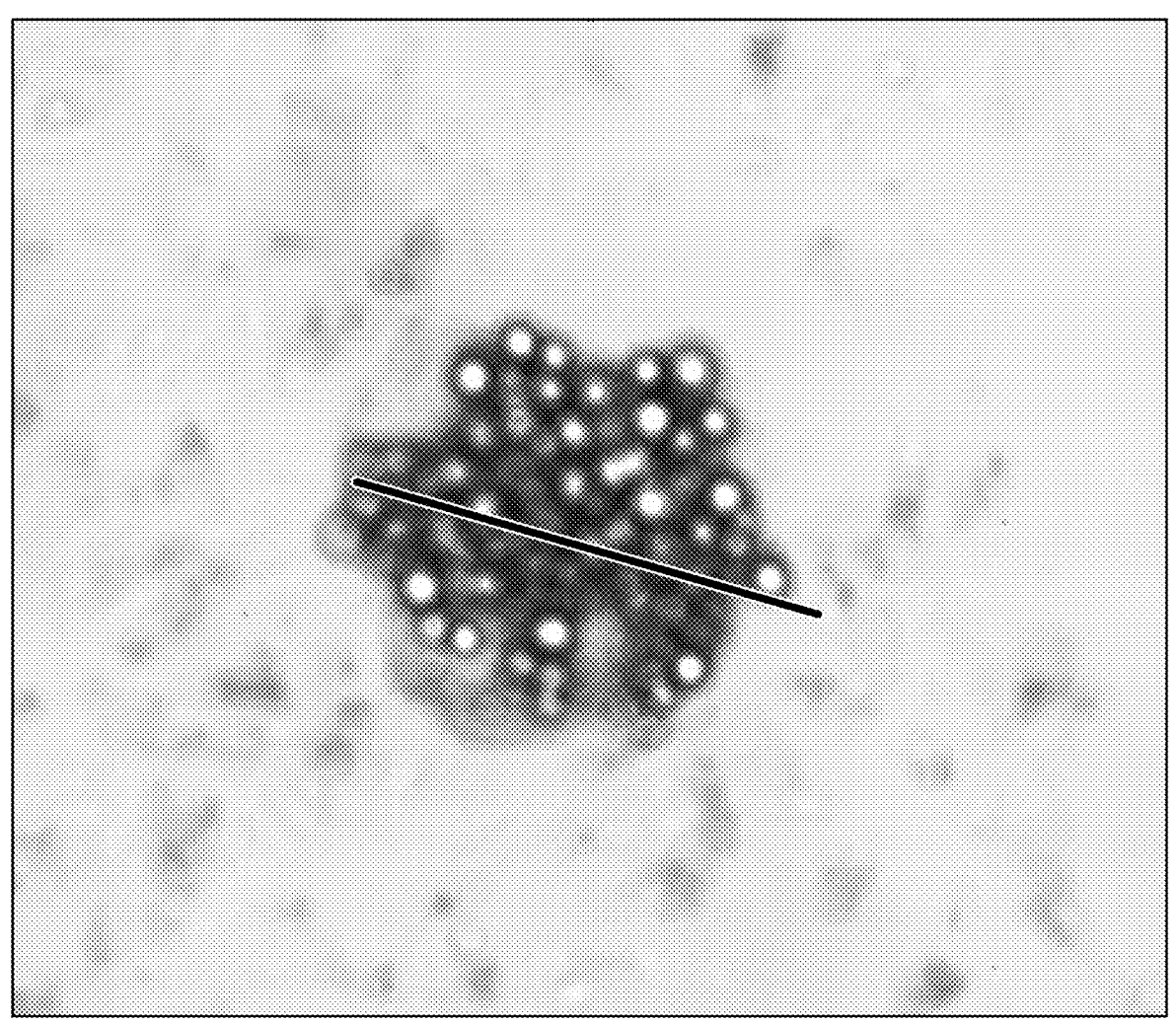
Figure 18:
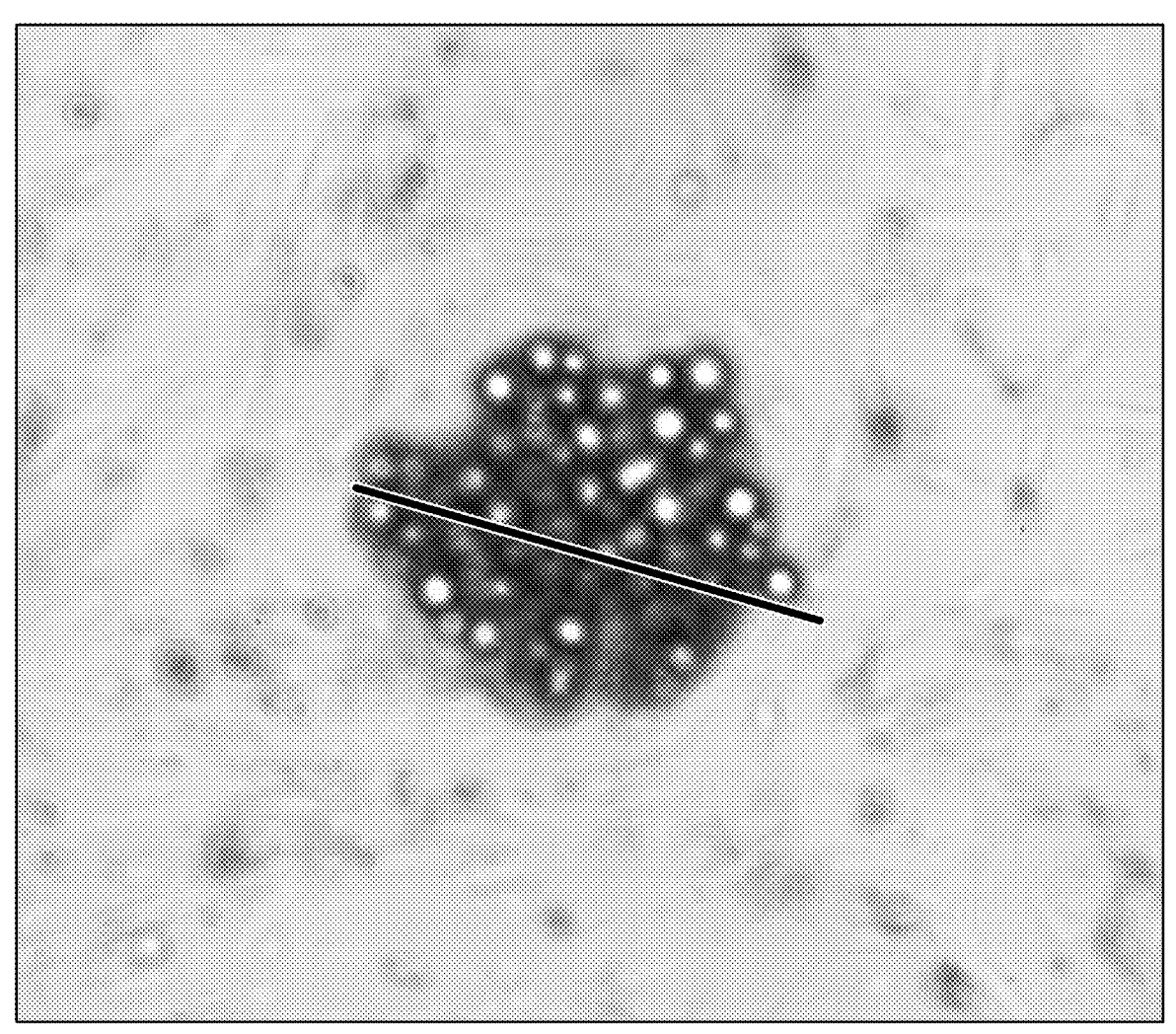
Figure 19:
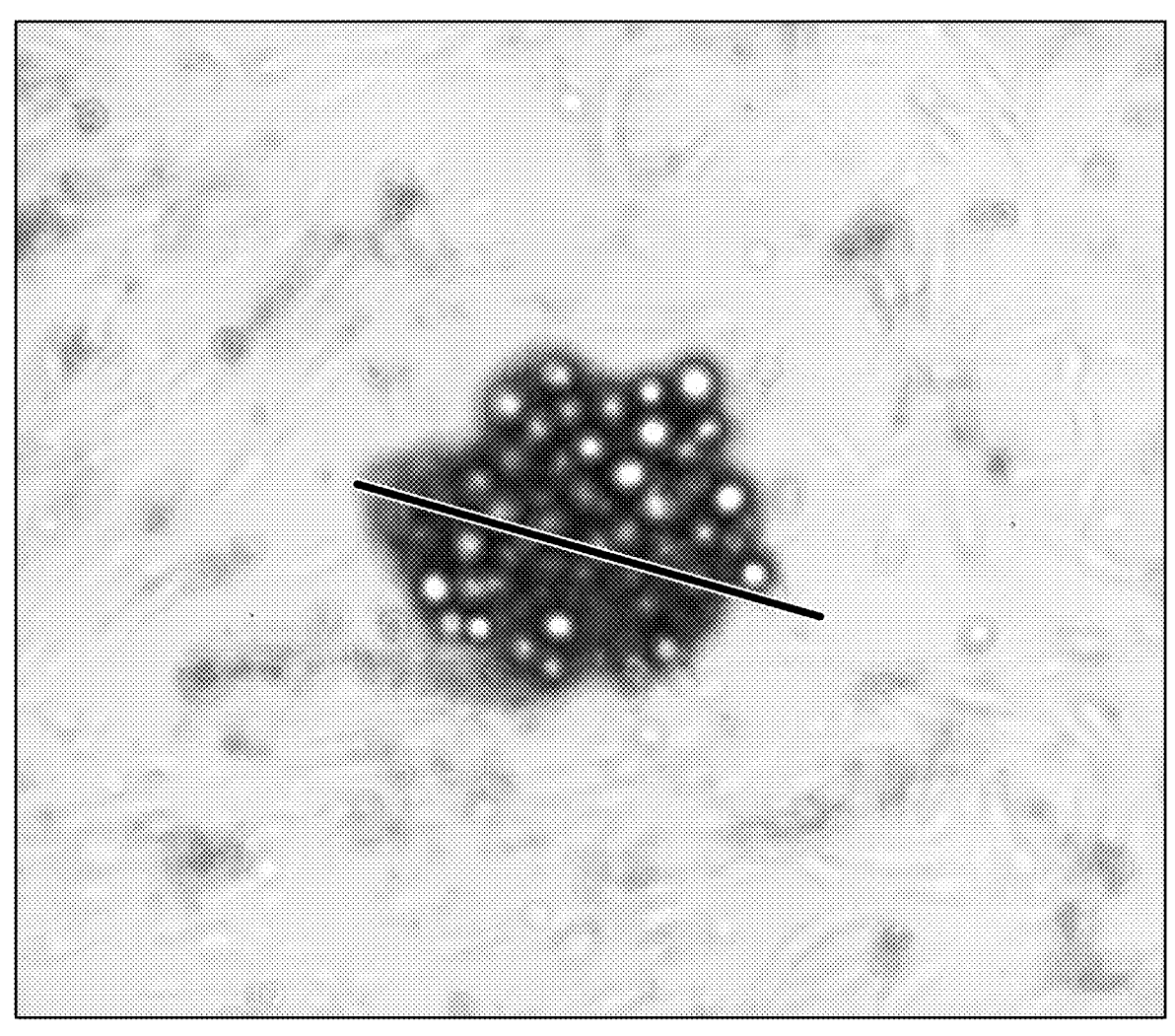
Figure 20:
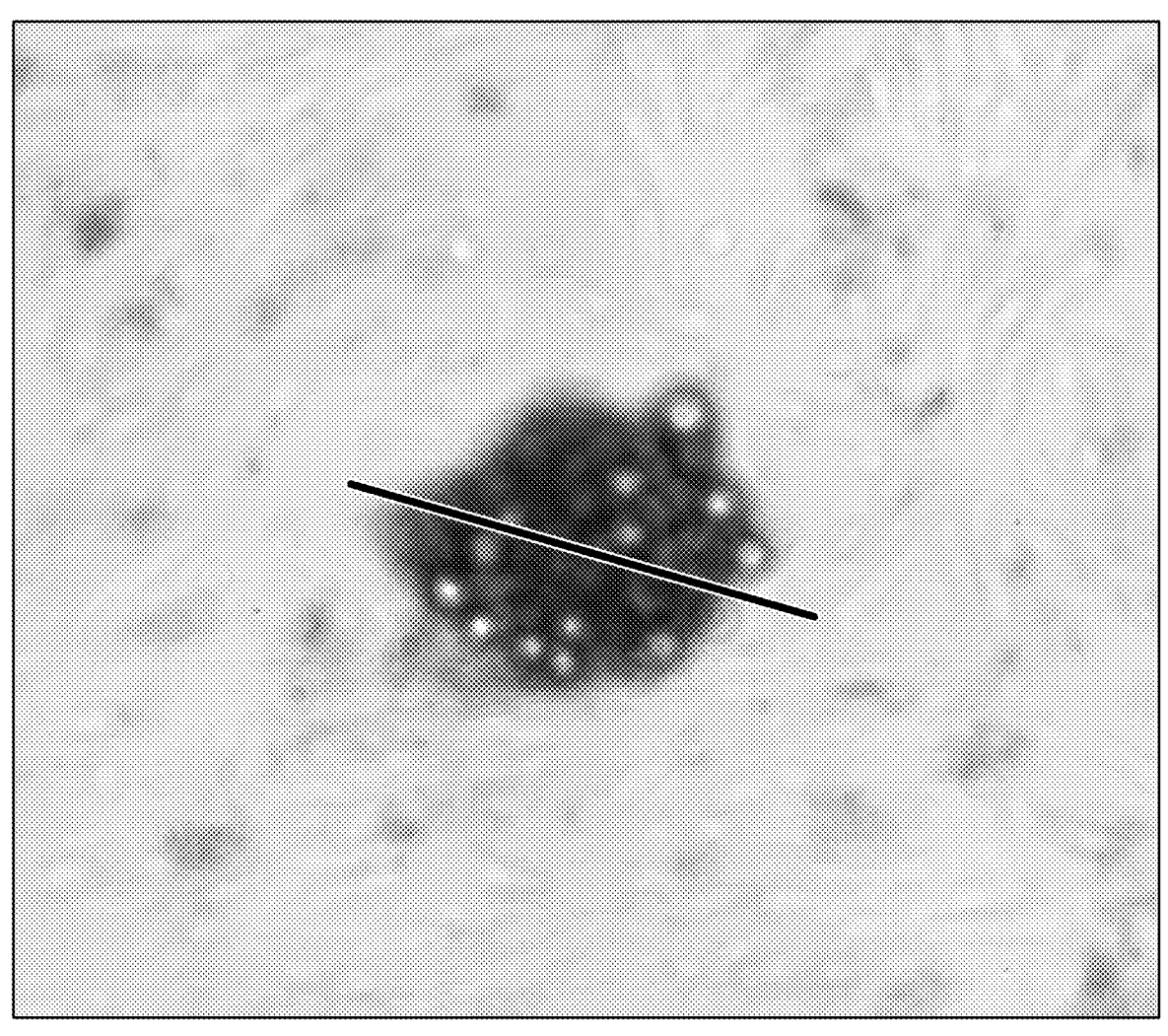
Figure 21:
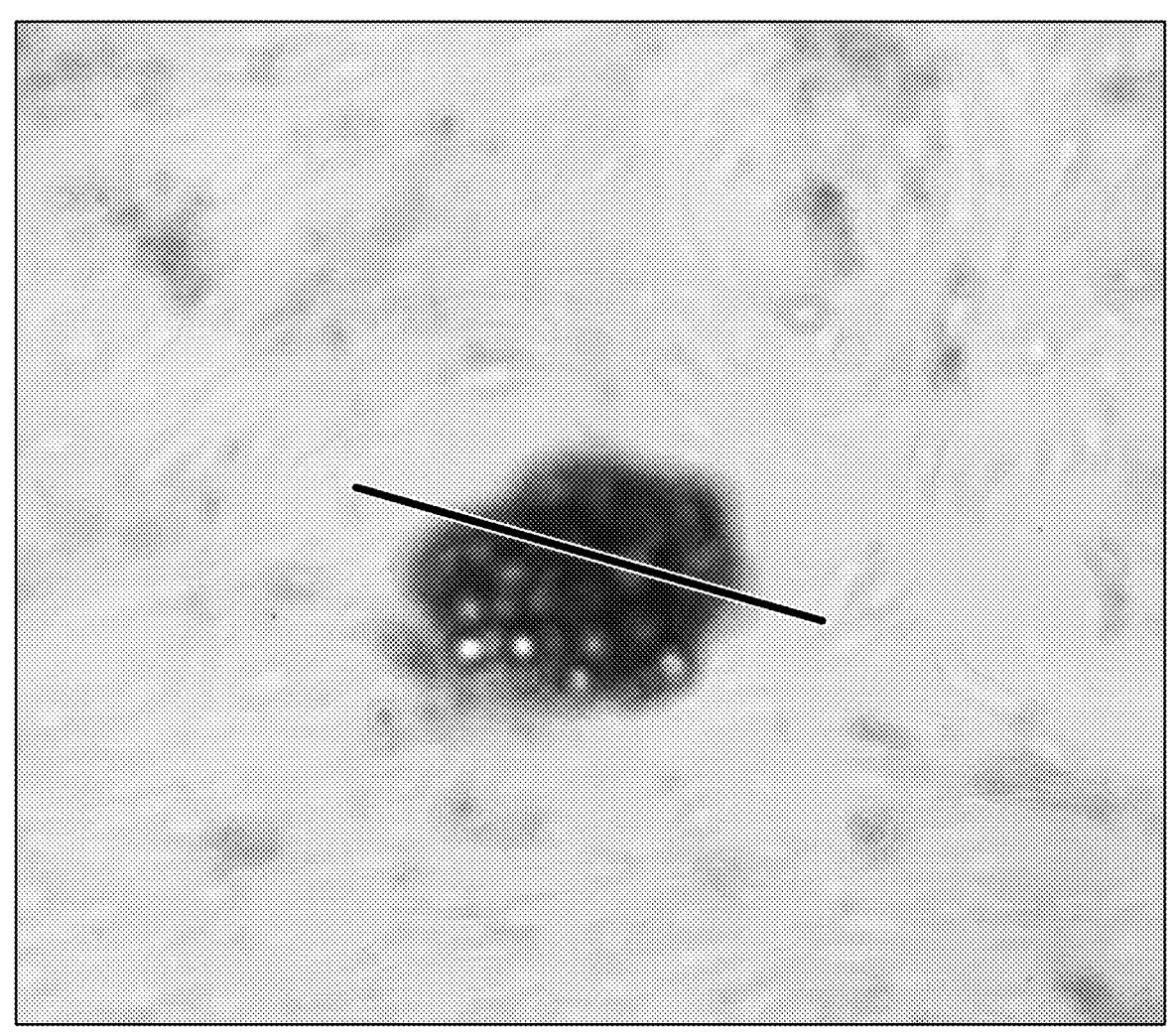

FIG. 6 demonstrates the presence of UCP1 24 hours after 1 µg, 5 µg and 10 µg doses for each 100 mg of ex vivo human WAT and the dose response curve at 1 µg, 5 µg and 10 µg doses. Untreated WAT did not express UCP1 protein. FIGS. 8 through 14 were generated using automated brightfield microscopy. These images show shrinkage of the transfected WAT in one day intervals from the start to the end point at t+6 days after treatment with a 1 µg dose of mRNA of SEQ ID NO: 130. FIGS. 15 through 21 show shrinkage of the transfected WAT in one day intervals from the start to the end point at t+6 days after treatment with a 5 µg dose of mRNA of SEQ ID NO: 130. The black line in FIG. 15 drawn diagonally across the cluster of cells is replicated in FIGS. 16 through 21. The length and position of the line as well as the magnification of the cell cluster depicted are held constant throughout FIGS. 15 through 21. The black line serves as a reference point to demonstrate the degree of shrinkage of the cell cluster over the period of treatment. In FIG. 15, the line spans the entire cluster. In FIG. 21, the line is roughly twice the diameter of the cluster.

Example 7

The sequence of mRNA of SEQ ID NO: 2 was created using A plasmid Editor (ApE). The coding sequence (CDS) was optimized using the GenScript Biotech Corporation GenSmart tool. The mRNA was manufactured by GeneFab Inc. using N1-methylpseudouridine as a substitute for uridine and packaged in LNP D as described above. 5 µg or 10 µg of the packaged mRNA was introduced to cultured, ex vivo human white adipose tissue that was prepared as described above. Treatment was performed by adding our drug test articles to the ex vivo fat culture medium (DMEM, 10% fetal bovine serum, and antibiotic and antifungal prophylactics.) After 24 hours, the culture medium was aspirated from the dish; cells were washed in chilled phosphate buffered saline (PBS) and PBS was aspirated completely after wash. A lysis buffer supplemented with protease and phosphatase inhibitors was added to the cell culture. The cells and cell lysate were transferred to a pre-chilled microcentrifuge tube. The lysate was incubated on ice for 15-30 mins and then centrifuged for 20 minutes to pellet cell debris. Supernatant was loaded into a new microcentrifuge tube and protein quantified. Western blot was performed to confirm the expression of UCP1 in the transfected WAT, as well as expected levels of housekeeping gene HSP90.

Figure 22:
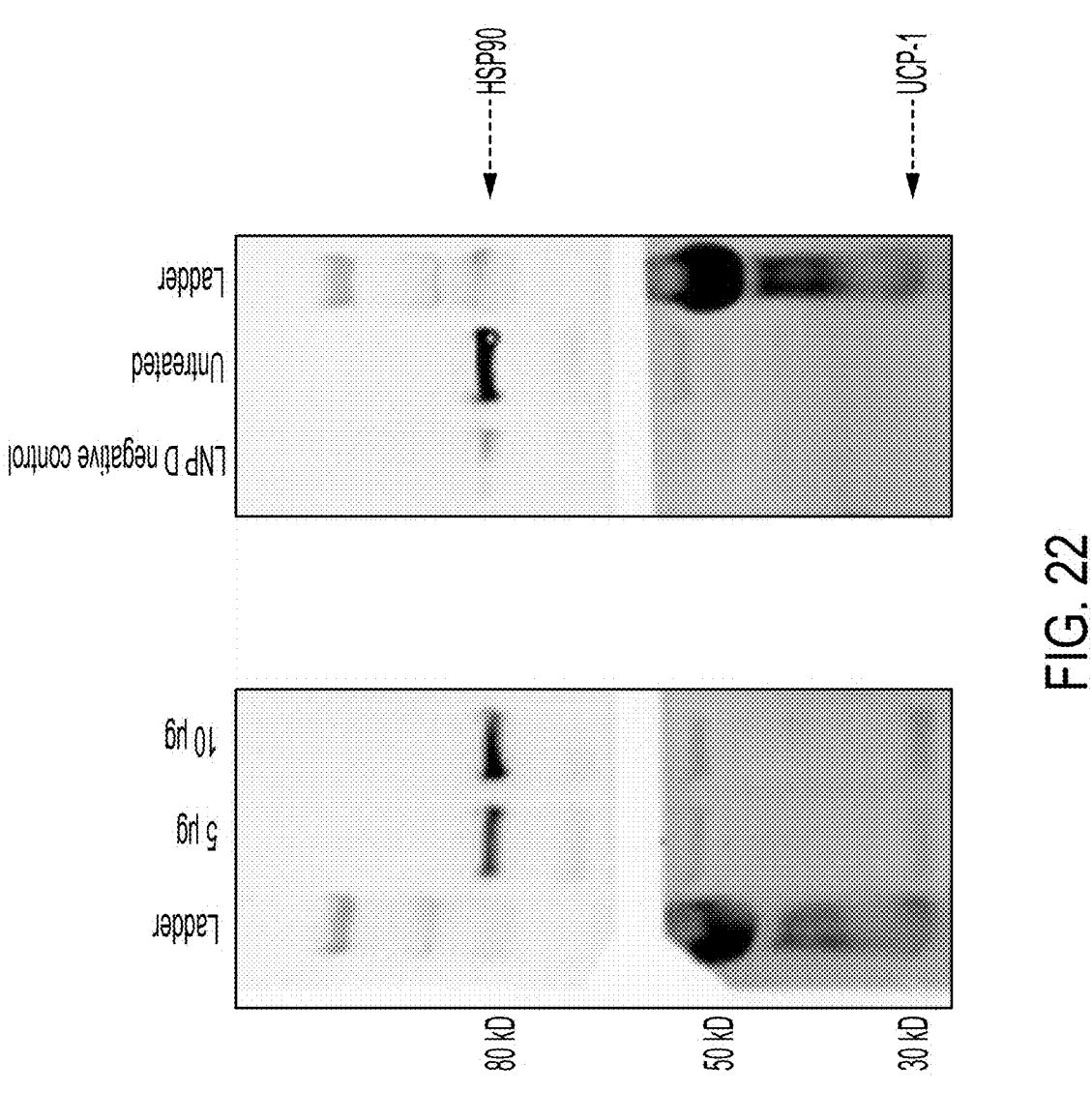
FIG. 22 is a Western Blot result showing dose respon-siveness of UCP1 expression 24 hours after transfection of cells derived from human white adipose tissue with 5 μg and 10 μg doses of SEQ ID NO: 130 encapsulated in LNP D.

FIG. 22 demonstrates expression of UCP1 after 24 hours of incubation. Negative control test articles (LNP D encapsulating synthetic mRNA encoding mCherry in lieu of UCP1) and untreated WAT did not express UCP1 protein.

Example 8

The sequence of mRNA of SEQ ID NO: 130 was created using A plasmid Editor (ApE). The coding sequence (CDS) was optimized using the GenScript Biotech Corporation GenSmart tool. The mRNA was manufactured by GeneFab Inc. using N1-methylpseudouridine as a substitute for uridine and packaged in LNP I as described above. One microgram of the packaged mRNA was added to a confluent culture of human adipose derived stem cells (ASCs) in the culture medium (DMEM, 10% fetal bovine serum, and antibiotic and antifungal prophylactics.) After 24 hours, the culture medium was aspirated from the dish; cells were washed in chilled phosphate buffered saline (PBS) and PBS was aspirated completely after wash. A lysis buffer supplemented with protease and phosphatase inhibitors was added to the cell culture. The cells and cell lysate were transferred to a pre-chilled microcentrifuge tube. The lysate was incubated on ice for 15-30 mins and then centrifuged for 20 minutes to pellet cell debris. Supernatant was loaded into a new microcentrifuge tube and protein quantified. Western blot was performed to confirm the expression of UCP1 in the transfected WAT, as well as expected levels of housekeeping genes heat shock protein 90 (HSP90) and beta-actin (β-actin).

Figure 23:
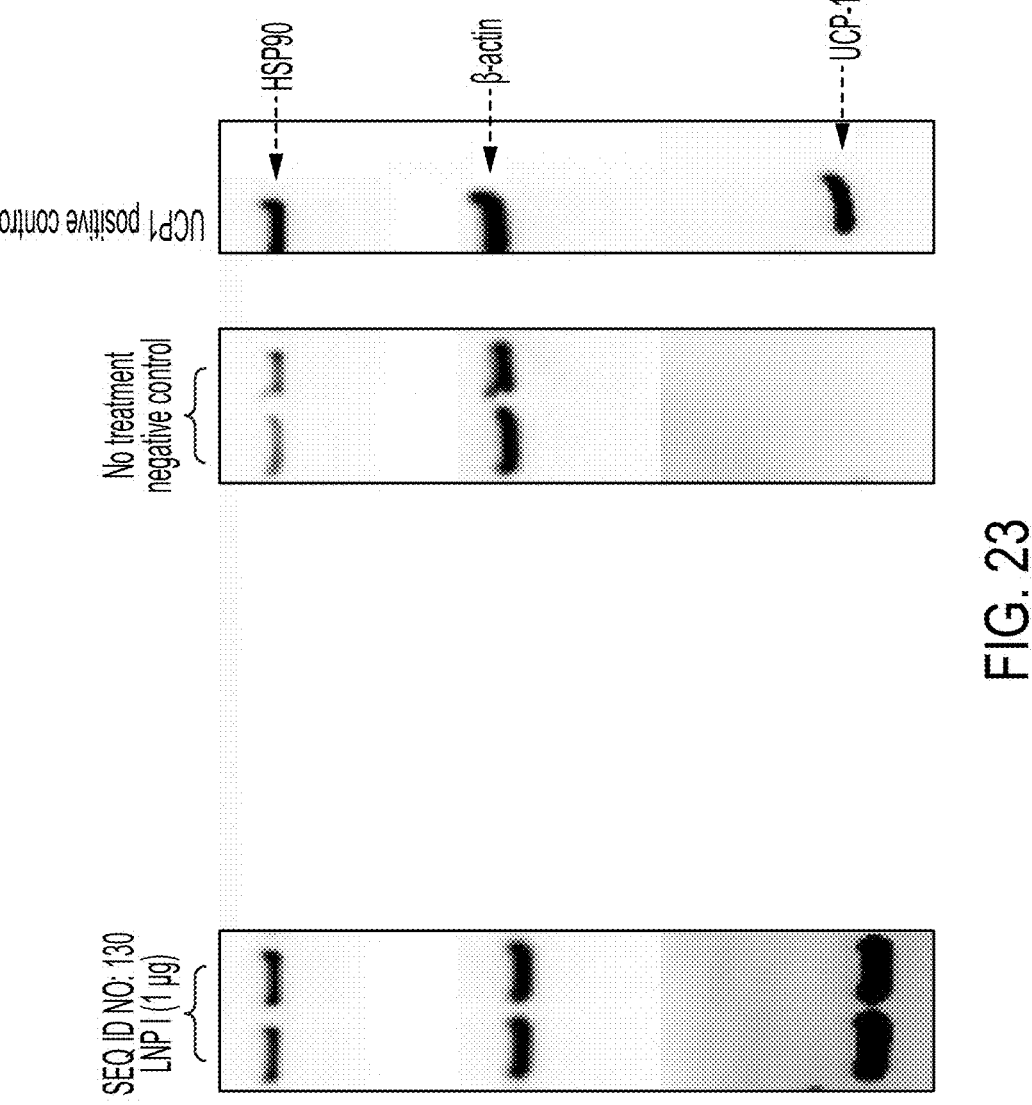
FIG. 23 is a Western Blot result showing UCP1 expres-sion 24 hours after transfection of cells derived from human white adipose tissue with 1 μg of SEQ ID NO: 130 encap-sulated in LNP I.

FIG. 23 demonstrates the expression level of UCP1 24 hours after adding 1 μg of mRNA.

Figure 24:
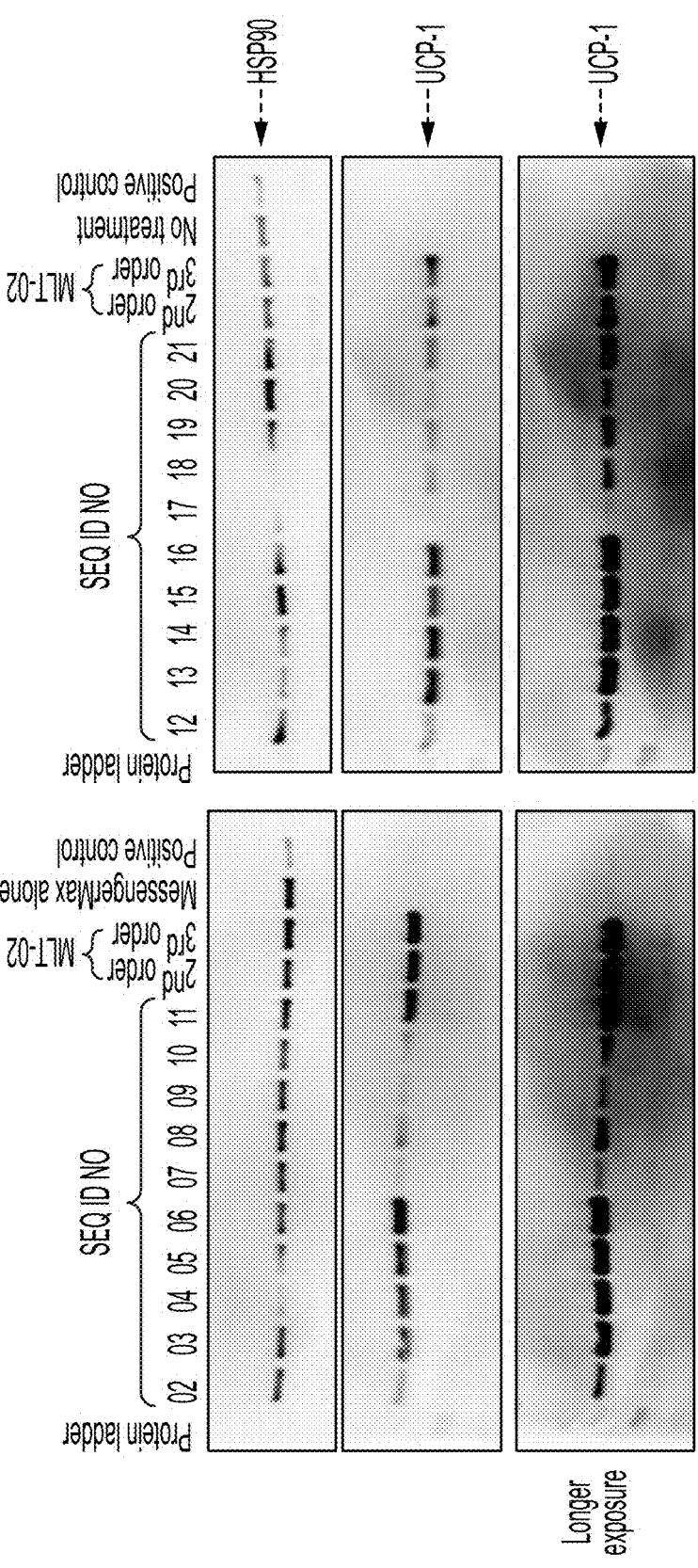
FIG. 24 is a Western Blot Result showing UCP1 expres-sion 24 hours after transfection of cells derived from human white adipose tissue with 1 μg of mRNA of SEQ ID NOs: 2 through 21 encapsulated with MessengerMAX™ trans-fection agent.

FIG. 24 demonstrates the expression level of UCP1 24 hours after adding 1 μg doses of mRNA of SEQ ID NO: 2 through 21 encapsulated in MessengerMax™ transfection agent to 100 mg of ex vivo human WAT. As shown in the controls untreated WAT did not express UCP1 protein.

Figure 25:
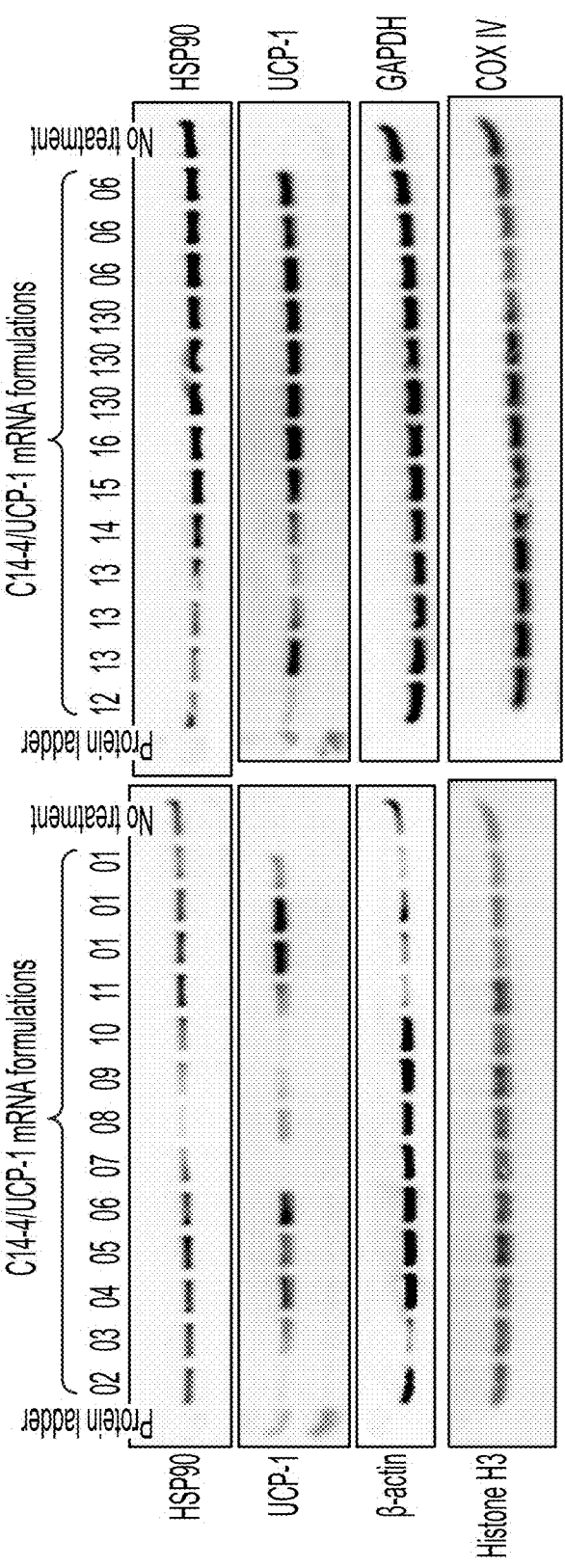
FIG. 25 is a Western Blot Result showing UCP1 expres-sion 24 hours after transfection of cells derived from human white adipose tissue with 1 μg of mRNA of SEQ ID NOs: 130 and 2 through 16, encapsulated in LNP I. SEQ ID NOs: 130, 1, 6, and 13 were run in triplicate.

FIG. 25 demonstrates the expression level of UCP1 24 hours after adding 1 μg doses of mRNA of SEQ ID NO: 2 through 16 as well as SEQ ID NO: 130 and 1 which, along with SEQ ID NO: 6 were run in triplicate, encapsulated in LNP I in 100 mg of ex vivo human WAT.

Figure 26:
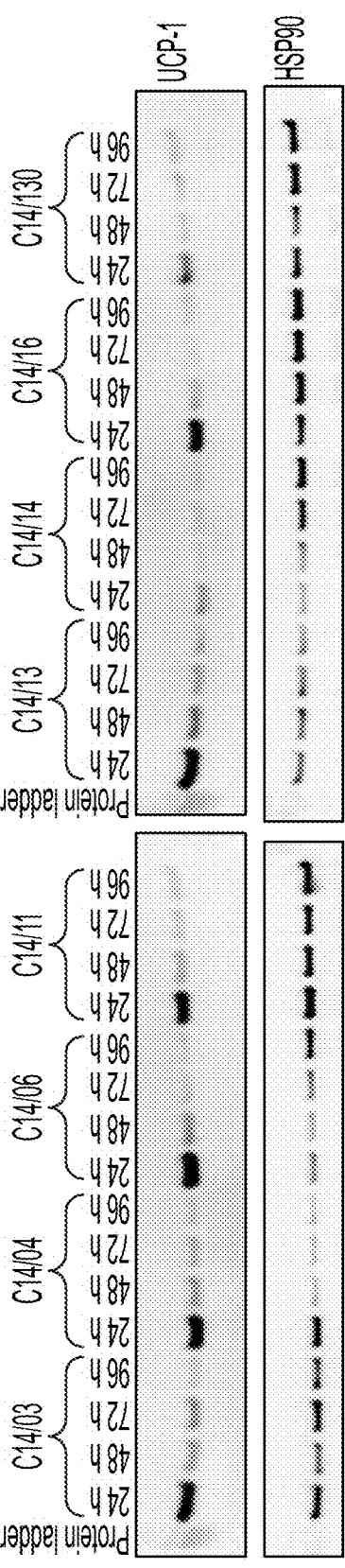
FIG. 26 is a Western Blot Result showing UCP1 expres-sion at 24, 48, 72 and 96 hours after transfection of cells derived from human white adipose tissue with 1 μg of mRNA of SEQ ID NOs: 3, 4, 6, 11, 13, 14, 16, and 130.

FIG. 26 demonstrates the presence of UCP1 at time points 24, 48, 72 and 96 hours post transfection of 100 mg of ex vivo human WAT with 1 μg mRNA of SEQ ID NO: 3, 4, 6, 11, 13, 14, 16 and 130 encapsulated in LNP I.

Figure 27:
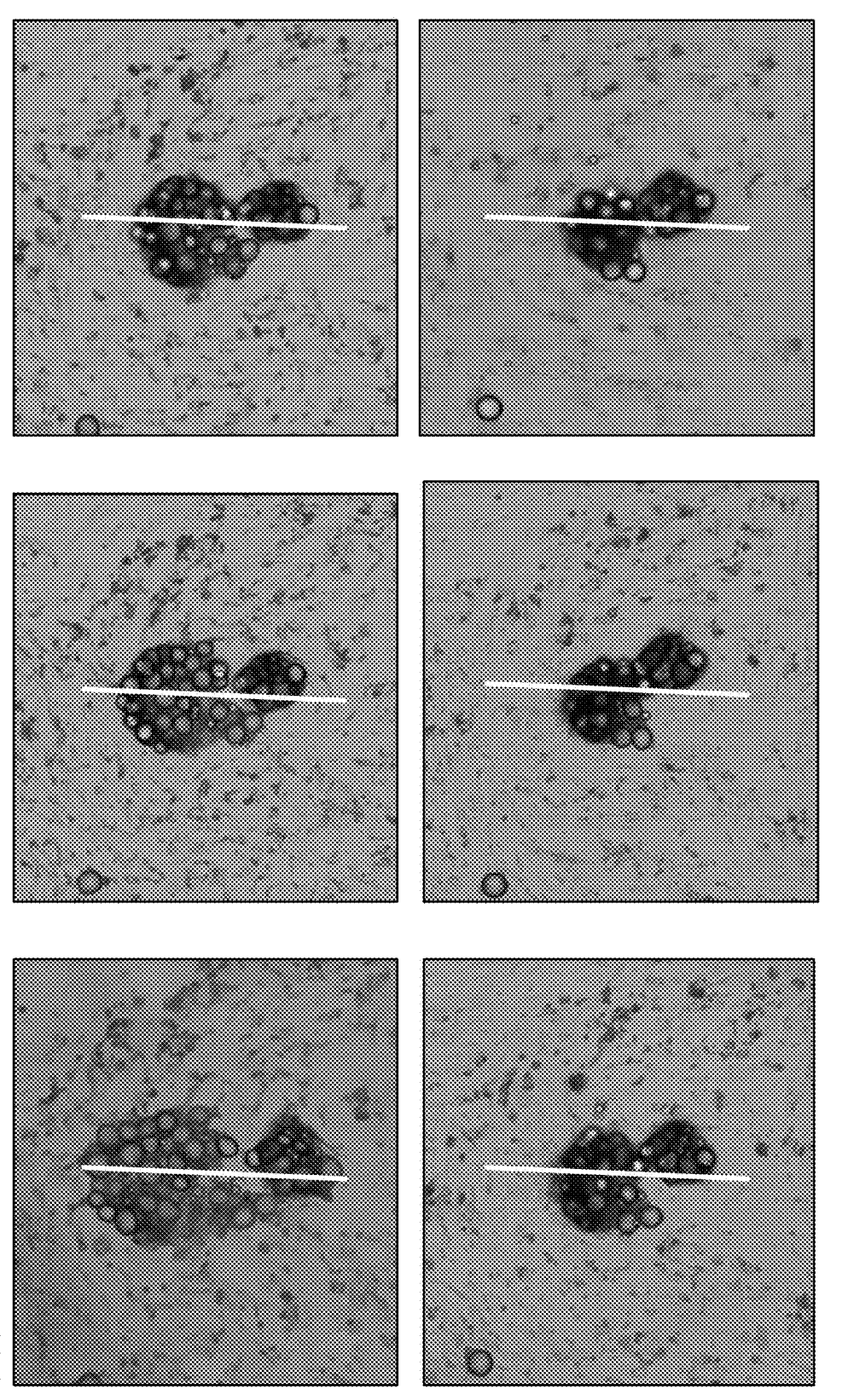
FIG. 27 is a series of time lapse images of cells derived from human white adipose tissue beginning at 24 hours after transfection with 10 μg of mRNA of SEQ ID NO: 2 encapsulated in LNP ID I (C14-4). Top row, from left to right: Day 1, Day 2, Day 3. Bottom row, from left to right: Day 4, Day 5, Day 6.

FIG. 27 was generated using automated brightfield microscopy. These images, from left to right and top to bottom, show shrinkage of the transfected WAT as observed in visual microscopy in one day intervals from the start to the end point at t+6 days after treatment as described above with a 10 μg dose of mRNA of SEQ ID NO: 130 encapsulated in LNP I of component ratio (C14-4:DSPC:Cholesterol:PEG/Lipid Conjugate) of 35:16:46.5:2.5. The white line in the upper left panel of FIG. 27 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly twice the diameter of the cluster.

Figure 28:
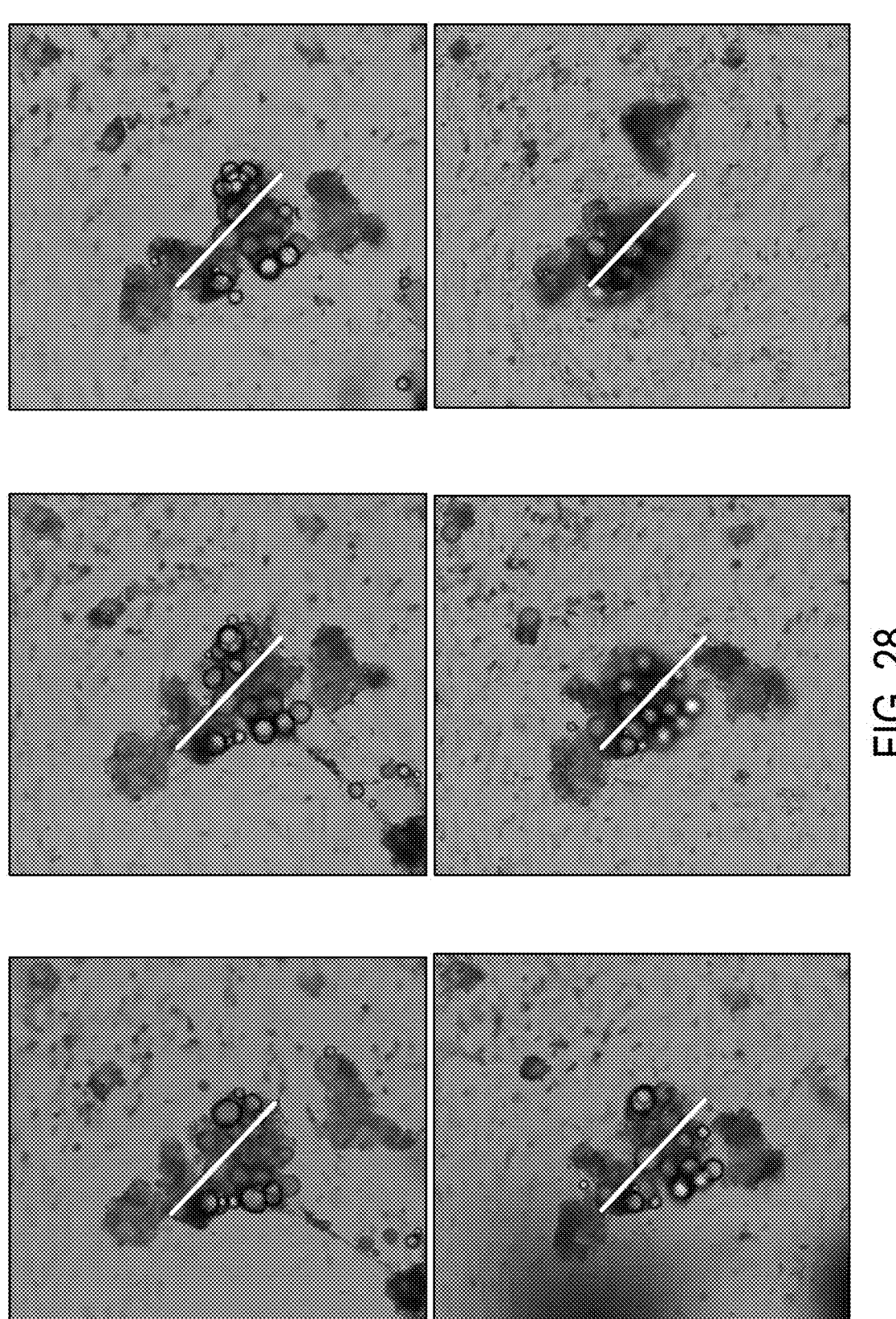
FIG. 28 is a series of time lapse images of cells derived from human white adipose tissue beginning at 24 hours after transfection with 10 μg of mRNA of SEQ ID NO: 3 encapsulated in LNP ID I (C14-4). Top row, from left to right: Day 1, Day 2, Day 3. Bottom row, from left to right: Day 4, Day 5, Day 6.

FIG. 28 was generated using automated brightfield microscopy. These images, read from left to right and top to bottom, show shrinkage of the transfected WAT in one day intervals from the start to the end point at t+6 days after treatment as described above with a 10 μg dose of mRNA of SEQ ID NO: 3 encapsulated in LNP I of component ratio (C14-4:DSPC:Cholesterol:PEG/Lipid Conjugate) of 35:16:46.5:2.5. The white line in the upper left panel of FIG. 28 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly one and a half times the diameter of the cluster.

Figure 29:
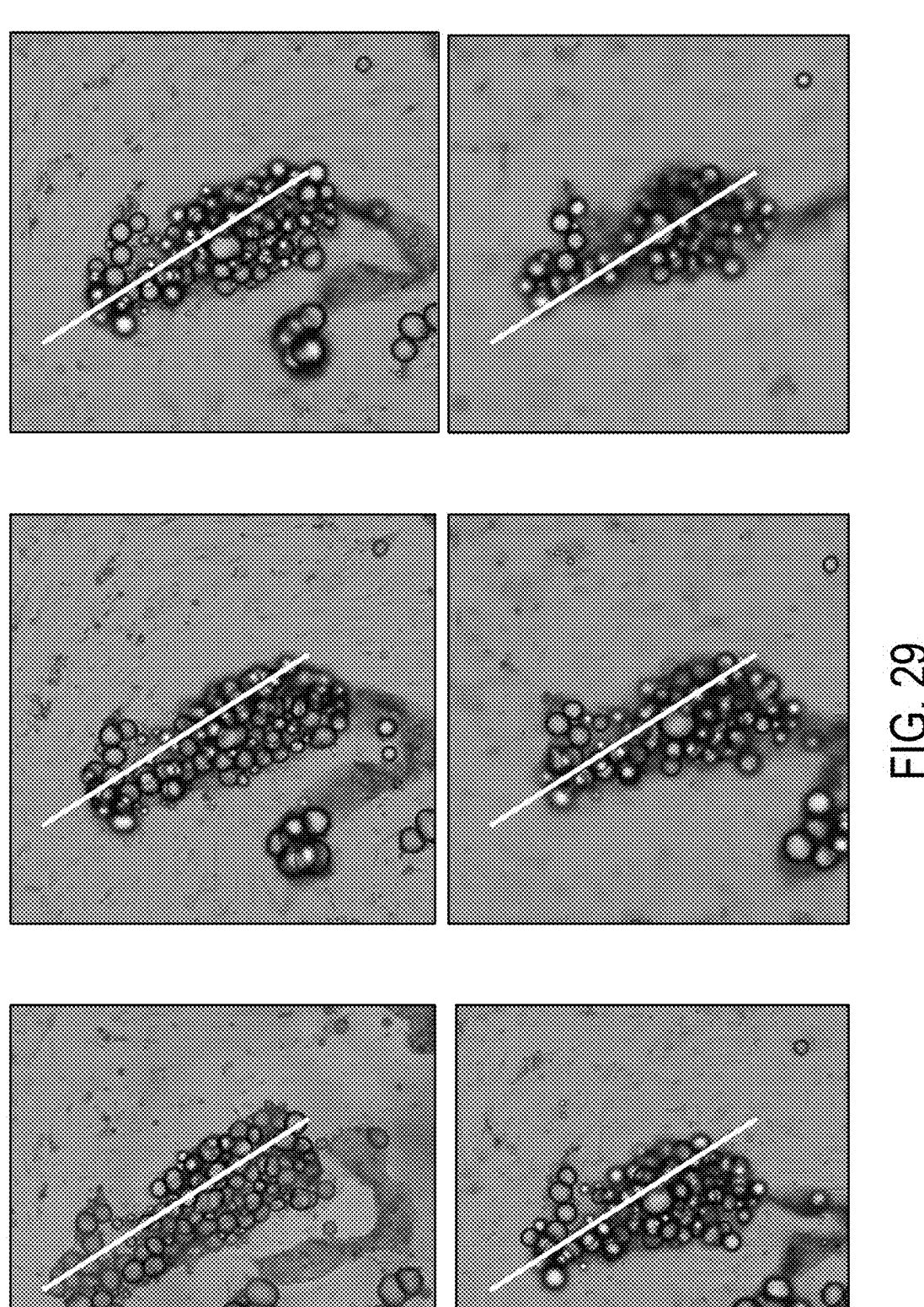
FIG. 29 is a series of time lapse images of cells derived from human white adipose tissue beginning at 24 hours after transfection with 10 μg of mRNA of SEQ ID NO: 4 encapsulated in LNP C14-4. Top row, from left to right: Day 1, Day 2, Day 3. Bottom row, from left to right: Day 4, Day 5, Day 6.

FIG. 29 was generated using automated brightfield microscopy. These images, read from left to right and top to bottom, show shrinkage of the transfected WAT in one day intervals from the start to the end point at t+6 days after treatment as described above with a 10 μg dose of mRNA of SEQ ID NO: 4 encapsulated in LNP I of component ratio (C14-4:DSPC:Cholesterol:PEG/Lipid Conjugate) of 35:16:46.5:2.5. The white line in the upper left panel of FIG. 29 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly one and a half times the diameter of the cluster.

Figure 30:
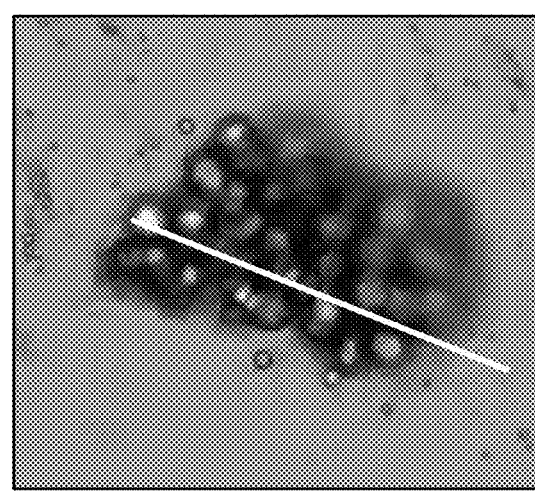
FIG. 30 is a series of time lapse images of cells derived from human white adipose tissue beginning at 24 hours after transfection with 2 μg of mRNA of SEQ ID NO: 6 encap-sulated in LNP C14-4. Top row, from left to right: Day 1, Day 2, Day 3. Bottom row, from left to right: Day 4, Day 5, Day 6.
Figure 30:
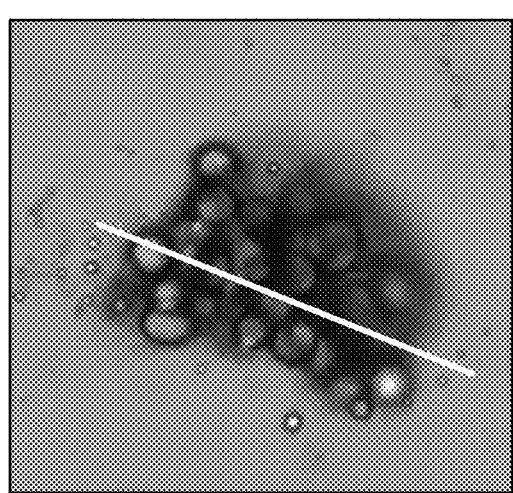
Figure 30:
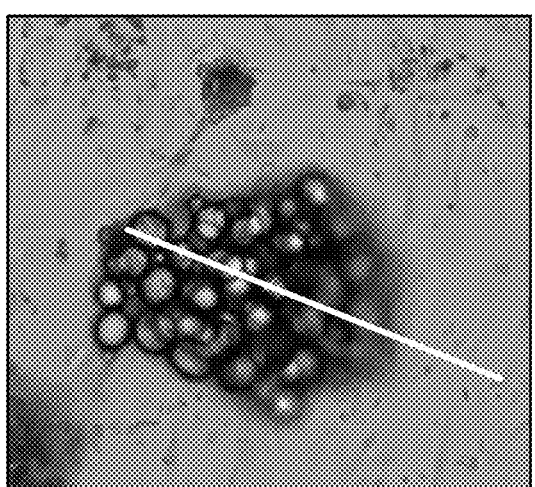
Figure 30:
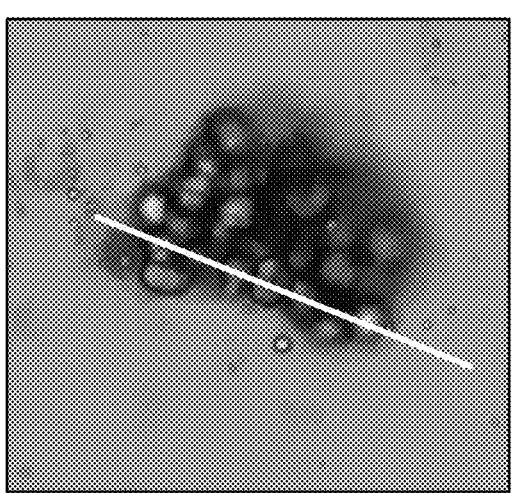
Figure 30:
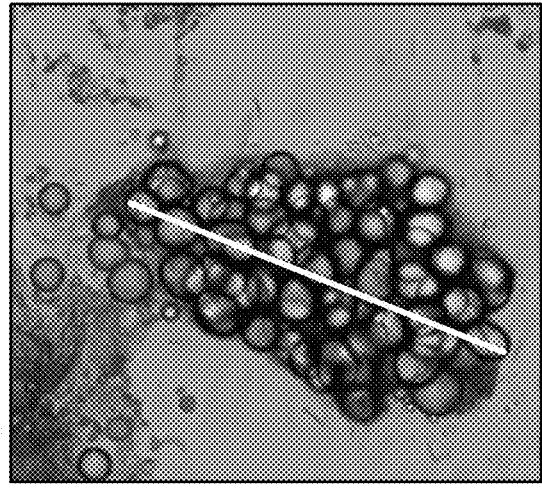
Figure 30:
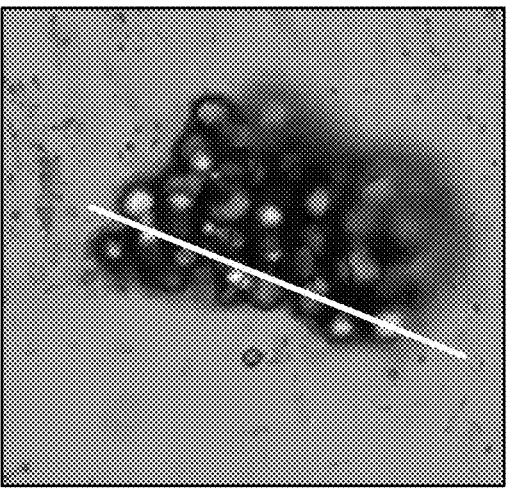

FIG. 30 was generated using automated brightfield microscopy. These images, read from left to right and top to bottom, show shrinkage of the transfected WAT in one day intervals from the start to the end point at t+6 days after treatment as described above with a 2 μg dose of mRNA of SEQ ID NO: 6 encapsulated in LNP I of component ratio (C14-4:DSPC:Cholesterol:PEG/Lipid Conjugate) of 35:16:46.5:2.5. The white line in the upper left panel of FIG. 30 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly one and a half times the diameter of the cluster.

Figure 31:
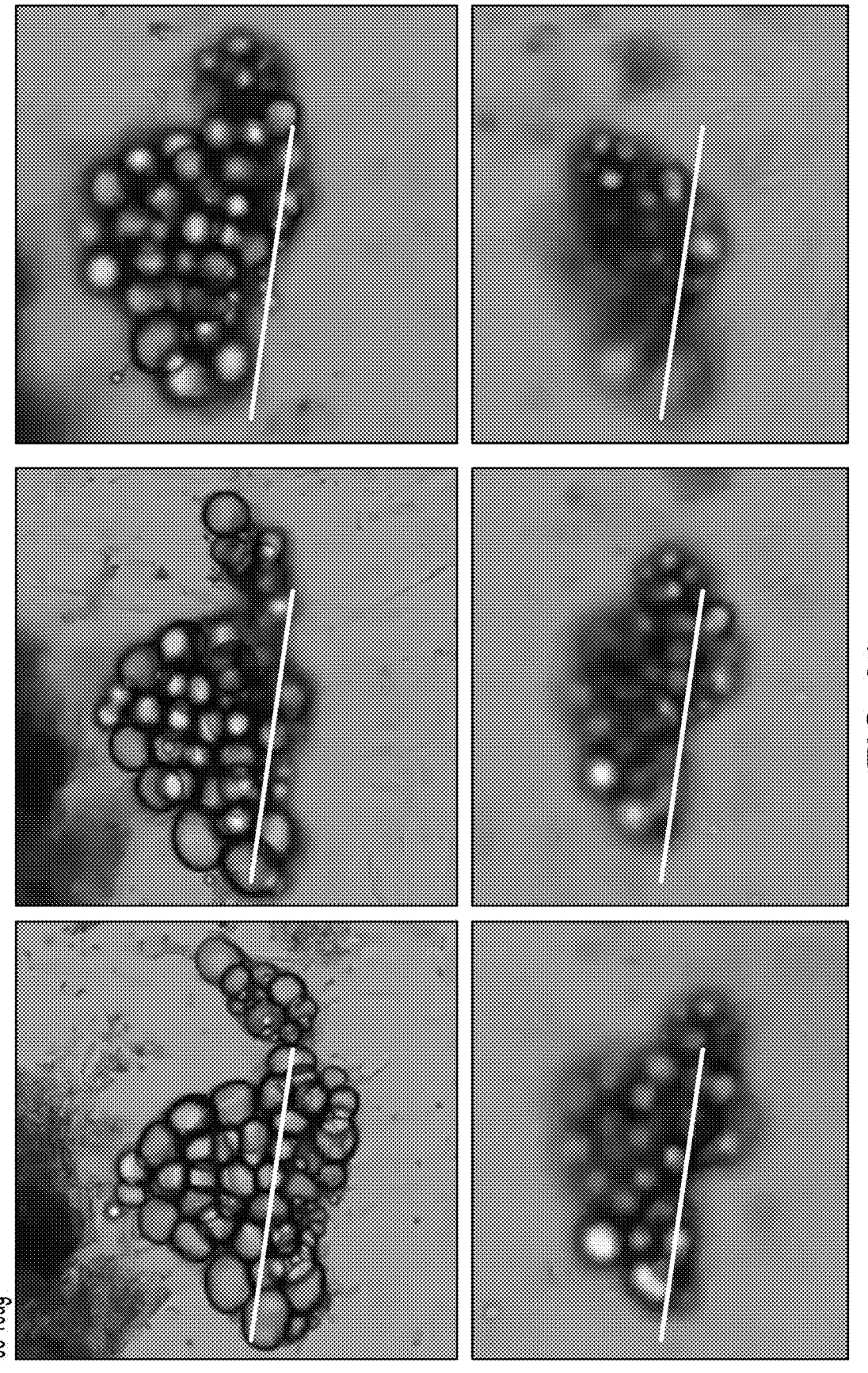
FIG. 31 is a series of time lapse images of cells derived from human white adipose tissue beginning at 24 hours after transfection with 10 μg of mRNA of SEQ ID NO: 6 encapsulated in LNP C14-4. Top row, from left to right: Day 1, Day 2, Day 3. Bottom row, from left to right: Day 4, Day 5, Day 6.

FIG. 31 was generated using automated brightfield microscopy. These images, read from left to right and top to bottom, show shrinkage of the transfected WAT in one day intervals from the start to the end point at t+6 days after treatment as described above with a 10 μg dose of mRNA of SEQ ID NO: 6 encapsulated in LNP I of component ratio (C14-4:DSPC:Cholesterol:PEG/Lipid Conjugate) of 35:16:46.5:2.5. The white line in the upper left panel of FIG. 31 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly one and a half times the diameter of the cluster.

Figure 32:
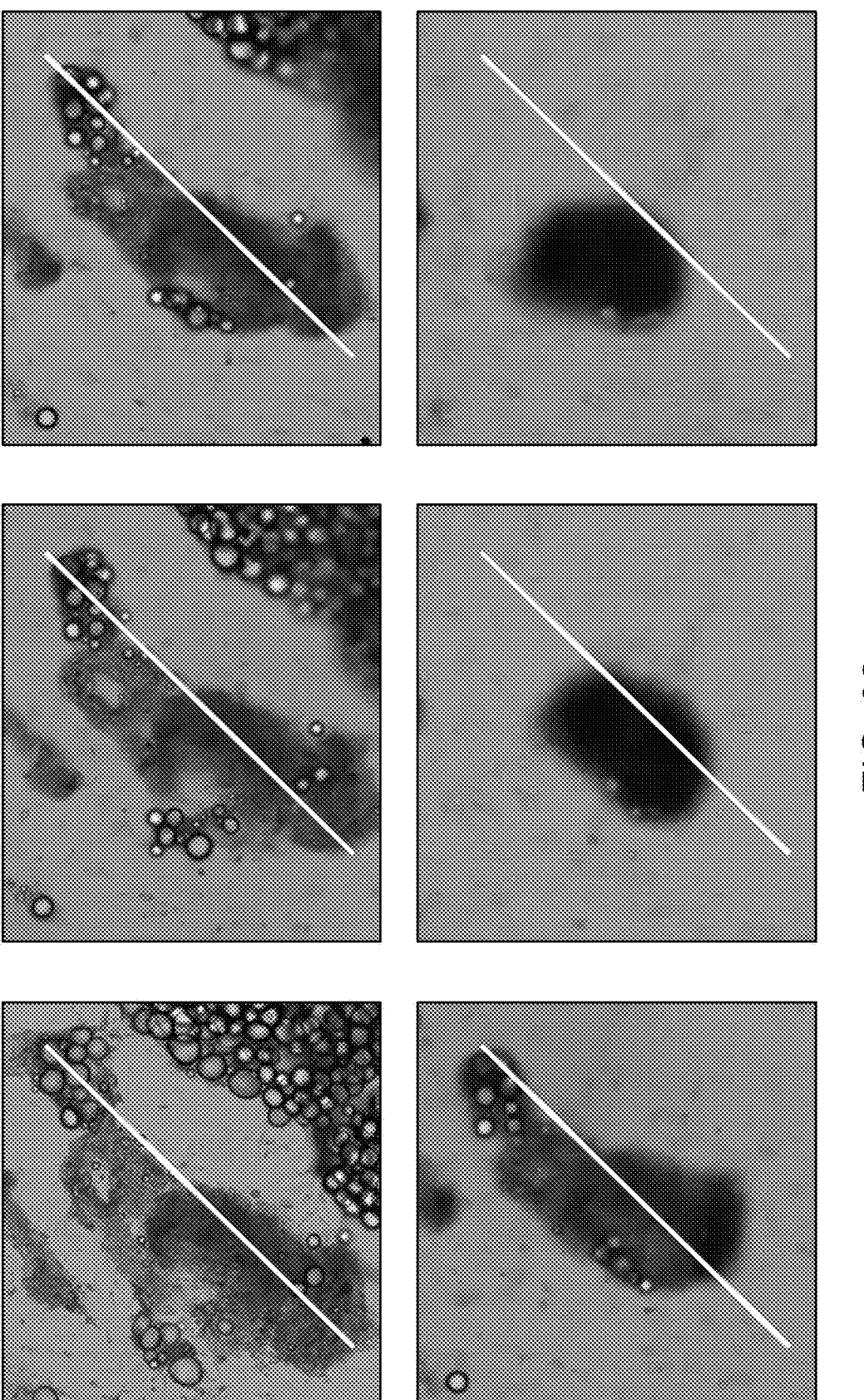
FIG. 32 is a series of time lapse images of cells derived from human white adipose tissue beginning at 24 hours after transfection with 10 μg of mRNA of SEQ ID NO: 14 encapsulated in LNP C14-4. Top row, from left to right: Day 1, Day 2, Day 3. Bottom row, from left to right: Day 4, Day 5, Day 6.

FIG. 32 was generated using automated brightfield microscopy. These images, read from left to right and top to bottom, show shrinkage of the transfected WAT in one day intervals from the start to the end point at t+6 days after treatment as described above with a 10 μg dose of mRNA of SEQ ID NO: 14 encapsulated in LNP I of component ratio (C14-4:DSPC:Cholesterol:PEG/Lipid Conjugate) of 35:16: 46.5:2.5. The white line in the upper left panel of FIG. 32 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly twice the diameter of the cluster.

Figure 33:
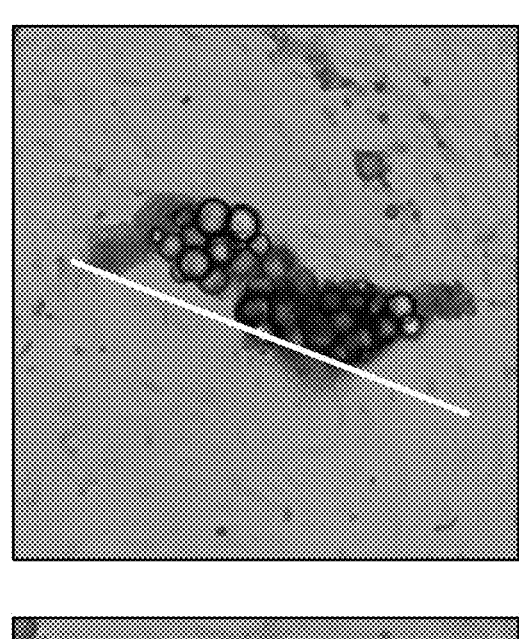
FIG. 33 is a series of time lapse images of cells derived from human white adipose tissue beginning at 24 hours after transfection with 2 μg of mRNA of SEQ ID NO: 16 encapsulated in LNP C14-4. Top row, from left to right: Day 1, Day 2, Day 3. Bottom row, from left to right: Day 4, Day 5, Day 6.
Figure 33:
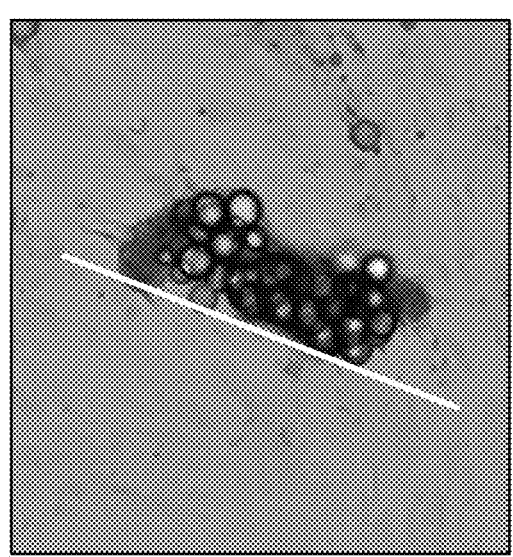
Figure 33:
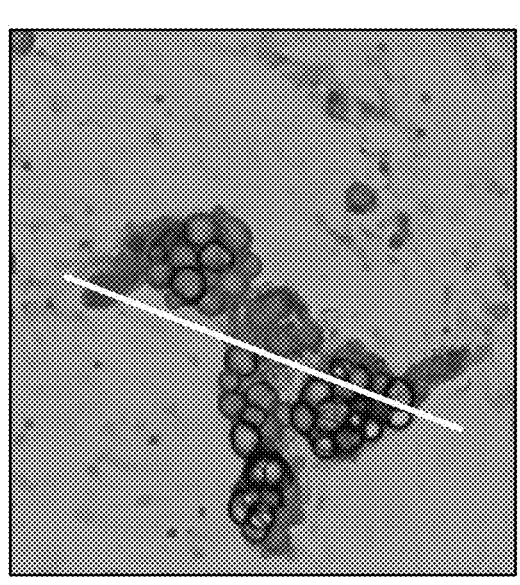
Figure 33:
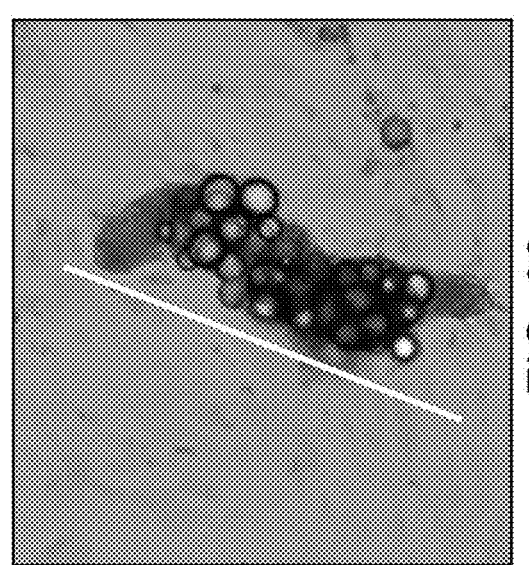
Figure 33:
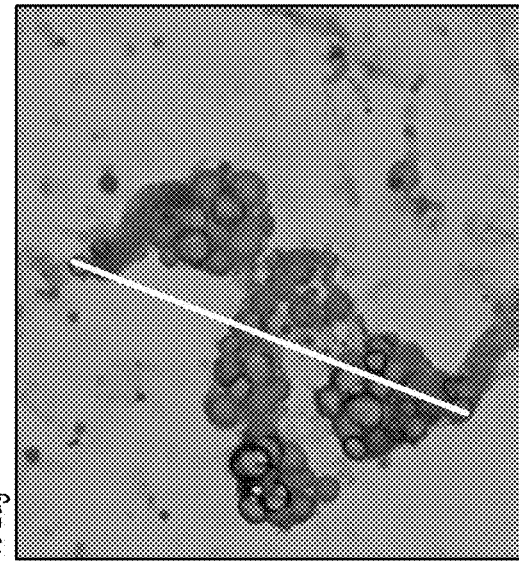
Figure 33:
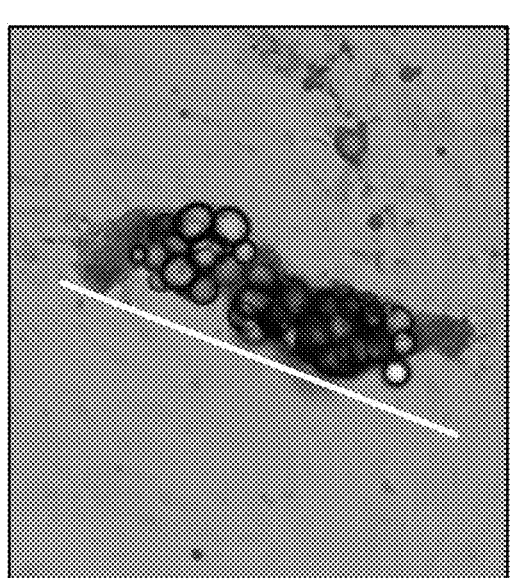

FIG. 33 was generated using automated brightfield microscopy. These images, read from left to right and top to bottom, show shrinkage of the transfected WAT in one day intervals from the start to the end point at t+6 days after treatment as described above with a 2 μg dose of mRNA of SEQ ID NO: 16 encapsulated in LNP I of component ratio (C14-4:DSPC:Cholesterol:PEG/Lipid Conjugate) of 35:16: 46.5:2.5. The white line in the upper left panel of FIG. 31 drawn diagonally across the cluster of cells is replicated in each of the succeeding images. The length and position of the line as well as the magnification of the cell cluster depicted are held constant throughout the images. The white line serves as a reference point to demonstrate the degree of shrinkage of the cell cluster over the period of treatment. In the first image, the line spans the entire cluster. In the last image, the line is roughly one and a half times the diameter of the cluster.

Example 9

Synthetic mRNA of SEQ ID NO: 130 expressing UCP1 was synthesized via in vitro transcription from a linearized DNA plasmid. The synthetic mRNA was encapsulated into lipid nanoparticles of LNP I. Subcutaneous fat was donated by a patient undergoing elective surgery under an IRB-approved protocol. The fat was stabilized for long-term ex vivo culture. The ex vivo fat was treated with the packaged mRNA at a dose of 10 μg per 100 mg of ex vivo fat. Brightfield microscopy images were captured every 4 to 6 hours using an automated system for a total of 6 days (144 hours). In FIG. 27, every treated fat cluster shrank significantly with a majority of the unilocular adipocytes shrinking to the point where they could no longer be visually identified as mature, unilocular adipocytes.

Example 10

Synthetic mRNA of SEQ ID NO: 3 expressing UCP1 was synthesized via in vitro transcription from a linearized DNA plasmid. The synthetic mRNA was encapsulated into lipid nanoparticles of LNP I, yielding a drug candidate test article. Subcutaneous fat was donated by a patient undergoing elective surgery under an IRB-approved protocol. The fat was stabilized for long-term ex vivo culture. The ex vivo fat was treated with the drug candidate test article at a dose of 10 μg drug candidate per 100 mg of ex vivo fat. Brightfield microscopy images were captured every 4 to 6 hours using an automated system for a total of 6 days (144 hours). In FIG. 28, every treated fat cluster shrank significantly with a majority of the unilocular adipocytes shrinking to the point where they could no longer be visually identified as mature, unilocular adipocytes.

Example 11

Synthetic mRNA of SEQ ID NO: 4 expressing UCP1 was synthesized via in vitro transcription from a linearized DNA plasmid. The synthetic mRNA was encapsulated into lipid nanoparticles of LNP I. Subcutaneous fat was donated by a patient undergoing elective surgery under an IRB-approved protocol. The fat was stabilized for long-term ex vivo culture. The ex vivo fat was treated with the packaged mRNA at a dose of 10 μg per 100 mg of ex vivo fat. Brightfield microscopy images were captured every 4 to 6 hours using an automated system for a total of 6 days (144 hours). In FIG. 29, every treated fat cluster shrank significantly with a majority of the unilocular adipocytes shrinking to the point where they could no longer be visually identified as mature, unilocular adipocytes.

Example 12

Synthetic mRNA of SEQ ID NO: 6 expressing UCP1 was synthesized via in vitro transcription from a linearized DNA plasmid. The synthetic mRNA was encapsulated into lipid nanoparticles of LNP I, yielding a drug candidate test article. Subcutaneous fat was donated by a patient undergoing elective surgery under an IRB-approved protocol. The fat was stabilized for long-term ex vivo culture. The ex vivo fat was treated with the packaged mRNA at a dose of 2 μg per 100 mg of ex vivo fat. Brightfield microscopy images were captured every 4 to 6 hours using an automated system for a total of 6 days (144 hours). In FIG. 30, every treated fat cluster shrank significantly with a majority of the unilocular adipocytes shrinking to the point where they could no longer be visually identified as mature, unilocular adipocytes.

Example 13

Synthetic mRNA of SEQ ID NO: 6 expressing UCP1 was synthesized via in vitro transcription from a linearized DNA plasmid. The synthetic mRNA was encapsulated into lipid nanoparticles of LNP I. Subcutaneous fat was donated by a patient undergoing elective surgery under an IRB-approved protocol. The fat was stabilized for long-term ex vivo culture. The ex vivo fat was treated with the packaged mRNA at a dose of 10 μg per 100 mg of ex vivo fat. Brightfield microscopy images were captured every 4 to 6 hours using an automated system for a total of 6 days (144 hours). In FIG. 31, every treated fat cluster shrank significantly with a majority of the unilocular adipocytes shrinking to the point where they could no longer be visually identified as mature, unilocular adipocytes.

Example 14

Synthetic mRNA of SEQ ID NO: 14 expressing UCP1 was synthesized via in vitro transcription from a linearized DNA plasmid. The synthetic mRNA was encapsulated into lipid nanoparticles of LNP I. Subcutaneous fat was donated by a patient undergoing elective surgery under an IRB-approved protocol. The fat was stabilized for long-term ex vivo culture. The ex vivo fat was treated with the packaged mRNA at a dose of 10 μg per 100 mg of ex vivo fat. Brightfield microscopy images were captured every 4 to 6 hours using an automated system for a total of 6 days (144 hours). In FIG. 32, every treated fat cluster shrank significantly with a majority of the unilocular adipocytes shrinking to the point where they could no longer be visually identified as mature, unilocular adipocytes.

Example 15

Synthetic mRNA of SEQ ID NO: 16 expressing UCP1 was synthesized via in vitro transcription from a linearized DNA plasmid. The synthetic mRNA was encapsulated into lipid nanoparticles of LNP I. Subcutaneous fat was donated by a patient undergoing elective surgery under an IRB-approved protocol. The fat was stabilized for long-term ex vivo culture. The ex vivo fat was treated with the packaged mRNA at a dose of 2 µg per 100 mg of ex vivo fat. Brightfield microscopy images were captured every 4 to 6 hours using an automated system for a total of 6 days (144 hours). In FIG. 33, every treated fat cluster shrank significantly with a majority of the unilocular adipocytes shrinking to the point where they could no longer be visually identified as mature, unilocular adipocytes.

SEQUENCES

Sequence total quantity: 130 (Sequences are shown 5' to 3')

| SEQ ID NO | | RNA Sequence |
|---|---|---|
| 130 | mol_type = RNA origin = synthetic construct | GAGACCCAAGCUGGCUAGCGGAAUUCGUCGACUGGAUCCGGUAC CGAGGAGAUCUGCCGCCGCGAUCGCCAUGGGCGGGCUGACAGCC AGCGACGUGCACCCAACCCUGGGGAGUGCAGCUGUUUUCCGCCGG CAUUGCUGCCUGUCUGGCUGAUGUGAUCACUUUCCCACUGGACA CAGCUAAAGUGCGGCUGCAGGUGCAGGGCGAGUGCCCAACAAGC UCUGUGAUCAGGUACAAGGGCGUGCUGGGGACCAUCACCGCCGU GGUGAAGACCGAGGGCAGAAUGAAACUGUAUAGUGGGUCUUCCCG CCGGCCUGCAGAGACAGAUUUCUAGCGCCUCACUGCGCAUUGGC CUGUAUGAUACAGUGCAGGAGUUUCUGACUGCCGGCAAGGAAAC UGCUCCAUCCCUGGGCAGCAAAAUCCUGGCCGGACUCACAACUG GCGGCGUGGCCGUCUUCAUCGGGCAGCCCACUGAGGUGGUGAAG GUGCGCCUGCAGGCCCAGAGCCACUUGCAUGGGAUCAAACCCAG AUACACAGGAACCUACAACGCUUACAGAAUCAUCGCCACCACCG AGGGCCUGACUGGGCUGUGGAAGGGCACUACCCCAAACCUGAUG CGGAGUGUGAUCAUUAAUUGUACUGAGCUGGUGACCUAUGAUC UGAUGAAGGAGGCCUUUGUGAAGAACAACAUCCUGGCCGACGAC GUGCCUUGUCACCUGGUGAGCGCCCUGAUCGCCGGCUUCUGCGC CACAGCCAUGAGCUCCCCCGUGGACGUGGUGAAGACAAGAUUCA UCAAUAGCCCACCUGGCCAGUAUAAAUCCGUGCCUAAUUGCGCC AUGAAGGUGUUCACCAAUGAGGGGCCCACCGCCUUUUUCAAGGG GCUGGUGCCCUCCUUCCUGAGGCUGGGCAGUUGGAACGUGAUCA UGUUCGUGUGUUUCGAACAGCUGAAAAGAGAGCUGUCCAAGUCU AGACAGACCAUGGACUGCGCCACAUGAUGACCCGGGAGGGCCCG CGGCCGCUCGAGUCUAGAGGGCCCGUUUAAACGUCUGAGUGGGC GGCGAAUUCAAAAAAAAAAAAAAAAAAAAAAAAAAAAAAAAAAA AAAAAAAAAAAAAAAAAAAAAAAAAAAAAAAAAAAA |
| 1 | mol_type = RNA origin = synthetic construct | GGAGAAUUCGUCGACUGGAUCCGGUACCGAGGAGAUCUGCCGCC GCGAUCGCCAUGGGCGGGCUGACAGCCAGCGACGUGCACCCAAC CCUGGGGAGUGCAGCUGUUUUCCGCCGGCAUUGCUGCCUGUCUGG CUGAUGUGAUCACUUUCCCACUGGACACAGCUAAAGUGCGGCUG CAGGUGCAGGGCGAGUGCCCAACAAGCUCUGUGAUCAGGUACAA GGGCGUGCUGGGGACCAUCACCGCCGUGGUGAAGACCGAGGGCA GAAUGAAACUGUAUAGUGGGUCUUCCCGCCGGCCUGCAGAGACAG AUUUCUAGCGCCUCACUGCGCAUUGGCCUGUAUGAUACAGUGCA GGAGUUUCUGACUGCCGGCAAGGAAACUGCUCCAUCCCUGGGCA GCAAAAUCCUGGCCGGACUCACAACUGGCGGCGUGGCCGUCUUC AUCGGGCAGCCCACUGAGGUGGUGAAGGUGCGCCUGCAGGCCCA GAGCCACUUGCAUGGGAUCAAACCCAGAUACACAGGAACCUACA ACGCUUACAGAAUCAUCGCCACCACCGAGGGCCUGACUGGGCUG UGGAAGGGCACUACCCCAAACCUGAUGCGGAGUGUGAUCAUUAA UUGUACUGAGCUGGUGACCUAUGAUCUGAUGAAGGAGGCCUUU GUGAAGAACAACAUCCUGGCCGACGACGUGCCUUGUCACCUGGU GAGCGCCCUGAUCGCCGGCUUCUGCGCCACAGCCAUGAGCUCCC CCGUGGACGUGGUGAAGACAAGAUUCAUCAAUAGCCCACCUGGC CAGUAUAAAUCCGUGCCUAAUUGCGCCAUGAAGGUGUUCACCAA UGAGGGGCCCACCGCCUUUUUCAAGGGGCUGGUGCCCUCCUUCC UGAGGCUGGGCAGUUGGAACGUGAUCAUGUUCGUGUGUUUCGA ACAGCUGAAAAGAGAGCUGUCCAAGUCUAGACAGACCAUGGACU GCGCCACAUGAUGACCCGGGGAUCCAAAAAAAAAAAAAAAAAAAA AAAAAAAAAAAAAAAAAAAAAAAAAAAAAAAAAAAAAAAAAAAA AAAAAAAAAAAAAAAAAAAAAAAAAAAAGAGAGCUCUAGAGU CGACCUGCAGGCAUGCAAGCUUCUCGAGAUGUGAGCAAAAGGCC AGCAAAAGGCCAGGAACCGUAAAAAGGCCGCGUUGCUGGCGUUU UUCCAUAGGCUCCGCCCCCCUGACGAGCAUCACAAAAAUCGACG CUCAAGUCAGAGGUGGCGAAACCCGACAGGACUAUAAAGAUACC AGGCGUUUCCCCCUGGAAGCUCCCUCGUGCGCUCUCCUGUUCCG ACCCUGCCGCUUACCGGAUACCUGUCCGCCUUUCUCCCUUCGGG AAGCGUGGCGCUUUCUCAUAGCUCACGCUGUAGGUAUCUCAGUU CGGUGUAGGUCGUUCGCUCCAAGCUGGGCUGUGUGCACGAACCC |

-continued

| SEQ ID NO | | RNA Sequence |
|---|---|---|
| | | CCCGUUCAGCCCGACCGCUGCGCCUUAUCCGGUAACUAUCGUCU |
| | | UGAGUCCAACCCGGUAAGACACGACUUAUCGCCACUGGCAGCAG |
| | | CCACUGGUAACAGGAUUAGCAGAGCGAGGUAUGUAGGCGGUGCU |
| | | ACAGAGUUCUUGAAGUGGUGGCCUAACUACGGCUACACUAGAAG |
| | | AACAGUAUUUGGUAUCUGCGCUCUGCUGAAGCCAGUUACCUUCG |
| | | GAAAAAGAGUUGGUAGCUCUUGAUCCGGCAAACAAACCACCGCU |
| | | GGUAGCGGUGGUUUUUUUGUUUGCAAGCAGCAGAUUACGCGCA |
| | | GAAAAAAAGGAUCUCAAGAAGAUCCUUUGAUCUUUUCUACGGG |
| | | GUCUGACGCUCAGUGGAACGAAAACUCACGUUAAGGGAUUUUGG |
| | | UCAUGAGCCUAGGCGCCGUCCCGUCAAGUCAGCGUAAUGCUCUG |
| | | CCAGUGUUACAACCAAUUAACCAAUUCUGAUUAGAAAAACUCAU |
| | | CGAGCAUCAAAUGAAACUGCAAUUUAUUCAUAUCAGGAUUAUCA |
| | | AUACCAUAUUUUUGAAAAAGCCGUUUCUGUAAUGAAGGAGAAA |
| | | ACUCACCGAGGCAGUUCCAUAGGAUGGCAAGAUCCUGGUAUCGG |
| | | UCUGCGAUUCCGACUCGUCCAACAUCAAUACAACCUAUUAAUUU |
| | | CCCCUCGUCAAAAAUAAGGUUAUCAAGUGAGAAAUCACCAUGAG |
| | | UGACGACUGAAUCCGGUGAGAAUGGCAAAAGCUUAUGCAUUUCU |
| | | UUCCAGACUUGUUCAACAGGCCAGCCAUUACGCUCGUCAUCAAA |
| | | AUCACUCGCAUCAACCAAACCGUUAUUCAUUCGUGAUUGCGCCU |
| | | GAGCGAGACGAAAUACGCGAUCGCUGUUAAAAGGACAAUUACAA |
| | | ACAGGAAUCGAAUGCAACCGGCGCAGGAACACUGCCAGCGCAUC |
| | | AACAAUAUUUUCACCUGAAUCAGGAUAUUCUUCUAAUACCUGGA |
| | | AUGCUGUUUUCCCGGGGAUCGCAGUGGUGAGUAACCAUGCAUCA |
| | | UCAGGAGUACGGAUAAAAUGCUUGAUGGUCGGAAGAGGCAUAA |
| | | AUUCCGUCAGCCAGUUUAGUCUGACCAUCUCAUCUGUAACAUCA |
| | | UUGGCAACGCUACCUUUGCCAUGUUUCAGAAACAACUCUGGCGC |
| | | AUCGGGCUUCCCAUAAAGUCGAUAGAUUGUCGCACCUGAUUGCC |
| | | CGACAUUAUCGCGAGCCCAUUUAUACCCAUAUAAAUCAGCAUCC |
| | | AUGUUGGAAUUUAAUCGCGGCCUUGAGCAAGACGUUUCCCGUUG |
| | | AAUAUGGCUCAUAACACCCCUUGUAUUACUGUUUAUGUAAGCAG |
| | | ACAGUUUUAUUGUUCAUGAUGAUAUAUUUUUAUCUUGUGCAAU |
| | | GUAACAUCAGAGAUUUUGAGACACAACGUG |
| 2 | mol_type = RNA origin = synthetic construct | AUGGGCGGGCUGACAGCCAGCGACGUGCACCCAACCCUGGGGAGU |
| | | GCAGCUGUUUUCCGCCGGCAUUGCUGCCUGUCUGGCUGAUGUGA |
| | | UCACUUUCCCACUGGACACAGCUAAAGUGCGGCUGCAGGUGCAG |
| | | GGCGAGUGCCCAACAAGCUCUGUGAUCAGGUACAAGGGCGUGCU |
| | | GGGGACCAUCACCGCCGUGGUGAAGACCGAGGGCAGAAUGAAAC |
| | | UGUAUAGUGGUCUUCCCGCCGGCCUGCAGAGACAGAUUUCUAGC |
| | | GCCUCACUGCGCAUUGGCCUGUAUGAUACAGUGCAGGAGUUUCU |
| | | GACUGCCGGCAAGGAAACUGCUCCAUCCCUGGGCAGCAAAAUCC |
| | | UGGCCGGACUCACAACUGGCGGCGUGGCCGUCUUCAUCGGGCAG |
| | | CCCACUGAGGUGGUGAAGGUGCGCCUGCAGGCCCAGAGCCACUU |
| | | GCAUGGGAUCAAACCCAGAUACACAGGAACCUACAACGCUUACA |
| | | GAAUCAUCGCCACCACCGAGGGCCUGACUGGGCUGUGGAAGGGC |
| | | ACUACCCCAAACCUGAUGCGGAGUGUGAUCAUUAAUUGUACUGA |
| | | GCUGGUGACCUAUGAUCUGAUGAAGGAGGCCUUUGUGAAGAAC |
| | | AACAUCCUGGCCGACGACGUGCCUUGUCACCUGGUGAGCGCCCU |
| | | GAUCGCCGGCUUCUGCGCCACAGCCAUGAGCUCCCCCGUGGACG |
| | | UGGUGAAGACAAGAUUCAUCAAUAGCCCACCUGGCCAGUAUAAA |
| | | UCCGUGCCUAAUUGCGCCAUGAAGGUGUUCACCAAUGAGGGGCC |
| | | CACCGCCUUUUUCAAGGGGCUGGUGCCCUCCUUCCUGAGGCUGG |
| | | GCAGUUGGAACGUGAUCAUGUUCGUGUGUUUCGAACAGCUGAA |
| | | AAGAGAGCUGUCCAAGUCUAGACAGACCAUGGACUGCGCCACAU |
| | | GAUGAC |
| 3 | mol_type = RNA origin = synthetic construct | CGCCAUGGGCGGGCUGACAGCCAGCGACGUGCACCCAACCCUGG |
| | | GAGUGCAGCUGUUUUCCGCCGGCAUUGCUGCCUGUCUGGCUGAU |
| | | GUGAUCACUUUCCCACUGGACACAGCUAAAGUGCGGCUGCAGGU |
| | | GCAGGGCGAGUGCCCAACAAGCUCUGUGAUCAGGUACAAGGGCG |
| | | UGCUGGGGACCAUCACCGCCGUGGUGAAGACCGAGGGCAGAAUG |
| | | AAACUGUAUAGUGGUCUUCCCGCCGGCCUGCAGAGACAGAUUUC |
| | | UAGCGCCUCACUGCGCAUUGGCCUGUAUGAUACAGUGCAGGAGU |
| | | UUCUGACUGCCGGCAAGGAAACUGCUCCAUCCCUGGGCAGCAAA |
| | | AUCCUGGCCGGACUCACAACUGGCGGCGUGGCCGUCUUCAUCGG |
| | | GCAGCCCACUGAGGUGGUGAAGGUGCGCCUGCAGGCCCAGAGCC |
| | | ACUUGCAUGGGAUCAAACCCAGAUACACAGGAACCUACAACGCU |
| | | UACAGAAUCAUCGCCACCACCGAGGGCCUGACUGGGCUGUGGAA |
| | | GGGCACUACCCCAAACCUGAUGCGGAGUGUGAUCAUUAAUUGUA |
| | | CUGAGCUGGUGACCUAUGAUCUGAUGAAGGAGGCCUUUGUGAA |
| | | GAACAACAUCCUGGCCGACGACGUGCCUUGUCACCUGGUGAGCG |
| | | CCCUGAUCGCCGGCUUCUGCGCCACAGCCAUGAGCUCCCCCGUG |
| | | GACGUGGUGAAGACAAGAUUCAUCAAUAGCCCACCUGGCCAGUA |
| | | UAAAUCCGUGCCUAAUUGCGCCAUGAAGGUGUUCACCAAUGAGG |

-continued

| SEQ ID NO | | RNA Sequence |
|---|---|---|
| | | GGCCCACCGCCUUUUUCAAGGGGCUGGUGCCCUCCUUCCUGAGG CUGGGCAGUUGGAACGUGAUCAUGUUCGUGUGUUUCGAACAGCU GAAAAGAGAGCUGUCCAAGUCUAGACAGACCAUGGACUGCGCCA CAUGAUGAC |
| 4 | mol_type = RNA origin = synthetic construct | CAAGAUGGGCGGGCUGACAGCCAGCGACGUGCACCCAACCCUGG GAGUGCAGCUGUUUUCCGCCGGCAUUGCUGCCUGUCUGGCUGAU GUGAUCACUUUCCCACUGGACACAGCUAAAGUGCGGCUGCAGGU GCAGGGCGAGUGCCCAACAAGCUCUGUGAUCAGGUACAAGGGCG UGCUGGGGACCAUCACCGCCGUGGUGAAGACCGAGGGCAGAAUG AAACUGUAUAGUGGUCUUCCCGCCGGCCUGCAGAGACAGAUUUC UAGCGCCUCACUGCGCAUUGGCCUGUAUGAUACAGUGCAGGAGU UUCUGACUGCCGGCAAGGAAACUGCUCCAUCCCUGGGCAGCAAA AUCCUGGCCGGACUCACAACUGGCGGCGUGGCCGUCUUCAUCGG GCAGCCCACUGAGGUGGUGAAGGUGCGCCUGCAGGCCCAGAGCC ACUUGCAUGGGAUCAAACCCAGAUACACAGGAACCUACAACGCU UACAGAAUCAUCGCCACCACCGAGGGCCUGACUGGGCUGUGGAA GGGCACUACCCCAAACCUGAUGCGGAGUGUGAUCAUUAAUUGUA CUGAGCUGGUGACCUAUGAUCUGAUGAAGGAGGCCUUUGUGAA GAACAACAUCCUGGCCGACGACGUGCCCUUGUCACCUGGUGAGCG CCCUGAUCGCCGGCUUCUGCGCCACAGCCAUGAGCUCCCCCGUG GACGUGGUGAAGACAAGAUUCAUCAAUAGCCCACCUGGCCAGUA UAAAUCCGUGCCUAAUUGCGCCAUGAAGGUGUUCACCAAUGAGG GGCCCACCGCCUUUUUCAAGGGGCUGGUGCCCUCCUUCCUGAGG CUGGGCAGUUGGAACGUGAUCAUGUUCGUGUGUUUCGAACAGCU GAAAAGAGAGCUGUCCAAGUCUAGACAGACCAUGGACUGCGCCA CAUGAUGAC |
| 5 | mol_type = RNA origin = synthetic construct | AGAGGGUCCUGCUGGCGCGAGGGUGGGUAGGAGGGGACGCGGG GACUCGGCCCCCAACACCGCGCUCCGUCUGCAGCCGCCGCCUCUG CACCGCCGCUGCCCGGCGGUCGGUUCAAAAAACAGAAAUCGGGU UUGCUGCCCGGCGGACAGGCGUGAAGAGCAAGGGAAAGGAACUU CCUCCACCUUCGGGGCUGGAGCCCUUUUCCUCUGCAUCUCCAGU CUCUGAGUGAAGAUGGGGGGCUGACAGCCAGCGACGUGCACCC AACCCUGGGAGUGCAGCUGUUUUCCGCCGGCAUUGCUGCCUGUC UGGCUGAUGUGAUCACUUUCCCACUGGACACAGCUAAAGUGCGG CUGCAGGUGCAGGGCGAGUGCCCAACAAGCUCUGUGAUCAGGUA CAAGGGCGUGCUGGGGACCAUCACCGCCGUGGUGAAGACCGAGG GCAGAAUGAAACUGUAUAGUGGUCUUCCCGCCGGCCUGCAGAGA CAGAUUUCUAGCGCCUCACUGCGCAUUGGCCUGUAUGAUACAGU GCAGGAGUUUCUGACUGCCGGCAAGGAAACUGCUCCAUCCCUGG GCAGCAAAAUCCUGGCCGGACUCACAACUGGCGGCGUGGCCGUC UUCAUCGGGCAGCCCACUGAGGUGGUGAAGGUGCGCCUGCAGGC CCAGAGCCACUUGCAUGGGAUCAAACCCAGAUACACAGGAACCU ACAACGCUUACAGAAUCAUCGCCACCACCGAGGGCCUGACUGGG CUGUGGAAGGGCACUACCCCAAACCUGAUGCGGAGUGUGAUCAU UAAUUGUACUGAGCUGGUGACCUAUGAUCUGAUGAAGGAGGCC UUUGUGAAGAACAACAUCCUGGCCGACGACGUGCCUUGUCACCU GGUGAGCGCCCUGAUCGCCGGCUUCUGCGCCACAGCCAUGAGCU CCCCCGUGGACGUGGUGAAGACAAGAUUCAUCAAUAGCCCACCU GGCCAGUAUAAAUCCGUGCCUAAUUGCGCCAUGAAGGUGUUCAC CAAUGAGGGGCCCACCGCCUUUUUCAAGGGGCUGGUGCCCUCCU UCCUGAGGCUGGGCAGUUGGAACGUGAUCAUGUUCGUGUGUUUC GAACAGCUGAAAAGAGAGCUGUCCAAGUCUAGACAGACCAUGGA CUGCGCCACAUGAUGAC |
| 6 | mol_type = RNA origin = synthetic construct | ACAGCACCCUCCUGAAAACUGCAGCUUCCUUCUCACCUUGAAGA AUAAUCCUAGAAAACUCACAAAAUGGGCGGGCUGACAGCCAGCG ACGUGCACCCAACCCUGGGAGUGCAGCUGUUUUCCGCCGGCAUU GCUGCCUGUCUGGCUGAUGUGAUCACUUUCCCACUGGACACAGC UAAAGUGCGGCUGCAGGUGCAGGGCGAGUGCCCAACAAGCUCUG UGAUCAGGUACAAGGGCGUGCUGGGGACCAUCACCGCCGUGGUG AAGACCGAGGGCAGAAUGAAACUGUAUAGUGGUCUUCCCGCCGG CCUGCAGAGACAGAUUUCUAGCGCCUCACUGCGCAUUGGCCUGU AUGAUACAGUGCAGGAGUUUCUGACUGCCGGCAAGGAAACUGCU CCAUCCCUGGGCAGCAAAAUCCUGGCCGGACUCACAACUGGCGG CGUGGCCGUCUUCAUCGGGCAGCCCACUGAGGUGGUGAAGGUGC GCCUGCAGGCCCAGAGCCACUUGCAUGGGAUCAAACCCAGAUAC ACAGGAACCUACAACGCUUACAGAAUCAUCGCCACCACCGAGGG CCUGACUGGGCUGUGGAAGGGCACUACCCCAAACCUGAUGCGGA GUGUGAUCAUUAAUUGUACUGAGCUGGUGACCUAUGAUCUGAU GAAGGAGGCCUUUGUGAAGAACAACAUCCUGGCCGACGACGUGC CUUGUCACCUGGUGAGCGCCCUGAUCGCCGGCUUCUGCGCCACA GCCAUGAGCUCCCCCGUGGACGUGGUGAAGACAAGAUUCAUCAA UAGCCCACCUGGCCAGUAUAAAUCCGUGCCUAAUUGCGCCAUGA AGGUGUUCACCAAUGAGGGGCCCACCGCCUUUUUCAAGGGGCUG |

-continued

| SEQ ID NO | | RNA Sequence |
|---|---|---|
| | | GUGCCCUCCUUCCUGAGGCUGGGCAGUUGGAACGUGAUCAUGUU |
| | | CGUGUGUUUCGAACAGCUGAAAAGAGAGCUGUCCAAGUCUAGAC |
| | | AGACCAUGGACUGCGCCACAUGAUGAC |
| 7 | mol_type = RNA origin = synthetic construct | AUGGGCGGGCUGACAGCCAGCGACGUGCACCCAACCCUGGGAGU |
| | | GCAGCUGUUUUCCGCCGGCAUUGCUGCCUGUCUGGCUGAUGUGA |
| | | UCACUUUCCCACUGGACACAGCUAAAGUGCGGCUGCAGGUGCAG |
| | | GGCGAGUGCCCAACAAGCUCUGUGAUCAGGUACAAGGGCGUGCU |
| | | GGGGACCAUCACCGCCGUGGUGAAGACCGAGGGCAGAAUGAAAC |
| | | UGUAUAGUGGGUCUUCCCGCCGGCCUGCAGAGACAGAUUUCUAGC |
| | | GCCUCACUGCGCAUUGGCCUGUAUGAUACAGUGCAGGAGUUUCU |
| | | GACUGCCGGCAAGGAAACUGCUCCAUCCCUGGGCAGCAAAAUCC |
| | | UGGCCGGACUCACAACUGGCGGCGUGGCCGUCUUCAUCGGGCAG |
| | | CCCACUGAGGUGGUGAAGGUGCGCCUGCAGGCCCAGAGCCACUU |
| | | GCAUGGGAUCAAACCCAGAUACACAGGAACCUACAACGCUUACA |
| | | GAAUCAUCGCCACCACCGAGGGCCUGACUGGGCUGUGGAAGGGC |
| | | ACUACCCCAAACCUGAUGCGGAGUGUGAUCAUUAAUUGUACUGA |
| | | GCUGGUGACCUAUGAUCUGAUGAAGGAGGCCUUUGUGAAGAAC |
| | | AACAUCCUGGCCGACGACGUGCCUUGUCACCUGGUGAGCGCCCU |
| | | GAUCGCCGGCUUCUGCGCCACAGCCAUGAGCUCCCCCGUGGACG |
| | | UGGUGAAGACAAGAUUCAUCAAUAGCCCACCUGGCCAGUAUAAA |
| | | UCCGUGCCUAAUUGCGCCAUGAAGGUGUUCACCAAUGAGGGGCC |
| | | CACCGCCUUUUUCAAGGGGCUGGUGCCCUCCUUCCUGAGGCUGG |
| | | GCAGUUGGAACGUGAUCAUGUUCGUGUGUUUCGAACAGCUGAA |
| | | AAGAGAGCUGUCCAAGUCUAGACAGACCAUGGACUGCGCCACAU |
| | | GAUGACUCAGCUUCAAGAAAAUGAUGUAACAUACCAGUGGGAA |
| | | UCUUGCUGACUGGAUCAUAAAAACAAACAAAACUUAUUCACUUA |
| | | UUUUAACCUAAAAAGAUAAAGGAAUUUUGGCAGAGAAUUUUGG |
| | | ACUUUUUUAUAUAAAAAAGAGGAAAAUUAAUGCCUAUUUCAUA |
| | | UAACUUUUUUUUUUUCUCAGUGUCUUAAGAAGGGGAAAGCAAA |
| | | ACAUUCAGCAUAUACCCUGGCAAAUGUAAUGCAGAUAAGCUACU |
| | | GCAUUUGACCAUUUCUGGAGUGCAAUUGUGUGAAUGAAUGUGA |
| | | AGAACUUUAACAUGUUUUAAUUACAAUUCCAACUGGUGGAAAA |
| | | GAAACUGAGUGAAAUGCAGUUUAUAUUUAUAAAAUACUUAAAAA |
| | | UGAAGUUAUUAAAAAUAUUAGUUUUUAUUAACCACAGUUGUCA |
| | | GUUAAUAUAUUCAAUAAAGUAUUGCUAAUACCUUUUAAA |
| 8 | mol_type = RNA origin = synthetic construct | CGCCAUGGGCGGGCUGACAGCCAGCGACGUGCACCCAACCCUGG |
| | | GAGUGCAGCUGUUUUCCGCCGGCAUUGCUGCCUGUCUGGCUGAU |
| | | GUGAUCACUUUCCCACUGGACACAGCUAAAGUGCGGCUGCAGGU |
| | | GCAGGGCGAGUGCCCAACAAGCUCUGUGAUCAGGUACAAGGGCG |
| | | UGCUGGGGACCAUCACCGCCGUGGUGAAGACCGAGGGCAGAAUG |
| | | AAACUGUAUAGUGGGUCUUCCCGCCGGCCUGCAGAGACAGAUUUC |
| | | UAGCGCCUCACUGCGCAUUGGCCUGUAUGAUACAGUGCAGGAGU |
| | | UUCUGACUGCCGGCAAGGAAACUGCUCCAUCCCUGGGCAGCAAA |
| | | AUCCUGGCCGGACUCACAACUGGCGGCGUGGCCGUCUUCAUCGG |
| | | GCAGCCCACUGAGGUGGUGAAGGUGCGCCUGCAGGCCCAGAGCC |
| | | ACUUGCAUGGGAUCAAACCCAGAUACACAGGAACCUACAACGCU |
| | | UACAGAAUCAUCGCCACCACCGAGGGCCUGACUGGGCUGUGGAA |
| | | GGGCACUACCCCAAACCUGAUGCGGAGUGUGAUCAUUAAUUGUA |
| | | CUGAGCUGGUGACCUAUGAUCUGAUGAAGGAGGCCUUUGUGAA |
| | | GAACAACAUCCUGGCCGACGACGUGCCUUGUCACCUGGUGAGCG |
| | | CCCUGAUCGCCGGCUUCUGCGCCACAGCCAUGAGCUCCCCCGUG |
| | | GACGUGGUGAAGACAAGAUUCAUCAAUAGCCCACCUGGCCAGUA |
| | | UAAAUCCGUGCCUAAUUGCGCCAUGAAGGUGUUCACCAAUGAGG |
| | | GGCCCACCGCCUUUUUCAAGGGGCUGGUGCCCUCCUUCCUGAGG |
| | | CUGGGCAGUUGGAACGUGAUCAUGUUCGUGUGUUUCGAACAGCU |
| | | GAAAAGAGAGCUGUCCAAGUCUAGACAGACCAUGGACUGCGCCA |
| | | CAUGAUGACUCAGCUUCAAGAAAAUGAUGUAACAUACCAGUGGG |
| | | AAUCUUGCUGACUGGAUCAUAAAAACAAACAAAACUUAUUCACU |
| | | UAUUUUAACCUAAAAAGAUAAAGGAAUUUUGGCAGAGAAUUUU |
| | | GGACUUUUUUAUAUAAAAAAGAGGAAAAUUAAUGCCUAUUUCA |
| | | UAUAACUUUUUUUUUUUCUCAGUGUCUUAAGAAGGGGAAAGCA |
| | | AAACAUUCAGCAUAUACCCUGGCAAAUGUAAUGCAGAUAAGCUA |
| | | CUGCAUUUGACCAUUUCUGGAGUGCAAUUGUGUGAAUGAAUGU |
| | | GAAGAACUUUAACAUGUUUUAAUUACAAUUCCAACUGGUGGAA |
| | | AAGAAACUGAGUGAAAUGCAGUUUAUAUUUAUAAAAUACUUAAA |
| | | AAUGAAGUUAUUAAAAAUAUUAGUUUUUAUUAACCACAGUUGU |
| | | CAGUUAAUAUAUUCAAUAAAGUAUUGCUAAUACCUUUUAAA |
| 9 | mol_type = RNA origin = synthetic construct | CAAGAUGGGCGGGCUGACAGCCAGCGACGUGCACCCAACCCUGG |
| | | GAGUGCAGCUGUUUUCCGCCGGCAUUGCUGCCUGUCUGGCUGAU |
| | | GUGAUCACUUUCCCACUGGACACAGCUAAAGUGCGGCUGCAGGU |
| | | GCAGGGCGAGUGCCCAACAAGCUCUGUGAUCAGGUACAAGGGCG |
| | | UGCUGGGGACCAUCACCGCCGUGGUGAAGACCGAGGGCAGAAUG |
| | | AAACUGUAUAGUGGGUCUUCCCGCCGGCCUGCAGAGACAGAUUUC |

-continued

| SEQ ID NO | | RNA Sequence |
|---|---|---|

UAGCGCCUCACUGCGCAUUGGCCUGUAUGAUACAGUGCAGGAGU
UUCUGACUGCCGGCAAGGAAACUGCUCCAUCCCUGGGCAGCAAA
AUCCUGGCCGGACUCACAACUGGCGGCGUGGCCGUCUUCAUCGG
GCAGCCCACUGAGGUGGUGAAGGUGCGCCUGCAGGCCCAGAGCC
ACUUGCAUGGGAUCAAACCCAGAUACACAGGAACCUACAACGCU
UACAGAAUCAUCGCCACCACCGAGGGCCUGACUGGGCUGUGGAA
GGGCACUACCCCAAACCUGAUGCGGAGUGUGAUCAUUAAUUGUA
CUGAGCUGGUGACCUAUGAUCUGAUGAAGGAGGCCUUUGUGAA
GAACAACAUCCUGGCCGACGACGUGCCUUGUCACCUGGUGAGCG
CCCUGAUCGCCGGCUUCUGCGCCACAGCCAUGAGCUCCCCCGUG
GACGUGGUGAAGACAAGAUUCAUCAAUAGCCCACCUGGCCAGUA
UAAAUCCGUGCCUAAUUGCGCCAUGAAGGUGUUCACCAAUGAGG
GGCCCACCGCCUUUUUCAAGGGGCUGGUGCCCUCCUUCCUGAGG
CUGGGCAGUUGGAACGUGAUCAUGUUCGUGUGUUUCGAACAGCU
GAAAAGAGAGCUGUCCAAGUCUAGACAGACCAUGGACUGCGCCA
CAUGAUGACUCAGCUUCAAGAAAAUGAUGUAACAUACCAGUGGG
AAUCUUGCUGACUGGAUCAUAAAAACAAACAAAACUUAUUCACU
UAUUUUAACCUAAAAAGAUAAAGGAAUUUUGGCAGAGAAUUUU
GGACUUUUUAUAUAAAAAAGAGGAAAAUUAAUGCCUAUUUCA
UAUAACUUUUUUUUUUUCUCAGUGUCUUAAGAAGGGGAAAGCA
AAACAUUCAGCAUAUACCCUGGCAAAUGUAAUGCAGAUAAGCUA
CUGCAUUUGACCAUUUCUGGAGUGCAAUUGUGUGAAUGAAUGU
GAAGAACUUUAACAUGUUUUAAUUACAAUUCCAACUGGUGGAA
AAGAAACUGAGUGAAAUGCAGUUUAUAUUUAUAAAUACUUAAA
AAUGAAGUUAUUAAAAAUAUUAGUUUUUAUUAACCACAGUUGU
CAGUUAAUAUAUUCAAUAAAGUAUUGCUAAUACCUUUUAAA

| 10 | mol_type = RNA origin = synthetic construct | AGAGGGUCCUGCUGGCGCGAGGGUGGGUAGGAGGGGACGCGGG GACUCGGCCCCCAACACCGCGCUCCGUCUGCAGCCGCCGCCUCUG CACCGCCGCUGCCCGGCGGUCGGUUCAAAAAACAGAAAUCGGGU UUGCUGCCCGGCGGACAGGCGUGAAGAGCAAGGGAAAGGAACUU CCUCCACCUUCGGGGCUGGAGCCCUUUUUCCUCUGCAUCUCCAGU CUCUGAGUGAAGAUGGGCGGGCUGACAGCCAGCGACGUGCACCC AACCCUGGGGAGUGCAGCUGUUUUCCGCCGGCAUUGCUGCCUGUC UGGCUGAUGUGAUCACUUUCCCACUGGACACAGCUAAAGUGCGG CUGCAGGUGCAGGGCGAGUGCCCAACAAGCUCUGUGAUCAGGUA CAAGGGCGUGCUGGGGGACCAUCACCGCCGUGGUGAAGACCGAGG GCAGAAUGAAACUGUAUAGUGGGUCUUCCCGCCGGCCUGCAGAGA CAGAUUUCUAGCGCCUCACUGCGCAUUGGCCUGUAUGAUACAGU GCAGGAGUUUCUGACUGCCGGCAAGGAAACUGCUCCAUCCCUGG GCAGCAAAAUCCUGGCCGGACUCACAACUGGCGGCGUGGCCGUC UUCAUCGGGCAGCCCACUGAGGUGGUGAAGGUGCGCCUGCAGGC CCAGAGCCACUUGCAUGGGAUCAAACCCAGAUACACAGGAACCU ACAACGCUUACAGAAUCAUCGCCACCACCGAGGGCCUGACUGGG CUGUGGAAGGGCACUACCCCAAACCUGAUGCGGAGUGUGAUCAU UAAUUGUACUGAGCUGGUGACCUAUGAUCUGAUGAAGGAGGCC UUUGUGAAGAACAACAUCCUGGCCGACGACGUGCCUUGUCACCU GGUGAGCGCCCUGAUCGCCGGCUUCUGCGCCACAGCCAUGAGCU CCCCCGUGGACGUGGUGAAGACAAGAUUCAUCAAUAGCCCACCU GGCCAGUAUAAAUCCGUGCCUAAUUGCGCCAUGAAGGUGUUCAC CAAUGAGGGGGCCCACCGCCUUUUUCAAGGGGCUGGUGCCCUCCU UCCUGAGGCUGGGCAGUUGGAACGUGAUCAUGUUCGUGUGUUUC GAACAGCUGAAAAGAGAGCUGUCCAAGUCUAGACAGACCAUGGA CUGCGCCACAUGAUGACUCAGCUUCAAGAAAAUGAUGUAACAUA CCAGUGGGAAUCUUGCUGACUGGAUCAUAAAAACAAACAAAACU UAUUCACUUAUUUUAACCUAAAAAGAUAAAGGAAUUUUGGCAG AGAAUUUUGGACUUUUUUAUAUAAAAAAGAGGAAAAUUAAUGC CUAUUUCAUAUAACUUUUUUUUUUUCUCAGUGUCUUAAGAAGG GGAAAGCAAAACAUUCAGCAUAUACCCUGGCAAAUGUAAUGCAG AUAAGCUACUGCAUUUGACCAUUUCUGGAGUGCAAUUGUGUGA AUGAAUGUGAAGAACUUUAACAUGUUUUAAUUACAAUUCCAAC UGGUGGAAAAGAAACUGAGUGAAAUGCAGUUUAUAUUUAUAAA UACUUAAAAAUGAAGUUAUUAAAAAUAUUAGUUUUUAUUAACC ACAGUUGUCAGUUAAUAUAUUCAAUAAAGUAUUGCUAAUACCU UUUAAA |
| 11 | mol_type = RNA origin = synthetic construct | ACAGCACCCUCCUGAAAACUGCAGCUUCCUUCUCACCUUGAAGA AUAAUCCUAGAAAACUCACAAAAUGGGCGGGCUGACAGCCAGCG ACGUGCACCCAACCCUGGGGAGUGCAGCUGUUUUCCGCCGGCAUU GCUGCCUGUCUGGCUGAUGUGAUCACUUUCCCACUGGACACAGC UAAAGUGCGGCUGCAGGUGCAGGGCGAGUGCCCAACAAGCUCUG UGAUCAGGUACAAGGGCGUGCUGGGGGACCAUCACCGCCGUGGUG AAGACCGAGGGCAGAAUGAAACUGUAUAGUGGGUCUUCCCGCCGG CCUGCAGAGACAGAUUUCUAGCGCCUCACUGCGCAUUGGCCUGU AUGAUACAGUGCAGGAGUUUCUGACUGCCGGCAAGGAAACUGCU CCAUCCCUGGGGCAGCAAAAUCCUGGCCGGACUCACAACUGGCGG |

-continued

| SEQ ID NO | | RNA Sequence |
|---|---|---|
| | | CGUGGCCGUCUUCAUCGGGCAGCCCACUGAGGUGGUGAAGGUGC |
| | | GCCUGCAGGCCCAGAGCCACUUGCAUGGGAUCAAACCCAGAUAC |
| | | ACAGGAACCUACAACGCUUACAGAAUCAUCGCCACCACCGAGGG |
| | | CCUGACUGGGCUGUGGAAGGGCACUACCCCAAACCUGAUGCGGA |
| | | GUGUGAUCAUUAAUUGUACUGAGCUGGUGACCUAUGAUCUGAU |
| | | GAAGGAGGCCUUUGUGAAGAACAACAUCCUGGCCGACGACGUGC |
| | | CUUGUCACCUGGUGAGCGCCCUGAUCGCCGGCUUCUGCGCCACA |
| | | GCCAUGAGCUCCCCCGUGGACGUGGUGAAGACAAGAUUCAUCAA |
| | | UAGCCCACCUGGCCAGUAUAAAUCCGUGCCUAAUUGCGCCAUGA |
| | | AGGUGUUCACCAAUGAGGGGCCCACCGCCUUUUUCAAGGGGCUG |
| | | GUGCCCUCCUUCCUGAGGCUGGGCAGUUGGAACGUGAUCAUGUU |
| | | CGUGUGUUUCGAACAGCUGAAAAGAGAGCUGUCCAAGUCUAGAC |
| | | AGACCAUGGACUGCGCCACAUGAUGACUCAGCUUCAAGAAAAUG |
| | | AUGUAACAUACCAGUGGGAAUCUUGCUGACUGGAUCAUAAAAAC |
| | | AAACAAAACUUAUUCACUUAUUUUAACCUAAAAAAGAUAAAGGA |
| | | AUUUUGGCAGAGAAUUUUGGACUUUUUUUAUAUAAAAAAGAGGA |
| | | AAAUUAAUGCCUAUUUCAUAUAACUUUUUUUUUUUUCUCAGUGU |
| | | CUUAAGAAGGGGAAAGCAAAACAUUCAGCAUAUACCCUGGCAAA |
| | | UGUAAUGCAGAUAAGCUACUGCAUUUGACCAUUUCUGGAGUGCA |
| | | AUUGUGUGAAUGAAUGUGAAGAACUUUAACAUGUUUUAAUUAC |
| | | AAUUCCAACUGGUGGAAAAGAAACUGAGUGAAAUGCAGUUUAU |
| | | AUUUAUAAAUACUUAAAAAUGAAGUUAUUAAAAAUAUUAGUUU |
| | | UUAUUAACCACAGUUGUCAGUUAAUAUAUUCAAUAAAGUAUUG |
| | | CUAAUACCUUUUAAA |
| 12 | mol_type = RNA origin = synthetic construct | AUGGGCGGGCUGACAGCCAGCGACGUGCACCCAACCCUGGGGAGU |
| | | GCAGCUGUUUUCCGCCGGCAUUGCUGCCUGUCUGGCUGAUGUGA |
| | | UCACUUUCCCACUGGACACAGCUAAAGUGCGGCUGCAGGUGCAG |
| | | GGCGAGUGCCCAACAAGCUCUGUGAUCAGGUACAAGGGCGUGCU |
| | | GGGGACCAUCACCGCCGUGGUGAAGACCGAGGGCAGAAUGAAAC |
| | | UGUAUAGUGGGUCUUCCCGCCGGCCUGCAGAGACAGAUUUCUAGC |
| | | GCCUCACUGCGCAUUGGCCUGUAUGAUACAGUGCAGGAGUUUCU |
| | | GACUGCCGGCAAGGAAACUGCUCCAUCCCUGGGCAGCAAAAUCC |
| | | UGGCCGGACUCACAACUGGCGGCGUGGCCGUCUUCAUCGGGCAG |
| | | CCCACUGAGGUGGUGAAGGUGCGCCUGCAGGCCCAGAGCCACUU |
| | | GCAUGGGAUCAAACCCAGAUACACAGGAACCUACAACGCUUACA |
| | | GAAUCAUCGCCACCACCGAGGGCCUGACUGGGCUGUGGAAGGGC |
| | | ACUACCCCAAACCUGAUGCGGAGUGUGAUCAUUAAUUGUACUGA |
| | | GCUGGUGACCUAUGAUCUGAUGAAGGAGGCCUUUGUGAAGAAC |
| | | AACAUCCUGGCCGACGACGUGCCUUGUCACCUGGUGAGCGCCCU |
| | | GAUCGCCGGCUUCUGCGCCACAGCCAUGAGCUCCCCCGUGGACG |
| | | UGGUGAAGACAAGAUUCAUCAAUAGCCCACCUGGCCAGUAUAAA |
| | | UCCGUGCCUAAUUGCGCCAUGAAGGUGUUCACCAAUGAGGGGCC |
| | | CACCGCCUUUUUCAAGGGGCUGGUGCCCUCCUUCCUGAGGCUGG |
| | | GCAGUUGGAACGUGAUCAUGUUCGUGUGUUUCGAACAGCUGAA |
| | | AAGAGAGCUGUCCAAGUCUAGACAGACCAUGGACUGCGCCACAU |
| | | GAUGACCUCGAGCUGGUACUGCAUGCACGCAAUGCUAGCUGCCC |
| | | CUUUCCCGUCCUGGGUACCCCGAGUCUCCCCCGACCUCGGGUCCC |
| | | AGGUAUGCUCCCACCUCCACCUGCCCCACUCACCACCUCUGCUAG |
| | | UUCCAGACACCUCCCAAGCACGCAGCAAUGCAGCUCAAAACGCU |
| | | UAGCCUAGCCACACCCCCACGGGAAACAGCAGUGAUUAACCUUU |
| | | AGCAAUAAACGAAAGUUUAACUAAGCUAUACUAACCCCAGGGUU |
| | | GGUCAAUUUCGUGCCAGCCACACCCUGGAGCUAGC |
| 13 | mol_type = RNA origin = synthetic construct | CGCCAUGGGCGGGCUGACAGCCAGCGACGUGCACCCAACCCUGG |
| | | GAGUGCAGCUGUUUUCCGCCGGCAUUGCUGCCUGUCUGGCUGAU |
| | | GUGAUCACUUUCCCACUGGACACAGCUAAAGUGCGGCUGCAGGU |
| | | GCAGGGCGAGUGCCCAACAAGCUCUGUGAUCAGGUACAAGGGCG |
| | | UGCUGGGGACCAUCACCGCCGUGGUGAAGACCGAGGGCAGAAUG |
| | | AAACUGUAUAGUGGGUCUUCCCGCCGGCCUGCAGAGACAGAUUUC |
| | | UAGCGCCUCACUGCGCAUUGGCCUGUAUGAUACAGUGCAGGAGU |
| | | UUCUGACUGCCGGCAAGGAAACUGCUCCAUCCCUGGGCAGCAAA |
| | | AUCCUGGCCGGACUCACAACUGGCGGCGUGGCCGUCUUCAUCGG |
| | | GCAGCCCACUGAGGUGGUGAAGGUGCGCCUGCAGGCCCAGAGCC |
| | | ACUUGCAUGGGAUCAAACCCAGAUACACAGGAACCUACAACGCU |
| | | UACAGAAUCAUCGCCACCACCGAGGGCCUGACUGGGCUGUGGAA |
| | | GGGCACUACCCCAAACCUGAUGCGGAGUGUGAUCAUUAAUUGUA |
| | | CUGAGCUGGUGACCUAUGAUCUGAUGAAGGAGGCCUUUGUGAA |
| | | GAACAACAUCCUGGCCGACGACGUGCCUUGUCACCUGGUGAGCG |
| | | CCCUGAUCGCCGGCUUCUGCGCCACAGCCAUGAGCUCCCCCGUG |
| | | GACGUGGUGAAGACAAGAUUCAUCAAUAGCCCACCUGGCCAGUA |
| | | UAAAUCCGUGCCUAAUUGCGCCAUGAAGGUGUUCACCAAUGAGG |
| | | GGCCCACCGCCUUUUUCAAGGGGCUGGUGCCCUCCUUCCUGAGG |
| | | CUGGGCAGUUGGAACGUGAUCAUGUUCGUGUGUUUCGAACAGCU |
| | | GAAAAGAGAGCUGUCCAAGUCUAGACAGACCAUGGACUGCGCCA |
| | | CAUGAUGACCUCGAGCUGGUACUGCAUGCACGCAAUGCUAGCUG |

-continued

| SEQ ID NO | | RNA Sequence |
|---|---|---|
| | | CCCCUUUCCCGUCCUGGGUACCCCGAGUCUCCCCCGACCUCGGGU |
| | | CCCAGGUAUGCUCCCACCUCCACCUGCCCCACUCACCACCUCUGC |
| | | UAGUUCCAGACACCUCCCAAGCACGCAGCAAUGCAGCUCAAAAC |
| | | GCUUAGCCUAGCCACACCCCCACGGGAAACAGCAGUGAUUAACC |
| | | UUUAGCAAUAAACGAAAGUUUAACUAAGCUAUACUAACCCCAGG |
| | | GUUGGUCAAUUUCGUGCCAGCCACACCCUGGAGCUAGC |
| 14 | mol_type = RNA origin = synthetic construct | CAAGAUGGGCGGGCUGACAGCCAGCGACGUGCACCCAACCCUGG |
| | | GAGUGCAGCUGUUUUCCGCCGGCAUUGCUGCCUGUCUGGCUGAU |
| | | GUGAUCACUUUCCCACUGGACACAGCUAAAGUGCGGCUGCAGGU |
| | | GCAGGGCGAGUGCCCAACAAGCUCUGUGAUCAGGUACAAGGGCG |
| | | UGCUGGGGACCAUCACCGCCGUGGUGAAGACCGAGGGCAGAAUG |
| | | AAACUGUAUAGUGGUCUUCCCGCCGGCCUGCAGAGACAGAUUUC |
| | | UAGCGCCUCACUGCGCAUUGGCCUGUAUGAUACAGUGCAGGAGU |
| | | UUCUGACUGCCGGCAAGGAAACUGCUCCAUCCCUGGGCAGCAAA |
| | | AUCCUGGCCGGACUCACAACUGGCGGCGUGGCCGUCUUCAUCGG |
| | | GCAGCCCACUGAGGUGGUGAAGGUGCGCCUGCAGGCCCAGAGCC |
| | | ACUUGCAUGGGAUCAAACCCAGAUACACAGGAACCUACAACGCU |
| | | UACAGAAUCAUCGCCACCACCGAGGGCCUGACUGGGCUGUGGAA |
| | | GGGCACUACCCCAAACCUGAUGCGGAGUGUGAUCAUUAAUUGUA |
| | | CUGAGCUGGUGACCUAUGAUCUGAUGAAGGAGGCCUUUGUGAA |
| | | GAACAACAUCCUGGCCGACGACGUGCCUUGUCACCUGGUGAGCG |
| | | CCCUGAUCGCCGGCUUCUGCGCCACAGCCAUGAGCUCCCCCGUG |
| | | GACGUGGUGAAGACAAGAUUCAUCAAUAGCCCACCUGGCCAGUA |
| | | UAAAUCCGUGCCUAAUUGCGCCAUGAAGGUGUUCACCAAUGAGG |
| | | GGCCCACCGCCUUUUUCAAGGGGCUGGUGCCCUCCUUCCUGAGG |
| | | CUGGGCAGUUGGAACGUGAUCAUGUUCGUGUGUUUCGAACAGCU |
| | | GAAAAGAGAGCUGUCCAAGUCUAGACAGACCAUGGACUGCGCCA |
| | | CAUGAUGACCUCGAGCUGGUACUGCAUGCACGCAAUGCUAGCUG |
| | | CCCCUUUCCCGUCCUGGGUACCCCGAGUCUCCCCCGACCUCGGGU |
| | | CCCAGGUAUGCUCCCACCUCCACCUGCCCCACUCACCACCUCUGC |
| | | UAGUUCCAGACACCUCCCAAGCACGCAGCAAUGCAGCUCAAAAC |
| | | GCUUAGCCUAGCCACACCCCCACGGGAAACAGCAGUGAUUAACC |
| | | UUUAGCAAUAAACGAAAGUUUAACUAAGCUAUACUAACCCCAGG |
| | | GUUGGUCAAUUUCGUGCCAGCCACACCCUGGAGCUAGC |
| 15 | mol_type = RNA origin = synthetic construct | AGAGGGUCCUGCUGGCGCGAGGGUGGGGUAGGAGGGGACGCGGG |
| | | GACUCGGCCCCCAACACCGCGCUCCGUCUGCAGCCGCCGCCUCUG |
| | | CACCGCCGCUGCCCGGCGGUCGGGUCAAAAAACAGAAAUCGGGU |
| | | UUGCUGCCCGGCGGACAGGCGUGAAGAGCAAGGGAAAGGAACUU |
| | | CCUCCACCUUCGGGGCUGGAGCCCUUUUCCUCUGCAUCUCCAGU |
| | | CUCUGAGUGAAGAUGGGCGGGCUGACAGCCAGCGACGUGCACCC |
| | | AACCCUGGGAGUGCAGCUGUUUUCCGCCGGCAUUGCUGCCUGUC |
| | | UGGCUGAUGUGAUCACUUUCCCACUGGACACAGCUAAAGUGCGG |
| | | CUGCAGGUGCAGGGCGAGUGCCCAACAAGCUCUGUGAUCAGGUA |
| | | CAAGGGCGUGCUGGGGACCAUCACCGCCGUGGUGAAGACCGAGG |
| | | GCAGAAUGAAACUGUAUAGUGGUCUUCCCGCCGGCCUGCAGAGA |
| | | CAGAUUUCUAGCGCCUCACUGCGCAUUGGCCUGUAUGAUACAGU |
| | | GCAGGAGUUUCUGACUGCCGGCAAGGAAACUGCUCCAUCCCUGG |
| | | GCAGCAAAAUCCUGGCCGGACUCACAACUGGCGGCGUGGCCGUC |
| | | UUCAUCGGGCAGCCCACUGAGGUGGUGAAGGUGCGCCUGCAGGC |
| | | CCAGAGCCACUUGCAUGGGAUCAAACCCAGAUACACAGGAACCU |
| | | ACAACGCUUACAGAAUCAUCGCCACCACCGAGGGCCUGACUGGG |
| | | CUGUGGAAGGGCACUACCCCAAACCUGAUGCGGAGUGUGAUCAU |
| | | UAAUUGUACUGAGCUGGUGACCUAUGAUCUGAUGAAGGAGGCC |
| | | UUUGUGAAGAACAACAUCCUGGCCGACGACGUGCCUUGUCACCU |
| | | GGUGAGCGCCCUGAUCGCCGGCUUCUGCGCCACAGCCAUGAGCU |
| | | CCCCCGUGGACGUGGUGAAGACAAGAUUCAUCAAUAGCCCACCU |
| | | GGCCAGUAUAAAUCCGUGCCUAAUUGCGCCAUGAAGGUGUUCAC |
| | | CAAUGAGGGGCCCACCGCCUUUUUCAAGGGGCUGGUGCCCUCCU |
| | | UCCUGAGGCUGGGCAGUUGGAACGUGAUCAUGUUCGUGUGUUUC |
| | | GAACAGCUGAAAAGAGAGCUGUCCAAGUCUAGACAGACCAUGGA |
| | | CUGCGCCACAUGAUGACCUCGAGCUGGUACUGCAUGCACGCAAU |
| | | GCUAGCUGCCCCUUUCCCGUCCUGGGUACCCCGAGUCUCCCCCGA |
| | | CCUCGGGUCCCAGGUAUGCUCCCACCUCCACCUGCCCCACUCACC |
| | | ACCUCUGCUAGUUCCAGACACCUCCCAAGCACGCAGCAAUGCAG |
| | | CUCAAAACGCUUAGCCUAGCCACACCCCCACGGGAAACAGCAGU |
| | | GAUUAACCUUUAGCAAUAAACGAAAGUUUAACUAAGCUAUACU |
| | | AACCCCAGGGUUGGUCAAUUUCGUGCCAGCCACACCCUGGAGCU |
| | | AGC |
| 16 | mol_type = RNA origin = synthetic construct | ACAGCACCCUCCUGAAAACUGCAGCUUCCUUCUCACCUUGAAGA |
| | | AUAAUCCUAGAAAACUCACAAAAUGGGCGGGCUGACAGCCAGCG |
| | | ACGUGCACCCAACCCUGGGAGUGCAGCUGUUUUCCGCCGGCAUU |
| | | GCUGCCUGUCUGGCUGAUGUGAUCACUUUCCCACUGGACACAGC |
| | | UAAAGUGCGGCUGCAGGUGCAGGGCGAGUGCCCAACAAGCUCUG |

-continued

| SEQ ID NO | | RNA Sequence |
|---|---|---|
| | | UGAUCAGGUACAAGGGCGUGCUGGGGGACCAUCACCGCCGUGGUG |
| | | AAGACCGAGGGCAGAAUGAAACUGUAUAGUGGGUCUUCCCGCCGG |
| | | CCUGCAGAGACAGAUUUCUAGCGCCUCACUGCGCAUUGGCCUGU |
| | | AUGAUACAGUGCAGGAGUUUCUGACUGCCGGCAAGGAAACUGCU |
| | | CCAUCCCUGGGCAGCAAAAUCCUGGCCGGACUCACAACUGGCGG |
| | | CGUGGCCGUCUUCAUCGGGCAGCCCACUGAGGUGGUGAAGGUGC |
| | | GCCUGCAGGCCCAGAGCCACUUGCAUGGGAUCAAACCCAGAUAC |
| | | ACAGGAACCUACAACGCUUACAGAAUCAUCGCCACCACCGAGGG |
| | | CCUGACUGGGCUGUGGAAGGGCACUACCCCAAACCUGAUGCGGA |
| | | GUGUGAUCAUUAAUUGUACUGAGCUGGUGACCUAUGAUCUGAU |
| | | GAAGGAGGCCUUUGUGAAGAACAACAUCCUGGCCGACGACGUGC |
| | | CUUGUCACCUGGUGAGCGCCCUGAUCGCCGGCUUCUGCGCCACA |
| | | GCCAUGAGCUCCCCCGUGGACGUGGUGAAGACAAGAUUCAUCAA |
| | | UAGCCCACCUGGCCAGUAUAAAUCCGUGCCUAAUUGCGCCAUGA |
| | | AGGUGUUCACCAAUGAGGGGCCCACCGCCUUUUUCAAGGGGCUG |
| | | GUGCCCUCCUUCCUGAGGCUGGGCAGUUGGAACGUGAUCAUGUU |
| | | CGUGUGUUUCGAACAGCUGAAAAGAGAGCUGUCCAAGUCUAGAC |
| | | AGACCAUGGACUGCGCCACAUGAUGACCUCGAGCUGGUACUGCA |
| | | UGCACGCAAUGCUAGCUGCCCCUUUCCCGUCCUGGGUACCCCGA |
| | | GUCUCCCCCGACCUCGGGUCCCAGGUAUGCUCCCACCUCCACCUG |
| | | CCCCACUCACCACCUCUGCUAGUUCCAGACACCUCCCAAGCACGC |
| | | AGCAAUGCAGCUCAAAACGCUUAGCCUAGCCACACCCCCACGGG |
| | | AAACAGCAGUGAUUAACCUUUAGCAAUAAACGAAAGUUUAACU |
| | | AAGCUAUACUAACCCCAGGGUUGGUCAAUUUCGUGCCAGCCACA |
| | | CCCUGGAGCUAGC |
| 17 | mol_type = RNA origin = synthetic construct | AUGGGCGGGCUGACAGCCAGCGACGUGCACCCAACCCUGGGGAGU |
| | | GCAGCUGUUUUCCGCCGGCAUUGCUGCCUGUCUGGCUGAUGUGA |
| | | UCACUUUCCCACUGGACACAGCUAAAGUGCGGCUGCAGGUGCAG |
| | | GGCGAGUGCCCAACAAGCUCUGUGAUCAGGUACAAGGGCGUGCU |
| | | GGGGACCAUCACCGCCGUGGUGAAGACCGAGGGCAGAAUGAAAC |
| | | UGUAUAGUGGGUCUUCCCGCCGGCCUGCAGAGACAGAUUUCUAGC |
| | | GCCUCACUGCGCAUUGGCCUGUAUGAUACAGUGCAGGAGUUUCU |
| | | GACUGCCGGCAAGGAAACUGCUCCAUCCCUGGGCAGCAAAAUCC |
| | | UGGCCGGACUCACAACUGGCGGCGUGGCCGUCUUCAUCGGGCAG |
| | | CCCACUGAGGUGGUGAAGGUGCGCCUGCAGGCCCAGAGCCACUU |
| | | GCAUGGGAUCAAACCCAGAUACACAGGAACCUACAACGCUUACA |
| | | GAAUCAUCGCCACCACCGAGGGCCUGACUGGGCUGUGGAAGGGC |
| | | ACUACCCCAAACCUGAUGCGGAGUGUGAUCAUUAAUUGUACUGA |
| | | GCUGGUGACCUAUGAUCUGAUGAAGGAGGCCUUUGUGAAGAAC |
| | | AACAUCCUGGCCGACGACGUGCCUUGUCACCUGGUGAGCGCCCU |
| | | GAUCGCCGGCUUCUGCGCCACAGCCAUGAGCUCCCCCGUGGACG |
| | | UGGUGAAGACAAGAUUCAUCAAUAGCCCACCUGGCCAGUAUAAA |
| | | UCCGUGCCUAAUUGCGCCAUGAAGGUGUUCACCAAUGAGGGGCC |
| | | CACCGCCUUUUUCAAGGGGCUGGUGCCCUCCUUCCUGAGGCUGG |
| | | GCAGUUGGAACGUGAUCAUGUUCGUGUGUUUCGAACAGCUGAA |
| | | AAGAGAGCUGUCCAAGUCUAGACAGACCAUGGACUGCGCCACAU |
| | | GAUGACGCGCUCGCUUUCUUGCUGUCCAAUUUCUAUUAAAGGUUCC |
| | | UUUGUUCCCUAAGUCCAACUACUAAACUGGGGGAUAUUAUGAAG |
| | | GGCCUUGAGCAUCUGGAUUCUGCCUGCUCGCUUUCUUGCUGUCC |
| | | AAUUUCUAUUAAAGGUUCCUUUGUUCCCUAAGUCCAACUACUAA |
| | | ACUGGGGGAUAUUAUGAAGGGCCUUGAGCAUCUGGAUUCUGCCU |
| 18 | mol_type = RNA origin = synthetic construct | CGCCAUGGGCGGGCUGACAGCCAGCGACGUGCACCCAACCCUGG |
| | | GAGUGCAGCUGUUUUCCGCCGGCAUUGCUGCCUGUCUGGCUGAU |
| | | GUGAUCACUUUCCCACUGGACACAGCUAAAGUGCGGCUGCAGGU |
| | | GCAGGGCGAGUGCCCAACAAGCUCUGUGAUCAGGUACAAGGGCG |
| | | UGCUGGGGACCAUCACCGCCGUGGUGAAGACCGAGGGCAGAAUG |
| | | AAACUGUAUAGUGGGUCUUCCCGCCGGCCUGCAGAGACAGAUUUC |
| | | UAGCGCCUCACUGCGCAUUGGCCUGUAUGAUACAGUGCAGGAGU |
| | | UUCUGACUGCCGGCAAGGAAACUGCUCCAUCCCUGGGCAGCAAA |
| | | AUCCUGGCCGGACUCACAACUGGCGGCGUGGCCGUCUUCAUCGG |
| | | GCAGCCCACUGAGGUGGUGAAGGUGCGCCUGCAGGCCCAGAGCC |
| | | ACUUGCAUGGGAUCAAACCCAGAUACACAGGAACCUACAACGCU |
| | | UACAGAAUCAUCGCCACCACCGAGGGCCUGACUGGGCUGUGGAA |
| | | GGGCACUACCCCAAACCUGAUGCGGAGUGUGAUCAUUAAUUGUA |
| | | CUGAGCUGGUGACCUAUGAUCUGAUGAAGGAGGCCUUUGUGAA |
| | | GAACAACAUCCUGGCCGACGACGUGCCUUGUCACCUGGUGAGCG |
| | | CCCUGAUCGCCGGCUUCUGCGCCACAGCCAUGAGCUCCCCCGUG |
| | | GACGUGGUGAAGACAAGAUUCAUCAAUAGCCCACCUGGCCAGUA |
| | | UAAAUCCGUGCCUAAUUGCGCCAUGAAGGUGUUCACCAAUGAGG |
| | | GGCCCACCGCCUUUUUCAAGGGGCUGGUGCCCUCCUUCCUGAGG |
| | | CUGGGCAGUUGGAACGUGAUCAUGUUCGUGUGUUUCGAACAGCU |
| | | GAAAAGAGAGCUGUCCAAGUCUAGACAGACCAUGGACUGCGCCA |
| | | CAUGAUGACGCGCUCGCUUUCUUGCUGUCCAAUUUCUAUUAAAGGU |
| | | UCCUUUGUUCCCUAAGUCCAACUACUAAACUGGGGGAUAUUAUG |

-continued

| SEQ ID NO | | RNA Sequence |
|---|---|---|
| | | AAGGGCCUUGAGCAUCUGGAUUCUGCCUGCUCGCUUUCUUGCUG<br>UCCAAUUUCUAUUAAAGGUUCCUUUGUUCCCUAAGUCCAACUAC<br>UAAACUGGGGGAUAUUAUGAAGGGCCUUGAGCAUCUGGAUUCU<br>GCCU |
| 19 | mol_type = RNA<br>origin = synthetic construct | CAAGAUGGGCGGGCUGACAGCCAGCGACGUGCACCCAACCCUGG<br>GAGUGCAGCUGUUUUCCGCCGGCAUUGCUGCCUGUCUGGCUGAU<br>GUGAUCACUUUCCCACUGGACACAGCUAAAGUGCGGCUGCAGGU<br>GCAGGGCGAGUGCCCAACAAGCUCUGUGAUCAGGUACAAGGGCG<br>UGCUGGGGACCAUCACCGCCGUGGUGAAGACCGAGGGCAGAAUG<br>AAACUGUAUAGUGGUCUUCCCGCCGGCCUGCAGAGACAGAUUUC<br>UAGCGCCUCACUGCGCAUUGGCCUGUAUGAUACAGUGCAGGAGU<br>UUCUGACUGCCGGCAAGGAAACUGCUCCAUCCCUGGGCAGCAAA<br>AUCCUGGCCGGACUCACAACUGGCGGCGUGGCCGUCUUCAUCGG<br>GCAGCCCACUGAGGUGGUGAAGGUGCGCCUGCAGGCCCAGAGCC<br>ACUUGCAUGGGAUCAAACCCAGAUACACAGGAACCUACAACGCU<br>UACAGAAUCAUCGCCACCACCGAGGGCCUGACUGGGCUGUGGAA<br>GGGCACUACCCCAAACCUGAUGCGGAGUGUGAUCAUUAAUUGUA<br>CUGAGCUGGUGACCUAUGAUCUGAUGAAGGAGGCCUUUGUGAA<br>GAACAACAUCCUGGCCGACGACGUGCCUUGUCACCUGGUGAGCG<br>CCCUGAUCGCCGGCUUCUGCGCCACAGCCAUGAGCUCCCCCGUG<br>GACGUGGUGAAGACAAGAUUCAUCAAUAGCCCACCUGGCCAGUA<br>UAAAUCCGUGCCUAAUUGCGCCAUGAAGGUGUUCACCAAUGAGG<br>GGCCCACCGCCUUUUUCAAGGGGCUGGUGCCCUCCUUCCUGAGG<br>CUGGGCAGUUGGAACGUGAUCAUGUUCGUGUGUUUCGAACAGCU<br>GAAAAGAGAGCUGUCCAAGUCUAGACAGACCAUGGACUGCGCCA<br>CAUGAUGACGCUCGCUUUCUUGCUGUCCAAUUUCUAUUAAAGGU<br>UCCUUUGUUCCCUAAGUCCAACUACUAAACUGGGGGAUAUUAUG<br>AAGGGCCUUGAGCAUCUGGAUUCUGCCUGCUCGCUUUCUUGCUG<br>UCCAAUUUCUAUUAAAGGUUCCUUUGUUCCCUAAGUCCAACUAC<br>UAAACUGGGGGAUAUUAUGAAGGGCCUUGAGCAUCUGGAUUCU<br>GCCU |
| 20 | mol_type = RNA<br>origin = synthetic construct | AGAGGGUCCUGCUGGCGCGAGGGUGGGUAGGAGGGGACGCGGG<br>GACUCGGCCCCCAACACCGCGCUCCGUCUGCAGCCGCCGCCUCUG<br>CACCGCCGCUGCCCGGCGGUCGGUUCAAAAAACAGAAAUCGGGU<br>UUGCUGCCCGGCGGACAGGCGUGAAGAGCAAGGGAAAGGAACUU<br>CCUCCACCUUCGGGGCUGGAGCCCUUUUCCUCUGCAUCUCCAGU<br>CUCUGAGUGAAGAUGGGCGGGCUGACAGCCAGCGACGUGCACCC<br>AACCCUGGGGAGUGCAGCUGUUUUCCGCCGGCAUUGCUGCCUGUC<br>UGGCUGAUGUGAUCACUUUCCCACUGGACACAGCUAAAGUGCGG<br>CUGCAGGUGCAGGGCGAGUGCCCAACAAGCUCUGUGAUCAGGUA<br>CAAGGGCGUGCUGGGGACCAUCACCGCCGUGGUGAAGACCGAGG<br>GCAGAAUGAAACUGUAUAGUGGUCUUCCCGCCGGCCUGCAGAGA<br>CAGAUUUCUAGCGCCUCACUGCGCAUUGGCCUGUAUGAUACAGU<br>GCAGGAGUUUCUGACUGCCGGCAAGGAAACUGCUCCAUCCCUGG<br>GCAGCAAAAUCCUGGCCGGACUCACAACUGGCGGCGUGGCCGUC<br>UUCAUCGGGCAGCCCACUGAGGUGGUGAAGGUGCGCCUGCAGGC<br>CCAGAGCCACUUGCAUGGGAUCAAACCCAGAUACACAGGAACCU<br>ACAACGCUUACAGAAUCAUCGCCACCACCGAGGGCCUGACUGGG<br>CUGUGGAAGGGCACUACCCCAAACCUGAUGCGGAGUGUGAUCAU<br>UAAUUGUACUGAGCUGGUGACCUAUGAUCUGAUGAAGGAGGCC<br>UUUGUGAAGAACAACAUCCUGGCCGACGACGUGCCUUGUCACCU<br>GGUGAGCGCCCUGAUCGCCGGCUUCUGCGCCACAGCCAUGAGCU<br>CCCCCGUGGACGUGGUGAAGACAAGAUUCAUCAAUAGCCCACCU<br>GGCCAGUAUAAAUCCGUGCCUAAUUGCGCCAUGAAGGUGUUCAC<br>CAAUGAGGGGCCCACCGCCUUUUUCAAGGGGCUGGUGCCCUCCU<br>UCCUGAGGCUGGGCAGUUGGAACGUGAUCAUGUUCGUGUGUUUC<br>GAACAGCUGAAAAGAGAGCUGUCCAAGUCUAGACAGACCAUGGA<br>CUGCGCCACAUGAUGACGCUCGCUUUCUUGCUGUCCAAUUUCUA<br>UUAAAGGUUCCUUUGUUCCCUAAGUCCAACUACUAAACUGGGGG<br>AUAUUAUGAAGGGCCUUGAGCAUCUGGAUUCUGCCUGCUCGCUU<br>UCUUGCUGUCCAAUUUCUAUUAAAGGUUCCUUUGUUCCCUAAGU<br>CCAACUACUAAACUGGGGGAUAUUAUGAAGGGCCUUGAGCAUCU<br>GGAUUCUGCC |
| 21 | mol_type = RNA<br>origin = synthetic construct | ACAGCACCCUCCUGAAAACUGCAGCUUCCUUCUCACCUUGAAGA<br>AUAAUCCUAGAAAACUCACAAAAUGGGCGGGCUGACAGCCAGCG<br>ACGUGCACCCAACCCUGGGGAGUGCAGCUGUUUUCCGCCGGCAUU<br>GCUGCCUGUCUGGCUGAUGUGAUCACUUUCCCACUGGACACAGC<br>UAAAGUGCGGCUGCAGGUGCAGGGCGAGUGCCCAACAAGCUCUG<br>UGAUCAGGUACAAGGGCGUGCUGGGGACCAUCACCGCCGUGGUG<br>AAGACCGAGGGCAGAAUGAAACUGUAUAGUGGUCUUCCCGCCGG<br>CCUGCAGAGACAGAUUUCUAGCGCCUCACUGCGCAUUGGCCUGU<br>AUGAUACAGUGCAGGAGUUUCUGACUGCCGGCAAGGAAACUGCU<br>CCAUCCCUGGGCAGCAAAAUCCUGGCCGGACUCACAACUGGCGG |

-continued

| SEQ ID NO | | RNA Sequence |
|---|---|---|

CGUGGCCGUCUUCAUCGGGCAGCCCACUGAGGUGGUGAAGGUGC
GCCUGCAGGCCCAGAGCCACUUGCAUGGGAUCAAACCCAGAUAC
ACAGGAACCUACAACGCUUACAGAAUCAUCGCCACCACCGAGGG
CCUGACUGGGCUGUGGAAGGGCACUACCCCAAACCUGAUGCGGA
GUGUGAUCAUUAAUUGUACUGAGCUGGUGACCUAUGAUCUGAU
GAAGGAGGCCUUUGUGAAGAACAACAUCCUGGCCGACGACGUGC
CUUGUCACCUGGUGAGCGCCCUGAUCGCCGGCUUCUGCGCCACA
GCCAUGAGCUCCCCCGUGGACGUGGUGAAGACAAGAUUCAUCAA
UAGCCCACCUGGCCAGUAUAAAUCCGUGCCUAAUUGCGCCAUGA
AGGUGUUCACCAAUGAGGGGCCCACCGCCUUUUUCAAGGGGCUG
GUGCCCUCCUUCCUGAGGCUGGGCAGUUGGAACGUGAUCAUGUU
CGUGUGUUUCGAACAGCUGAAAAGAGAGCUGUCCAAGUCUAGAC
AGACCAUGGACUGCGCCACAUGAUGACGCUCGCUUUCUUGCUGU
CCAAUUUCUAUUAAAGGUUCCUUUGUUCCUAAGUCCAACUACU
AAACUGGGGGAUAUUAUGAAGGGCCUUGAGCAUCUGGAUUCUG
CCUGCUCGCUUUCUUGCUGUCCAAUUUCUAUUAAAGGUUCCUUU
GUUCCCUAAGUCCAACUACUAAACUGGGGGAUAUUAUGAAGGGC
CUUGAGCAUCUGGAUUCUGCCU

| 22 | mol_type = RNA origin = synthetic construct | AUGGGCGGCCUGACUGCCAGCGACGUGCACCCCACCCUCGGCGU GCAGCUGUUUAGCGCCGGAAUCGCCGCCGUCUGGCUGAUGUGA UUACCUUCCCUCUGGACACCGCCAAGGUGCGGCUGCAGGUGCAA GGCGAGUGCCCUACCAGCAGCGUGAUUAGAUACAAGGGAGUUCU GGGCACCAUCACAGCUGUGGGUGAAGACAGAAGGCAGAAUGAAAC UGUACAGCGGCCUGCCAGCCGGCCUGCAGAGACAGAUCUCUAGC GCCAGCCUGAGGAUCGGCCUGUAUGAUACCGUGCAGGAGUUCCU GACAGCCGGAAAGGAAACCGCUCCUAGCCUGGGCUCUAAGAUCC UGGCUGGUCUGACCACAGGCGGAGUGGCCGUGUUCAUCGGCCAG CCUACAGAGGUGGUCAAAGUCCGGCUGCAAGCCCAGUCUCACCU GCAUGGCAUCAAGCCCAGAUACACCGGCACCUACAACGCCUACA GAAUCAUCGCCACCACCGAGGGCUUGACAGGCCUGUGGAAGGGC ACAACACCUAAUCUGAUGCGGAGCGUGAUCAUCAACUGCACCGA ACUGGUGACCUACGACCUGAUGAAAGAGGCCUUCGUGAAAAACA ACAUCCUGGCUGAUGACGUGCCCUGCCACCUGGUGUCCGCUCUG AUCGCCGGCUUCUGCGCCACAGCCAUGAGCUCUCCCGUGGACGU CGUGAAGACCAGAUUCAUCAAUAGCCCUCCUGGACAGUACAAGU CCGUGCCCAACUGUGCCAUGAAGGUGUUCACCAACGAGGGACCU ACAGCAUUUUUCAAGGGCCUGGUGCCAUCAUUCCUGAGACUGGG CUCCUGGAACGUGAUCAUGUUUGUGUGCUUCGAGCAGCUGAAGC GGGAACUGAGCAAGAGCAGACAGACCAUGGACUGCGCCACCUGA |

| 23 | mol_type = RNA origin = synthetic construct | AUGGGCGGCCUGACCGCAUCUGAUGUGCAUCCAACACUGGGCGU UCAACUGUUCAGCGCCGGAAUCGCCGCCGUGCUGGCUGAUGUGA UCACAUUCCCCCUGGACACCGCCAAGGUGCGGCUGCAGGUGCAG GGCGAGUGCCCUACAAGCAGCGUGAUCAGAUACAAGGGCGUGCU GGGAACAAUCACCGCCGUGGUCAAGACCGAAGGGAGAAUGAAAC UGUACAGCGGCCUGCCUGCCGGACUCCAGAGACAGAUUAGCUCC GCUUCUCUGCGGAUCGGCCUGUACGAUACCGUGCAGGAGUUCCU GACCGCUGGCAAGGAGACAGCCCCUUCUCUGGGAAGCAAGAUCC UGGCCGGCCUCACAACCGGCGGAGUCGCCGUGUUCAUCGGCCAG CCUACCGAGGUGGUGAAGGUGCGCCUGCAGGCCCAGAGCCACCU GCACGGCAUCAAGCCUAGAUAUACAGGCACCUACAACGCCUACA GGAUCAUCGCUACCACCGAGGGCCUGACUGGACUGUGGAAGGGC ACAACCCCUAAUCUGAUGCGGAGCGUGAUUAUCAACUGCACCGA ACUGGUGACCUACGACCUGAUGAAAGAAGCUUUUGUGAAGAACA ACAUCCUGGCCGACGACGUCCCCUGUCACCUGGUGUCCGCCCUG AUCGCCGGCUUCUGCGCCACCGCCAUGAGCAGCCCCGUGGACGU GGUGAAAACAAGAUUCAUCAACAGCCCUCCUGGCCAAUACAAGU CCGUGCCCAACUGUGCCAUGAAAGUGUUCACCAACGAGGGCCCU ACCGCCUUUUUUAAGGGCCUGGUUCCAAGCUUCCUGAGACUGGG CAGCUGGAAUGUGAUCAUGUUCGUGUGCUUCGAGCAGCUGAAGC GGGAACUUUCUAAGAGCAGACAGACCAUGGACUGCGCCACCUGA |

| 24 | mol_type = RNA origin = synthetic construct | AUGGGCGGACUGACCGCUUCUGAUGUUCAUCCUACAUUGGGCGU GCAGCUGUUUCAGCGCCGGCAUCGCCGCUUGUCUGGCUGAUGUGA UCACAUUCCCUCUGGACACCGCAAAGGUGCGGCUGCAAGUGCAA GGCGAGUGCCCCACCAGCUCCGUGAUCCGGUACAAGGGAGUCCU GGGUACAAUCACCGCCGUGGUGAAAACCGAAGGCAGAAUGAAGC UGUACAGCGGCCUGCCAGCCGGCCUGCAGAGACAGAUCAGCAGC GCCAGCCUGCGGAUCGGCCUGUACGAUACCGUGCAGGAGUUCCU GACCGCUGGCAAGGAAACCGCCCCUUCUCUGGGAUCUAAAAUCC UGGCCGGGCUGACAACCGGCGGCGUGGCCGUGUUUAUCGGCCAG CCUACAGAGGUGGUCAAGGUGCGGCUGCAGGCCCAGAGCCACCU GCACGGCAUUAAGCCCAGAUACACCGGCACCUACAACGCCUAUA GAAUCAUCGCCACCACAGAAGGCCUGACAGGCCUGUGGAAGGGC ACAACCCCUAAUCUGAUGAGAUCUGUGAUCAUUAACUGCACCGA |

-continued

| SEQ ID NO | | RNA Sequence |
|---|---|---|
| | | GCUGGUGACCUACGACCUGAUGAAAGAAGCCUUUGUGAAGAACA |
| | | ACAUCCUGGCCGACGACGUGCCUUGCCACCUGGUGUCCGCCCUG |
| | | AUCGCCGGCUUCUGCGCCACAGCCAUGAGCAGCCCUGUGGACGU |
| | | GGUGAAGACCAGAUUCAUCAACAGCCCACCUGGACAGUACAAGU |
| | | CCGUGCCCAAUUGUGGCCAUGAAAGUGUUCACCAACGAGGGCCCU |
| | | ACCGCUUUUUUCAAGGGACUCGUCCCCAGCUUCCUGAGGCUCGG |
| | | CAGCUGGAACGUGAUCAUGUUCGUGUGCUUCGAGCAGCUGAAGA |
| | | GAGAGCUGAGCAAGAGCAGACAGACCAUGGACUGCGCCACAUGA |

| 25 | mol_type = RNA origin = synthetic construct | AUGGGCGGACUGACCGCCUCUGAUGUGCAUCCUACCCUGGGGCGU |
| | | CCAGCUGUUCAGCGCCGGAAUCGCCGCUUGUCUGGCUGAUGUGA |
| | | UCACCUUCCCCUGGACACAGCGAAGGUCAGACUGCAGGUGCAG |
| | | GGCGAGUGUCCUACCAGCAGCGUGAUUAGAUACAAGGGCGUGCU |
| | | GGGAACAAUCACAGCUGUGGUGAAGACAGAGGGCAGAAUGAAA |
| | | CUGUACAGCGGCCUGCCUGCCGGCCUGCAAAGACAGAUCAGCUC |
| | | CGCCAGCCUGCGGAUCGGCCUGUACGACACCGUGCAGGAGUUCC |
| | | UGACCGCCGGCAAGGAAACCGCCCCUAGCCUGGGCUCCAAGAUC |
| | | CUGGCCGGCUUGACCACCGGAGGCGUGGCCGUGUUCAUCGGCCA |
| | | GCCUACAGAAGUGGUGAAAGUGCGGCUGCAGGCCCAGAGCCACC |
| | | UGCACGGCAUCAAGCCUAGAUACACCGGCACCUACAACGCCUAC |
| | | CGGAUCAUCGCCACAACAGAAGGCCUGACAGGCCUGUGGAAGGG |
| | | CACAACCCCUAAUCUGAUGAGAAGCGUGAUCAUCAACUGCACCG |
| | | AGCUCGUGACCUAUGAUCUGAUGAAAGAGGCCUUCGUGAAGAAC |
| | | AACAUCCUGGCCGACGACGUGCCAUGCCACCUGGUGUCCGCCCU |
| | | GAUUGCCGGCUUCUGCGCCACCGCCAUGAGCUCUCCUGUGGACG |
| | | UUGUGAAAACCCGCUUUAUCAACAGCCCCCCCGGCCAAUACAAG |
| | | AGCGUGCCCAAUUGCGCCAUGAAGGUCUUUACCAACGAGGGUCC |
| | | UACAGCUUUCUUCAAGGGACUGGUUCCAUCUUUUCUGAGACUCG |
| | | GCAGCUGGAACGUGAUCAUGUUCGUGUGCUUCGAGCAGCUGAAG |
| | | CGGGAACUGAGCAAGUCUAGACAGACCAUGGACUGCGCUACCUG |
| | | A |

| 26 | mol_type = RNA origin = synthetic construct | AUGGGCGGACUGACCGCUUCUGAUGUGCAUCCCACCCUGGGGCGU |
| | | UCAACUGUUCAGCGCCGGCAUCGCCCGCUUGUCUGGCAGAUGUGA |
| | | UCACCUUUCCACUGGACACAGCCAAGGUGCGGCUGCAGGUGCAG |
| | | GGCGAGUGCCCCACCUCCUCCGUGAUUAGAUACAAGGGCGUUCU |
| | | CGGAACCAUCACAGCCGUGGUGAAGACCGAAGGCAGAAUGAAGC |
| | | UGUACAGCGGCCUGCCUGCCGGACUGCAGAGACAGAUCAGCAGC |
| | | GCCCUCUCGCGGAUCGGCCUGUAUGAUACAGUGCAGGAGUUCCU |
| | | GACAGCCGGUAAGGAAACCGCCCCUAGCCUGGGGAUCUAAGAUCC |
| | | UGGCCGGACUGACCACAGGCGGCGUCGCCGUGUUCAUCGGCCAG |
| | | CCUACAGAGGUGGUGAAGGUGCGGCUUCAAGCCCAGAGCCACCU |
| | | GCACGGCAUCAAGCCUAGAUACACCGGCACAUACAACGCCUACA |
| | | GAAUCAUCGCUACCACCGAGGGCCUGACAGGCCUGUGGAAGGGC |
| | | ACCACCCCUAAUCUGAUGAGAAGCGUGAUCAUCAACUGUACAGA |
| | | ACUGGUGACCUACGACCUGAUGAAAGAGGCCUUUGUGAAAAACA |
| | | ACAUCCUCGCUGACGACGUGCCCUGCCACCUGGUCAGCGCCCUG |
| | | AUCGCCGGCUUCUGCGCCACCGCCAUGAGCUCUCCUGUGGACGU |
| | | GGUCAAAACCAGAUUCAUCAAUAGCCCCCCUGGACAGUACAAGA |
| | | GCGUGCCUAACUGCGCCAUGAAAGUGUUCACCAACGAGGGCCCU |
| | | ACAGCUUUUUUCAAGGGCCUGGUGCCAAGCUUCCUGAGACUGGG |
| | | CAGCUGGAACGUGAUUAUGUUCGUGUGCUUCGAGCAGCUGAAGC |
| | | GGGAACUGAGCAAGUCCCGCCAGACCAUGGACUGCGCCACCUGA |

| 27 | mol_type = RNA origin = synthetic construct | AUGGGCGGCCUGACCGCCAGCGACGUGCACCCCACACUGGGGCGU |
| | | GCAGCUGUUCAGCGCCCGGCAUCGCCGCCUGCCUGGCUGAUGUGA |
| | | UUACAUUCCCUCUGGAUACAGCCAAGGUGCGGCUGCAGGUGCAG |
| | | GGCGAGUGCCCUACCAGCAGCGUGAUCCGGUACAAGGGCGUGCU |
| | | GGGCACCAUCACCGCAGUGGUCAAGACCGAGGGCAGAAUGAAGC |
| | | UGUACAGCGGCCUCCCCGCCGGACUGCAAAGACAGAUCAGCUCU |
| | | GCUUCUCUGAGAAUCGGACUCUAUGAUACCGUGCAGGAGUUCCU |
| | | GACCGCUGGCAAGGAAACCGCCCCUUCCCUGGGGAUCUAAGAUCC |
| | | UGGCCGGCCUGACAACCGGCGGAGUGGCCGUGUUCAUCGGCCAG |
| | | CCUACCGAAGUGGUGAAGGUCAGGCUGCAGGCCCAGAGCCAUCU |
| | | GCACGGCAUCAAACCCAGAUACACCGGCACCUACAACGCCUACA |
| | | GAAUCAUCGCCACCACCGAAGGCCUGACAGGCCUGUGGAAGGGC |
| | | ACCACACCUAAUCUGAUGAGAAGCGUGAUCAUCAACUGCACCGA |
| | | GCUGGUUACAUACGACCUGAUGAAAGAGGCCUUUGUGAAGAACA |
| | | ACAUCCUGGCCGACGACGUGCCCUGUCACCUGGUGUCCGCCCUG |
| | | AUCGCUGGCUUCUGCGCCACAGCCAUGAGCUCUCCUGUGGACGU |
| | | GGUGAAAACCAGAUUCAUCAACAGCCCCUCCUGGCCAGUACAAGU |
| | | CCGUGCCCAAAUUGUGGCCAUGAAAGUUUUCACCAACGAGGGACCU |
| | | ACAGCUUUUUUCAAGGGACUGGUCCCAAGCUUCCUGCGGCUGGG |
| | | CAGCUGGAACGUGAUCAUGUUCGUGUGCUUUGAGCAGCUGAAGC |
| | | GGGAACUGAGCAAGAGCAGACAAACAAUGGACUGCGCCACCUGA |

-continued

| SEQ ID NO | | RNA Sequence |
|---|---|---|
| 28 | mol_type = RNA origin = synthetic construct | AUGGGCGGACUGACCGCUAGCGACGUGCACCCCACACUGGGAGU GCAGCUGUUCAGCGCCGGCAUCGCCGCCUGCCUGGCUGAUGUGA UCACAUUCCCCCUGGACACCGCCAAGGUGCGGCUGCAAGUGCAG GGCGAGUGCCCUACCAGCUCCGUGAUCAGAUACAAGGGCGUGCU GGGCACCAUCACCGCUGUGGUCAAGACCGAAGGCAGAAUGAAAC UGUACAGCGGCCUGCCUGCCGGCCUGCAGAGACAGAUCAGCUCC GCCAGCCUGCGGAUCGGCCUGUAUGAUACCGUUCAGGAGUUCCU CACCGCCGGAAAAGAGACAGCCCCUUCUCUGGGCUCUAAGAUCC UGGCCGGACUCACCACAGGCGGCGUGGCCGUGUUCAUCGGACAG CCUACAGAAGUGGUGAAGGUGCGGCUUCAGGCCCAGAGCCAUCU GCACGGCAUCAAGCCUAGAUACACCGGCACAUACAACGCCUACA GAAUCAUCGCCACCACCGAGGGCCUGACAGGCCUGUGGAAGGGC ACCACCCCUAAUCUGAUGAGAAGCGUGAUUAUCAACUGCACCGA GCUGGUGACCUACGACCUGAUGAAGGAAGCUUUUGUGAAAAACA ACAUCCUGGCCGAUGACGUCCCAUGUCACCUGGUCAGCGCCCUG AUCGCCGGCUUCUGCGCCACAGCUAUGAGCUCUCCAGUGGACGU GGUGAAGACCAGAUUCAUCAACAGCCCUCCUGGCCAGUACAAGU CCGUGCCCAAUUGUGCCAUGAAAGUGUUUACCAACGAGGGUCCU ACUGCCUUCUUCAAGGGACUGGUGCCCAGCUUUCUGAGACUGGG CAGCUGGAACGUGAUCAUGUUCGUGUGCUUCGAGCAGCUGAAGC GGGAACUGAGCAAGUCUAGGCAAACAAUGGACUGCGCCACAUGA |
| 29 | mol_type = RNA origin = synthetic construct | AUCGCCGCUUGUCUGGCUGAUGUCAUCACCUUCCCUCUGGACAC CGCCAAGGUGCGGCUGCAGGUGCAGGGCGAGUGCCCCACCAGCU CUGUGAUUCGGUACAAGGGCGUCCUGGGCACCAUCACAGCUGUU GUGAAGACCGAGGGCAGAAUGAAACUGUACAGCGGCCUGCCUGC CGGACUGCAAAGACAGAUCUCUUCUGCUUCCCUGAGAAUCGGCC UGUAUGAUACCGUGCAGGAGUUCCUCACAGCCGGCAAGGAGACA GCCCCUAGCCUGGGCUCCAAGAUCCUGGCCGGCCUGACCACAGG CGGCGUCGCCGUGUUCAUCGGCCAGCCUACCGAGGUGGUGAAGG UGCGGCUGCAGGCCCAGAGCCAUCUGCACGGCAUUAAGCCUAGA UACACCGGCACAUACAACGCCUACAGAAUCAUCGCCACAACAGA AGGCCUGACAGGCCUGUGGAAGGGCACCACCCCUAACCUGAUGA GAAGCGUGAUCAUCAAUUGCACCGAACUGGUGACCUACGACCUG AUGAAGGAAGCCUUUGUGAAGAACAACAUCCUGGCCGACGACGU UCCAUGUCACCUGGUGUCUGCCCUGAUCGCCGGAUUUUGCGCCA CAGCCAUGAGCUCCCCCGUGGACGUGGUGAAAAACCAGAUUCAUC AACAGCCCUCCAGGCCAGUACAAAAGCGUGCCUAAUUGCGCCAU GAAAGUGUUCACCAACGAGGGACCUACCGCUUUUUUCAAGGGCC UUGUGCCCAGCUUCCUGAGGCUGGGCAGCUGGAACGUGAUCAUG UUCGUGUGCUUCGAGCAGCUGAAGCGGGAACUGAGCAAGAGCAG ACAGACCAUGGACUGCGCCACCUGA |
| 30 | mol_type = RNA origin = synthetic construct | AUGGGCGGCCUGACUGCUUCUGAUGUGCACCCCACACUGGGCGU CCAACUGUUCAGCGCCGGCAUCGCCGCCUGCUUGGCUGACGUGA UCACCUUUCCUCUGGACACCGCAAAGGUGCGGCUGCAGGUGCAG GGCGAGUGCCCUACAAGCUCUGUGAUCCGGUACAAGGGCGUUCU GGGAACCAUCACAGCUGUGGUCAAGACCGAGGGGAAGAAUGAAAC UGUACAGCGGCCUGCCUGCCGGCCUGCAAAGACAGAUCAGCUCC GCCAGCCUGCGGAUCGGCCUUUAUGAUACCGUGCAGGAGUUCCU GACCGCCGGCAAGGAAACCGCCCCUAGCCUGGGCAGCAAGAUCC UGGCCGGCCUGACAACAGGAGGCGUGGCCGUGUUCAUCGGACAG CCUACCGAAGUGGUGAAGGUGCGCCUGCAGGCCCAGAGCCACCU GCACGGCAUCAAGCCUAGAUACACACAGGCACAUACAACGCUUACA GAAUCAUCGCCACCACAGAGGGCCUGACCGGCCUGUGGAAGGGC ACCACCCCUAAUCUGAUGAGAAGCGUGAUUAUCAACUGCACCGA ACUGGUGACCUACGACCUGAUGAAGAGGCCUUUGUGAAGAACA ACAUCCUGGCCGACGACGUGCCAUGUCAUCUGGUGUCCGCCCUG AUCGCCGGAUUCUGCGCUACCGCCAUGAGCUCCCCUGUGGACGU GGUGAAAACCAGAUUCAUCAACAGCCCCCCCGGCCAGUACAAGA GCGUGCCCAAUUGCGCCAUGAAAGUGUUCACCAACGAGGGCCCU ACCGCCUUCUUCAAGGGCCUCGUUCCAAGCUUCCUGAGACUGGG AUCUUGGAACGUGAUUAUGUUCGUGUGUGUUUUGAGCAGCUGAAG CGGGAACUGUCUAAGUCAAGACAGACAAUGGAUUGCGCCACAUG A |
| 31 | mol_type = RNA origin = synthetic construct | AUGGGCGGCCUGACCGCUAGCGACGUGCAUCCUACACUGGGGCGU GCAGCUGUUCAGCGCUGGCAUCGCCGCCUGCCUGGCCGAUGUUA UCACCUUCCCCCUGGAUACCGCCAAGGUCAGACUGCAAGUGCAG GGCGAAUGUCCUACAAGCAGCGUGAUCAGAUACAAGGGCGUGCU GGGAACCAUCACAGCCGUGGUGAAAACAGAGGGCAGAAUGAAGC UGUACAGCGGCCUUGCCUGCCGGACUUCAAAGACAGAUCAGCUCU GCCUUCUCUGCGGAUCGGACUGUACGAUACAGUGCAGGAGUUCCU GACCGCCGGCAAGGAAACCGCCCCUAGCCUGGGCUCCAAGAUCC UGGCUGGACUGACAACUGGAGGAGUGGCCGUGUUCAUCGGCCAG CCUACCGAGGUGGUGAAGGUGCGGCUGCAGGCCCAGAGCCACCU |

-continued

| SEQ ID NO | | RNA Sequence |
|---|---|---|
| | | GCACGGCAUCAAGCCCAGAUAUACAGGCACCUACAACGCCUACC |
| | | GGAUUAUCGCCACCACCGAAGGCCUGACCGGCCUGUGGAAGGGC |
| | | ACCACACCUAAUCUGAUGAGGUCCGUGAUUAUCAAUUGCACCGA |
| | | GCUGGUGACCUACGACCUGAUGAAAGAGGCCUUUGUGAAGAACA |
| | | ACAUCCUGGCUGACGACGUGCCUUGCCACCUGGUGUCCGCCCUG |
| | | AUCGCCGGCUUCUGCGCCACAGCCAUGAGCUCUCCAGUGGACGU |
| | | UGUGAAGACAAGAUUCAUCAACAGCCCCCCCGGCCAGUACAAAA |
| | | GCGUGCCUAACUGUGCCAUGAAAGUCUUUACCAACGAGGGCCCU |
| | | ACCGCCUUCUUUAAGGGCCUCGUGCCAAGCUUCCUGAGACUGGG |
| | | CAGCUGGAACGUGAUCAUGUUCGUGUGCUUCGAGCAGCUGAAGC |
| | | GGGAACUGUCUAAGAGCAGACAGACCAUGGACUGCGCCACCUGA |
| 32 | mol_type = RNA origin = synthetic construct | AUGGGCGGCCUGACAGCCAGCGACGUCCACCCCACCCUGGGCGU GCAGCUGUUCAGCGCCGGCAUCGCUGCUUGUCUGGCUGAUGUGA UCACUUUUCCACUGGAUACCGCAAAGGUGCGGCUGCAGGUGCAG GGCGAGUGCCCUACCAGCUCUGUGAUCAGAUACAAGGGCGUGCU GGGAACAAUCACCGCCGUUGUUAAGACAGAAGGCAGAAUGAAGC UGUACAGCGGCCUGCCUGCUGGCCUUCAGAGACAGAUCAGCAGC GCCUCUCUGCGGAUCGGCCUGUACGACACCGUGCAGGAGUUCCU GACCGCCGGCAAGGAAACCGCCCCUAGCCUGGGAUCUAAGAUCC UGGCCGGCCUGACAACCGGAGGAGUCGCCGUGUUCAUCGGCCAG CCUACCGAGGUGGUGAAAGUGCGCCUGCAGGCCCAGAGCCACCU GCACGGCAUCAAGCCUAGAUAUACAGGCACAUACAACGCCUACA GGAUCAUCGCCACCACCGAGGGCCUGACCGGACUCUGGAAGGGC ACCACCCCUAACCUGAUGCGGUCCGUGAUUAUCAAUUGUACCGA GCUGGUGACCUACGACCUGAUGAAGGAAGCCUUCGUGAAAAACA ACAUCCUGGCCGACGACGUGCCCUGCCAUCUGGUGUCCGCCCUG AUCGCCGGCUUCUGCGCCACAGCCAUGAGCUCUCCAGUGGAUGU GGUGAAAACCAGAUUCAUCAACAGCCCCCCCGGACAAUACAAGU CCGUGCCUAAUUGCGCCAUGAAAGUGUUCACCAACGAGGGCCCU ACAGCUUUUUUCAAGGGCCUGGUCCCUAGCUUUCUGAGACUGGG CAGCUGGAACGUGAUUAUGUUCGUGUGCUUCGAGCAGCUGAAGC GGGAACUGAGCAAGAGCAGACAAACAAUGGACUGCGCCACAUGA |
| 33 | mol_type = RNA origin = synthetic construct | AUGGGAGGCCUGACAGCCUUCUGAUGUGCACCCCACCCUGGGCGU GCAACUGUUCAGCGCCGGCAUCGCCGUUUGCCUUGCCUGGCUGAUGUGA UCACAUUCCCCCUGGACACCGCCAAGGUGCGGCUUCAGGUGCAG GGAGAAUGUCCUACCAGCAGCGUGAUCAGAUACAAGGGCGUGCU GGGCACAAUCACAGCUGUGGUCAAGACCGAAGGCAGAAUGAAAC UGUACAGCGGCCUGCCUGCCGGCCUGCAGAGACAGAUCAGCUCC GCCAGCCUGAGGAUCGGCCUGUACGACACCGUGCAGGAGUUCCU GACCGCCGGCAAGGAGACAGCCCCUAGCCUGGGCAGCAAGAUCC UGGCCGGCCUCACAACCGGAGGAGUGGCCGUGUUCAUCGGCCAG CCUACCGAGGUGGUGAAGGUCAGACUGCAGGCCCAGAGCCCACCU GCACGGCAUUAAGCCUAGAUACACCGGCACCUAUAAUGCCUACC GGAUCAUCGCCACCACCGAGGGACUGACCGGCCUCUGGAAGGGC ACAACACCUAACCUGAUGCGGGAGCGUGAUCAUCAACUGCACCGA GCUGGUUACAUACGACCUGAUGAAGGAAGCCUUUGUGAAAAACA ACAUCCUGGCUGAUGAUGUUCCAUGUCAUCUGGUGUCCGCCCUG AUCGCCGGCUUCUGCGCCACUGCCAUGAGCUCUCCUGUGGACGU GGUGAAAACCAGAUUCAUUAACAGCCCUCCAGGCCAAUACAAGA GCGUGCCCAAUUGCGCCAUGAAGGUUUUCACCAACGAGGGCCCU ACCGCUUUUUUCAAAGGCCUGGUGCCUUCUUUUUCUGAGACUGGG AUCUUGGAACGUGAUCAUGUUCGUGUGCUUCGAGCAGCUGAAGC GGGAACUGUCUAAGAGCAGACAGACCAUGGACUGCGCCACAUGA |
| 34 | mol_type = RNA origin = synthetic construct | AUGGGCGGACUUACAGCCAGUGAUGUGCAUCCUACCCUGGGCGU UCAACUGUUCAGCGCCGGAAUCGCCGCUUGUCUGGCUGAUGUGA UCACCUUCCCCCUGGACACCGCCAAGGUGCGGCUGCAGGUGCAG GGCGAGUGCCCUACAAGCAGCGUGAUUAGAUACAAGGGCGUGCU GGGCACCAUCACAGCCGUGGUGAAAACCGAAGGUAGAAUGAAGC UGUACAGCGGCCUGCCUGCCGGCCUGCAAAGGCAGAUCAGCUCU GCCUCUCUGCGGAUCGGCCUCUAUGAUACAGUGCAGGAGUUCCU GACCGCCGGCAAGGAAACCGCUCCUUCUCUGGGCAGCAAGAUCC UGGCCGGACUGACAACCGGCGGCUGGGCCGUGUUUAUCGGACAG CCAACAGAAGUGGUCAAAGUGCGGCUGCAGGCCCAGAGCCACCU GCACGGCAUCAAGCCUAGAUACACCGGCACAUACAACGCCUACA GAAUCAUCGCCACCACUGAGGGCCUCACCGGCCUGUGGAAGGGC ACCACACCUAAUCUGAUGAGAAGCGUGAUUAUCAACUGUACCGA GCUGGUCACCUACGACCUGAUGAAAGAGGCCUUUGUGAAGAACA ACAUCCUGGCCGACGACGUCCCCUGCCACCUGGUGUCCGCCCUG AUCGCCGGCUUCUGCGCCACAGCUAUGAGCUCUCCCUGUGGACGU GGUGAAGACCAGAUUCAUCAAUAGCCCCCCCGGCCAGUACAAGA |

-continued

| SEQ ID NO | | RNA Sequence |
|---|---|---|
| | | GCGUGCCUAACUGCGCCAUGAAAGUGUUCACCAACGAGGGCCCU |
| | | ACCGCCUUUUUCAAGGGCCUGGUUCCAAGCUUCCUGAGACUGGG |
| | | AUCUUGGAACGUGAUCAUGUUCGUGUGCUUCGAGCAGCUGAAGC |
| | | GGGAACUGAGCAAGUCCAGACAGACCAUGGACUGCGCCACAUGA |
| 35 | mol_type = RNA origin = synthetic construct | AUGGGUGGCCUGACAGCCUCCGACGUGCAUCCUACCCUGGGGAGU |
| | | GCAACUGUUCAGCGCCGGCAUCGCCGCUUGUCUCGGCUGAUGUGA |
| | | UUACCUUCCCCCUGGACACAGCCAAGGUGAGACUGCAAGUGCAG |
| | | GGCGAGUGCCCCACAAGCAGCGUGAUCCGGUACAAGGGCGUGCU |
| | | GGGCACCAUCACCGCUGUGGGUUAAGACAGAAGGCAGAAUGAAGC |
| | | UGUACAGCGGCCUGCCUGCCGGCCUGCAGAGACAGAUCAGCUCU |
| | | GCCUCUCUGCGGAUCGGCCUCUAUGAUACCGUGCAGGAGUUCCU |
| | | GACCGCCGGAAAGGAGACAGCCCCUUCUCUGGGAAGCAAGAUCC |
| | | UGGCCGGCCUGACAACCGGCGAGUGGCCGUCUUCAUCGGCCAG |
| | | CCUACAGAAGUGGUGAAGGUGCGGCUGCAGGCCCAGAGCCACCU |
| | | GCACGGCAUCAAGCCCAGAUACACCGGAACCUACAACGCCUACA |
| | | GAAUCAUCGCCACCACCGAGGGCCUCACAGGCCUGUGGAAAGGC |
| | | ACCACCCCUAAUCUGAUGAGGUCCGUGAUCAUCAACUGCACCGA |
| | | ACUGGUGACCUACGACCUGAUGAAAGAGGCCUUUGUGAAAAACA |
| | | ACAUCCUGGCCGACGAUGUGCCAUGCCACCUGGUCAGCGCCCUG |
| | | AUCGCUGGCUUUUGCGCAACCGCCAUGAGCUCCCCAGUGGACGU |
| | | GGUGAAGACAAGAUUCAUUAACAGCCCUCCUGGCCAGUACAAGA |
| | | GCGUCCCCAAUUGCGCCAUGAAAGUGUUCACCAACGAGGGACCU |
| | | ACAGCUUUCUUCAAGGGCCUGGUGCCUAGCUUCCUGAGACUGGG |
| | | CAGCUGGAACGUGAUCAUGUUCGUUUGUUUUGAGCAGCUGAAGC |
| | | GGGAACUGAGCAAGUCUAGACAGACCAUGGACUGCGCCACCUGA |
| 36 | mol_type = RNA origin = synthetic construct | AUGGGCGGACUGACCGCCUCUGAUGUGCACCCCACCCUGGGGAGU |
| | | GCAGCUGUUCAGCGCCGGUAUCGCCCGCUUGUCUGGCCGACGUGA |
| | | UUACAUUCCCCCUGGACACCGCGAAGGUGCGGCUGCAAGUGCAG |
| | | GGCGAGUGCCCCUACAAGCUCUGUUAUUAGAUAUAAGGGCGUGCU |
| | | GGGCACCAUCACCGCCGUGGUGAAAACCGAGGGCAGAAUGAAGC |
| | | UGUACAGCGGCCUGCCUGCCGGACUGCAGAGACAGAUCAGCAGC |
| | | GCCAGCCUGAGGAUCGGCCUCUACGAUACCGUGCAGGAGUUCCU |
| | | GACCGCCGGCAAGGAGACAGCCCCUAGCCUGGGCUCCAAGAUCC |
| | | UCGCCGGCCUGACCACAGGCGGCGUCGCCGUGUUCAUCGGCCAA |
| | | CCUACCGAAGUGGUCAAAGUGCGGCUGCAGGCCCAGAGCCACCU |
| | | GCACGGCAUCAAGCCCAGAUACACCGGAACCUACAACGCCUACA |
| | | GAAUCAUCGCCACAACAGAAGGCCUGACAGGCCUGUGGAAGGGC |
| | | ACCACACCUAACCUGAUGCGGAGCGUGAUCAUCAAUUGCACUGA |
| | | GCUGGUUACAUACGACCUGAUGAAGGAAGCCUUCGUGAAAAACA |
| | | ACAUCCUGGCUGAUGACGUGCCUUGUCAUCUGGUGUCCGCCCUG |
| | | AUCGCCGGAUUUUGCGCCACCGCUAUGAGCUCUCCAGUGGACGU |
| | | GGUCAAGACCAGAUUCAUCAAUUCUCCUCCUGGCCAGUACAAGU |
| | | CCGUGCCAAACUGCGCUAUGAAAGUGUUUACCAACGAGGGACCU |
| | | ACCGCUUUUUUCAAGGGCCUGGUGCCCAGCUUCCUGAGACUGGG |
| | | CAGCUGGAACGUGAUCAUGUUCGUGUGCUUCGAGCAGCUGAAGC |
| | | GGGAACUGAGCAAGAGCAGACAGACCAUGGACUGCGCCACCUGA |
| 37 | mol_type = RNA origin = synthetic construct | AUGGGCGGCCUGACCGCUAGCGACGUGCACCCCACACUGGGGCGU |
| | | UCAGCUGUUCAGCGCCGGCAUCGCCGCCUGUCUGGCUGAUGUGA |
| | | UUACCUUCCCCCUGGACACAGCCAAGGUGCGGCUGCAAGUGCAG |
| | | GGCGAGUGCCCUACCAGCAGCGUGAUCAGAUAUAAGGGCGUGCU |
| | | GGGCACCAUCACCGCCGUGGUGAAGACCGAAGGCAGAAUGAAGC |
| | | UGUACAGCGGCCUGCCUGCCGGACUUCAAAGACAGAUCAGCUCC |
| | | GCUUCUCUGCGGAUUGGACUCUACGACACCGUGCAGGAGUUCCU |
| | | GACCGCCGGAAAAGAGACAGCCCCUUCUCUGGGAUCUAAGAUCC |
| | | UGGCCGGCCUGACAACCGGAGGCGUGGCCGUGUUUAUCGGACAG |
| | | CCUACAGAAGUGGUGAAGGUGAGGCUGCAGGCCCAGAGCCAUCU |
| | | GCACGGCAUCAAGCCCAGAUACACCGGCACAUACAACGCCUACC |
| | | GGAUCAUCGCCACCACCGAGGGCCUCACAGGCCUGUGGAAGGGC |
| | | ACCACCCCUAAUCUGAUGAGAUCUGUGAUCAUCAAUUGCACCGA |
| | | GCUGGUCACCUACGAUCUGAUGAAAGAAGCCUUCGUCAAGAACA |
| | | ACAUCCUGGCGGAUGACGUUCCAUGUCACCUGGUGUCCGCCCUG |
| | | AUCGCCGGCUUCUGCGCCACAGCCAUGAGCUCCCCUGUGGACGU |
| | | CGUGAAAACGAGAUUCAUCAACAGCCCUCCAGGCCAGUACAAGA |
| | | GCGUGCCUAACUGCGCCAUGAAAGUGUUCACCAACGAGGGUCCU |
| | | ACCGCUUUUUUCAAGGGCCUGGUGCCCAGCUUUCUGAGACUGGG |
| | | CAGCUGGAACGUGAUCAUGUUCGUGUGCUUCGAGCAGCUGAAGC |
| | | GGGAACUGAGCAAGUCUAGACAGACCAUGGACUGCGCCUACAUGA |
| 38 | mol_type = RNA origin = synthetic construct | AUGGGCGGACUGACCGCCUCUGAUGUGCCAUCCUACCCUGGGGCGU |
| | | UCAGCUCUUUAGCGCCGGAAUCGCCCGCUUGUCUGGCCGAUGUCA |
| | | UCACCUUCCCCCUGGACACCGCCAAGGUGCGGCUGCAAGUGCAG |
| | | GGCGAGUGUCCUACCAGCAGCGUGAUCCGGUACAAGGGCGUGCU |
| | | GGGCACUAUCACAGCUGUGGGUGAAGACCGAGGGCAGAAUGAAAC |

-continued

| SEQ ID NO | | RNA Sequence |
|---|---|---|
| | | UGUACAGCGGCCUGCCAGCCGGCCUGCAGAGACAGAUUUCCAGC |
| | | GCUAGCCUGAGAAUCGGCCUGUAUGAUACCGUGCAGGAGUUCCU |
| | | GACCGCAGGCAAGGAAACCGCCCCUAGCCUGGGCAGCAAGAUCC |
| | | UGGCCGGCCUGACAACCGGCGGCGUGGCCGUGUUUAUUGGACAG |
| | | CCUACAGAGGUGGUGAAGGUGAGGCUGCAGGCCCAGAGCCACCU |
| | | GCACGGCAUCAAGCCCAGAUACACCGGCACCUACAACGCCUACA |
| | | GAAUCAUCGCCACAACCGAAGGCCUGACAGGACUGUGGAAGGGC |
| | | ACCACACCUAAUCUGAUGAGAAGCGUGAUCAUCAAUUGCACCGA |
| | | GCUGGUGACCUACGACCUGAUGAAGGAAGCCUUUGUGAAGAACA |
| | | ACAUCCUGGCCGACGACGUGCCCUGCCACCUGGUGUCCGCCCUG |
| | | AUCGCUGGCUUCUGCGCCACAGCCAUGAGCUCUCCUGUGGACGU |
| | | GGUCAAAACCAGAUUCAUCAACAGCCCUCCCGGCCAGUACAAAA |
| | | GCGUCCCAAACUGCGCCAUGAAAGUGUUCACCAACGAGGGACCU |
| | | ACAGCUUUCUUCAAGGGACUUGUGCCUUCCUUCCUGCGGCUGGG |
| | | CAGCUGGAACGUGAUCAUGUUCGUGUGCUUCGAGCAGCUGAAGC |
| | | GGGAACUGCUCUAAGUCUAGACAAACAAUGGACUGCGCCACCUGA |
| 39 | mol_type = RNA origin = synthetic construct | AUGGGCGGGCUCACAGCUUCUGAUGUGCAUCCUACACUGGGCGU |
| | | CCAGCUGUUCAGCGCCGGAAUCGCCCGCUUGUCUGGCCGAUGUGA |
| | | UCACCUUCCCCCUGGACACCGCCAAGGUGCGGCUGCAGGUGCAG |
| | | GGCGAGUGCCCUACCAGCUCUGUGAUCCGCUACAAGGGCGUGCU |
| | | GGGCACCAUCACAGCUGUGGUGAAGACCGAAGGCAGAAUGAAAC |
| | | UGUACAGCGGCCUGCCUGCCGGCCUGCAAAGACAAAUCAGCAGC |
| | | GCCAGCCUGAGAAUCGGACUGUAUGAUACAGUGCAGGAGUUCCU |
| | | GACUGCUGGCAAGGAGACAGCCCCUAGCCUGGGAAGCAAGAUCC |
| | | UUGCCGGACUGACCACCGGCGGCGUGGCCGUGUUUAUCGGCCAG |
| | | CCUACCGAAGUGGUUAAGGUGCGGCUGCAGGCCCAGAGCCACCU |
| | | GCACGGCAUCAAGCCUAGAUACACCGGCACCUACAACGCUUACA |
| | | GAAUUAUCGCCACAACCGAAGGUCUGACAGGACUGUGGAAGGGC |
| | | ACCACCCCUAACCUGAUGCGGAGCGUCAUCAUUAACUGCACCGA |
| | | GCUGGUUACAUACGACCUGAUGAAAGAGGCCUUUGUGAAGAACA |
| | | ACAUCCUGGCCGACGACGUCCCAUGUCACCUGGUGUCCGCCCUG |
| | | AUCGCCGGCUUCUGCGCCACAGCCAUGAGCUCUCCCUGUGGACGU |
| | | GGUGAAGACAAGAUUCAUCAACAGCCCCCCCGGCCAGUACAAGU |
| | | CUGUGCCAAAUUGCGCCAUGAAAGUGUUCACCAACGAGGGCCCU |
| | | ACCGCUUUUUUCAAGGGCCUGGUGCCCUCUUUCCUCAGACUGGG |
| | | CAGCUGGAAUGUGAUCAUGUUCGUGUGCUUCGAGCAGCUGAAGC |
| | | GGGAACUGAGCAAAUCCAGACAGACCAUGGACUGCGCCACCUGA |
| 40 | mol_type = RNA origin = synthetic construct | AUGGGCGGCCUGACCGCCAGCGACGUGCAUCCUACACUAGGCGU |
| | | GCAGCUGUUCAGCGCCGGCAUCGCCGCCUGCCUGGCUGAUGUGA |
| | | UUACCUUCCCCCUGGACACCGCCAAGGUGCGGCUGCAAGUGCAG |
| | | GGCGAGUGUCCUACCAGCAGCGUGAUCAGAUACAAGGGAGUGCU |
| | | GGGAACAAUCACCGCCGUGGUGAAAACCGAGGGAAGAAUGAAGC |
| | | UGUACAGCGGCCUCCCCGCCGGCCUGCAGAGACAGAUCAGCUCU |
| | | GCUUCUCUGCGGAUCGCCGUGUAUGAUACCGUGCAGGAGUUCCU |
| | | GACAGCUGGCAAGGAGACAGCCCCUAGCCUGGGCAGCAAGAUCC |
| | | UGGCCGGACUCACAACCGGCGGCGAGUGGCCGUGUUUAUUGGCCAG |
| | | CCUACAGAAGUGGUCAAAGUGCGGCUGCAGGCCCAGAGCCACCU |
| | | GCACGGCAUCAAGCCCAGAUACACCGGCACCUACAACGCCUACA |
| | | GAAUCAUCGCCACAACAGAAGGCCUGACCGGACUGUGGAAGGGC |
| | | ACCACCCCUAAUCUGAUGAGGUCCGUGAUCAUCAACUGCACCGA |
| | | ACUGGUCACCUACGACCUGAUGAAAGAGGCCUUUGUCAAGAACA |
| | | ACAUCCUGGCCGAUGACGUGCCUUGUCACCUGGUGUCCGCCCUG |
| | | AUCGCCGGCUUCUGCGCCACAGCUAUGAGCUCUCCUGUGGACGU |
| | | GGUUAAGACCAGAUUCAUCAACAGCCCUCCAGGCCAAUACAAGU |
| | | CCGUGCCAAAUUGCGCCAUGAAGGUGUUCACCAACGAGGGUCCU |
| | | ACCGCUUUUUUCAAGGGCCUGGUGCCCAGCUUCCUGAGACUGGG |
| | | CUCUUGGAACGUGAUCAUGUUCGUGUGCUUCGAGCAGCUGAAGC |
| | | GGGAACUGAGCAAAGCAGACAGACCAUGGACUGCGCUACAUGA |
| 41 | mol_type = RNA origin = synthetic construct | AUGGGCGGCCUGACCGCUUCCGAUGUGCACCCCACCUGGGCGU |
| | | GCAGCUGUUCAGCGCCGGCAUCGCCGCUUGUCUGGCCGACGUGA |
| | | UCACUUUUCCACUGGACACAGCCAAGGUGCGGCUGCAAGUGCAG |
| | | GGCGAGUGCCCCACCAGCUCCGUGAUCCGGUACAAAGGCGUGCU |
| | | GGGCACCAUCACCGCCGUGGUGAAGACAGAAGGCAGAAUGAAAC |
| | | UGUACAGCGGCCUGCCUGCCGGCCUGCAGAGGCAGAUCAGCAGC |
| | | GCCUCUCUGCGGAUCGACUGUACGACACCGUGCAGGAGUUCCU |
| | | GACGGCCGGAAAAGAGACAGCCCCUAGCCUCGGCAGCAAGAUCC |
| | | UGGCCGGCCUCACCACCGGCGGCGUGUGGCCGUGUUCAUUGGACAA |
| | | CCUACCGAAGUGGUGAAGGUCAGACUGCAGGCCCAGAGCCACCU |
| | | GCAUGGCAUCAAGCCUAGAUACACCGGAACAUACAACGCCUACA |
| | | GAAUCAUUGCCACCACCGAGGGACUGACAGGCCUGUGGAAGGGC |
| | | ACCACACCUAAUCUGAUGAGAAGCGUGAUCAUCAAUUGUACCGA |
| | | GCUGGUUACAUAUGACCUGAUGAAGGAAGCCUUCGUGAAAAACA |
| | | ACAUCCUUGCUGAUGAUGUGCCCUGCCACCUGGUGUCCGCCCUG |

-continued

| SEQ ID NO | | RNA Sequence |
|---|---|---|
| | | AUCGCCGGCUUCUGCGCCACCGCAAUGAGCAGCCCUGUGGACGU |
| | | CGUGAAGACCAGAUUCAUCAACAGCCCCCCUGGCCAGUACAAGA |
| | | GCGUGCCUAACUGCGCCAUGAAGGUGUUCACCAACGAGGGCCCU |
| | | ACAGCUUUUUUCAAGGGCCUGGUCCCAUCUUUUUCUGAGACUGGG |
| | | AUCUUGGAACGUGAUCAUGUUCGUGUGCUUCGAGCAGCUGAAGC |
| | | GGGAACUGAGCAAGUCUAGACAGACCAUGGACUGCGCUACAUGA |
| 42 | mol_type = RNA origin = synthetic construct | AUGGGCGGCCUGACCGCUAGCGACGUGCAUCCUACCCUGGGGAGU |
| | | GCAGCUGUUCAGUGCCGGCAUCGCUGCUUGUCUGGCUGAUGUGA |
| | | UCACCUUCCCCCUGGACACCGCAAAGGUGCGGCUGCAAGUGCAG |
| | | GGAGAAUGUCCUACAAGCUCCGUGAUUAGAUAUAAGGGCGUGCU |
| | | GGGUACCAUUACAGCCGUGGUCAAAACCGAAGGCAGAAUGAAAC |
| | | UGUACAGCGGCCUCCCCUGCCGGCCUGCAGCGCCAGAUCAGCAGC |
| | | GCCAGCCUGCGGAUCGGACUGUACGAUACCGUGCAGGAGUUCCU |
| | | GACCGCCGGCAAGGAAACCGCCCCUAGCCUGGGCUCCAAGAUCC |
| | | UGGCCGGCCUGACAACAGGCGGAGUGGCCGUCUUUAUCGGCCAG |
| | | CCUACAGAGGUGGUGAAGGUUAGACUGCAGGCCCAGAGCCACCU |
| | | GCACGGAAUCAAGCCCAGAUACACCGGCACCUACAACGCCUACA |
| | | GAAUCAUCGCCACCACAGAGGGCCUGACAGGCCUGUGGAAGGGC |
| | | ACAACCCCUAAUCUGAUGCGGAGCGUGAUCAUCAACUGCACCGA |
| | | GCUGGUGACCUACGAUCUGAUGAAAGAGGCCUUUGUGAAGAACA |
| | | ACAUCCUGGCCGACGACGUGCCGUGCCACCUGGUGUCUGCCCUG |
| | | AUCGCCGGCUUCUGCGCCACCGCCAUGAGCUCUCCAGUGGACGU |
| | | GGUGAAAAACCAGAUUCAUCAACAGCCCUCCAGGCCAAUACAAGU |
| | | CCGUGCCCAAUUGCGCCAUGAAGGUGUUCACCAACGAGGGCCCU |
| | | ACAGCUUUUUUCAAGGGCCUGGUCCCCAGCUUCCUGAGACUGGG |
| | | AUCUUGGAACGUGAUCAUGUUCGUGUGCUUCGAGCAGCUCAAGC |
| | | GGGAACUGUCUAAGAGCAGACAGACCAUGGACUGCGCCACAUGA |
| 43 | mol_type = RNA origin = synthetic construct | AUGGGAGGCCUGACCGCAUCUGAUGUGCACCCUACACUGGGGAGU |
| | | GCAGCUGUUCAGCGCCGGAAUCGCCGCUUGUCUGGCCGAUGUGA |
| | | UUACCUUCCCCCUGGACACCGCCAAGGUGCGCCUGCAGGUGCAG |
| | | GGCGAGUGCCCUACCAGCUCUGUGAUCAGAUACAAAGGCGUGCU |
| | | GGGCACCAUCACCGCUGUGGUCAAGACAGAGGGCAGAAUGAAAC |
| | | UGUACAGCGGCCUCCCCGCCGGCCUGCAAAGACAGAUCAGCAGC |
| | | GCCAGCCUGAGAAUCGGCCUGUAUGACACCGUGCAGGAGUUCCU |
| | | GACAGCUGGCAAGGAAACCGCCCCUAGCCUGGGCAGCAAGAUCC |
| | | UGGCCGGUCUUACAACCGGCGGCGUGGCCGUGUUCAUCGGCCAA |
| | | CCUACAGAAGUGGUGAAGGUGCGGCUGCAGGCCCAGAGCCACCU |
| | | GCAUGGCAUCAAGCCUAGAUACACCGGAACAUACAACGCCUACC |
| | | GGAUCAUCGCCACCACCGAGGGCCUGACAGGCCUCUGGAAGGGC |
| | | ACCACCCCUAAUCUGAUGAGAUCCGUGAUCAUCAACUGCACCGA |
| | | GCUGGUCACCUACGACCUGAUGAAAGAAGCCUUUGUGAAGAACA |
| | | ACAUCCUGGCUGAUGACGUUCCAUGCCACCUGGUGUCUGCCCUG |
| | | AUCGCCGGCUUCUGCGCCACAGCCAUGAGCUCUCCCUGUGGACGU |
| | | GGUGAAGACCAGAUUCAUCAAUAGCCCUCCAGGACAGUACAAGU |
| | | CCGUCCCUAACUGCGCCAUGAAAGUGUUCACCAACGAGGGCCCC |
| | | ACAGCUUUUUUCAAGGGCCUGGUGCCCAGCUUCCUGCGGCUGGG |
| | | AUCUUGGAACGUGAUUAUGUUCGUUUGUUUUUGAGCAGCUGAAG |
| | | CGGGAACUGAGCAAGAGCAGACAGACCAUGGACUGCGCCACCUG |
| | | A |
| 44 | mol_type = RNA origin = synthetic construct | AUGGGCGGACUGACCGCUUCUGAUGUGCAUCCCACACUGGGGCGU |
| | | GCAACUGUUCAGCGCCGGAAUCGCCGCAUGCCUGGCUGAUGUUA |
| | | UUACCUUCCCCUCUGGAUACCGCCAAGGUGCGGCUGCAAGUGCAG |
| | | GGCGAGUGUCCUACCAGCAGCGUGAUCAGAUACAAGGGCGUGCU |
| | | GGGAACCAUCACCGCCGUGGUGAAGACAGAGGGCAGAAUGAAAC |
| | | UGUAUUCUGGCCUGCCUGCCGGCCUGCAGAGACAGAUCUCCAGC |
| | | GCCAGCCUGCGGAUCGGCCUGUACGACACCGUGCAGGAGUUCCU |
| | | GACAGCUGGCAAGGAAACCGCCCCUAGCCUGGGCUCUAAGAUCC |
| | | UGGCUGGCCUGACCACAGGCCGGCGUGGCCGUUUUUAUUGGCCAG |
| | | CCUACCGAGGUGGUGAAGGUGCGCCUCCAGGCCCAGAGCCACCU |
| | | GCACGGCAUCAAGCCCAGAUACACCGGCACAUACAACGCCUACA |
| | | GAAUCAUCGCCACAACAGAGGGCCUGACCGGACUGUGGAAGGGA |
| | | ACAACCCCUAACCUGAUGCGGAGCGUGAUCAUCAAUUGCACCGA |
| | | ACUGGUGACCUACGACCUGAUGAAAGAAGCCUUCGUGAAAAACA |
| | | ACAUCCUGGCCGACGACGUGCCAUGCCACCUGGUGUCCGCCCUG |
| | | AUCGCCGGCUUCUGCGCCACAGCCAUGAGCAGCCCUGUGGACGU |
| | | GGUCAAGACCAGAUUCAUCAACAGCCCCCCCGGCCAGUACAAGU |
| | | CCGUGCCUAAUUGUGCCAUGAAAGUGUUCACCAACGAGGGGUCCU |
| | | ACAGCUUUUUUCAAGGGCCUUGUGCCAUCUUUUCUGAGACUGGG |
| | | CAGCUGGAACGUGAUCAUGUUCGUCUGCUUCGAGCAGCUGAAGC |
| | | GGGAACUGAGCAAGAGCAGACAGACCAUGGACUGCGCCACCUGA |

-continued

| SEQ ID NO | | RNA Sequence |
| --- | --- | --- |
| 45 | mol_type = RNA origin = synthetic construct | AUGGGAGGCCUGACCGCUUCUGAUGUGCAUCCCACCCUGGGCGU CCAGCUGUUCAGCGCCGGCAUCGCCGCUUGUCUGGCUGAUGUGA UUACAUUCCCCCUGGACACCGCCAAGGUGCGGCUGCAGGUGCAG GGCGAGUGCCCCACCCAGCAGCGUGAUCAGAUAUAAGGGCGUUCU GGGCACCAUCACCGCCGUGGUCAAGACCGAAGGCAGAAUGAAAC UGUACAGCGGCCUGCCUGCCGGCCUGCAAAGACAGAUCAGCAGC GCCAGCCUCAGGAUCGGCCUGUACGACACAGUGCAGGAGUUCCU GACAGCUGGCAAGGAAACCGCCCCUUCUCUGGGCAGCAAGAUCC UGGCCGGACUGACCACCGGCGGCGUGGCCGUCUUUAUCGGACAG CCUACAGAAGUGGUGAAGGUGCGGCUGCAGGCCCAGAGCCACCU GCACGGCAUUAAGCCUAGAUACACCGGCACAUACAACGCCUACA GAAUCAUCGCCACCACAGAGGGCCUGACAGGCCUGUGGAAGGGC ACCACCCCUAAUCUGAUGCGGAGCGUGAUCAUCAAUUGUACCGA GCUGGUGACCUACGAUCUGAUGAAAGAGGCCUUCGUGAAAAACA ACAUCCUGGCCGACGACGUGCCCUGCCUGACCUCGUGUCCGCCCUG AUCGCCGGCUUCUGCGCCACAGCCAUGAGCUCUCCUGUGGACGU CGUGAAGACCAGAUUCAUCAACAGCCCUCCUGGACAGUACAAGU CCGUGCCAAACUGCGCCAUGAAAGUGUUCACCAACGAGGGUCCU ACCGCUUUUUUCAAGGGCCUGGUGCCAUCUUUUCUGAGACUGGG AUCCUGGAACGUGAUCAUGUUCGUGUGCUUCGAGCAGCUCAAGC GGGAACUGAGCAAGAGCAGACAAACAAUGGACUGCGCUACAUGA |
| 46 | mol_type = RNA origin = synthetic construct | AUGGGCGGCCUUACAGCUAGCGACGUGCACCCUACCCUGGGGAGU GCAGCUGUUCAGCGCCGGGAAUCGCCGCCUGCCUGGCUGAUGUGA UCACAUUCCCCCUGGACACCGCCAAGGUGCGGCUGCAAGUGCAG GGCGAGUGCCCCACCCAGCAGCGUGAUCCGGUACAAAGGCGUGCU GGGAACCAUCACCGCCGUGGUGAAGACAGAAGGAAGAAUGAAAC UGUACUCAGGCCUGCCUGCCGGCCUGCAACGCCAGAUCAGCUCU GCUUCUCUGAGAAUCGGACUGUAUGAUACCGUGCAGGAGUUCCU GACCGCUGGCAAGGAAACCGCCCCUAGCCUGGGCAGCAAGAUCC UGGCCGGCCUGACAACAGGUGGCGUCGCCGUGUUCAUCGGCCAG CCUACUGAGGUGGUGAAGGUUAGACUGCAGGCCCAGAGCCAUCU GCACGGCAUCAAGCCCAGAUACACCGGCACCUACAACGCCUACA GAAUCAUCGCCACAACCGAGGGCCUGACCGGCCUCUGGAAGGGC ACAACCCCUAAUCUGAUGAGAAGCGUGAUCAUCAACUGCACCGA GCUGGUGACCUACGAUCUGAUGAAGGAAGCCUUUGUGAAGAACA ACAUCCUGGCCGACGACGUGCCUUGCCACCUCGUGUCCGCCCUG AUUGCCGGCUUCUGCGCCACCGCCAUGAGCAGCCCUGUGGACGU GGUGAAAAACCAGAUUCAUCAACAGCCCACCUGGCCAGUACAAGU CCGUGCCCAACUGCGCCAUGAAGGUGUUCACCAAUGAGGGACCU ACAGCAUUCUUCAAGGGCCUGGUCCCAUCUUUUCUGCGGCUGGG CUCCUGGAACGUGAUCAUGUUCGUUUGUUUUGAGCAGCUGAAAC GGGAACUGAGCAAGUCUAGACAGACCAUGGACUGUGUCUACAUGA |
| 47 | mol_type = RNA origin = synthetic construct | AUGGGCGGCCUGACCGCUUCUGAUGUGCACCCCACACUGGGGAGU CCAGCUGUUCAGCGCCGGCAUCGCCGCUUGUCUGGCCGAUGUGA UUACUUUUUCCACUGGACACCGCCAAGGUGCGGCUGCAGGUGCAA GGCGAGUGCCCUACCAGCAGCGUGAUCAGAUACAAGGGCGUGCU GGGCACCAUCACCGCUGUUGUGAAGACCGAAGGCAGAAUGAAAC UGUACAGCGGCCUGCCUGCCGGACUGCAAAGACAGAUCAGCUCC GCCAGCCUGCGCAUCGGACUGUACGAUACCGUGCAGGAGUUCCU GACAGCCGGCAAGGAAGACAGCCCCUAGCCUGGGCUCUAAGAUCC UGGCUGGCCUGACCACAGGCGGAGUGGCCGUCUUCAUCGGCCAG CCUACCGAGGUGGUCAAAGUGCGGCUGCAGGCCCAGAGCCACCU GCAUGGCAUCAAGCCCCGGUAUACAGGCACCUACAACGCCUACA GAAUCAUUGCCACAACAGAGGGCCUGACCGGCCUGUGGAAGGGA ACCACCCCCAAUCUGAUGAGAAGCGUGAUCAUCAACUGCACCGA ACUGGUGACCUACGACCUGAUGAAGGAAGCCUUCGUGAAAAACA ACAUCCUCGCCGACGACGUGCCUUGUCACCUGGUGUCCGCCCUG AUCGCCGGCUUCUGCGCCACCGCCAUGAGCUCCCCUGUGGACGU GGUGAAGACAAGAUUCAUCAACAGCCCUCCUGGCCAGUACAAGA GCGUGCCAAAUUGCGCCAUGAAGGUGUUUACCAACGAGGGCCCU ACAGCUUUUUUCAAGGGCCUUGUGCCCAGCUUCCUGAGACUCGG AUCUUGGAACGUGAUCAUGUUCGUCUGCUUCGAGCAGCUGAAGC GGGAACUGUCUAAAAGCAGACAGACCAUGGACUGCGCAACAUGA |
| 48 | mol_type = RNA origin = synthetic construct | AUGGGCGGACUCACCGCCAGCGACGUGCACCCAACCCUGGGGCGU GCAGCUGUUCAGCGCCGGAAUCGCCGCUUGUCUGGCCGACGUGA UUACCUUCCCUCUCGGAUACAGCCAAGGUGCGGCUGCAGGUGCAG GGCGAGUGCCCCACCAGCAGCGUCAUCCGGUAUAAGGGCGUUCU GGGCACCAUCACAGCUGUGGUGAAGACCGAAGGUAGAAUGAAGC UGUACAGCGGCCUCCCUGCCGGCCUGCAAAGACAGAUCAGCUCU GCUUCUCUGCGGAUCGGACUGUACGACACCGUCCAGGAGUUCCU GACAGCUGGCAAGGAGACAGCCCCUUCUCUGGGGAUCCAAGAUCC UGGCCGGCCUGACAACAGGCGGCGUGGCCGUCUUUAUUGGCCAG CCUACCGAAGUGGUGAAGGUGAGACUGCAGGCCCAGAGUCCCACCU |

| SEQ ID NO | | RNA Sequence |
|---|---|---|
| | | GCAUGGCAUCAAGCCUAGAUACACCGGCACUUACAACGCCUACA |
| | | GAAUCAUCGCAACCACCGAAGGCCUGACCGGCCUGUGGAAGGGA |
| | | ACAACCCCUAACCUGAUGAGAAGCGUGAUCAUCAAUUGCACCGA |
| | | GCUGGUGACCUACGACCUGAUGAAAGAGGCCUUUGUGAAAAACA |
| | | ACAUCCUGGCUGAUGAUGUGCCCUGCCACCUUGUGUCCGCCCUG |
| | | AUCGCCGGAUUUUGUGCCACCGCCAUGAGCUCUCCUGUGGACGU |
| | | GGUGAAAACCAGAUUCAUCAACAGCCCCCCCGGCCAGUACAAGA |
| | | GCGUGCCUAACUGCGCCAUGAAAGUGUUCACCAACGAGGGCCCU |
| | | ACAGCCUUCUUCAAGGGCCUGGUGCCAAGCUUCCUGAGGCUGGG |
| | | CAGCUGGAAUGUGAUCAUGUUCGUGUGCUUCGAGCAGCUGAAGC |
| | | GGGAACUGAGCAAGUCAAGACAAACAAUGGACUGCGCCACCUGA |
| 49 | mol_type = RNA origin = synthetic construct | AUGGGCGGCCUCACCGCCUCUGAUGUGCACCCUACACUGGGCGU |
| | | GCAGCUGUUCAGCGCCGGAAUCGCCGCCUUGUCUGGCUGAUGUGA |
| | | UUACCUUCCCCUGGACACAGCAAAGGUGCGGCUGCAAGUGCAA |
| | | GGCGAGUGCCCUACCAGCUCCGUGAUCAGAUACAAAGGCGUCCU |
| | | GGGCACCAUCACCGCUGUGGUCAAGACCGAAGGCAGAAUGAAGC |
| | | UGUACAGCGGCCUGCCUGCUGGCCUGCAGAGACAGAUCAGCAGC |
| | | GCCAGCCUGAGAAUCGGCCUGUAUGAUACCGUGCAGGAGUUCCU |
| | | GACCGCCGGCAAGGAAACCGCCCCUUCUCUGGGAAGCAAGAUCC |
| | | UGGCCGGACUGACAACCGGCGGAGUGGCCGUGUUUAUCGGACAG |
| | | CCUACAGAAGUGGUGAAAGUGCGGCUGCAGGCCCAGAGCCACCU |
| | | GCACGGCAUCAAGCCCAGAUACACCGGCACCUACAACGCCUACA |
| | | GAAUCAUCGCCACCACAGAGGGCCUGACCGGCCUGUGGAAGGGG |
| | | ACAACCCCUAAUCUGAUGCGGAGCGUGAUCAUCAACUGCACUGA |
| | | GCUGGUCACAUACGACCUGAUGAAAGAGGCCUUUGUGAAGAACA |
| | | ACAUCCUGGCCGACGACGUGCCAUGUCAUCUCGUGUCCGCCCUG |
| | | AUUGCCGGCUUCUGCGCCACCGCCAUGAGCAGCCCUGUGGACGU |
| | | CGUGAAGACAAGAUUCAUCAACAGCCCCCCCGGCCAGUACAAGU |
| | | CCGUGCCAAAUUGCGCCAUGAAAGUGUUCACCAACGAGGGCCCU |
| | | ACAGCUUUUUUCAAGGGCCUGGUUCCUAGCUUCCUGAGGCUGGG |
| | | AUCUUGGAACGUGAUCAUGUUCGUGUGCUUCGAGCAGCUGAAGC |
| | | GGGAACUGUCUAAGUCAAGACAGACCAUGGACUGCGCCACAUGA |
| 50 | mol_type = RNA origin = synthetic construct | AUGGGCGGCUUGACAGCUAGCGACGUGCACCCAACCCUGGGCGU |
| | | CCAGCUGUUCAGCGCUGGAAUCGCCGCUUGUCUGGCCGACGUGA |
| | | UCACAUUUCCUCUGGACACCGCCAAGGUUAGACUGCAAGUGCAG |
| | | GGCGAGUGCCCUACCAGCUCCGUGAUCAGAUACAAGGGCGUGCU |
| | | GGGAACCAUCACCGCCGUGGUCAAGACCGAAGGUAGAAUGAAGC |
| | | UGUACAGCGGCCUGCCUGCCGGCCUUCAGCGGCAGAUCAGCUCU |
| | | GCCUCUCUGCGCAUCGGCCUGUACGAUACCGUGCAGGAGUUUCU |
| | | GACCGCAGGCAAGGAAACAGCCCCUAGCCUGGGCAGCAAGAUUC |
| | | UGGCCGGACUGACUACAGGCGGAGUGGCCGUGUUCAUCGGGCAG |
| | | CCCACAGAGGUGGUGAAGGUGCGGCUGCAGGCCCAGAGCCACCU |
| | | GCAUGGCAUCAAGCCCAGAUACACAGGCACAUACAACGCCUACA |
| | | GAAUCAUUGCUACAACCGAGGGCCUGACCGGCCUGUGGAAGGGC |
| | | ACCACACCUAAUCUGAUGCGGUCCGUGAUCAUCAACUGCACCGA |
| | | ACUGGUGACCUAUGAUCUGAUGAAAGAGGCCUUUGUGAAGAAC |
| | | AACAUCCUCGCCGAUGACGUCCCUUGCCACCUGGUGUCCGCCCU |
| | | GAUCGCCGGCUUCUGCGCCACCGCCAUGAGCAGCCCUGUGGACG |
| | | UGGUGAAAACCAGAUUCAUCAAUAGCCCCCCCGGCCAAUACAAA |
| | | AGCGUGCCUAACUGUGCCAUGAAAGUGUUCACCAACGAGGGCCC |
| | | UACCGCUUUCUUCAAGGGCCUGGUGCCAAGUUUUCCUGAGACUGG |
| | | GAUCUUGGAACGUGAUCAUGUUCGUGUGCUUCGAGCAGCUGAAG |
| | | CGGGAACUGAGCAAGUCUAGACAGACCAUGGACUGCGCCACAUG |
| | | A |
| 51 | mol_type = RNA origin = synthetic construct | AUGGGCGGACUGACAGCCUCUGAUGUGCACCCCACACUGGGCGU |
| | | CCAGCUGUUCAGCGCCGGCAUCGCCGCUUGUCUGGCCGACGUGA |
| | | UCACCUUCCCACUGGACACCGCAAAGGUGCGGCUGCAGGUGCAA |
| | | GGCGAGUGUCCUACCAGCAGCGUGAUCGCUACAAGGGCGUGCU |
| | | GGGCACCAUCACCGCCGUUGUGAAGACCGAAGGCAGAAUGAAGC |
| | | UGUACAGCGGCCUUCCUGCCGGACUGCAAAGACGAUCAGCUCC |
| | | GCUUCUCUGCGGAUCGGACUGUAUGAUACAGUGCAGGAGUUCCU |
| | | GACAGCUGGGAAAGAGACAGCCCCUAGCCUGGGCAGCAAGAUCC |
| | | UGGCUGGACUGACCACCGGCGGCGUGGCCGUGUUUAUCGGCCAG |
| | | CCUACCGAGGUGGUGAAGGUGAGACUGCAGGCCCAGAGCCACCU |
| | | GCACGGCAUCAAGCCUAGAUACACCGGCACAUACAACGCCUACA |
| | | GAAUCAUCGCCACAACAGAAGGCCUGACCGGCCUGUGGAAGGGC |
| | | ACCACACCUAAUCUGAUGCGGAGCGUGAUUAUCAAUUGCACCGA |
| | | GCUGGUGACCUACGACCUGAUGAAAGAAGCCUUCGUGAAGAACA |
| | | ACAUCCUGGCCGAUGACGUUCCAUGCCAUCUGGUGUCCGCCCUG |
| | | AUCGCCGGCUUCUGCGCCACCGCCAUGUCCAGCCCCGUGGACGU |
| | | GGUGAAAACCAGAUUCAUCAACAGCCCUCCUGGACAGUACAAGU |
| | | CCGUGCCUAACUGCGCCAUGAAGGUGUUCACCAACGAGGGCCCC |
| | | ACCGCUUUUUUUAAGGGCCUGGUCCCCAGCUUCCUGAGACUCGG |

| SEQ ID NO | | RNA Sequence |
|---|---|---|
| | | AUCUUGGAACGUGAUUAUGUUCGUGUGCUUCGAGCAGCUGAAGC GGGAAUUGUCUAAAAGCAGACAGACCAUGGACUGCGCCACAUGA |
| 52 | mol_type = RNA origin = synthetic construct | AUGGGAGGCCUGACCGCUAGCGACGUGCACCCCACACUGGGCGU UCAGCUGUUCAGCGCCGGCAUCGCCGCUUGUCUGGCUGAUGUUA UUACCUUCCCCCUGGACACCGCCAAGGUGAGACUGCAAGUGCAG GGCGAAUGUCCUACCAGCUCUGUGAUCCGGUACAAGGGCGUGCU GGGCACAAUCACCGCAGUGGUCAAGACAGAAGGCAGAAUGAAGC UGUACAGCGGCCUGCCUGCCGGCCUGCAGAGACAAAUCAGCUCU GCCUCCCUGAGAAUCGGCCUGUAUGAUACCGUGCAGGAGUUCCU GACCGCCGGAAAAGAGACAGCCCCUAGCCUGGGCAGCAAGAUCC UGGCCGGACUUACCACAGGCGGCGUGGCCGUGUUCAUUGGACAG CCUACCGAGGUGGUGAAAGUGCGGCUGCAGGCCCAGAGCCACCU GCACGGCAUCAAGCCUAGAUACACCGGAACUUACAACGCCUACA GAAUCAUCGCCACCACCGAAGGCCUGACCGGCCUGUGGAAGGGU ACAACCCCUAAUCUGAUGCGGAGCGUGAUCAUCAACUGCACCGA GCUGGUGACCUACGAUCUGAUGAAAGAGGCCUUUGUCAAGAACA ACAUCCUGGCCGACGACGUGCCUUGCCAUCUGGGUGUCCGCCCUG AUCGCCGGCUUCUGCGCCACAGCUAUGAGCUCCCCUGUGGACGU GGUGAAGACCAGAUUCAUCAACAGCCCCCCCGGCCAGUACAAGA GCGUGCCAAAUUGCGCCAUGAAAGUCUUUACCAACGAGGGCCCU ACAGCUUUUUUCAAGGGACUCGUGCCAUCAUUCCUGCGGCUGGG CUCUUGGAACGUGAUCAUGUUCGUGUGCUUCGAGCAGCUGAAGA GGGAACUGAGCAAGUCUAGACAGACCAUGGACUGCGCCACAUGA |
| 53 | mol_type = RNA origin = synthetic construct | AUGGGCGGACUGACAGCUAGCGACGUGCACCCUACCCUGGGGCGU CCAGCUGUUCAGCGCCGGAAUCGCCGCUUGUCUGGCCGAUGUGA UUACAUUCCCCCUGGAUACCGCCAAGGUGCGGCUGCAAGUGCAG GGCGAGUGCCCUACCUCCAGCGUGAUCCGGUACAAGGGAGUGCU GGGAACAAUCACCGCCGUGGUGAAGACCGAAGGCAGAAUGAAAC UGUACAGCGGCCUCCCCGCCGGCCUUCAAAGACAGAUCAGCUCU GCCAGCCUGCGGAUCGGCCUGUACGACACAGUGCAGGAGUUCCU GACCGCCGGCAAGGAAACCGCCCCUUCUCUGGGUUCUAAGAUCC UGGCUGGCCUGACCACCGGCGGCGUGGCCGUGUUUAUUGGACAG CCUACCGAGGUGGUGAAGGUGCGGCUGCAGGCCCAGAGCCAUCU GCACGGCAUCAAGCCCAGAUACACCGGCACCUACAACGCCUACA GAAUCAUCGCUACCACCGAGGGCCUGACCGGCCUGUGGAAGGGC ACAACACCUAAUCUGAUGAGAAGCGUGAUCAUCAACUGUACAGA ACUGGUGACUUAUGAUCUGAUGAAAGAAGCCUUUGUGAAGAAC AACAUCCUGGCCGACGACGUGCCCAUGCCACCUGGUGUCCGCCCU GAUCGCCGGCUUCUGCGCCACCGCCAUGAGCAGCCCCGUGGACG UGGUCAAAACCAGAUUCAUCAACAGCCCUCCUGGCCAGUACAAG UCCGUUCCAAAUUGCGCCAUGAAAGUGUUCACCAACGAGGGCCC UACAGCUUUUUUCAAGGGCCUGGUCCCUAGCUUCCUGAGACUCG GAUCUUGGAACGUGAUCAUGUUCGUGUGCUUCGAGCAGCUGAAG AGGGAGCUGAGCAAGAGCAGACAGACCAUGGACUGCGCAACAUG A |
| 54 | mol_type = RNA origin = synthetic construct | AUCGCUGCUUGUCUGGCCGACGUGAUUACAUUCCCCUCUGGACAC CGCCAAGGUGCGGCUCCAGGUGCAAGGCGAAUGUCCUACCAGCU CCGUGAUCCGGUACAAAGGCGUCCUGGGGAACCAUCACCGCCGUG GUGAAAACCGAGGGCCAGAAUGAAACUGUACAGCGGCCUGCCUGU CGGACUGCAAAGACAGAUCAGCAGCGCCGCCAGCCUGCGGAUCGGCC UUUAUGAUACCGUGCAGGAGUUCCUGACCGCCGGCAAGGAGACU GCCCCUAGCCUGGGCUCUAAGAUCCUGGCUGGCCUGACAACCGG CGGCGUCGCCGUGUUCAUCGGACAGCAGCCUACCGAGGUGGUGAAGG UUAGACUGCAGGCCCAGAGCCACCUGCACGGCAUCAAGCCAAGA UACACCGGCACCUACAACGCCUACAGAAUCAUCGCCACAACCGA GGGCCUCACAGGGCUGUGGAAGGGCACCACACCUAAUCUGAUGA GAAGCGUGAUCAUCAAUUGCACCGAACUGGUUACAUACGACCUG AUGAAGGAAGCCUUUGUGAAGAACAACAUCCUGGCGGAUGACGU GCCCUGCCAUCUGGUGUCCGCCCUGAUCGCCGGCUUCUGCGCCA CAGCUAUGAGCUCCCCUGUGGACGUGGUGAAGACCAGAUUCAUU AACAGCCCCCCCGGCCAGUACAAGAGCGUGCCAAACUGCGCCAU GAAAGUGUUCACCAACGAGGGUCCUACAGCUUUUUUCAAGGGCC UGGUGCCUAGCUUUCUGAGGCUGGGCUCUUGGAACGUGAUCAUG UUCGUCUGCUUCGAGCAGCUGAAGCGGGAACUGAGCAAGUCUAG ACAGACCAUGGACUGCGCCACAUGA |
| 55 | mol_type = RNA origin = synthetic construct | AUGGGCGGACUGACAGCCAGCGACGUGCACCCCACCCUGGGGAGU GCAGCUGUUCAGCGCCGGCAUCGCCGCUUGCCUGGCUGAUGUGA UCACUUUUCCACUGGACACCGCAAAGGUGAGACUGCAGGUGCAG GGCGAAUGUCCUACAAGCAGCGUGAUUAGAUACAAGGGCGUGCU GGGCACAAUCACGGCUGUGGUCAAGACCGAGGGCAGAAUGAAGC UGUACAGCGGCUUGCCUGCCGGCCUCCAGAGGCAGAUCAGCUCC GCCUCUCUGCGGAUCGGCCUCUACGACACCGUGCAGGAGUUCCU |

-continued

| SEQ ID NO | RNA Sequence |
|---|---|

|  | GACAGCCGGGAAGGAGACAGCCCCUUCUCUGGGCAGCAAGAUCC
UGGCCGGACUGACCACCGGCGGCGUGGCCGUGUUCAUUGGACAG
CCCACCGAAGUGGUGAAAGUUCGGCUGCAAGCCCAGAGCCAUCU
GCACGGCAUCAAGCCCAGAUACACCGGCACCUACAACGCCUACA
GAAUCAUCGCCACAACAGAAGGCCUGACCGGCCUGUGGAAGGGC
ACCACCCCUAACCUGAUGCGGUCCGUGAUCAUCAAUUGCACCGA
GCUGGUCACCUAUGAUCUGAUGAAAGAGGCCUUCGUGAAGAACA
ACAUCCUGGCCGACGACGUCCCAUGCCACCUGGUGUCCGCCCUG
AUCGCCGGCUUCUGCGCUACAGCCAUGAGCUCUCCUGUUGAUGU
GGUGAAAACCAGAUUCAUCAACAGCCCUCCUGGCCAGUACAAAA
GCGUGCCUAAUUGUGCCAUGAAGGUGUUCACCAACGAGGGACCU
ACCGCCUUUUUCAAGGGCCUGGUGCCCAGCUUUCUGAGACUGGG
AUCUUGGAACGUGAUCAUGUUCGUGUGCUUCGAGCAGCUGAAGC
GGGAACUGAGCAAGAGCAGACAAACAAUGGACUGCGCUACCUGA |
| 56 | mol_type = RNA origin = synthetic construct | AUGGGCGGACUGACCGCCUCUGAUGUGCACCCUACCCUGGGCGU
GCAACUGUUCAGCGCCGGCAUCGCCCGCUUGUCUGGCCGACGUGA
UUACAUUCCCUCUGGACACCGCCAAGGUGCGGCUGCAAGUGCAG
GGCGAAUGCCCUACCUCCAGCGUUAUCCGGUACAAGGGAGUUCU
GGGCACCAUCACAGCUGUGGUGAAAACCGAGGGCAGAAUGAAGC
UGUACAGCGGCCUCUCCCGCCGGACUGCAGAGACAGAUCAGCAGC
GCCUCUCUGAGGAUCGGCCUAUAUGACACCGUGCAGGAGUUCCU
GACAGCCGGCAAGGAAACAGCCCCUAGCCUGGGCAGCAAGAUCC
UGGCCGGCCUGACCACCGGCGGCGUGGCCGUCUUUAUCGGCCAG
CCUACAGAGGUGGUGAAAGUGCGGCUGCAGGCCCAGAGCCACCU
GCACGGCAUUAAGCCUAGAUACACCGGCACCUACAACGCCUACA
GAAUCAUCGCCACAACCGAAGGCCUGACAGGCCUGUGGAAGGGC
ACAACACCUAACCUGAUGCGGAGCGUGAUCAUCAAUUGCACCGA
ACUGGUCACCUACGACCUGAUGAAAGAGGCCUUUGUGAAGAACA
ACAUCCUGGCUGAUGAUGUGCCAUGUCAUCUGGUCUCCGCCCUG
AUCGCCGGUUUCUGCGCCACCGCUAUGAGCUCUCCCUGUGGACGU
GGUGAAGACCAGAUUCAUCAACAGCCCCCCCGGCCAGUACAAGU
CUGUGCCCAAAUUGCGCUAUGAAAGUGUUCACCAACGAGGGACCU
ACAGCUUUUUUCAAGGGCCUGGUGCCCAGCUUCCUCAGACUGGG
AUCUUGGAACGUGAUCAUGUUCGUGUGCUUCGAGCAGCUGAAGA
GAGAGCUGAGCAAGAGCAGACAGACCAUGGACUGCGCCACCUGA |
| 57 | mol_type = RNA origin = synthetic construct | AUGGGAGGACUGACCGCCAGCGACGUGCACCCUACCCUGGGAGU
GCAGCUGUUCAGCGCCGGAAUCGCCGCCCUGCCUGGGCCGAUGUCA
UCACCUUCCCCCUGGAUACAGCUAAGGUGCGGCUGCAGGUGCAG
GGCGAGUGCCCCACAAGCAGCGUGAUUAGAUACAAGGGCGUGCU
GGGCACAAUCACAGCUGUGGUGAAGACCGAGGGCAGAAUGAAAC
UGUACAGCGGCCUGCCUGCCGGCCUGCAAAGACAGAUCAGCAGC
GCCUCUCUGCGGAUCGGCCUCUACGACACCGUGCAGGAGUUCCU
GACCGCCGGCAAGGAAACCGCCCCUAGCCUGGGCUCCAAGAUCC
UGGCUGGACUGACCACCGGCGGCGUGGCCGUGUUCAUCGGCCAA
CCUACAGAGGUGGUCAAAGUGCGGCUGCAGGCCCAGAGCCACCU
GCAUGGCAUCAAGCCUAGAUACACCGGCACCUACAACGCCUACA
GAAUCAUCGCCACCACAGAAGGCCUGACCGGCCUGUGGAAGGGC
ACGACUCCUAAUCUGAUGCGGAGCGUGAUCAUCAACUGCACCGA
ACUGGUGACCUAUGACCUGAUGAAAGAGGCCUUUGUGAAAAACA
ACAUCCUUGCUGAUGACGUUCCAUGUCACCUGGUGUCCGCCCUG
AUCGCCGGCUUCUGCGCCACAGCCAUGUCUUCUCCUGUGGACGU
GGUGAAGACAAGAUUUAUCAACAGCCCUCCAGGCCAGUACAAGA
GCGUGCCCAAUUGCGCCAUGAAGGUGUUCACCAACGAAGGCCCU
ACCGCUUUUUUCAAGGGACUGGUCCCCAGCUUCCUGAGACUGGG
UUCUUGGAACGUGAUUAUGUUCGUGUGCUUCGAGCAGCUGAAGC
GCGAGCUGAGCAAGUCCAGACAGACCAUGGACUGUGCCACAUGA |
| 58 | mol_type = RNA origin = synthetic construct | AUGGGCGGACUGACCGCUUCUGAUGUGCACCCUACCCUGGGCGU
GCAGCUGUUCUCCGCCGGCAUCGCCGCUUGUCUGGCCGACGUGA
UUACUUUUCCACUGGACACCGCAAAGGUCAGACUGCAGGUGCAG
GGCGAGUGCCCCACAAGCAGCGUGAUCAGAUAUAAGGGCGUGCU
GGGAACCAUCACCGCCGUGGUGAAGACCGAGGGCAGAAUGAAGC
UGUACAGCGGCCUCUCCCGCCGGCCUGCAGAGACAGAUCAGCUCU
GCCAGCCUGCGGAUCGGACUCUACGAUACAGUGCAGGAGUUCCU
GACCGCUGGCAAGGAAACCGCCCCUAGCCUGGGUUCUAAGAUCC
UGGCCGGACUGACCACCGGAGGAGUGGCCGUGUUCAUCGGCCAA
CCUACCGAGGUGGUCAAGGUGCGGCUGCAAGCCCAGAGCCAUCU
GCACGGCAUCAAGCCUAGAUACACCGGCACAUACAACGCCUACA
GAAUUAUCGCCACCACAGAAGGCCUGACAGGCCUGUGGAAGGGC
ACCACCCCUAAUCUGAUGCGGAGCGUUAUCAUCAACUGCACCGA
ACUGGUGACCUACGACCUGAUGAAAGAGGCCUUCGUGAAGAACA
ACAUCCUGGCUGAUGACGUGCCCUGCCACCUGGUGUCCGCCCUG
AUCGCCGGCUUCUGCGCCACAGCCAUGAGCAGCCCUGUGGACGU
GGUGAAAACAAGAUUCAUCAACAGCCCUCCUGGCCAGUACAAGA |

-continued

| SEQ ID NO | | RNA Sequence |
|---|---|---|
| | | GCGUGCCAAACUGUGCCAUGAAAGUCUUUACCAACGAGGGCCCU |
| | | ACAGCUUUUUUCAAGGGCCUAGUGCCCUCCUUCCUGAGGCUGGG |
| | | CUCUUGGAAUGUGAUCAUGUUCGUGUGCUUCGAGCAGCUGAAGC |
| | | GGGAACUGAGCAAAAGCAGACAGACAAUGGACUGCGCCACAUGA |
| 59 | mol_type = RNA origin = synthetic construct | AUGGGCGGCCUGACCGCCAGUGAUGUGCACCCCACCCUGGGUGU |
| | | UCAACUGUUCUCUGCCGGAAUCGCCGCCUGCCUGGCCGACGUGA |
| | | UCACCUUUCCACUGGACACCGCCAAGGUGAGGCUGCAGGUGCAG |
| | | GGCGAGUGUCCUACAAGCAGCGUGAUCAGAUACAAGGGCGUGCU |
| | | GGGCACCAUCACCGCUGUGGUCAAGACAGAGGGCAGAAUGAAAC |
| | | UGUACAGCGGCCUGCCUGCCGGCCUCCAGCGGCAGAUCAGCUCC |
| | | GCCUCUCUUCGGAUCGGCCUCUACGACACCGUGCAGGAGUUCCU |
| | | GACAGCUGGCAAGGAAACCGCCCCUUCUCUGGGAUCUAAGAUCC |
| | | UGGCUGGCCUGACCACAGGAGGAGUGGCCGUGUUUAUCGGCCAG |
| | | CCUACCGAAGUGGUGAAGGUGCGGCUGCAGGCCCAGAGCCAUCU |
| | | GCACGGCAUCAAGCCUAGAUAUACAGGCACCUACAACGCCUACA |
| | | GAAUCAUCGCGACAACCGAGGGCCUGACCGGCCUGUGGAAGGGC |
| | | ACAACACCUAAUCUGAUGAGAAGCGUGAUUAUUAACUGCACCGA |
| | | GCUGGUUACAUACGAUCUGAUGAAAGAAGCCUUCGUGAAGAACA |
| | | ACAUCCUGGCCGAUGACGUGCCUUGUCACCUGGUGUCCGCUCUG |
| | | AUCGCCGGCUUCUGCGCCACGGCCAUGAGCUCCCCUGUGGACGU |
| | | GGUCAAAACCAGAUUCAUCAACAGCCCCCCCGGCCAGUACAAGA |
| | | GCGUGCCCAAUUGCGCCAUGAAAGUCUUUACCAACGAGGGACCU |
| | | ACCGCUUUCUUCAAGGGCCUGGUGCCAAGCUUCCUGAGACUGGG |
| | | CAGCUGGAACGUGAUCAUGUUCGUGUGCUUCGAGCAGCUGAAGC |
| | | GGGAACUGAGCAAGAGCAGACAAACAAUGGACUGCGCCACCUGA |
| 60 | mol_type = RNA origin = synthetic construct | AUGGGCGGCCUGACAGCCAGUGAUGUGCACCCCACCCUGGGCGU |
| | | GCAACUGUUCAGCGCCGGCAUCGCAGCCUGCCUGGCCGACGUGA |
| | | UCACAUUUCCAUUGGACACAGCCAAGGUGAGACUGCAGGUGCAG |
| | | GGCGAGUGCCCCACAAGCAGCGUGAUUCGGUACAAGGGCGUGCU |
| | | GGGCACCAUCACCGCCGUGGUCAAGACCGAAGGCAGGAUGAAAC |
| | | UGUACAGCGGCCUGCCUGCCGGCCUGCAGAGACAGAUCAGCUCU |
| | | GCUAGCCUGAGAAUCGGACUCUACGACACCGUCCAGGAGUUCCU |
| | | GACUGCUGGCAAGGAAACCGCCCCUUCUCUGGGAAGCAAGAUCC |
| | | UGGCCGGACUCACUACCGGCGGAGUGGCCGUGUUCAUCGGCCAG |
| | | CCUACAGAGGUGGUGAAAGUGCGGCUGCAAGCCCAGAGCCAUCU |
| | | GCACGGCAUCAAGCCUAGAUACACCGGCACCUACAACGCCUACA |
| | | GAAUCAUCGCCACCACAGAAGGCCUGACCGGCCUGUGGAAGGGC |
| | | ACAACCCCUAAUCUGAUGCGGUCUGUGAUCAUCAAUUGCACAGA |
| | | GCUGGUGACCUAUGACCUGAUGAAAGAAGCCUUCGUGAAGAACA |
| | | ACAUCCUGGCUGAUGAUGUGCCCUGUCACCUGGUCUCCGCCCUG |
| | | AUCGCCGGCUUCUGCGCCACCGCCAUGUCCAGCCCUGUGGACGU |
| | | GGUGAAGACAAGAUUCAUCAACAGCCCACCUGGCCAGUACAAGU |
| | | CUGUUCCCAACUGUGCUAUGAAAGUGUUUACCAACGAGGGACCU |
| | | ACCGCUUUUUUCAAGGGACUGGUGCCUAGCUUCCUGCGGCUGGG |
| | | CUCCUGGAACGUGAUCAUGUUCGUGUGCUUCGAGCAGCUGAAGA |
| | | GAGAGCUGAGCAAGAGCAGACAGACCAUGGACUGCGCCACAUGA |
| 61 | mol_type = RNA origin = synthetic construct | AUGGGCGGCCUGACCGCCUCUGAUGUGCACCCUACCCUGGGCGU |
| | | GCAGCUGUUCAGCGCCGGAAUCGCCGCCUGUCUGGCCGACGUGA |
| | | UCACCUUUCCACUGGACACCGCUAAAGUGCGGCUGCAGGUGCAA |
| | | GGCGAGUGCCCUACAAGCUCUGUGAUCAGAUACAAGGGAGUGCU |
| | | GGGCACCAUCACAGCCGUGGUGAAGACCGAAGGCAGAAUGAAAC |
| | | UGUACAGCGGCCUGCCUGCCUGGACUGCAAAGACAGAUCAGCUCU |
| | | GCUAGCCUGAGGAUCGGACUUUAUGAUACCGUGCAGGAGUUCCU |
| | | GACAGCCGGCAAAGAGACAGCCCCUAGCCUGGGCUCCAAGAUCC |
| | | UGGCCGGCCUGACCACAGGAGGCGUCGCCGUGUUCAUCGGCCAG |
| | | CCUACAGAAGUGGUCAAGGUGCGGCUACAGGCCCAGAGCCACCU |
| | | GCACGGCAUCAAGCCCAGAUACACCGGCACCUACAACGCCUACC |
| | | GGAUCAUCGCCACAACCGAGGGCCUGACCGGCCUCUGGAAGGGC |
| | | ACAACCCCUAACCUGAUGCGCAGCGUGAUCAUCAAUUGCACCGA |
| | | ACUGGUCACCUACGACCUGAUGAAAGAAGCCUUCGUGAAGAACA |
| | | ACAUCCUGGCUGAUGACGUGCCCUGCCAUCUGGUGUCCGCCCUG |
| | | AUCGCCGGCUUCUGCGCCACCGCCAUGAGCAGCCCCGUGGACGU |
| | | GGUUAAGACAAGAUUCAUUAACUCCCCUCCAGGCCAGUACAAGA |
| | | GCGUGCCUAAUUGCGCCAUGAAGGUGUUCACCAACGAGGGACCU |
| | | ACAGCUUUUUUCAAGGGCCUGGUGCCCAGCUUCCUGAGACUGGG |
| | | CAGCUGGAACGUGAUUAUGUUCGUGUGUGUUUUGAGCAGCUGAAG |
| | | CGGGAGCUGUCUAAGUCCAGACAGACCAUGGACUGCGCAACAUG |
| | | A |

-continued

| SEQ ID NO | | RNA Sequence |
|---|---|---|
| 62 | mol_type = RNA origin = synthetic construct | AUGGGCGGACUGACAGCCAGUGAUGUGCACCCCACCCUGGGAGU UCAGCUGUUCAGCGCUGGAAUCGCCGCCUGCCUGGCCGACGUGA UUACAUUUCCUCUGGACACCGCCAAGGUGCGGCUGCAAGUGCAG GGCGAGUGUCCUACAAGCAGCGUGAUCCGGUACAAGGGCGUGCU GGGAACCAUCACAGCUGUGGUGAAAACCGAGGGAAGAAUGAAGC UGUACAGCGGCCUGCCUGCUGGCCUGCAGAGACAGAUCAGCUCC GCUUCUCUGCGGAUCGGCCUUUAUGAUACCGUGCAGGAGUUCCU GACAGCUGGCAAGGAAACCGCCCCUAGCCUGGGCUCUAAAAUCC UGGCUGGCCUGACCACCGGUGGCGUGGCCGUGUUCAUCGGCCAG CCUACAGAAGUGGUCAAGGUGCGGCUGCAGGCCCAGAGCCACCU GCACGGCAUCAAGCCCAGAUACACCGGCACAUACAACGCCUACA GAAUCAUCGCCACCACCGAGGGCCUAACCGGCCUGUGGAAGGGC ACCACCCCUAAUCUGAUGAGAAGCGUGAUCAUCAACUGCACCGA ACUGGUGACCUACGACCUCAUGAAGGAAGCCUUUGUGAAGAACA ACAUCCUGGCCGAUGACGUGCCCUGCCAUCUGGUCUCCGCCCUG AUCGCCGGCUUCUGCGCCACAGCCAUGAGCAGCCCCGUGGACGU GGUGAAGACAAGAUUCAUCAACAGCCCUCCUGGCCAGUACAAGA GCGUGCCAAAUUGUGCCAUGAAAGUGUUUACCAACGAGGGCCCU ACCGCCUUCUUCAAGGGACUGGUUCCAUCCUUCCUGAGGCUGGG CAGCUGGAACGUGAUCAUGUUCGUGUGCUUCGAGCAGCUGAAGA GAGAGCUGUCUAAAUCUAGACAAACAAUGGACUGCGCCACCUGA |
| 63 | mol_type = RNA origin = synthetic construct | AUGGGAGGCCUGACCGCUAGCGACGUGCACCCUACACUGGGCGU GCAGCUGUUCAGCGCCGGCAUCGCCGCAUGCCUGGCUGAUGUGA UCACCUUCCCCCUGGAUACCGCCAAGGUGCGGCUGCAAGUGCAG GGCGAGUGCCCUACAAGCUCCGUGAUCAGAUACAAGGGAGUGCU GGGCACAAUCACAGCUGUGGUGAAAACCGAGGGCAGAAUGAAGC UGUACAGCGGCCUGCCUGCCGGACUUCAGAGACAGAUUAGCAGU GCCUCUCUGAGAAUCGGCCUGUAUGAUACAGUGCAGGAGUUCCU GACAGCCGGCAAAGAGACAGCUCCUUCCCUGGGCAGCAAGAUCC UGGCCGGCCUGACCACCGGCGGCGUGGCCGUGUUCAUCGGCGACAG CCUACCGAAGUGGUCAAAGUGCGGCUGCAGGCCCAGAGCCACCU GCAUGGCAUCAAGCCUCGGUACACCGGCACCUACAACGCCUACA GAAUCAUCGCCACCACAGAAGGCCUGACCGGACUGUGGAAGGGA ACCACCCCUAACCUGAUGAGAAGCGUGAUCAUCAAUUGCACUGA GCUGGUGACCUACGACCUGAUGAAGGAAGCCUUCGUUAAGAACA ACAUCCUCGCCGACGACGUCCCCUGUCACCUGGUCAGCGCCCUG AUCGCCGGCUUCUGCGCCACCGCCAUGAGCUCUCCAGUGGACGU GGUGAAGACCAGAUUCAUCAACAGCCCCCCUGGCCAGUACAAAA GCGUGCCUAAUUGCGCCAUGAAGGUGUUUACCAACGAGGGCCCU ACAGCUUUUUUCAAGGGCCUGGUGCCAUCUUUCCUGCGCCUCGG AAGCUGGAACGUGAUUAUGUUCGUUUGUUUUGAGCAGCUGAAG CGGGAACUGUCUAAGUCCAGACAAACAAUGGACUGCGCCACCUG A |
| 64 | mol_type = RNA origin = synthetic construct | AUGGGCGGCCUGACAGCCUCUGAUGUGCACCCUACCCUGGGGAGU GCAGCUGUUCAGCGCCGGCAUCGCCGCCUUGUCUGGCCGAUGUGA UCACCUUUCCUCUGGACACCGCUAAGGUGCGCCUGCAGGUGCAG GGCGAGUGUCCUACCAGCAGCGUGAUCAGAUACAAGGGCGUGCU GGGCACCAUCACAGCAGUGGUCAAAACCGAGGGCAGAAUGAAAC UGUACAGCGGCCUCCCCGCCGGCCUGCAAAGACAAAUCAGCUCU GCCAGCCUGCGGAUUGGCCUGUAUGACACCGUACAGGAGUUCCU GACAGCCGGAAAGGAAACCGCCCCUUCUCUGGGGAUCCAAGAUCC UGGCCGGCCUGACCACUGGCGGAGUGGCCGUGUUCAUCGGCCAG CCUACCGAGGUGGUGAAGGUGCGGCUGCAGGCCCAGAGCCACCU GCAUGGCAUCAAGCCUCUAGAUACACAGGCACGUACAACGCCUACA GAAUCAUCGCCACCACCGAAGGACUGACCGGCCUGUGGAAGGGC ACAACCCCUAACCUGAUGAGAAGCGUCAUCAUCAACUGCACCGA ACUGGUCACAUACGACCUGAUGAAAGAGGCCUUUGUGAAGAACA AUAUCCUGGCCGACGAUGUGCCCAUGCCACCUGGUGUCCGCCCUC AUCGCCGGCUUCUGCGCUACCGCUAUGAGCUCCCCUGUGGACGU GGUGAAGACCCGGUUCAUCAACAGCCCCCCUGGCCAGUACAAAA GCGUGCCAAAUUGCGCCAUGAAGGUGUUCACAAACGAGGGACCU ACAGCUUUUUUCAAGGGCCUGGUUCCCAGCUUCCUGAGACUGGG CUCUUGGAACGUGAUCAUGUUCGUGUGCUUCGAGCAGCUGAAGC GGGAACUGAGCAAGAGCAGACAGACCAUGGACUGCGCCACAUGA |
| 65 | mol_type = RNA origin = synthetic construct | AUGGGCGGACUGACCGCUUCUGAUGUGCACCCUACACUGGGCGU CCAACUGUUCUCUGCCGGCAUCGCCGCCUUGUCUGGCUGAUGUGA UCACAUUCCCCCUGGACACCGCCAAGGUGCGCCUGCAGGUGCAG GGCGAGUGCCCUACCUCUAGCGUGAUUCGGUACAAGGGCGUGCU GGGCACCAUCACAGCCGUUGUGAAGACCGAAGGCAGAAUGAAAC UGUACUCCGGCCUCCCCUGCCGGCCUGCAAAGACAGAUCAGCAGC GCCCAGCCUCAGAAUUGGCCUGUAUGAUACCGUGCAGGAGUUCCU GACCGCCGGCAAGGAGACAGCCCCUAGCCUGGGCAGCAAGAUCC UGGCCGGCCUGACAACCGGCGGAGUCGCCGUGUUUAUCGGACAG |

-continued

| SEQ ID NO | | RNA Sequence |
|---|---|---|
| | | CCUACCGAGGUGGUGAAAGUGCGGCUGCAGGCCCAGAGCCACCU |
| | | GCACGGCAUCAAGCCCAGAUACACCGGCACCUACAACGCCUACC |
| | | GGAUCAUCGCCACCACCGAAGGCCUGACCGGACUGUGGAAGGGC |
| | | ACAACCCCUAAUCUGAUGCGGAGCGUGAUCAUCAACUGCACAGA |
| | | ACUGGUCACCUACGACCUGAUGAAGGAAGCCUUCGUGAAGAACA |
| | | ACAUCCUGGCCGACGACGUUCCAUGUCAUCUGGUGUCCGCCCUG |
| | | AUCGCCGGCUUCUGCGCGACCGCUAUGAGCAGCCCUGUGGACGU |
| | | GGUGAAGACAAGAUUCAUCAACAGCCCCCCCGGCCAGUACAAGU |
| | | CCGUGCCUAAUUGCGCCAUGAAAGUGUUCACCAACGAGGGCCCU |
| | | ACAGCUUUUUUCAAGGGACUGGUGCCAUCUUUUCUGAGACUGGG |
| | | AAGCUGGAACGUGAUCAUGUUCGUGUGCUUCGAGCAGCUGAAGA |
| | | GAGAGCUGAGCAAAAGCAGACAGACGAUGGACUGCGCCACAUGA |
| 66 | mol_type = RNA origin = synthetic construct | AUGGGCGGACUGACCGCUUCUGAUGUGCAUCCCACCCUGGGGAGU |
| | | GCAGCUGUUCAGCGCCGGCAUCGCUGCUUGUCUGGCCGACGUGA |
| | | UCACCUUCCCCCUGGACACCGCCAAGGUGCGCCUGCAAGUGCAG |
| | | GGCGAGUGCCCUACCAGCAGCGUGAUCAGAUACAAGGGCGUGCU |
| | | GGGCACAAUCACCGCCGUGGUGAAGACCGAGGGCAGAAUGAAAC |
| | | UGUAUAGUGGCCUGCCUGCCGGUCUCCAGCGGCAGAUUAGCUCU |
| | | GCCAGCCUGCGGAUCGGCCUGUACGACACCGUGCAGGAGUUUCU |
| | | GACAGCAGGCAAAGAGACAGCCCCUUCUCUCGGAAGCAAGAUCC |
| | | UGGCCGGCCUGACCACCGGCGGCGUGGCCGUGUUUAUCGGACAA |
| | | CCUACAGAAGUGGUGAAAGUGCGGCUGCAGGCCCAGAGCCACCU |
| | | GCACGGCAUCAAGCCUAGAUACACCGGAACAUACAACGCCUACA |
| | | GAAUCAUCGCCACCACCGAAGGCCUGACCGGCUUAUGGAAGGGC |
| | | ACCACACCUAAUCUGAUGAGAAGCGUGAUUAUCAACUGUACAGA |
| | | GCUGGUGACCUACGACCUGAUGAAGGAAGCCUUCGUGAAGAACA |
| | | ACAUCCUGGCUGAUGAUGUGCCAUGCCACCUGGUGUCCGCCCUG |
| | | AUCGCCGGCUUCUGCGCCACCGCCAUGAGCAGCCCUGUCGACGU |
| | | CGUGAAGACAAGAUUCAUCAACAGCCCCCCCGGCCAGUACAAGU |
| | | CCGUGCCAAAUUGCGCCAUGAAAGUUUUCACCAACGAGGGCCCU |
| | | ACAGCUUUUUUCAAGGGACUGGUCCCUAGCUUCCUGAGACUGGG |
| | | CUCCUGGAACGUGAUCAUGUUCGUGUGCUUCGAGCAGCUGAAGC |
| | | GGGAACUGUCUAAGAGCAGACAGACCAUGGACUGCGCCACGUGA |
| 67 | mol_type = RNA origin = synthetic construct | AUGGGCGGACUGACAGCCUCUGAUGUGCACCCCACCCUGGGGAGU |
| | | GCAGCUGUUCAGCGCCGGCAUCGCCGCUUGUCUGGCCGACGUGA |
| | | UUACCUUCCCCUCUGGACACCGCAAAGGUGGAGGCUGCAGGUUCAG |
| | | GGCGAGUGCCCUACCAGCAGUGUGAUCCGGUACAAGGGCGUACU |
| | | GGGCACCAUCACCGCUGUGGUGAAGACAGAAGGCAGAAUGAAAC |
| | | UGUACAGCGGCCUUCCCGCCGGCCUGCAAAGACAGAUCAGCAGC |
| | | GCCUCUCUGCGGAUCGGCCUGUAUGAUACAGUGCAGGAGUUCCU |
| | | GACAGCCGGCAAGGAAACCGCCCCUAGCCUGGGAUCUAAGAUCC |
| | | UGGCUGGACUGACCACCGGCGGCGUGGCCGUGUUCAUCGGCCAA |
| | | CCUACCGAGGUGGUCAAGGUGCGGCUGCAGGCCCAGAGCCACCU |
| | | GCAUGGCAUCAAGCCUAGAUACACCGGCACAUACAACGCCUACA |
| | | GAAUCAUCGCCACCACCGAGGGCCUCACCGGCCUGUGGAAGGGA |
| | | ACAACCCCUAAUCUGAUGAGAAGCGUGAUCAUCAAUUGCACGGA |
| | | GCUGGUGACCUACGACCUGAUGAAGGAAGCCUUUGUGAAAAACA |
| | | ACAUCCUGGCCGAUGACGUGCCAUGUCACCUGGUGUCCGCCCUG |
| | | AUCGCCGGCUUUUGCGCCACCGCUAUGAGCUCUCCUGUGGACGU |
| | | GGUGAAAACAAGAUUCAUCAACAGCCCUCCAGGCCAGUACAAGU |
| | | CCGUCCCCAACUGCGCCAUGAAAGUGUUCACCAACGAGGGCCCU |
| | | ACAGCUUUUUUCAAGGGACUGGUCCCCAGCUUCCUGAGACUGGG |
| | | CAGCUGGAACGUGAUUAUGUUCGUGUGCUUCGAGCAGCUGAAGC |
| | | GGGAACUGAGCAAGUCCAGACAGACCAUGGACUGCGCCACAUGA |
| 68 | mol_type = RNA origin = synthetic construct | AUGGGAGGACUGACAGCCUCUGAUGUGCAUCCCACCCUGGGGCGU |
| | | GCAGCUGUUCAGCGCCGGCAUCGCCGCUUGUCUGGCCGAUGUGA |
| | | UUACCUUCCCCCUGGACACCGCCAAGGUGCGGCUGCAGGUUCAG |
| | | GGCGAGUGCCCCACAAGCAGCGUGAUCAGAUACAAGGGCGUGCU |
| | | GGGCACCAUCACCGCAGUGGUGAAGACAGAAGGCAGAAUGAAAC |
| | | UGUACAGCGGCCUGCCUGCCGGCCUGCAAAGACAGAUCAGCUCC |
| | | GCCAGCCUGAGAAUCGGCCUGUAUGAUACCGUGCAGGAGUUCCU |
| | | CACAGCCGGCAAGGAAACCGCCCCUUCUCUGGGGGUCCAAGAUCC |
| | | UGGCUGGCCUGACCACAGGAGGCGUCGCCGUGUUUAUCGGACAG |
| | | CCUACAGAGGUGGUGAAGGUGCGGCUGCAGGCCCAGAGCCACCU |
| | | GCACGGCAUCAAGCCUAGAUACACCGGCACCUACAACGCCUACA |
| | | GAAUCAUCGCCACCACCGAAGGCCUGACCGGCCUCUGGAAGGGA |
| | | ACCACCCCUAAUCUGAUGCGGAGCGUGAUCAUCAACUGCACCGA |
| | | GCUGGUGACCUACGACCUGAUGAAGGAGGCCUUUGUGAAGAACA |
| | | ACAUCCUGGCCGACGACGUGCCUUGUCACCUGGUCAGCGCCCUG |
| | | AUCGCCGGCUUCUGCGCUACAGCUAUGAGCUCUCCUGUGGACGU |
| | | GGUGAAGACCAGAUUCAUUAACAGCCCCACCUGGCCAGUACAAGU |
| | | CCGUGCCAAAUUGCGCCAUGAAAGUCUUCACCAACGAGGGGACCU |
| | | ACAGCUUUUUUCAAGGGCCUGGUGCCCAGCUUCCUGAGGCUGGG |

-continued

| SEQ ID NO | | RNA Sequence |
|---|---|---|
| | | CUCUUGGAACGUGAUCAUGUUCGUGUGCUUCGAGCAGCUGAAGC |
| | | GGGAACUGUCUAAAAGCAGACAAACAAUGGACUGCGCCACAUGA |
| 69 | mol_type = RNA origin = synthetic construct | AUGGGCGGACUCACAGCCAGCGACGUACAUCCUACACUGGGCGU |
| | | GCAGCUGUUCAGCGCCGGCAUCGCUGCCUGCCUGGCUGAUGUGA |
| | | UCACCUUCCCCCUGGAUACAGCAAAGGUUAGACUGCAAGUGCAG |
| | | GGCGAGUGCCCCACAAGCAGCGUGAUCCGGUACAAAGGCGUGCU |
| | | GGGAACCAUUACAGCUGUGGUGAAGACAGAGGGCAGAAUGAAG |
| | | CUGUAUUCUGGCCUGCCUGCCGGCCUGCAGAGACAGAUCAGCUC |
| | | UGCUAGCCUGCGGAUCGGCCUGUACGACACCGUGCAGGAGUUCC |
| | | UCACAGCCGGAAAGGAAACCGCCCCUUCUCUGGGCAGCAAGAUC |
| | | CUGGCCGGCCUGACCACAGGCGGCGUGGCCGUGUUUAUUGGACA |
| | | ACCUACAGAGGUGGUCAAGGUCAGACUGCAGGCCCAGAGCCACC |
| | | UGCACGGCAUCAAACCUAGAUACACCGGCACCUACAACGCCUAC |
| | | AGAAUCAUCGCCACCACCGAGGGCCUGACCGGCCUUUGGAAGGG |
| | | CACCACCCCUAAUCUGAUGCGCAGCGUGAUCAUCAAUUGUACCG |
| | | AACUGGUGACAUACGACCUGAUGAAAGAAGCCUUUGUGAAAAAC |
| | | AACAUCCUGGCCGACGAUGUGCCAUGCCACCUGGUGUCCGCCCU |
| | | GAUCGCCGGCCUUCUGCGCCACCGCUAUGAGCUCCCCUGUGGACG |
| | | UGGUGAAGACCAGAUUCAUCAACAGCCCCCCCGGCCAGUACAAG |
| | | UCCGUGCCCAACUGUGCCAUGAAGGUCUUCACUAACGAGGGUCC |
| | | UACCGCCUUUUUCAAGGGACUGGUUCCAAGCUUCCUGAGGCUGG |
| | | GCUCUUGGAACGUGAUCAUGUUCGUGUGCUUCGAGCAGCUGAAG |
| | | CGGGAACUGAGCAAGAGCCGGCAGACCAUGGACUGCGCCACCUG |
| | | A |
| 70 | mol_type = RNA origin = synthetic construct | AUGGGGAGGUCUCACAGCCAGCGACGUACACCCCACAUUAGGGGU |
| | | UCAGCUCUUUAGUGCAGGCAUAGCCGCUUGCCUCGCUGAUGUUA |
| | | UUACUUUUCCCCUCGACACUGCUAAGGUGCGACUGCAAGUACAG |
| | | GGCGAAUGCCCUACUUCAUCAGUGAUUCGAUACAAGGGCGUAUU |
| | | GGGCACUAUUACUGCCGUCGUGAAAACAGAAGGCCGUAUGAAGC |
| | | UGUAUAGUGGGCUGCCAGCGGGAUUGCAGAGGCAGAUCAGCUCU |
| | | GCAUCUCUGCGAAUCGGACUGUACGACACCGUUCAAGAGUUCCU |
| | | UACCGCAGGAAAGGAGACAGCACCUAGCCUAGGGUCCAAAAUCU |
| | | UGGCAGGUCUCACUACAGGGGGCGUAGCUGUUUUCAUCGGACAA |
| | | CCCACAGAAGUUGUAAAGGUCCGACUCCAAGCACAGAGCCAUCU |
| | | UCACGGGAUCAAACCUCGCUACACUGGCACGUACAACGCUUACA |
| | | GGAUCAUCGCCACUACAGAGGGUUUAACAGGGCUUUGGAAGGGG |
| | | ACAACACCUAAUCUGAUGCGAUCCGUGAUUAUUAACUGCACCGA |
| | | AUUGGUGACUUACGAUCUCAUGAAGGAGGCCUUCGUGAAGAACA |
| | | ACAUCUUGGCGGACGACGUGCCUUGUCAUUUAGUCUCUGCACUG |
| | | AUAGCCGGAUUCUGUGCCACCGCCAUGUCGAGCCCUGUUGACGU |
| | | CGUGAAGACGCGAUUUAUCAAUUCUCCUCCUCUGGUCAAUAUAAGA |
| | | GUGUCCUAAUUGUGCCAUGAAGGUCUUCACAAACGAGGGCCCU |
| | | ACAGCCUUUUUCAAGGGACUCGUCCCAUCCUUUUCUACGGCUCGG |
| | | UUCUUGGAACGUCAUCAUGUUCGUGUGUUUCGAACAACUGAAAC |
| | | GAGAGCUGUCCAAAAGUAGGCAGACCAUGGACUGCGCUACUUGA |
| 71 | mol_type = RNA origin = synthetic construct | AUGGGCGGUCUAACGGCCUCUGACGUCCAUCCCACACUUUGGGGU |
| | | GCAGCUCUUCAGUGCGGGGAUCGCCGCCUGCUUGGCCGAUGUCA |
| | | UUACUUUUCCUCUGGACACAGCAAAGGUGCGAUUGCAGGUUCAA |
| | | GGAGAAUGCCCCACCUCCUCCGUCAUUCGAUAUAAAGGCGUUUU |
| | | GGGGACGAUCACUGCCGUGGUGAAGACGGAGGGCCGUAUGAAAU |
| | | UGUACAGCGGGCUGCCAGCAGGCCUGCAGAGGCAGAUAAGCUCC |
| | | GCAUCAUUGCGAAUCGGCCUGUACGACACAGUGCAAGAAUUUCU |
| | | UACUGCCGGAAAGGAGACAGCACCCAGUUUGGGGAGCAAAAUCC |
| | | UCGCCGGGCUGACCACAGGCGGCGUCGCUGUAUUUAUUGGACAG |
| | | CCUACUGAAGUGGUAAAGGUACGACUCCAGGCCCAGUCUCAUCU |
| | | GCACGGAAUCAAGCCUAGAUACACUGGGACAUAUAACGCUUACA |
| | | GGAUCAUCGCUACAACAGAAGGCCUCACUGGACUUUGGAAGGGC |
| | | ACAACUCCUAAUUUAAUGCGAUCAGUCAUCAUCAAUUGCACCGA |
| | | GUUGGUCACAUACGACCUAAUGAAGGAGGCCUUCGUGAAAAACA |
| | | AUAUACUCGCAGAUGACGUUCCUUGUCACUUAGUGUCUGCGCUG |
| | | AUCGCCGGAUUUUGUGCCACCGCCAUGUCUAGCCCUGUUGAUGU |
| | | CGUGAAGACAAGGUUUAUCAAUUCACCACCUGGCCAGUAUAAAU |
| | | CUGUUCCUAAUUGUGCAAUGAAGGUGUUCACGAAUGAAGGUCCA |
| | | ACAGCAUUCUUCAAGGGGCUUGUCCCUUCAUUUCUGCGACUGGG |
| | | AUCAUGGAACGUGAUCAUGUUUGUGUGUUUUGAACAACUGAAA |
| | | AGAGAGCUGUCGAAGUCCAGGCAGACAAUGGACUGCGCCACCUG |
| | | A |
| 72 | mol_type = RNA origin = synthetic construct | AUGGGCGGACUGACCGCUUCCGACGUACACCCUACCUUAGGAGU |
| | | GCAGCUCUUCAGUGCAGGAAUCGCCGCUUGCCUUGCUGAUGUCA |
| | | UUACUUUUCCAUUAGACACCGCCAAGGUGCGGCUACAGGUUCAG |
| | | GGCGAAUGUCCCACUUCUUCCGUCAUUCGGUACAAAGGCGUUCU |
| | | GGGAACGAUCACAGCUGUCGUGAAAACCGAAGGGCCGUAUGAAGC |

-continued

| SEQ ID NO | | RNA Sequence |
|---|---|---|
| | | UGUACAGCGGGCUUCCAGCAGGACUUCAGAGGCAGAUCAGCUCG<br>GCGUCCUUACGCAUCGGACUCUACGACACAGUCCAAGAAUUCCU<br>CACAGCUGGAAAGGAAACUGCCCCUAGCCUGGGGGAGCAAAAUAC<br>UGGCCGGGCUCACAACAGGCGGCGUUGCUGUGUUUAUUGGACAG<br>CCCACUGAGGUUGUCAAGGUCCGCCUGCAAGCCCAAAGCCACCU<br>UCACGGGAUUAAGCCUCGCUACACUGGAACAUACAAUGCAUAUA<br>GAAUCAUCGCCACCACCGAAGGCCUAACUGGACUGUGGAAAGGG<br>ACAACACCUAACUUAAUGCGGUCAGUUAUUAUUAACUGCACUGA<br>GUUAGUGACUUACGAUCUCAUGAAGGAAGCAUUCGUGAAGAAC<br>AACAUUUUGGCAGAUGACGUUCCUUGUCAUUUGGUUUCCGCAUU<br>AAUAGCCGGGUUUUGUGCUACCGCCAUGUCUUCCCCAGUCGACG<br>UCGUGAAGACAAGGUUUAUAAAUUCCCCACCUGGCCAGUAUAAA<br>AGUGUCCCUAACUGUGCAAUGAAAGUCUUCACAAACGAGGGCCC<br>UACCGCCUUCUUCAAGGGGCUUGUUCCCUCUUUUCUGCGACUCG<br>GCUCAUGGAACGUCAUCAUGUUUGUCUGUUUUGAACAGCUGAAA<br>AGGGAGCUAUCAAAGUCAAGACAGACCAUGGACUGCGCCACCUG<br>A |
| 73 | mol_type = RNA<br>origin = synthetic construct | AUGGGCGGCCUGACCGCUUCAGACGUUCACCCGACGUUGGGAGU<br>GCAGCUAUUCAGCGCAGGAAUAGCCGCUUGCUUAGCAGAUGUGA<br>UUACUUUCCCUCUCGAUACUGCUAAGGUCCGCCUUCAAGUUCAG<br>GGCGAAUGCCCUACUUCUUCCGUGAUUCGCUAUAAGGGCGUACU<br>GGGAACUAUUACAGCUGUCGUGAAAACAGAAGGCCGCAUGAAAC<br>UCUACAGCGGACUCCCUGCCGGGUUACAAAGACAAAUCAGCUCA<br>GCUUCCCUGCGGAUCGGCUUGUACGACACCGUUCAGGAAUUCCU<br>CACAGCCGGAAAGGAGACUGCACCUAGUUUAGGAAGCAAAAUUC<br>UCGCAGGGCUUACCACAGGUGGCGUCGCCGUUUUCAUUGGACAA<br>CCAACCGAAGUAGUUAAGGUCCGACUCCAAGCUCAAUCUCACCU<br>ACACGGAAUUAAGCCUCGCUACACUGGCACGUAUAACGCUUAUA<br>GGAUUAUCGCUACAACAGAAGGAUUAACGGGCCUGUGGAAGGGC<br>ACCACCCCCAAUUUAAUGCGAUCAGUCAUCAUCAACUGCACCGA<br>GUUGGUAACAUACGAUCUCAUGAAGGAAGCCUUUGUGAAAAAC<br>AACAUACUGGCAGACGACGUCCCUUGUCAUUUGGUUUCUGCGCU<br>CAUCGCAGGGUUUUGUGCUACCGCCAUGUCUAGCCCUGUUGACG<br>UUGUCAAGACACGAUUUAUAAACUCUCCACCAGGCCAGUAUAAA<br>UCUGUCCCUAAUUGUGCCAUGAAGGUCUUCACAAACGAGGGUCC<br>CACUGCUUUCUUCAAGGGGCUUGUUCCCUCGUUUCUGCGGCUUG<br>GAUCCUGGAAUGUUAUCAUGUUUGUGUGCUUUGAACAGUUGAA<br>AAGAGAGUUGUCCAAAUCCAGGCAGACUAUGGACUGCGCCACAU<br>AG |
| 74 | mol_type = RNA<br>origin = synthetic construct | AUGGGAGGGCUCACAGCAAGCGACGUGCAUCCAACCUUAGGAGU<br>ACAGCUCUUCAGUGCAGGAAUCGCCGCUUGCCUAGCCGAUGUCA<br>UUACCUUUCCACUGGACACCGCUAAGGUUCGCCUGCAAGUUCAG<br>GGCGAGUGUCCUACCUCUUCUGUAAUUCGAUAUAAAGGCGUGUU<br>GGGGACAAUCACAGCUGUCGUGAAAACAGAAGGCCGCAUGAAGC<br>UCUACAGCGGACUGCCAGCAGGUUUGCAACGGCAGAUAAGCUCA<br>GCAUCCCUCCGUAUCGGGCUGUACGACACAGUUCAGGAAUUCCU<br>CACUGCCGGGAAAGAGACAGCCCCUAGCUUGGGGAGCAAAAUUU<br>UGGCCGGGCUCACUACAGGUGGCGUCGCUGUGUUCAUUGGACAA<br>CCCACUGAGGUGGUGAAGGUACGACUCCAGGCUCAAAGCCAUUU<br>ACACGGGAUUAAACCACGCUACACUGGAACUUACAACGCAUACA<br>GAAUCAUCGCUACCACAGAAGGUUUGACGGGACUUUGGAAAGGG<br>ACAACACCUAAUUUAAUGCGAUCUGUCAUCAUCAAUUGCACUGA<br>AUUGGUGACUUAUGACCUGAUGAAAGAAGCAUUUGUUAAAAAU<br>AACAUCCUGGCGGAUGAUGUCCCUUGUCAUUUGGUAUCAGCACU<br>CAUUGCAGGGUUUUGUGCCCACCGCCAUGUCUUCCCCAGUUGAUG<br>UUGUAAAGACACGGUUCAUAAACUCACCUCCAGGCCAGUAUAAG<br>AGUGUCCCCAAUUGUGCAAUGAAAGUGUUCACAAACGAAGGUCC<br>AACUGCAUUCUUCAAGGGGCUUGUUCCCUCUUUUCCUUCGUCUCG<br>GAUCCUGGAACGUGAUAAUGUUUGUGUGCUUUUGAACAACUUAA<br>ACGAGAGCUUUCUAAAAGUAGGCAGACUAUGGACUGUGCAACGU<br>AG |
| 75 | mol_type = RNA<br>origin = synthetic construct | AUGGGCGGCCUCACCGCAUCAGACGUCCAUCCAACAUUGGGGGU<br>GCAGCUCUUCAGUGCCGGCAUCGCUGCCUGUCUCGCCGACGUCA<br>UUACCUUUCCGUUAGAUACUGCAAAGGUCCGCCUGCAGGUUCAA<br>GGCGAGUGCCCAACUUCCUCCGUUAUUCGCUACAAGGGCGUGCU<br>GGGAACAAUCACCGCAGUGGUGAAAACAGAGGGCCGAAUGAAGC<br>UCUACUCCGGGCUACCAGCAGGCUUGCAGAGGCAAAUCAGUUCU<br>GCAUCCCUGCGCAUCGGUCUAUACGACACUGUUCAGGAGUUCCU<br>CACCGCCGGGAAGGAGACAGCCCCUAGUUUGGGCAGCAAAAUAC<br>UCGCCGGGCUCACAACAGGUGGCGUUGCCGUUUUCAUCGGACAA<br>CCAACCGAGGUCGUGAAGGUGCGACUGCAAGCACAAAGCCAUCU<br>CCACGGGAUCAAGCCUAGAUACACUGGAACUUACAACGCCUACA<br>GGAUCAUCGCUACAACCGAAGGCUUAACUGGACUCUGGAAAGGG |

-continued

| SEQ ID NO | | RNA Sequence |
|---|---|---|
| | | ACAACCCCUAACUUAAUGCGAAGCGUCAUAAUCAACUGUACAGA |
| | | ACUAGUCACAUACGAUCUCAUGAAAGAAGCCUUUGUGAAAAAUA |
| | | AUAUCCUGGCAGAUGACGUUCCUUGUCACCUGGUCUCAGCACUG |
| | | AUCGCCGGAUUUUGCGCUACUGCAAUGUCUUCUCCCUGUUGAUGU |
| | | UGUGAAAACACGGUUCAUAAAUUCUCCUCCAGGUCAGUAUAAGA |
| | | GUGUUCCUAAUUGUGCCAUGAAAGUCUUCACUAACGAAGGUCCU |
| | | ACAGCAUUCUUUAAGGGACUCGUUCCCUCUUUUUCUCCGUCUUGG |
| | | CUCAUGGAACGUUAUCAUGUUUGUGUGUUUUGAACAGCUGAAG |
| | | AGGGAGCUGUCCAAAUCAAGACAAACCAUGGACUGCGCCACAUG |
| | | A |
| 76 | mol_type = RNA origin = synthetic construct | AUGGGAGGGCUUACUGCUAGUGACGUCCACCCUACCCUCGGAGU |
| | | UCAGCUCUUCAGUGCCGGAAUCGCCGCGUGCCUCGCCGACGUGA |
| | | UUACCUUUCCACUAGACACCGCUAAGGUGCGGCUGCAAGUCCAG |
| | | GGCGAGUGUCCUACAUCCUCCGUCAUUCGCUAUAAAGGCGUUUU |
| | | GGGCACCAUCACGGCUGUAGUCAAAACAGAGGGCCGUAUGAAGC |
| | | UCUACAGCGGGCUGCCCGCCGGGUUGCAGAGACAAAAUAAGCUCU |
| | | GCUUCUCUGCGGAUCGGUCUGUACGACACUGUUCAGGAGUUCCU |
| | | CACUGCUGGUAAGGAGACAGCACCUAGCUUGGGUAGUAAAAUUC |
| | | UCGCAGGGCUCACUACAGGCGGCGUCGCCGUAUUCAUUGGACAG |
| | | CCCACCGAAGUUGUGAAGGUACGACUGCAAGCUCAGUCCCAUCU |
| | | GCACGGGAUAAAACCUCGUUACACUGGCACUUACAAUGCUUACA |
| | | GGAUAAUAGCUACAACAGAAGGCUUAACGGGACUCUGGAAGGG |
| | | GACAACACCAAAUUUAAUGCGAUCUGUUAUCAUCAACUGCACUG |
| | | AACUCGUGACCUAUGAUCUGAUGAAGGAAGCCUUUGUGAAAAAC |
| | | AACAUCCUGGCCGACGACGUUCCCUGUCACUUAGUGUCUGCACU |
| | | CAUCGCCGGCUUCUGUGCCACCGCUAUGUCCUCCCUGUGGACG |
| | | UUGUGAAGACACGCUUCAUAAAUUCCCCUCCUGGCCAAUACAAA |
| | | AGCGUGCCUAACUGUGCCAUGAAGGUUUUCACAAACGAGGGCCC |
| | | UACUGCUUUUUUCAAAGGCCUCGUUCCUUCCUUUCUUCGGCUCG |
| | | GGUCCUGGAAUGUCAUCAUGUUCGUGUGUUUUGAGCAGUUAAA |
| | | GAGAGAGCUUAGCAAAUCCAGGCAGACCAUGGACUGCGCCACCU |
| | | GA |
| 77 | mol_type = RNA origin = synthetic construct | AUGGGGGGGACUGACCGCCAGCGACGUGCACCCUACUCUGGGGAGU |
| | | CCAGCUCUUCAGUGCCGGUAUCGCCGCCUGUCUUGCCGAUGUUA |
| | | UAACAUUUCCCCUGGACACAGCUAAGGUCCGACUUCAAGUUCAA |
| | | GGCGAAUGUCCCACUUCUUCUGUCAUCCGGUACAAAGGCGUACU |
| | | GGGAACCAUCACAGCAGUGGGUGAAAACCGAAGGCCGUAUGAAGC |
| | | UUUACAGCGGACUCCCAGCAGGACUGCAGAGGCAAAUAAGCUCG |
| | | GCAUCACUGCGGAUCGGCCUCUACGAUACCGUCCAGGAGUUUCU |
| | | GACCGCCGGAAAAGAAACAGCUCCUAGUUUGGGCAGUAAAAUAC |
| | | UCGCCGGGCUCACUACAGGUGGCGUUGCCGUUUUCAUAGGACAA |
| | | CCAACAGAAGUGGUCAAGGUCAGACUACAGGCUCAAAGUCACCU |
| | | UCACGGGAUUAAAACCUCGCUAUACCGGAACUUAUAACGCUUAUA |
| | | GGAUCAUAGCCACGACAGAAGGCUUGACUGGGCUCUGGAAGGGG |
| | | ACAACACCUAACUUAAUGCGAUCCGUGAUCAUAAAUUGUACUGA |
| | | GCUCGUGACUUACGAUCUCAUGAAAGAGGCGUUCGUAAAAAAUA |
| | | ACAUAUUGGCAGAUGAUGUUCCCUGUCACUUAGUUUCCGCACUG |
| | | AUCGCCGGGUUUUGUGCAACAGCUAUGUCUUCUCCCUGUCGACGU |
| | | UGUCAAAACACGGUUCAUAAAUUCUCCUCCGGGCCAAUAUAAAA |
| | | GUGUCCCUAACUGUGCCAUGAAAGUCUUCACGAAUGAGGGGCCU |
| | | ACAGCCUUCUUUAAGGGACUGGUCCCCUCGUUUCUUCGCCUCGG |
| | | UUCAUGGAAUGUUAUCAUGUUCGUGUGUUUUGAGCAGUUAAAG |
| | | CGGGAGCUGAGCAAGAGUAGACAAACAAUGGACUGCGCCACCUG |
| | | A |
| 78 | mol_type = RNA origin = synthetic construct | AUGGGCGGAUUGACCGCCAGCGAUGUGCAUCCCACGUUAGGUGU |
| | | GCAGCUCUUUAGCGCAGGUAUUGCCGCGUGCUUAGCGGAUGUGA |
| | | UUACGUUUCCCCUCGACACGGCUAAGGUACGGCUUCAAGUCCAG |
| | | GGCGAGUGCCCAACUUCUUCCGUAAUUCGCUACAAAGGCGUUCU |
| | | CGGAACCAUCACAGCCGUGGUGAAGACAGAAGGCCGCAUGAAAC |
| | | UUUACAGCGGACUGCCAGCCGGCUUGCAGAGGCAGAUAAGCUCG |
| | | GCCUCUCUCCGCAUCGGUUUGUACGACACGGUUCAGGAGUUCCU |
| | | UACUGCUGGAAAGGAGACAGCACCCAGUCUGGGGAGCAAAAUCC |
| | | UAGCCGGGCUUACAACAGGUGGUGUGGGCUGUCUUCAUUGGACAG |
| | | CCCACUGAGGUUGUUAAGGUACGGCUGCAGGCUCAAAGCCACCU |
| | | CCACGGCAUCAAACCACGCUAUACCGGUACAUAUAACGCCUACA |
| | | GGAUCAUUGCGACUACAGAAGGACUCACAGGACUGUGGAAGGGG |
| | | ACGACUCCUAAUUUAAUGCGGUCUGUGAUCAUCAACUGCACCGA |
| | | ACUGGUCACUUACGAUCUAAUGAAAGAGGCUUUCGUGAAAAAU |
| | | AAUAUCUUGGCCGAUGACGUGCCUUGUCACCUCGUUUCUGCGCU |
| | | CAUCGCCGGAUUCUGUGCAACCGCCAUGUCUUCUCCGGUUGACG |
| | | UUGUCAAAACACGAUUUAUAAACUCACCACCAGGCCAAUACAAA |

-continued

| SEQ ID NO | | RNA Sequence |
|---|---|---|
| | | AGCGUCCCCAACUGUGCAAUGAAAGUCUUCACAAACGAAGGCCC |
| | | GACAGCGUUCUUUAAGGGGCUCGUCCCCUCCUUUCUUCGGCUCG |
| | | GUUCCUGGAAUGUUAUAAUGUUUGUGUGUUUUUGAACAGCUAAA |
| | | AAGGGGAGCUGUCAAAAUCCAGGCAAACAAUGGACUGUGCAACAU |
| | | GA |
| 79 | mol_type = RNA origin = synthetic construct | AUGGGGGGACUGACAGCCAGUGAUGUGCAUCCCACUCUGGGGUGU UCAGCUUUUCAGCGCCGGGAUUGCCGCAUGUCUCGCUGAUGUAA UUACUUUUCCUCUCGACACAGCUAAAGUCCGCCUGCAGGUUCAG GGAGAGUGUCCAACGUCCUCCGUGAUUCGGUAUAAAGGAGUUUU AGGAACAAUCACAGCAGUGGUGAAGACCGAGGGCCGGAUGAAGC UCUACAGCGGGCUCCCGGCAGGAUUGCAGAGGCAAAUCAGUUCU GCCUCUCUCCGUAUCGGCCUGUACGAUACUGUACAAGAAUUCCU CACCGCCGGAAAGGAGACAGCACCCAGUUUGGGGAGUAAAAUUC UGGCAGGGCUGACCACAGGCCGGCGUGGCUGUUUUCAUUGGACAG CCUACCGAGGUGGUCAAGGUCCGAUUGCAGGCUCAAUCUCAUCU UCACGGCAUAAAACCUAGAUAUACUGGGACAUACAACGCUUACA GGAUCAUCGCAACCACAGAAGGCCUGACUGGACUAUGGAAAGGG ACAACACCCAAUUUAAUGCGAUCAGUCAUUAUCAACUGCACUGA AUUGGUAACAUACGAUCUCAUGAAGGAAGCUUUCGUGAAGAAU AACAUCCUCGCAGAUGACGUUCCCUGUCACCUUGUGUCUGCACU GAUCGCCGGAUUUUGUGCCACCGCGAUGUCUUCCCCGGUCGAUG UUGUGAAGACACGAUUCAUAAAUUCUCCACCAGGCCAAUACAAA AGCGUUCCCAACUGUGCCAUGAAAGUAUUUACAAACGAAGGCCC GACAGCUUUCUUUAAGGGGCUCGUCCCCUCAUUUCUUCGACUCG GUUCCUGGAAUGUAAUCAUGUUUGUGUGUUUCGAACAAUUAAA AAGGGGAGCUGAGUAAAAGUAGACAAACCAUGGACUGCGCCACCU AG |
| 80 | mol_type = RNA origin = synthetic construct | AUGGGUGGGUCUCACAGCCAGUGACGUUCAUCCCACUCUGGGGGU UCAGCUUUUCAGUGCAGGAAUCGCCGCCUGCCUCGCCGACGUGA UCACCUUUCCGUUGGACACUGCCAAAGUACGCCUACAGGUCCAG GGCGAGUGUCCUACUUCUUCCGUGAUUCGGUAUAAGGGGUGUGCU AGGAACCAUCACUGCCGUGGUGAAAACAGAGGGCCGUAUGAAAC UCUACAGCGGGUUGCCUGCCGGGCUACAGAGGCAGAUCAGCUCA GCUUCUUUGAGAAUCGGUCUCUACGACACGGUCCAGGAAUUUCU UACUGCCGGGAAGGAGACUGCACCUAGUCUGGGGCAGCAAAAUUU UAGCGGGGCUCACAACAGGCGGCGUGGCUGUAUUCAUUGGACAA CCCACAGAGGUUGUGAAGGUCCGACUGCAGGCUCAAAGCCAUCU GCACGGCAUUAAACCUCGCUACACUGGCACUUACAAUGCUUACC GAAUCAUUGCUACAACUGAGGGCCUUACUGGACUCUGGAAAGGC ACAACUCCCAAUUUAAUGCGAUCCGUAAUCAUCAAUUGCACUGA ACUCGUGACUUACGACCUCAUGAAGGAAGCUUUUGUGAAAAAUA ACAUCCUGGCAGAUGACGUCCCUUGUCACUUGGUUUCUGCUCUU AUCGCAGGAUUCUGCGCAACCGCCAUGUCAUCUCCAGUGGACGU UGUGAAGACAAGGUUCAUAAAUUCCCCUCCCGGUCAAUAUAAAA GUGUCCCCAAUUGUGCCAUGAAGGUGUUCACAAACGAAGGCCCA ACCGCCUUUUUUAAGGGGCUUGUUCCAUCUUUUCUGCGCUCUCGG AUCCUGGAACGUCAUCAUGUUCGUGUGUGUUUUGAACAAUUGAAA AGGGAGUUGUCGAAGUCCAGGCAAACAAUGGAUUGUGCAACGU AA |
| 81 | mol_type = RNA origin = synthetic construct | AUGGGCGGACUCACGGCUUCCGACGUCCAUCCCACCCUGGGGGGU GCAGCUCUUCAGCGCAGGCAUUGCCGCGUGUCUCGCCGAUGUUA UUACUUUUCCACUUGACACCGCUAAGGUGCGAUUACAGGUCCAG GGCGAAUGCCCAACAUCUUCCGUGAUCCGGUAUAAAGGGUGUCCU GGGAACCAUUACCGCGGUGGUGAAGACAGAAGGCCGCAUGAAAC UGUACAGCGGGCUGCCGCAGGGCUGCAGAGACAAAUAAGCUCC GCAUCCCUCCGCAUCGGACUAUACGACACAGUUCAGGAAUUCCU CACGGCCGGGAAGGAGACAGCUCCUAGUCUGGGGAAGCAAGAUUC UUGCUGGGCUCACUACAGGCGGCGUCGCUGUCUUCAUUGGACAA CCUACUGAGGUGGUGAAGGUCCGACUGCAAGCCCAAUCCCACCU UCAUGGAAUCAAGCCUCGCUACACUGGGACAUAUAACGCCUAUA GAAUCAUUGCUACUACAGAAGGCUUGACUGGCCUUUGGAAAGGG ACAACUCCCAAUUUAAUGCGAAGCGUGAUUAUCAAUUGCACUGA ACUCGUGACUUACGAUCUCAUGAAGGAAGCAUUUGUGAAAAACA ACAUCCUGGCUGAUGACGUUCCAUGUCAUCUGGUAUCUGCACUG AUCGCCGGAUUUUGCGCUACUGCCAUGUCUAGCCCCUGUAGAUGU CGUCAAGACACGGUUCAUUAAAUUCUCCUCCAGGCCAAUACAAAA GUGUCCCCAAUUGUGCUAUGAAAGUGUUCACAAAUGAGGGCCCC ACAGCCUUCUUUAAGGGGCUCGUCCCCUCUUUUUCUGCGCCUCGG UUCCUGGAAUGUCAUCAUGUUUGUGUGCUUCGAGCAAUUGAAGC GAGAGUUGUCAAAGUCCCGGCAGACUAUGGAUUGUGCCACGUAA |

-continued

| SEQ ID NO | | RNA Sequence |
|---|---|---|
| 82 | mol_type = RNA origin = synthetic construct | AUGGGAGGCCUCACCGCUAGUGACGUGCACCCUACUCUGGGUGU ACAGCUCUUCAGUGCAGGAAUCGCCGCGUGCUUGGCCGAUGUUA UUACUUUUCCCCUGGACACAGCUAAGGUGCGCCUGCAGGUUCAG GGGGAGUGUCCCACCUCCUCCGUCAUCAGAUACAAAGGCGUUUU AGGAACCAUCACAGCCGUGGUAAAAACUGAGGGCCGCAUGAAGC UCUACAGCGGUCUCCCGGCAGGACUUCAGAGGCAGAUCAGCUCU GCAUCACUCCGUAUCGGGCUCUACGACACCGUUCAAGAGUUUCU UACAGCAGGAAAGGAGACUGCACCCAGUUUGGGAAGCAAAAUUC UGGCAGGUCUUACAACCGGCGGCGUGGCUGUGUUCAUCGGACAG CCCACUGAGGUGGUCAAGGUGCGGCUCCAGGCUCAAUCUCACUU GCACGGCAUCAAGCCUCGCUACACUGGCACGUACAAUGCUUACA GAAUCAUUGCAACUACAGAAGGCCUGACAGGACUUUGGAAGGGA ACAACUCCUAACCUUAUGCGAUCCGUUAUCAUUAACUGCACAGA GCUCGUCACAUAUGACCUCAUGAAGGAAGCGUUCUGUGAAAAAUA ACAUCCUUGCAGAUGACGUUCCUUGCCACUUGGUGUCCGCGCUG AUCGCCGGAUUCUGUGCUACCGCUAUGUCAAGCCCUGUCGACGU CGUGAAGACAAGGUUCAUCAAUUCCCCUCCAGGACAAUAUAAGA GUGUUCCUAACUGUGCAAUGAAAGUAUUCACAAACGAAGGCCCC ACCGCCUUCUUCAAGGGACUGGUUCCUUCUUUUUCUUCGACUCGG UUCCUGGAACGUUAUCAUGUUCGUGUGUUUUGAGCAAUUAAAA AGGGAGCUGUCAAAGUCCCGGCAGACAAUGGACUGUGCCACAUG A |
| 83 | mol_type = RNA origin = synthetic construct | AUGGGUGGUUUAACCGCAAGCGACGUCCACCCCACCCUAGGGGU GCAGCUCUUCAGUGCAGGAAUCGCCGCAUGUCUCGCCGACGUCA UUACAUUUCCCUUAGACACCGCUAAGGUGCGCCUCCAGGUCCAG GGCGAAUGUCCCACAUCUUCUGUAAUCCGCGUCUAUAAAGGCGUACU UGGAACAAUCACAGCUGUAGUGAAAACCGAGGGCCGGAUGAAAC UGUACAGUGGGCUGCCCGCAGGACUGCAGAGGCAGAUCAGCUCC GCAUCACUGCGAAUCGGGCUUUACGACACCGUGCAGGAAUUUCU CACUGCCGGAAAAGAGACUGCUCCCAGUCUGGGUAGCAAAAUUC UGGCCGGACUCACAACAGGCGGCGUAGCUGUCUUCAUUGGCCAG CCCACCGAGGUGGUUAAGGUCCGGCUGCAAGCCCAAUCCCACCU UCACGGUAUCAAGCCGCGUUACACUGGAACUUACAACGCUUACA GAAUUAUCGCUACCACCGAAGGCUUAACGGGACUCUGGAAGGGG ACAACUCCCAAUUUAAUGCGAUCCGUUAUCAUCAACUGCACCGA ACUAGUGACCUAUGACCUCAUGAAGGAAGCCUUCGUGAAAAACA ACAUCCUGGCAGACGACGUGCCCUGUCACCUGGUCUCUGCACUC AUCGCUGGAUUCUGUGCUACAGCAAUGUCAUCUCCUGUCGACGU UGUGAAGACACGAUUCAUCAACUCUCCACCUGGUCAGUAUAAAA GUGUCCCUAACUGUGCCAUGAAGGUCUUCACAAAUGAAGGCCCU ACCGCAUUCUUCAAGGGGCUCGUCCCCUCCUUUUUACGCCUCGG CUCCUGGAACGUUAUUAUGUUUGUAUGUUUUGAGCAACUCAAA AGGGAGCUGUCAAAUCCAGACAGACUAUGGACUGCGCCACAUG A |
| 84 | mol_type = RNA origin = synthetic construct | AUGGGUGGGCUGACCGCCAGCGAUGUUCAUCCGACUUUAGGUGU GCAACUCUUCAGUGCCGGCAUCGCCGCCUGCCUCGCUGAUGUGA UUACCUUUCCUCUUGAUACCGCUAAGGUACGGCUGCAGGUCCAA GGCGAAUGCCCCACCUCUUCCGUCAUUCGGUACAAAGGCGUGUU GGGAACAAUUACGGCAGUCGUGAAGACUGAAGGCCGAAUGAAAC UCUACAGUGGGCUGCCUGCUGGUUUUGCAGAGACAGAUAAGCUCA GCGUCUCUGCGAAUUGGGCUCUAUGACACGGUUCAGGAGUUCCU CACCGCUGGGAAGGAGACAGCUCCUAGUCUGGGAAGCAAAAUAC UCGCCGGACUAACAACCGGUGGCGUUGCUGUAUUCAUCGGACAG CCUACCGAAGUCGUUAAGGUCAGACUCCAGGCUCAGAGCCACCU GCAUGGCAUUAAGCCUCGCUACACAUGGUACCUACAACGCUUACA GGAUUAUCGCUACCACAGAAGGCCUGACUGGACUGUGGAAAGGG ACAACUCCUAAUUUAAUGCGCUCUGUUAUCAUCAACUGCACCGA AUUGGUCACUUACGAUCUCAUGAAGGAAGCGUUUGUGAAAAAAC AACAUCUUGGCUGAUGACGUUCCUUGUCACCUAGUUUCGGCACU GAUCGCUGGGUUUUGUGCCACCGCCAUGUCUUCUCCUGUCGACG UUGUCAAAACAAGGUUUAUAAACUCACCACCAGGUCAGUAUAAA AGUGUCCCUAACUGUGCCAUGAAAGUCUUCACCAACGAAGGGCC CACAGCUUUCUUCAAGGGGCUUGUCCCUUCGUUUCUACGACUCG GAUCUUGGAACGUGAUCAUGUUUGUCUGUUUCGAGCAAUUGAA GCGAGAGCUGUCUAAGUCUAGGCAGACAAUGGACUGCGCAACCU GA |
| 85 | mol_type = RNA origin = synthetic construct | AUGGGGGGGCUGACAGCUUCUGACGUACAUCCUACUCUGGGGGU CCAACUCUUCAGUGCCGGAAUCGCCGCUUGCCUCGCUGACGUUA UCACCUUCCCUUUAGACACAGCUAAAGUCCGACUGCAAGUUCAA GGCGAGUGCCCUACUUCUUUCCGUGAUCAGAUACAAGGGCGUGCU GGGUACAAUUACUGCGGUGGUGAAAACUGAAGGGCCGCAUGAAGC UCUAUAGCGGGCUGCCUGCAGGCUUGCAGAGGCAGAUAAGCUCA GCCUCCCUGCGGAUUGGUCUGUACGAUACUGUUCAGGAGUUCCU |

| SEQ ID NO | | RNA Sequence |
|---|---|---|
| | | UACCGCUGGAAAGGAGACAGCUCCCAGUUUAGGGAGCAAAAUCC |
| | | UGGCCGGACUCACUACAGGCGGCGUCGCUGUCUUCAUUGGACAG |
| | | CCCACAGAGGUUGUAAAGGUAAGGCUGCAAGCCCAAAGCCACCU |
| | | CCACGGCAUCAAACCUCGCUAUACUGGGACUUACAACGCUUACC |
| | | GAAUCAUAGCUACAACCGAAGGCUUAACUGGACUGUGGAAGGGC |
| | | ACAACACCAAACUUAAUGCGAUCAGUUAUUAUCAACUGCACCGA |
| | | ACUGGUUACUUAUGAUCUCAUGAAAGAAGCUUUUGUGAAAAAU |
| | | AACAUCCUCGCUGAUGACGUCCCUUGUCAUUUGGUGUCUGCAUU |
| | | AAUCGCCGGAUUUUGUGCGACCGCUAUGUCGAGUCCUGUCGACG |
| | | UUGUGAAAACACGAUUCAUAAAUUCACCUCCCGGGCAGUAUAAA |
| | | AGCGUUCCCAAUUGUGCCAUGAAGGUAUUCACCAACGAAGGUCC |
| | | UACGGCAUUCUUCAAGGGGCUGGUUCCUUCCUUUCUUCGGCUCG |
| | | GUUCCUGGAAUGUUAUCAUGUUUGUCUGUUUUGAACAGCUGAA |
| | | AAGGGAGCUAUCAAAGUCCAGGCAGACCAUGGACUGCGCUACUU |
| | | GA |
| 86 | mol_type = RNA origin = synthetic construct | AUGGGCGGACUCACAGCCUCGGACGUGCACCCCACACUGGGAGU |
| | | UCAGCUUUUCAGCGCAGGCAUAGCCGCCUGCCUCGCAGAUGUGA |
| | | UUACCUUUCCUCUAGACACUGCUAAGGUCCGCUUGCAAGUCCAG |
| | | GGCGAGUGCCCAACUUCUAGUGUGAUCCGAUAUAAGGGCGUGUU |
| | | GGGGACCAUUACGGCGGUCGUUAAAACAGAGGGCCGCAUGAAGC |
| | | UAUAUAGCGGGCUGCCAGCCGGCCUGCAGAGGCAGAUCAGCUCU |
| | | GCCUCCCUACGUAUCGGCCUGUAUGACACCGUUCAGGAGUUCCU |
| | | UACUGCAGGAAAAGAAACUGCUCCUAGCUUGGGCAGCAAAAUUC |
| | | UCGCCGGGCUCACUACAGGCGGCGUGGCUGUGUUCAUUGGACAG |
| | | CCUACUGAAGUGGUCAAGGUCCGACUGCAGGCUCAAAGCCACCU |
| | | CCAUGGCAUCAAACCUCGCUACACUGGCACAUAUAACGCUUACA |
| | | GAAUCAUAGCCACAACUGAAGGGCUCACAGGACUUUGGAAGGGG |
| | | ACAACACCUAACUUAAUGCGAUCUGUUAUCAUAAACUGCACCGA |
| | | ACUCGUAACGUAUGAUCUCAUGAAGGAGGCCUUCGUGAAAAACA |
| | | ACAUCCUGGCCGACGACGUUCCAUGUCAUUUGGUUUCCGCUCUC |
| | | AUCGCCGGGUUUUGUGCUACUGCUAUGUCAAGCCCUGUCGAUGU |
| | | UGUUAAGACACGAUUUAUAAACUCCCCACCUGGCCAGUAUAAGA |
| | | GCGUCCCCAACUGCGCCAUGAAGGUGUUCACAAACGAAGGGCCC |
| | | ACAGCGUUCUUUAAGGGGCUGGUCCCUUCUUUUCUACGGCUCGG |
| | | AUCCUGGAACGUUAUCAUGUUCGUGUGUUUCGAACAAUUAAAA |
| | | AGGGAGCUCUCCAAGUCACGGCAAACAAUGGACUGCGCUACAUA |
| | | G |
| 87 | mol_type = RNA origin = synthetic construct | AUGGGCGGUCUUACUGCUAGUGACGUGCACCCAACGCUGGGGGU |
| | | GCAACUCUUCAGUGCUGGCAUCGCCGCUUGCCUUGCCGACGUUA |
| | | UUACUUUUCCCUUAGAUACCGCUAAGGUGCGAUUGCAGGUCCAA |
| | | GGCGAAUGCCCUACAUCAUCAGUUAUUCGAUAUAAAGGGUGUUCU |
| | | AGGUACCAUUACCGCCGUGGUGAAAACCGAGGGCCGCAUGAAGC |
| | | UUUACAGCGGGCUUCCUGCCGGCCUACAGCGCCAGAUAAGCUCA |
| | | GCAUCUCUACGGAUCGGACUGUACGACACCGUGCAGGAGUUCCU |
| | | UACAGCCGGAAAGGAAACAGCUCCUAGUCUGGGCAGCAAAAUCC |
| | | UCGCCGGGCUCACCACAGGCGGUGUCGCUGUAUUCAUUGGUCAA |
| | | CCCACUGAGGUCGUAAAGGUCCGGCUGCAGGCUCAAAGUCACCU |
| | | GCACGGUAUAAAACCGCGGUACACUGGUACUUACAACGCCUAUA |
| | | GGAUCAUCGCUACAACGGAGGGCUUAACUGGAUUGUGGAAGGG |
| | | GACGACUCCUAACUUAAUGCGCUCUGUCAUCAUAAAUUUGCACCG |
| | | AACUGGUUACUUACGACCUCAUGAAGGAAGCCUUCGUGAAAAAC |
| | | AACAUCCUGGCAGAUGACGUUCCAUGCCACCUCGUGUCUGCACU |
| | | CAUCGCAGGAUUCUGUGCUACCGCUAUGUCUAGUCCAGUCGAUG |
| | | UUGUCAAGACACGGUUUAUCAAUUCACCACCAGGACAAUAUAAA |
| | | AGUGUCCCAAACUGUGCCAUGAAAGUCUUCACAAACGAGGGGCC |
| | | UACAGCAUUCUUCAAGGGGCUCGUCCCCUCUUUUCUGCGGCUCG |
| | | GGUCUUGGAACGUUAUCAUGUUUGUGUGUUUCGAACAGCUAAA |
| | | AAGGGAACUGUCCAAGUCAAGGCAAACAAUGGACUGCGCCACCU |
| | | AA |
| 88 | mol_type = RNA origin = synthetic construct | AUGGGGGGUCUGACCGCGAGCGACGUCCAUCCUACCCUGGGUGU |
| | | UCAGCUCUUCAGUGCGGGCAUCGCCGCGUGCCUGGCCGACGUUA |
| | | UUACCUUUCCCUUAGACACACAGCAAAGGUACGACUACAGGUACAA |
| | | GGCGAAUGUCCUACUUCUUCCGUUAUUCGCUAUAAGGGCGUCUU |
| | | GGGAACCAUUACUGCUGUGGUUAAAAACGGAAGGCCGCAUGAAGC |
| | | UGUAUAGCGGGCUGCCCGCGGGCCUUCAGAGGCAGAUCAGCUCG |
| | | GCCUCCCUGCGUAUUGGAUUGUACGACACAGUCCAAGAAUUCCU |
| | | UACCGCGGGAAAGAAACAGCACCUAGCCUGGGGCAGCAAAAUAC |
| | | UCGCCGGACUCACUACAGGCGGCGUGGCCGUGUUUAUUGGACAG |
| | | CCUACUGAGGUGGUCAAGGUCCGACUGCAGGCCCAGAGUCACUU |
| | | GCACGGCAUCAAACCACGGUAUACUGGCACGUACAACGCUUACA |
| | | GGAUCAUCGCAACCACCGAAGGCUUAACAGGACUCUGGAAGGGU |
| | | ACAACGCCUAAUUUAAUGCGCUCCGUCAUCAUAAAUUGCACCGA |
| | | GCUCGUGACUUAUGAUCUCAUGAAGGAAGCCUUUGUGAAGAAU |

| SEQ ID NO | | RNA Sequence |
|---|---|---|
| | | AACAUCCUGGCAGACGACGUUCCCUGUCACCUAGUAUCUGCACU CAUCGCAGGAUUCUGCGCCACCGCUAUGUCUUCUCCCGUAGAUG UCGUUAAGACGCGGUUUAUUAAUUCGCCACCCGGUCAAUAUAAA AGUGUCCCUAAUUGUGCCAUGAAGGUCUUUACAAACGAAGGCCC UACCGCCUUUUUUAAGGGGCUGGUUCCUUCUUUUUUUACGGCUCG GGUCGUGGAACGUCAUCAUGUUCGUGUGUUUGAACAGCUGAA ACGGGAACUUUCCAAAUCCAGGCAGACAAUGGACUGCGCUACUU GA |
| 89 | mol_type = RNA origin = synthetic construct | AUGGGUGGUCUGACCGCAAGUGACGUGCAUCCUACACUGGGGAGU GCAGCUCUUCAGUGCGGGCAUUGCCGCUUGCCUUGCCGAUGUAA UUACCUUUCCAUUAGACACAGCCAAGGUGCGCCUGCAGGUUCAG GGAGAAUGUCCAACGUCUUCCGUGAUUCGGUAUAAGGGCGUUCU GGGCACCAUUACGGCUGUGGUGAAAACAGAAGGCCGUAUGAAAC UUUACAGCGGACUCCCUGCAGGGCUACAGCGACAGAUCAGCUCU GCUUCUCUGCGUAUCGGUUUGUAUGACACAGUACAGGAGUUCCU CACUGCCGGAAAGGAGACUGCACCCAGUUUAGGCAGCAAAAUCC UUGCAGGGCUCACAACAGGUGGCGUUGCCGUUUUUAUCGGACAG CCCACAGAAGUGGUGAAGGUACGACUGCAAGCUCAGAGUCACCU GCACGGGAUCAAGCCUCGCUAUACUGGAACUUAUAACGCUUAUA GAAUCAUUGCUACUACAGAAGGUCUAACUGGACUCUGGAAAGGG ACAACACCUAAUUUAAUGCGAUCUGUUAUCAUCAACUGCACAGA ACUGGUGACUUAUGACCUCAUGAAGGAAGCUUUUGUGAAAAAC AACAUCCUCGCAGACGACGUUCCUUGUCACCUGGUGUCUGCACU CAUUGCAGGGUUUUGUGCAACCGCCAUGUCUUCUCCUGUUGACG UUGUCAAAACACGUUUUAUAAACUCACCUCCUGGACAGUACAAG AGUGUCCCCAAUUGUGCCAUGAAGGUAUUCACAAACGAAGGGCC CACCGCAUUCUUUAAGGGGCUGGUUCCCUCUUUUCUGCGCCUCG GUUCUUGGAACGUGAUAAUGUUUGUGUGCUUUGAACAGUUAAA AAGAGAACUAUCCAAAUCAAGGCAGACAAUGGACUGUGCCACAU GA |
| 90 | mol_type = RNA origin = synthetic construct | AUGGGAGGACUGACAGCCAGCGACGUUCACCCUACACUGGGGGU UCAGCUCUUCAGCGCGGGAAUCGCUGCUUGCCUCGCUGAUGUCA UUACUUUUUCCUCUUGAUACAGCUAAGGUCCGACUGCAAGUUCAG GGCGAAUGCCCUACUUCUUCCGUCAUCCGUCUACAAGGGCGUGCU GGGCACCAUCACAGCUGUCGUAAAAACAGAGGGCCGCAUGAAAU UAUAUAGCGGCUUGCCCGCAGGGCUGCAAAGGCAGAUCAGCUCU GCGUCCUCCGGAUCGGACUGUACGACACAGUGCAGGAAUUUCU UACGGCCGGAAAGGAGACUGCUCCUAGCUUGGGUAGCAAAAUUC UCGCCGGGCUGACCACAGGCGGUGUGGGCGUGGUUCAUCGGGCAG CCUACCGAGGUUGUUAAGGUGCGACUGCAGGCUCAAAGUCACCU GCAUGGAAUCAAGCCUCGCUACACUGGUACAUAUAACGCUUAUC GGAUUAUUGCAACCACUGAAGGCCUCACAGGCCUCUGGAAGGGC ACCACUCCUAAUUUAAUGCGAUCAGUCAUCAUAAAUUGCACCGA ACUCGUGACUUAUGAUCUCAUGAAGGAAGCUUUUGUAAAAAAC AACAUUCUGGCUGACGACGUUCCCUGCCAUCUGGUGUCGGCUCU CAUCGCAGGAUUUUGUGCAACCGCCAUGUCUUCUCCCUGUCGACG UUGUGAAAACAAGGUUUAUAAACUCACCACCUGGCCAAUAUAAG UCUGUUCCCAAUUGUGCCAUGAAGGUGUUCACAAAUGAAGGUCC CACAGCAUUCUUCAAAGGGCUUGUUCCCUCCUUUCUUCGGCUCG GGUCCUGGAACGUCAUCAUGUUCGUGUGCUUUGAACAGUUAAAA AGGGAACUGAGUAAGUCCAGGCAGACAAUGGACUGUGCUACAUG A |
| 91 | mol_type = RNA origin = synthetic construct | AUGGGUGGCCUAACUGCCAGUGACGUUCAUCCCACUUUGGGGAGU GCAGCUUUUCAGCGCAGGAAUUGCUGCUUGCCUUGCUGACGUUA UUACCUUUCCCUUAGAUACCGCGAAGGUCCGCUUGCAAGUCCAA GGCGAGUGCCCAACUUCAUCCGUCAUUCGCUACAAAGGCGUUCU GGGUACCAUCACAGCCGUCGUGAAGACCGAAGGCCGCAUGAAAC UCUAUAGCGGGCUGCCCGCGGGGCCUCCAGAGGCAAAUCAGCUCA GCUUCCUUGCGCAUCGGAUUAUACGACACUGUUCAAGAGUUUCU UACAGCCGGAAAGGAGACAGCGCCUAGUCUGGGGGAGUAAAAUCU UGGCCGGGCUCACAACAGGCGGCGUCGCCGUAUUCAUCGGACAG CCCACCGAAGUAGUCAAGGUCCGACUGCAGGCUCAAUCUCAUCU ACAUGGUAUCAAGCCCCGCUACACUGGCACAUAUAACGCUUAUA GAAUUAUUGCUACAACAGAAGGCUUAACUGGACUAUGGAAGGG CACUACACCUAAUUUGAUGCGGUCCGUCAUCAUCAAUUGCACCG AGCUCGUAACUUACGAUCUAAUGAAGGAGGCCUUCGUGAAAAAC AACAUUCUGGCCGAUGAUGUCCCUUGUCACUGGGUCUCUGCACU GAUCGCCGGAUUCUGUGCCACCGCCAUGUCUAGCCCUGUCGACG UCGUGAAAACGCGAUUCAUCAAUUCUCCCCCCGGUCAGUAUAAA UCUGUUCCCAAUUGUGCUAUGAAGGUGUUCACAAACGAAGGCCC |

| SEQ ID NO | RNA Sequence |
| --- | --- |
|  | AACUGCAUUCUUUAAAGGGCUAGUACCCUCUUUUCUGCGGCUUG GCUCCUGGAAUGUCAUCAUGUUCGUGUGUUUCGAACAACUGAAA AGGGGAGCUGUCCAAAUCCAGGCAGACUAUGGACUGCGCCACCUG A |
| 92 | mol_type = RNA origin = synthetic construct |

AUGGGUGGACUCACAGCUUCAGACGUCCAUCCAACCCUGGGAGU
GCAGCUCUUCAGUGCCGGAAUCGCCGCAUGCCUGGCAGACGUCA
UUACCUUUCCCCUGGAUACAGCCAAGGUGCGACUACAGGUUCAG
GGGGAAUGCCCUACAUCCUCUGUGAUCCGGUAUAAGGGCGUGCU
GGGGACCAUUACAGCCGUGGUAAAGACCGAGGGCCGCAUGAAGC
UUUAUAGCGGGCUCCCCGCCGGCUUGCAGAGGCAGAUCAGCUCC
GCAUCACUGCGAAUCGGGUUGUACGACACAGUGCAGGAAUUUCU
UACUGCUGGAAAAGAGACUGCCCCUAGUCUGGGCAGCAAAAUCC
UGGCCGGGCUGACUACAGGUGGCGUUGCUGUCUUUAUUGGACAG
CCCACUGAGGUUGUAAAGGUGCGACUGCAAGCUCAAUCCCACCU
CCACGGAAUUAAGCCACGCUAUACUGGAACGUAUAACGCCUAUA
GGAUCAUUGCUACAACAGAAGGUUUGACUGGGCUUUGGAAGGG
UACAACACCCAAUUUAAUGCGAUCCGUCAUUAUCAACUGCACCG
AACUAGUGACAUACGAUCUCAUGAAGGAAGCAUUUGUGAAAAA
UAACAUCCUGGCUGACGACGUUCCUUGUCACUUAGUAUCUGCAC
UGAUCGCUGGGUUUUGUGCAACCGCAAUGUCUUCCCCCGUCGAU
GUCGUCAAAACAAGAUUUAUAAAUUCUCCACCUGGACAAUAUAA
AAGUGUUCCCAACUGCGCUAUGAAGGUCUUCACAAACGAAGGCC
CAACCGCAUUCUUUAAGGGGCUAGUUCCUUCUUUUCUUCGGCUU
GGUUCUUGGAACGUCAUCAUGUUCGUGUGUUUCGAACAGUUGA
AGCGGGAGCUGUCAAAAUCGAGGCAGACCAUGGACUGCGCUACG
UAA

| 93 | mol_type = RNA origin = synthetic construct |

AUGGGGGGGACUGACUGCCUCGGACGUCCAUCCGACACUGGGUGU
GCAGCUCUUCAGUGCAGGGAUCGCUGCUUGUCUCGCCGACGUUA
UAACCUUUCCCCUAGACACGGCCAAGGUACGUCUACAGGUUCAG
GGCGAAUGCCCUACUUCUUUCUGUCAUUCGUUACAAAGGUGUGUU
AGGGACCAUAACAGCGGUAGUGAAGACCGAAGGCCGCAUGAAAC
UCUACAGCGGGCUUCCUGCCGGACUGCAACGGCAGAUUAGCUCU
GCAUCCCUGCGCAUUGGGCUGUACGACACUGUGCAGGAAUUCCU
CACAGCAGGAAAGGAGACAGCGCCUAGUCUGGGGGAGUAAAAUCC
UCGCAGGACUAACGACAGGUGGCGUCGCUGUGUUCAUUGGACAG
CCUACCGAGGUUGUGAAGGUAAGGCUGCAAGCCCAAUCACACCU
GCACGGAAUUAAGCCUCGCUACACUGGAACUUACAACGCCUACA
GGAUUAUUGCCACAACCGAGGGCCUUACUGGACUAUGGAAGGGG
ACAACACCUAAUCUUAUGCGAUCAGUUAUUAUCAACUGCACUGA
GUUGGUAACCUACGAUCUCAUGAAGGAAGCGUUCGUGAAAAACA
AUAUCCUGGCCGACGACGUGCCCUGCCAUUUGGUGUCUGCACUG
AUCGCAGGAUUUUGUGCUACCGCAAUGUCUUCUCCUGUCGAUGU
UGUGAAGACACGGUUUAUCAAUUCCCCACCGGGCCAGUAUAAAA
GUGUUCCUAACUGUGCCAUGAAAGUAUUCACAAACGAGGGCCCC
ACAGCCUUCUUCAAGGGGCUAGUUCCCUCAUUCCUUCGGCUCGG
GUCCUGGAAUGUCAUCAUGUUUGUGUGUUUUGAACAGUUAAAA
CGAGAGCUCUCGAAGUCCAGGCAGACAAUGGACUGUGCCACGUG
A

| 94 | mol_type = RNA origin = synthetic construct |

AUGGGCGGUCUCACGGCCUCAGACGUUCAUCCAACGCUGGGCGU
GCAGCUCUUCAGUGCAGGAAUCGCCGCUUGCCUGGCGAUGUCA
UUACCUUUCCUCUUGACACUGCCAAGGUGCGGUUGCAGGUCCAG
GGUGAAUGCCCAACUUCUUCUGUUAUUCGCUACAAAGGCGUUUU
GGGAACCAUCACCGCUGUGGUGAAAACAGAGGGUCGCAUGAAGC
UGUACAGCGGGCUGCCAGCGGGACUACAGCGACAGAUAAGCUCA
GCAUCACUUCGGAUUGGUCUGUAUGACACAGUUCAGGAGUUCCU
CACUGCUGGAAAGGAGACAGCACCUAGUCUGGGGUAGCAAAAUCC
UGGCUGGGCUAACAACAGGCGGCGUAGCUGUAUUUAUUGGACAA
CCCACUGAGGUGGUCAAGGUCCGACUGCAGGCCCAAUCUCACCU
GCAUGGCAUCAAGCCUCGCUACACUGGUACUUACAACGCUUACA
GGAUCAUAGCUACAACCGAAGGCCUAACUGGGCUGUGGAAGGGC
ACGACACCCAAUUUAAUGCGAUCCGUCAUCAUAAACUGCACCGA
ACUCGUUACAUAUGAUCUUUAUGAAGGAAGCAUUUGUGAAAAAU
AACAUCCUGGCAGAUGACGUUCCUUGUCAUCUGGUUUCUGCACU
CAUCGCGGGAUUUUGUGCUACCGCUAUGUCAAGUCCCGUCGACG
UCGUGAAGACACGGUUCAUAAAUUCCCCACCUGGCCAGUACAAA
AGUGUCCCCAACUGUGCAAUGAAAGUCUUCACAAACGAAGGCCC
CACAGCAUUCUUCAAGGGACUAGUUCCCUCCUUUCUACGCCUCG
GCUCUUGGAACGUAAUCAUGUUCGUGUGUUUUGAACAAUUAAA
AAGGGAGCUGUCUAAAUCACGUCAAACUAUGGACUGCGCCACAU
GA

-continued

| SEQ ID NO | | RNA Sequence |
|---|---|---|
| 95 | mol_type = RNA origin = synthetic construct | AUGGGAGGCCUAACAGCUUCUGAUGUCCACCCCACCCUUGGAGU GCAGCUCUUCAGUGCAGGUAUCGCUGCUUGCCUGGCCGAUGUUA UAACCUUUCCUCUGGAUACAGCCAAGGUGCGAUUGCAGGUCCAG GGCGAGUGCCCGACCUCAAGCGUGAUCCGAUAUAAAGGCGUGUU GGGAACUAUCACAGCCGUCGUGAAGACCGAAGGCCGAAUGAAGC UUUACAGCGGACUUCCUGCCGGCCUGCAGAGGCAGAUAAGCUCU GCAUCUCUCCGGAUCGGACUGUACGACACAGUCCAAGAGUUCCU UACUGCAGGAAAGGAGACUGCACCUAGUUUAGGGAGCAAGAUCU UGGCCGGACUCACAACAGGUGGCGUUGCUGUUUUUAUAGGACAG CCUACUGAAGUGGUGAAGGUGAGACUGCAGGCUCAAAGCCAUCU GCACGGCAUCAAACCUCGCUAUACUGGAACAUAUAAUGCUUAUA GGAUCAUUGCGACCACAGAGGGCCUCACAGGGCUGUGGAAAGGG ACAACCCCUAAUUUGAUGCGGUCAGUCAUCAUCAACUGCACUGA GCUAGUUACUUAUGAUCUCAUGAAAGAAGCAUUUGUCAAAAAU AACAUUCUGGCAGAUGAUGUGCCUUGUCACCUGGUGUCUGCAUU AAUCGCAGGAUUCUGCGCCACCGCUAUGUCAUCUCCUGUCGAUG UUGUGAAGACACGAUUCAUAAACUCCCCUCCUGGUCAAUAUAAG AGCGUUCCCAACUGCGCUAUGAAAGUCUUCACCAACGAGGGCCC AACAGCUUUCUUCAAGGGGCUCGUGCCCUCCUUUCUCCGACUGG GAUCCUGGAAUGUGAUCAUGUUUGUCUGCUUUGAGCAGUUGAA ACGGGAAUUGUCUAAAUCGAGGCAAACUAUGGACUGCGCCACAU GA |
| 96 | mol_type = RNA origin = synthetic construct | AUGGGCGGCCUGACAGCCUCAGACGUUCAUCCCACAUUGGGUGU UCAGCUCUUCAGUGCAGGUAUUGCCGCCUGUCUCGCCGAUGUAA UAACCUUUCCACUCGACACCGCUAAGGUCCGCCUUCAGGUUCAG GGCGAGUGCCCCACCAGUUCCGUUAUCAGAUACAAAGGUGUCCU AGGGACCAUUACAGCGGUGGUGAAGACCGAGGGCCGUAUGAAGC UCUAUAGCGGGCUGCCAGCAGGCCUCCAGCGCCAGAUAAGCUCU GCCUCCCUGCGGAUCGGCCUCUAUGACACAGUCCAAGAAUUCCU CACAGCUGGAAAGGAGACUGCGCCUAGUCUGGGUAGCAAGAUCC UUGCCGGACUCACCACAGGCGGCGUUGCUGUAUUCAUUGGACAG CCUACUGAAGUAGUCAAGGUUCGACUGCAGGCCCAAAGUCACCU CCACGGCAUUAAGCCUCGCUACACUGGUACGUAUAACGCUUAUA GAAUAAUAGCCACAACAGAAGGCUUAACGGGACUCUGGAAGGGG ACUACACCUAAUUUAAUGCGAUCCGUCAUCAUCAACUGCACUGA GCUUGUAACUUACGACCUCAUGAAGGAAGCCUUCGUGAAAAAUA ACAUUUUGGCUGAUGACGUUCCGUGUCACCUGGUGUCUGCACUC AUUGCAGGGUUCUGUGCCACCGCCAUGUCUUCUCCCGGUCGACGU UGUGAAGACGCGAUUCAUCAAUUCCCCUCCCGGUCAAUAUAAAU CUGUCCCCAAUUGUGCCAUGAAAGUAUUCACUAACGAGGGCCCA ACAGCCUUUUUCAAGGGGCUUGUUCCUUCCUUUUUGCGGCUCGG AUCUUGGAACGUUAUCAUGUUCGUGUGUUUUGAACAAUUGAAA CGGGAGUUGUCUAAGUCCCGCCAAACGAUGGACUGCGCUACCUG A |
| 97 | mol_type = RNA origin = synthetic construct | AUGGGUGGGCUGACCGCAAGUGACGUGCACCCCACGUUAGGGGU GCAACUCUUCAGUGCCGGAAUUGCCGCCUGCCUCGCGAUGUUA UUACUUUUCCUCUGGACACCGCGAAGGUACGGUUGCAAGUCCAA GGCGAAUGUCCAACCUCUUCCGUCAUUCGGUAUAAAGGCGUCCU UGGGACCAUCACUGCUGUCGUGAAAACGGAGGGCCGUAUGAAAC UCUACAGCGGGCUUCCUGCAGGCCUGCAAAGGCAGAUCAGUUCA GCUUCCCUGCGGAUCGGGCUGUAUGACACCGUGCAGGAAUUCCU UACUGCAGGUAAGGAGACCGCACCCAGUUUGGGGGUCCAAAAUCU UGGCAGGACUCACAACAGGAGGCGUUGCUGUAUUCAUCGGACAG CCCACCGAAGUGGUAAAGGUAAGACUGCAGGCCCAGUCUCACCU GCACGGCAUCAAGCCUCGCUACACUGGAACCUACAACGCCUACA GGAUCAUUGCCACCACUGAAGGUCUCACUGGAUUAUGGAAGGGG ACCACUCCCAAUUUAAUGCGAUCAGUCAUCAUAAAUUGCACCGA AUUGGUUACUUACGAUCUCAUGAAAGAAGCGUUUGUGAAAAAU AAUAUCCUUGCAGACGACGUUCCUUGUCACCUGGUAUCUGCGCU CAUCGCCGGAUUUUGCGCGACCGCCAUGUCUUCUCCUGUCGAUG UUGUCAAAACACGGUUUAUCAACUCUCCUCCUGGUCAAUAUAAA AGUGUUCCCAAUUGUGCCAUGAAGGUCUUCACCAACGAAGGCCC UACAGCAUUCUUUAAGGGGCUUGUUCCUUCCUUUUCUGCGCCUUG GUUCUUGGAAUGUCAUCAUGUUUGUCUGUUUCGAACAACUAAA AAGGGAGCUGAGCAAGAGUAGACAAACCAUGGACUGUGCAACAU GA |
| 98 | mol_type = RNA origin = synthetic construct | AUGGGUGGCCUUACCGCUUCGGACGUUCAUCCCACCCUGGGGCGU UCAGCUGUUUAGCGCCGGAAUAGCCGCAUGUCUCGCCGAUGUAA UCACCUUUCCUCUGGAUACCGCCAAGGUGCGCCUACAAGUCCAA GGCGAAUGCCCGACCUCUUCUGUUAUUCGGUAUAAAGGUGUCUU GGGAACCAUCACUGCAGUCGUAAAAACAGAAGGCCGUAUGAAAC UCUACAGCGGACUUCCUGCUGGGCUCCAGAGGCAGAUAAGCUCU GCCUCCUUGAGGAUUGGUCUGUACGACACCGUUCAGGAGUUCCU |

-continued

| SEQ ID NO | | RNA Sequence |
|---|---|---|
| | | UACAGCGGGAAAGGAGACAGCUCCCAGCUUAGGCAGCAAAAUAC |
| | | UUGCCGGGCUUACAACAGGUGGCGUGGCGGUGUUCAUUGGACAG |
| | | CCUACCGAGGUGGUAAAGGUGCGACUGCAGGCCCAGUCUCAUUU |
| | | GCAUGGGAUCAAGCCGCGCUACACUGGGACUUAUAACGCCUAUA |
| | | GAAUCAUUGCUACGACGGAGGGCUUAACUGGACUUUGGAAGGG |
| | | GACAACACCUAAUUUGAUGCGGUCGGUCAUAAUCAAUUGCACCG |
| | | AACUGGUGACUUAUGACCUCAUGAAAGAGGCUUUUGUGAAGAA |
| | | CAACAUCCUGGCUGACGACGUUCCUUGUCAUCUUUGUAUCAGCAC |
| | | UUAUCGCAGGAUUCUGUGCAACAGCAAUGUCCAGCCCUGUCGAU |
| | | GUUGUCAAAACACGGUUCAUAAAUUCUCCACCUGGCCAAUAUAA |
| | | AAGCGUCCCCAAUUGUGCCAUGAAAGUAUUCACAAACGAAGGGC |
| | | CAACCGCCUUCUUCAAGGGACUCGUCCCCUCCUUUCUCCGUCUC |
| | | GGAUCCUGGAAUGUUAUCAUGUUCGUGUGCUUUGAGCAAUUAA |
| | | AGCGAGAGCUCUCCAAGUCAAGGCAAACAAUGGACUGCGCUACA |
| | | UAG |
| 99 | mol_type = RNA origin = synthetic construct | AUGGGAGGUCUCACCGCAUCUGAUGUGCAUCCAACACUGGGGGU |
| | | UCAGCUCUUCAGUGCGGGAAUAGCCGCCUGUCUGGCUGAUGUUA |
| | | UUACCUUUCCCCUGGACACCGCAAAGGUACGACUCCAAGUCCAG |
| | | GGCGAAUGUCCGACCUCAUCGGUGAUUAGAUACAAAGGCGUGUU |
| | | GGGGACCAUCACCGCAGUCGUGAAAACAGAAGGCAGGAUGAAAC |
| | | UUUACAGUGGGCUGCCCGCAGGCCUGCAGAGGCAGAUCAGCUCU |
| | | GCAUCUCUACGCAUCGGCUUGUACGAUACCGUCCAGGAAUUCCU |
| | | GACAGCAGGCAAAGAAACCGCCCCCAGUCUGGGUAGUAAGAUUU |
| | | UGGCAGGGCUGACUACAGGUGGUGUCGCUGUCUUCAUCGGGCAA |
| | | CCCACUGAAGUGGUGAAGGUGCGACUGCAAGCUCAGAGUCACCU |
| | | GCACGGAAUAAAACCUCGCUAUACUGGUACCUACAACGCUUAUA |
| | | GAAUUAUCGCGACCACCGAAGGCCUCACUGGACUCUGGAAAGGG |
| | | ACGACACCUAACUUGAUGCGAUCCGUAAUCAUCAAUUGCACUGA |
| | | GCUAGUUACAUACGAUCUCAUGAAGGAGGCAUUCGUGAAAAACA |
| | | AUAUCCUGGCCGAUGACGUCCCUUGUCACUUGGUUUCCGCGCUC |
| | | AUCGCAGGAUUCUGUGCUACCGCCAUGUCAUCCCCCGUCGAUGU |
| | | CGUUAAAACUCGGUUCAUUAACUCACCCCCUGGCCAGUACAAAA |
| | | GUGUUCCUAACUGUGCCAUGAAGGUGUUCACAAAUGAGGGCCCC |
| | | ACAGCAUUCUUCAAGGGACUAGUCCCUUCUUUUCUUCGGCUCGG |
| | | CAGCUGGAAUGUCAUCAUGUUCGUGUGCUUCGAACAGCUAAAAC |
| | | GAGAGCUGUCCAAGUCAAGGCAAACCAUGGACUGUGCCACAUAG |
| 100 | mol_type = RNA origin = synthetic construct | AUGGGGGGGCUCACCGCCUCCGAUGUGCACCCCACCCUUGGAGU |
| | | UCAGCUCUUCAGUGCAGGAAUCGCCGCUUGCCUCGCCGAUGUUA |
| | | UUACUUUUCCCUUAGACACAGCGAAGGUACGCCUGCAGGUUCAA |
| | | GGCGAAUGUCCAACUUCAAGCGUGAUUCGAUACAAAGGCGUGCU |
| | | CGGAACAAUCACAGCUGUGGUGAAGACAGAGGGCCGAAUGAAGC |
| | | UGUACUCUGGUCUCCCCAGCAGGCCUCCAGAGGCAGAUCAGCUCC |
| | | GCAUCCUUGCGUAUCGGACUGUACGACACAGUCCAAGAAUUUCU |
| | | UACAGCUGGAAAGGAAACAGCUCCUAGUCUGGGAAGCAAAAUCC |
| | | UUGCAGGUCUUACCACAGGCGGCGUCGCCGUGUUCAUUGGACAG |
| | | CCUACUGAGGUUGUGAAGGUCCGACUGCAGGCUCAAUCCCAUCU |
| | | GCAUGGUAUUAAGCCACGCUACACUGGAACAUAUAACGCUUACA |
| | | GAAUCAUCGCAACCACAGAGGGCUUGACAGGACUCUGGAAAGGC |
| | | ACGACGCCCAAUUUAAUGCGAUCCGUCAUCAUCAACUGCACAGA |
| | | ACUGGUAACGUAUGAUCUCAUGAAAGAAGCUUUUGUGAAGAAU |
| | | AACAUCUUGGCAGACGACGUUCCAUGUCACCUGGUUUCUGCAUU |
| | | GAUCGCCGGAUUCUGUGCUACUGCUAUGUCAUCGCCUGUUGACG |
| | | UCGUAAAGACACGCUUUAUAAACUCCCCACCUGGUCAAUAUAAA |
| | | AGUGUCCCCAACUGUGCAAUGAAAGUCUUCACAAACGAAGGCCC |
| | | UACAGCAUUUUUUAAGGGACUGGUUCCCUCCUUUCUUCGUCUCG |
| | | GAUCCUGGAAUGUCAUUAUGUUUGUAUGCUUUGAACAGCUGAA |
| | | AAGAGAGCUGUCCAAAUCCAGACAAACAAUGGACUGUGCAACCU |
| | | GA |
| 101 | mol_type = RNA origin = synthetic construct | AUGGGCGGUCUGACAGCCAGCGACGUGCAUCCCACACUGGGGUGU |
| | | GCAGCUCUUCAGUGCAGGAAUUGCCGCUUGCCUCGCUGAUGUUA |
| | | UUACAUUUCCUCUAGAUACUGCCAAGGUACGAUUGCAGGUUCAA |
| | | GGCGAAUGCCCAACAAGUAGCGUUAUCCGAUAUAAAGGCGUGUU |
| | | GGGAACCAUCACCGCUGUAGUGAAAACCGAAGGCAGGAUGAAGC |
| | | UCUACAGCGGGCUCCCAGCCCGGCCUACAAAGGCAGAUAAGCUCC |
| | | GCCUCCUGCGUAUCGGAUUGUACGACACGGUCCAAGAGUUCCU |
| | | UACAGCGGGAAAAGAGACAGCGCCUAGCUUGGGGUCCAAAAUUC |
| | | UGGCCGGACUCACAACAGGAGGUGUGGCGUGUUCAUUGGACAG |
| | | CCUACAGAAGUUGUCAAGGUGCGACUACAGGCUCAAUCUCACCU |
| | | GCAUGGGAUAAAACCUCGCUACACUGGGACUUACAACGCUUACA |
| | | GGAUUAUUGCCACAACAGAAGGCCUGACGGGACUUUGGAAAGGU |
| | | ACAACACCUAAUUUAAUGCGUUCCGUUAUCAUCAAUUGCACUGA |
| | | GCUGGUCACUUACGAUCUCAUGAAGGAAGCAUUCGUGAAAAAUA |
| | | ACAUCUUGGCAGAUGACGUUCCCUGUCACUUGGUGUCCGCACUG |

| SEQ ID NO | | RNA Sequence |
|---|---|---|
| | | AUCGCAGGAUUCUGUGCCACUGCAAUGUCAAGCCCUGUCGAUGU |
| | | CGUGAAAACAAGGUUUAUCAAUUCCCCACCUGGUCAGUAUAAAU |
| | | CUGUUCCUAAUUGUGCCAUGAAGGUAUUCACCAACGAAGGCCCC |
| | | ACAGCCUUCUUUAAGGGACUGGUUCCCUCUUUUCUCCGGCUUGG |
| | | AUCCUGGAACGUCAUAAUGUUCGUAUGUUUUGAGCAGUUAAAA |
| | | AGAGAGCUGUCUAAAUCCAGGCAGACAAUGGACUGUGCUACAUA |
| | | G |
| 102 | mol_type = RNA origin = synthetic construct | AUGGGCGGACUUACAGCAUCUGACGUGCACCCUACAUUAGGUGU |
| | | UCAGCUCUUCAGUGCAGGCAUCGCUUGCCUCGCCGAUGUCA |
| | | UUACCUUUCCUCUGGAUACCGCUAAGGUACGCCUCCAGGUUCAG |
| | | GGCGAAUGCCCAACUUCCUCCGUGAUUCGAUAUAAGGGAGUUUU |
| | | GGGAACCAUUACGGCUGUGGUGAAGACUGAGGGCCGAAUGAAAC |
| | | UUUACAGCGGGCUGCCUGCGGGACUGCAGCGGCAGAUCAGCUCA |
| | | GCUUCGUUGCGGAUCGGGCUAUAUGACACCGUUCAGGAAUUCCU |
| | | UACGGCCGGAAAGGAAACCGCACCUAGUCUGGGGUAGUAAAAUUC |
| | | UUGCCGGGCUUACGACAGGCGGCGUCGCUGUGUUCAUUGGCCAA |
| | | CCCACUGAGGUGGUAAAGGUCCGGCUUCAGGCUCAAAGCCACCU |
| | | GCACGGAAUCAAGCCUCGCUACACUGGAACAUACAACGCUUACA |
| | | GGAUCAUAGCCACUACAGAAGGCCUGACAGGGCUUUGGAAGGGC |
| | | ACGACACCCAAUUUAAUGCGGUCUGUGAUCAUCAAUUGCACUGA |
| | | ACUGGUGACUUACGACCUCAUGAAGGAAGCUUUCGUGAAAAACA |
| | | ACAUACUGGCCGAUGACGUCCCAUGUCAUCUGGUGUCCGCAUUG |
| | | AUCGCCGGAUUUUGUGCUACAGCUAUGUCUUCCCCUGUCGACGU |
| | | CGUUAAGACACGAUUUAUAAACUCUCCACCAGGACAAUACAAGA |
| | | GUGUCCCCAAUUGCGCCAUGAAAGUCUUCACAAACGAAGGCCCU |
| | | ACAGCCUUCUUUAAGGGGCUCGUUCCCUCCUUUCUUCGGCUCGG |
| | | CUCUUGGAACGUCAUCAUGUUCGUGUGCUUCGAGCAACUGAAAC |
| | | GGGAGUUAUCCAAAAGUAGACAGACCAUGGACUGCGCUACUUGA |
| 103 | mol_type = RNA origin = synthetic construct | AUGGGCGGAUUAACUGCCAGUGACGUCCACCCCACUCUGGGGGU |
| | | ACAACUCUUCAGUGCCGGAAUCGCCGCUUGUCUCGCCGAUGUUA |
| | | UUACCUUUCCCUUAGACACCGCUAAGGUGCGCCUGCAAGUUCAA |
| | | GGCGAAUGCCCAACAUCAAGCGUUAUACGAUAUAAGGGCGUUCU |
| | | CGGGACCAUCACAGCUGUUGUAAAAACAGAAGGCCGUAUGAAAC |
| | | UCUACAGCGGACUGCCUGCCGGCCUGCAGAGGCAGAUCAGUUCG |
| | | GCGUCCUGCGCAUCGGUUUGUACGAUACCGUGCAAGAAUUCCU |
| | | GACCGCCGGAAAAGAGACAGCUCCCAGUUUGGGUAGUAAAAUUC |
| | | UGGCGGGGCUCACAACAGGUGGCGUUGCUGUGUUCAUCGGACAG |
| | | CCUACAGAGGUAGUCAAGGUCCGACUCCAGGCUCAAUCACACCU |
| | | GCACGGAAUCAAACCUCGCUACACUGGGACAUACAACGCUUACA |
| | | GGAUUAUCGCCACCACAGAAGGCUUGACUGGGUUGUGGAAGGGC |
| | | ACAACACCUAAUUUAAUGCGAUCUGUCAUAAUCAAUUGCACGGA |
| | | ACUAGUAACGUACGAUCUCAUGAAAGAAGCUUUUGUGAAAAAU |
| | | AACAUUCUGGCAGAUGACGUCCCCUGUCACUUGGGUGUCUGCACU |
| | | CAUAGCUGGAUUUUGUGCAACUGCUAUGUCAUCCCCCGUCGAUG |
| | | UCGUGAAAACACGGUUUAUCAAUUCACCACCAGGCCAAUACAAA |
| | | UCUGUACCUAAUUGUGCCAUGAAGGUGUUCACGAACGAAGGGCC |
| | | AACAGCCUUCUUCAAGGGGCUUGUUCCAUCCUUUCUCCGACUCG |
| | | GGUCAUGGAAUGUGAUCAUGUUCGUGUGUUUCGAGCAACUGAA |
| | | AAGAGAGUUGUCAAAGAGUAGACAAACGAUGGACUGCGCCACAU |
| | | GA |
| 104 | mol_type = RNA origin = synthetic construct | AUGGGGUGGAUUGACUGCCUCCGAUGUCCAUCCUACAUUGGGGGU |
| | | UCAGCUCUUCAGUGCGGGCAUCGCCGCUUGCCUUGCCGAUGUCA |
| | | UUACCUUUCCACUAGACACAGCUAAGGUACGUCUACAAGUCCAA |
| | | GGAGAAUGCCCCACCUCUUCUGUGAUUAGAUACAAGGGCGUACU |
| | | GGGAACCAUCACAGCUGUCGUGAAGACCGAGGGACGCAUGAAGC |
| | | UUUACAGCGGGCUGCCAGCAGGACUGCAGAGGCAGAUAAGCUCA |
| | | GCAUCCCUGCGAAUCGGACUAUACGACACAGUCCAGGAAUUUCU |
| | | UACUGCGGGAAAAGAGACAGCUCCCAGUUUAGGGAGUAAAAUAC |
| | | UCGCCGGGCUGACAACAGGCGGCGUUGCCGUUUCAUAGGACAG |
| | | CCGACUGAAGUGGUUAAGGUGCGACUCCAAGCUCAGUCUCACCU |
| | | GCAUGGUAUCAAACCUCGCUAUACUGGUACAUAUAACGCCUACA |
| | | GGAUUAUAGCCAACAACAGAAGGUUUGACUGGACUCUGGAAGGG |
| | | GACAACACCCAAUUUGAUGCGAUCCGUCAUUAUUAACUGCACCG |
| | | AGCUCGUAACCUAUGAUCUCAUGAAGGAGGCCUUUGUAAAAAAC |
| | | AACAUCCUGGCAGACGACGUUCCUUGCCACUUGGGUUUCAGCACU |
| | | CAUCGCCGGGUUCUGUGCUACCGCUAUGUCUAGCCCUGUGGAUG |
| | | UUGUCAAAACACGAUUCAUCAAUUCACCACCGGGCCAAUAUAAA |
| | | UCUGUCCCCAAUUGCGCCAUGAAGGUCUUCACAAAUGAAGGCCC |
| | | GACUGCCUUCUUCAAGGGGCUCGUUCCUUCUUUUCUCCGGCUCG |
| | | GGUCCUGGAAUGUGAUAAUGUUCGUGUGUUUCGAACAGCUGAA |
| | | AAGGGAGCUGUCAAAAUCAAGGCAAACCAUGGACUGCGCCACCU |
| | | GA |

-continued

| SEQ ID NO | | RNA Sequence |
|---|---|---|
| 105 | mol_type = RNA origin = synthetic construct | AUGGGAGGUCUGACAGCUUCAGACGUACACCCCACAUUAGGCGU GCAACUCUUCAGUGCCGGCAUAGCCGCUUGCCUCGCCGAUGUUA UUACCUUUCCUCUGGACACCGCUAAGGUGCGACUUCAGGUUCAG GGCGAGUGUCCAACCUCAUCCGUUAUUCGAUACAAAGGCGUGCU AGGAACCAUAACCGCCGUGGUCAAGACGGAAGGCCGUAUGAAAC UUUACAGCGGACUCCCAGCGGGACUCCAGAGACAAAUAAGCUCU GCAUCUCUUCGAAUCGGACUGUACGAUACCGUCCAGGAGUUUCU AACAGCUGGAAAGGAGACAGCACCUAGUUUGGGCAGCAAAAUUC UUGCCGGGCUCACUACAGGAGGCGUCGCCGUGUUUAUUGGACAG CCCACAGAGGUAGUGAAGGUGCGACUGCAGGCCCAAUCUCAUCU GCACGGAAUUAAACCGCGCUACACCGGUACAUAUAACGCCUACA GAAUCAUCGCUACCACAGAAGGUCUGACUGGGUUGUGGAAGGGG ACAACCCCCAAUUUAAUGCGAUCUGUGAUCAUCAACUGCACUGA GCUGGUCACUUACGAUCUCAUGAAAGAAGCAUUCGUGAAAAACA ACAUUUUGGCUGACGACGUCCCAUGUCAUUUAGUUUCUGCGCUC AUCGCUGGGGUUUUGUGCUACAGCAAUGUCUUCUCCCGUUGAUGU CGUCAAAACACGAUUCAUAAACUCUCCACCUGGCCAAUACAAAA GUGUUCCUAACUGUGCCAUGAAAGUCUUCACGAACGAAGGCCCC ACAGCCUUCUUCAAGGGGCUGGUUCCCUCCUUUCUUCGGCUCGG AUCCUGGAAUGUAAUCAUGUUUGUGUGCUUCGAACAGUUAAAA AGAGAGCUCUCAAAAUCAAGGCAGACAAUGGAUUGUGCCACUUG A |
| 106 | mol_type = RNA origin = synthetic construct | AUGGGUGGACUGACAGCUAGCGAUGUGCACCCCACACUGGGCGU GCAACUCUUCAGUGCUGGUAUUGCCGCUUGCCUCGCCGACGUCA UAACGUUUCCCUUAGACACUGCUAAAGUCCGGCUUCAGGUCCAG GGUGAAUGCCCAACCUCUUCAGUCAUCCGUUAUAAAGGCGUGCU GGGAACCAUCACAGCGGUGGUAAAAACAGAGGGCCGCAUGAAGC UGUAUAGCGGGCUCCCCGCAGGCCUCCAGAGGCAGAUAAGCUCU GCUUCUCUGCGGAUCGGUUUUGUAUGACACUGUUCAAGAAUUCCU UACCGCCGGCAAAGAAACCGCACCUAGUCUGGGUAGUAAAAUCC UCGCCGGGCUCACUACAGGCGGUGUCGCCGUAUUCAUCGGACAA CCUACCGAGGUGGUCAAGGUAAGACUGCAGGCCCAAAGCCACCU GCACGGCAUCAAACCUCGCUACACCGGCACUUACAACGCCUACA GGAUUAUAGCUACCACCGAAGGCUUGACGGGACUGUGGAAAGGC ACAACCCCAAAUUUAAUGCGGUCCGUUAUUAUCAACUGCACCGA GCUGGUAACUUAUGAUCUCAUGAAGGAAGCAUUUGUGAAAAAU AACAUCUUGGCAGACGACGUUCCAUGUCACUUGGUUUCGGCGCU AAUCGCCGGAUUUUGUGCUACAGCCAUGUCAUCCCCUGUCGAUG UCGUGAAGACAAGGUUCAUCAAUUCACCACCAGGUCAGUACAAA AGUGUCCCCAAUUGCGCAAUGAAAGUAUUCACAAACGAAGGCCC AACCGCGUUUUUUAAGGGGCUUGUUCCCUCCUUUCUGCGCCUCG GUUCUUGGAAUGUCAUCAUGUUUGUAUGCUUCGAGCAGCUGAA ACGGGAGCUGUCCAAGUCCAGACAGACUAUGGACUGUGCGACAU GA |
| 107 | mol_type = RNA origin = synthetic construct | AUGGGGGGGCUGACAGCUUCAGACGUUCACCCCACCUGGGGAGU UCAACUCUUUAGUGCUGGAAUCGCCGCCUGCCUCGCGAUGUCA UCACCUUUCCUCUGGAUACAGCAAAGGUGCGGCUUCAGGUUCAG GGCGAAUGUCCAACUUCUUCAGUGAUCCGCUAUAAAGGCGUCUU GGGAACCAUCACCGCAGUCGUGAAGACCGAAGGCCGAAUGAAGC UUUACAGCGGGCUGCCAGCCGGGCUGCAACGACAGAUAAGCUCA GCAUCCCUGCGUAUAGGCCUAUACGACACCGUCCAAGAGUUUCU CACUGCCGGAAAGGAGACAGCUCCCAGUCUGGGGAAGCAAGAUCU UAGCCGGACUCACCACAGGCGGCGUGGCCGUGUUCAUUGGACAA CCUACCGAGGUUGUUAAGGUGCGACUACAGGCUCAGAGCCAUCU GCAUGGGAUUAAACCACGCUAUACUGGAACUUACAACGCUUAUA GGAUUAUCGCCACCACUGAAGGAUUAACUGGACUUUGGAAGGGC ACAACACCCAACUUGAUGCGAUCAGUGAUCAUAAAAUUGCACCGA ACUGGUGACCUACGAUCUCAUGAAGGAGGCUUUCGUGAAGAACA ACAUACUUGCCGACGACGUUCCUUGUCACCUCGUCUCUGCGUUG AUCGCCGGGUUCUGCGCUACUGCUAUGUCAUCUCCCGUCGAUGU UGUGAAAACAAGGUUUAUCAAUUCGCCUCCAGGCCAGUAUAAAA GUGUCCCUAACUGUGCCAUGAAAGUGUUCACAAAUGAAGGCCCC ACAGCAUUUUUCAAGGGACUCGUUCCUUCCUUUCUUCGUCUCGG AUCCUGGAAUGUCAUCAUGUUUGUGUGCUUCGAGCAAUUGAAAC GAGAGCUGUCGAAGUCACGACAAACCAUGGACUGCGCAACCUGA |
| 108 | mol_type = RNA origin = synthetic construct | AUGGGUGGUCUCACUGCAAGCGACGUGCAUCCAACACUGGGGGU UCAGCUCUUCAGCGCCGGAAUCGCCGCUUGCCUUGCCGACGUCA UAACUUUUCCUUUAGAUACCGCUAAGGUACGCCUGCAAGUCCAG GGCGAGUGCCCCACAUCAAGUGUGAUUCGCUACAAAGGCGUUUU GGGGACCAUCACAGCCAGUGGUGAAGACGGAAGGCCGAAUGAAAC UUUAUAGCGGGACUGCCAGCAGGACUGCAGCGCCAAAUAAGCUCU GCUUCACUGCGUAUCGGUCUAUAUGAUACCGUGCAGGAAUUUCU UACUGCAGGAAAGGAGACGGCACCCAGUUUGGGGGAGCAAAAUCU |

-continued

| SEQ ID NO | | RNA Sequence |
|---|---|---|
| | | UGGCCGGCCUGACUACAGGCGGUGUCGCUGUAUUCAUUGGACAG |
| | | CCAACUGAAGUGGUGAAGGUGCGACUCCAGGCUCAAUCUCACCU |
| | | GCACGGUAUCAAACCCCGCUACACUGGCACAUAUAACGCUUACA |
| | | GGAUUAUCGCUACGACAGAAGGCUUAACGGGCCUCUGGAAAGGC |
| | | ACCACCCCUAAUUUAAUGCGAUCUGUCAUCAUCAAUUGCACUGA |
| | | ACUCGUAACGUAUGAUCUCAUGAAAGAAGCGUUUGUGAAAAAU |
| | | AAUAUCCUGGCGGACGACGUCCCUUGUCACCUGGUGUCUGCACU |
| | | UAUCGCCGGAUUUUGUGCCACCGCCAUGUCCAGUCCUGUUGACG |
| | | UUGUCAAAACAAGGUUCAUCAAUUCACCUCCUGGUCAAUAUAAA |
| | | AGUGUUCCCAACUGUGCCAUGAAAGUCUUCACAAAUGAAGGUCC |
| | | CACAGCUUUUUUUAAAGGACUAGUUCCUUCCUUCCUGCGGCUUG |
| | | GAUCCUGGAAUGUCAUCAUGUUUGUGUGUGUUUUGAACAGCUGAA |
| | | ACGGGAACUUAGUAAAUCCAGACAGACCAUGGACUGUGCCACCU |
| | | GA |
| 109 | mol_type = RNA origin = synthetic construct | AUGGGUGGUCUAACCGCUUCAGACGUGCAUCCUACUCUGGGGAGU |
| | | GCAGCUCUUCAGUGCAGGUAUCGCCGCUUGCCUUGCCGACGUGA |
| | | UCACCUUUCCCCUGGACACCGCUAAGGUGCGCCUGCAGGUCCAG |
| | | GGCGAAUGUCCUACAUCAAGCGUGAUUCGGUAUAAAGGCGUAUU |
| | | GGGAACCAUCACUGCUGUGGUAAAGACUGAAGGAAGAAUGAAG |
| | | CUAUACAGCGGGCUUCCAGCUGGACUUCAGAGGCAGAUCAGCUC |
| | | CGCUUCUUUGCGUAUCGGCCUGUACGACACCGUUCAGGAAUUUC |
| | | UCACUGCAGGAAAGGAGACAGCACCCAGCCUGGGCAGCAAAAUU |
| | | CUAGCCGGGCUCACCACAGGUGGCGUUGCUGUAUUUAUAGGGCA |
| | | ACCAACAGAGGUGGUCAAGGUGAGGCUGCAAGCUCAAUCCCACU |
| | | UACACGGUAUUAAGCCACGCUAUACUGGAACUUACAACGCCUAC |
| | | AGGAUUAUUGCUACAACAGAAGGUCUUACUGGACUUUGGAAGG |
| | | GGACAACACCUAAUUUAAUGCGGUCCGUGAUCAUUAACUGCACC |
| | | GAAUUGGUUACCUACGAUCUCAUGAAAGAAGCCUUUGUGAAGA |
| | | AUAACAUCUUGGCCGAUGACGUUCCUUGUCACCUCGUGUCUGCA |
| | | CUAAUAGCCGGAUUCUGUGCUACAGCUAUGUCAUCUCCUGUCGA |
| | | UGUUGUCAAAACGAGGUUUAUCAAUUCUCCUCCGGGUCAGUAUA |
| | | AAAGUGUCCCUAAUUGUGCCAUGAAAGUAUUCACGAACGAAGGA |
| | | CCCACCGCCUUCUUCAAGGGACUUGUUCCUUCUUUUCUCCGUCU |
| | | CGGUUCCUGGAAUGUCAUCAUGUUCGUGUGUGUUUUGAACAGCUGA |
| | | AAAGGGAACUUAGCAAAUCAAGACAAACUAUGGACUGUGCUACG |
| | | UGA |
| 110 | mol_type = RNA origin = synthetic construct | AUGGGGGGGUCUGACUGCCUCAGACGUUCAUCCGACACUGGGGGGU |
| | | GCAGCUCUUCAGUGCCGGCAUUGCCGCUUGCCUCGCCGAUGUCA |
| | | UUACUUUUCCUCUGGACACCGCGAAGGUCCGCCUGCAAGUUCAG |
| | | GGCGAGUGUCCUACAUCUUCCGUCAUCCGGUAUAAAGGCGUUCU |
| | | GGGAACCAUCACAGCCGUCGUGAAGACCGAGGGCCGAAUGAAGC |
| | | UUUACAGCGGGCUGCCUGCUCUGGGCUGCAGCGACAGAUAAGCUCC |
| | | GCUUCUCUUCGGAUCGGGCUGUACGACACAGUACAGGAGUUUCU |
| | | CACAGCUGGAAAGGAGACUGCACCCAGUUUGGGUAGUAAAAUUC |
| | | UCGCGGGGCUCACCACUGGCGGUGUCGCGUGUUUAUUGGUCAG |
| | | CCUACUGAGGUCGUCAAGGUCAGGCUGCAGGCUCAGAGCCAUCU |
| | | GCAUGGGAUCAAACCUCGCUACACUGGCACAUAUAAUGCCUACA |
| | | GGAUAAUUGCAACAACAGAAGGCCUGACUGGACUGUGGAAAGG |
| | | GACAACACCCAAUUUAAUGCGAUCCGUCAUCAUUAAUUGCACCG |
| | | AGCUCGUAACAUACGAUCUCAUGAAGAGGAGGCAUUUGUGAAAA |
| | | UAACAUUUUAGCAGAUGAUGUUCCAUGUCACCUGGUAUCAGCAC |
| | | UCAUCGCAGGAUUCUGUGCUACUGCUAUGUCUUCUCCCAGUGGAC |
| | | GUGGUGAAGACUCGGUUUAUCAAUUCUCCACCUGGCCAAUACAA |
| | | AAGUGUCCCUAACUGUGCCAUGAAGGUAUUCACUAACGAAGGCC |
| | | CGACUGCCUUCUUUAAGGGACUCGUCCCUUCUUUUCUGCGGCUU |
| | | GGCUCGUGGAACGUGAUUAUGUUUGUGUGUGUUUUGAACAGCUGA |
| | | AAAGGGAGCUAAGUAAGAGCAGGCAAACAAUGGACUGUGCCACU |
| | | UGA |
| 111 | mol_type = RNA origin = synthetic construct | AUGGGUGGGCUCACCGCAUCAGACGUUCACCCCACACUGGGGAGU |
| | | UCAACUCUUCAGUGCGGGCAUCGCCGCCUGCCUGGCUGACGUUA |
| | | UUACUUUUCCUCUGGACACAGCUAAGGUACGUUUACAGGUUCAA |
| | | GGAGAAUGUCCCACUUCUUCCGUGAUUCCGGUAUAAAGGCGUUUU |
| | | GGGGACUAUCACAGCCGUAGUGAAGACAGAAGGCCGCAUGAAGC |
| | | UCUACAGUGGUCUGCCAGCAGGCCUGCAGCGACAAAUCAGCUCU |
| | | GCUUCACUGCGUAUCGGUUUGUACGACACUGUGCAAGAAUUCCU |
| | | CACCGCAGGAAAGGAGACCGCACCCAGCUUAGGGAGCAAAAUCC |
| | | UUGCCGGGCUCACAACAGGCGGCGUCGCGUGUUCAUCGGACAG |
| | | CCUACAGAGGUGGUUAAGGUAAGACUUCAGGCCCAGUCACACCU |
| | | UCAUGGUAUAAAACCUCGCUAUACUGGAACGUACAAUGCUUACA |
| | | GGAUCAUCGCCACCACAGAAGGCCUCACAGGGCGUGGGAAAGGU |
| | | ACAACCCCUAAUUUGAUGCGAUCAGUCAUCAUCAAUUGCACUGA |
| | | GCUGGUGACUUACGAUCUCAUGAAGGAAGCUUUUGUCAAAAACA |
| | | ACAUACUGGCCGAUGACGUCCCAUGCCACCUGGUUUUCCGCACUC |

-continued

| SEQ ID NO | | RNA Sequence |
|---|---|---|
| | | AUCGCAGGAUUCUGUGCCACCGCAAUGUCUUCUCCUGUCGAUGU<br>CGUGAAGACACGAUUUAUCAAUUCACCUCCUGGACAGUACAAAU<br>CUGUCCCCAAUUGUGCCAUGAAAGUGUUCACAAACGAAGGGCCA<br>ACAGCCUUUUUUAAGGGGCUCGUGCCCUCCUUUCUUCGACUCGG<br>AUCUUGGAACGUCAUUAUGUUUGUGUGUUUUGAACAGUUAAAA<br>AGAGAGCUCUCCAAAUCUAGGCAGACAAUGGAUUGCGCCACUUA<br>G' |
| 112 | mol_type = RNA<br>origin = synthetic construct | AUGGGCGGUCUCACAGCUAGCGAUGUGCAUCCCACGCUGGGGGU<br>GCAACUUUUCAGCGCGGGCAUCGCCGCUUGCUUAGCUGAUGUCA<br>UUACCUUUCCCUUAGAUACGGCUAAGGUCCGCCUUCAGGUCCAG<br>GGCGAAUGUCCCACCUCAUCCGUGAUUCGCUAUAAGGGCGUAUU<br>AGGGACAAUCACAGCCGUCGUGAAGACCGAGGGCCGUAUGAAAC<br>UCUAUAGCGGGCUGCCCGCCGGAUUGCAGCGACAGAUCAGCUCU<br>GCAUCCCUGCGAAUUGGCCUGUAUGACACUGUGCAGGAAUUCCU<br>CACCGCCGGGAAAGAGACGGCGCCCAGUCUGGGCAGCAAGAUAC<br>UGGCCGGACUCACUACAGGUGGCGUGGCGGUGUUCAUUGGACAG<br>CCUACAGAGGUGGUUAAGGUUAGACUGCAGGCUCAAUCCCAUCU<br>GCACGGGAUCAAACCUCGCUAUACUGGCACUUAUAAUGCUUACA<br>GGAUCAUUGCCACGACAGAGGGCCUCACUGGACUUUGGAAAGGG<br>ACAACACCCAAUUUAAUGCGAAGCGUUAUCAUCAACUGCACCGA<br>GCUCGUGACCUAUGAUCUGAUGAAGGAAGCCUUUGUAAAAAACA<br>ACAUCCUGGCAGAUGACGUCCCAUGUCACUUGGUAUCUGCACUC<br>AUAGCUGGCUUUUGUGCUACCGCCAUGUCUUCCCCUGUGGAUGU<br>GGUAAAGACACGAUUCAUCAAUUCUCCCACCUGGUCAAUAUAAAA<br>GUGUUCCUAAUUGUGCCAAUGAAAGUAUUCACUAACGAAGGCCCA<br>ACAGCGUUCUUCAAGGGGCUCGUGCCAUCUUUUUCUGCGGCUCGG<br>GUCCUGGAAUGUCAUCAUGUUUGUGUGCUUCGAACAGUUAAAA<br>AGGGAACUGUCAAAUCAAGGCAGACAAUGGAUUGCGCUACUUG<br>A |
| 113 | mol_type = RNA<br>origin = synthetic construct | AUGGGCGGUCUGACCGCAUCUGACGUACAUCCUACCCUUGGGGU<br>GCAGCUCUUUAGUGCUGGAAUCGCCGCUUGCCUUGCGGACGUUA<br>UUACUUUUCCCUUAGAUACUGCUAAGGUGCGCCUCCAGGUCCAG<br>GGCGAGUGUCCUACAUCAUCCGUUAUUCGCUACAAGGGCGUAUU<br>AGGCACUAUUACAGCCGUGGUGAAAACCGAAGGCCGCAUGAAAU<br>UGUAUAGCGGGCUCCCUGCUGGUUUGCAAAGGCAGAUCAGCUCC<br>GCUUCUCUGCGGAUCGGUUUAUACGACACCGUUCAGGAGUUUCU<br>UACCGCAGGAAAGGAGACGGCACCUAGUUUAGGGAGCAAAAUUC<br>UCGCCGGGCUCACUACAGGUGGACGUCGCCGUAUUCAUCGGACAG<br>CCUACAGAGGUGGUAAAGGUACGCCUGCAAGCUCAGUCUCAUCU<br>GCACGGCAUUAAACCUCGCUACACUGGGACAUAUAACGCUUAUA<br>GGAUUAUCGCCACAACAGAAGGCCUAACGGGACUAUGGAAAGGC<br>ACAACCCCCAACUUAAUGCGGUCUGUCAUUAUCAACUGCACUGA<br>ACUCGUGACUUACGAUCUUAUGAAAGAAGCUUUCGUGAAGAACA<br>ACAUCCUGGCCGAUGAUGUUCCUUGUCACUUGGUGUCCGCACUU<br>AUCGCUGGAUUCUGUGCUACCGCUAUGUCAUCCCCUGUCGACGU<br>CGUUAAAACACGCUUCAUAAAUUCUCCCACCUGGUCAAUAUAAA<br>GUGUUCCCAAUUGUGCCAUGAAGGUGUUUACAAAUGAGGGACCC<br>ACAGCCUUUUUCAAGGGCCUGGUUCCAUCGUUUCUACGGCUCGG<br>AUCCUGGAACGUCAUCAUGUUCGUCUGUUUUGAGCAACUGAAAC<br>GGGAGCUUUCCAAAUCCAGACAGACGAUGGACUGUGCUACUUGA<br>' |
| 114 | mol_type = RNA<br>origin = synthetic construct | AUGGGGGGUUUAACCGCUUCAGAUGUGCAUCCAACGCUGGGGGU<br>GCAACUUUUCAGUGCAGGGAUUGCCGCUUGCCUCGCAGACGUCA<br>UUACUUUUCCAUUGGACACCGCAAAGGUGCGCCUGCAGGUCCAG<br>GGCGAAUGCCCAACUUCAUCGGUUAUCAGAUAUAAGGGCGUCUU<br>GGGAACCAUCACAGCCGUGGUGAAGACUGAAGGCAGGAUGAAAC<br>UCUACAGCGGGCUCCCAGCCGGCCUACAGCGGCAAAUCAGCUCC<br>GCAUCGCUGAGAAUCGGACUGUAUGACACCGUUCAAGAAUUCCU<br>AACCGCAGGAAAGGAGACAGCACCCAGUCUGGGAAGUAAAAUUC<br>UCGCUGGGCUGACUACUGGCGGCGUGGCCGUAUUCAUCGGACAA<br>CCUACUGAAGUGGUUAAGGUACGGCUACAAGCUCAAAGCCACCU<br>GCACGGCAUUAAACCACGCUAUACUGGCACUUACAAUGCUUAUA<br>GGAUAAUUGCAACAACAGAAGGCCUCACUGGACUUUGGAAGGGC<br>ACAACACCUAAUCUGAUGCGAUCUGUUAUUAUUAAUUGCACUGA<br>GCUCGUGACUUACGAUCUCAUGAAAGAGGCCUUUGUGAAGAAUA<br>AUAUCCUGGCAGACGACGUUCCUUGCCACCUUGUGUCCGCACUA<br>AUCGCGGGAUUCUGUGCCACCGCAAUGUCUAGCCCCUGUGGAUGU<br>UGUCAAAACACGGUUUAUAAACUCCCCUCCCGGCCAGUAUAAAA<br>GUGUCCCCAAUUGUGCAAUGAAGGUCUUCACUAAUGAAGGCCCC<br>ACAGCAUUUUUCAAAGGGCUGGUGCCCUCCUUUCUUCGGCUCGG<br>AUCGUGGAACGUGAUCAUGUUCGUGUGUUUCGAACAGCUGAAA<br>AGGGAGUUGUCAAAGAGCAGACAAACCAUGGACUGUGCUACCUG<br>A |

-continued

| SEQ ID NO | | RNA Sequence |
|---|---|---|
| 115 | mol_type = RNA origin = synthetic construct | AUGGGAGGUUUAACUGCCAGCGACGUUCAUCCAACUCUGGGGGU GCAGCUCUUCAGUGCAGGCAUCGCCGCAUGCCUCGCUGACGUGA UUACGUUUCCUUUAGACACCGCUAAGGUCCGUCUUCAAGUCCAA GGCGAAUGUCCUACUUCUUCCGUCAUUCGUUACAAGGGCGUGUU GGGGACCAUCACAGCCGUGGUGAAGACUGAAGGCAGGAUGAAAC UUUAUAGCGGGCUCCCUGCUGGCUUACAGAGGCAAAUCAGCUCU GCUUCACUCCGGAUUGGGCUCUACGACACUGUCCAGGAAUUUCU UACCGCCGGAAAGGAGACAGCUCCCAGCUUGGGGAGUAAAAUCC UCGCGGGACUCACUACAGGCGGCGUCGCCGUCUUCAUUGGGCAA CCCACUGAGGUGGUGAAGGUCCGGUUGCAGGCUCAAUCCCACCU UCACGGCAUUAAGCCUCGCUACACAGGCACAUACAACGCCUACA GAAUCAUUGCCACCACAGAAGGGUUAACCGGACUUUGGAAGGGG ACAACACCCAACUUAAUGCGAUCUGUCAUCAUCAAUUGCACUGA ACUCGUGACUUACGACCUCAUGAAGGAAGCCUUUGUGAAGAAUA ACAUCUUGGCCGACGACGUUCCUUGUCACCUGGUUUCUGCAUUA AUUGCUGGUUUUUGUGCUACUGCCAUGUCAUCUCCUGUUGAUGU CGUCAAAACACGGUUCAUCAACUCCCCUCCCGGGCAGUACAAAU CUGUCCCCAAUUGUGCCAUGAAAGUCUUCACAAACGAGGGUCCA ACCGCCUUCUUCAAAGGGCUUGUUCCCUCUUUUCUUCGUCUCGG CUCCUGGAACGUGAUCAUGUUCGUGUGCUUCGAACAGCUGAAGA GGGAACUGUCCAAAUCCAGGCAAACGAUGGAUUGUGCCACAUGA |
| 116 | mol_type = RNA origin = synthetic construct | AUGGGCGGUUUAACGGCAAGCGACGUGCAUCCCACGCUGGGCGU GCAGCUUUUCAGUGCCGGAAUCGCUGCUUGCUUAGCAGACGUUA UAACUUUUUCCCCUUGACACGGCCAAGGUCCGCCUGCAAGUCCAA GGCGAAUGUCCAACCUCAUCGGUUAUCCGCUAUAAAGGCGUUUU GGGAACUAUUACAGCCGUCUGUGAAGACCGAGGGCAGGAUGAAAC UUUACAGCGGGCUCCCUGCUGGUUUGCAGAGGCAGAUAAGCUCA GCAUCCCUUCGAAUUGGUCUGUACGACACCGUUCAGGAGUUCCU UACUGCGGGAAAGGAAACAGCCCCUAGUUUGGGCAGCAAAAUUC UGGCCGGGCUGACUACAGGUGGUGUCGCCGUAUUUAUUGGACAA CCCACAGAAGUAGUAAAGGUUCGACUGCAGGCCCAGAGCCAUUU GCAUGGAAUCAAGCCGCGCUACACUGGUACUUACAACGCCUAUA GAAUCAUCGCCACCACAGAGGGGAUUAACUGGACUUUGGAAGGGG ACAACCCCUAAUUUAAUGCGAUCAGUUAUCAUCAAUUGCACCGA GCUAGUGACGUACGAUCUCAUGAAAGAAGCAUUUGUCAAAAACA ACAUUUUGGCAGAUGACGUUCCAUGUCACUUGGUCUCUGCGUUA AUCGCCGGAUUUUGUGCAACCGCUAUGUCUUCUCCUGUCGACGU UGUGAAGACAAGGUUCAUAAACUCUCCACCUGGCCAAUAUAAAA GUGUCCCUAAUUGUGCCAUGAAAGUCUUUACUAAUGAAGGGCCU ACCGCAUUUUUUAAGGGGCUCGUUCCGUCCUUUUCUGCGGCUCGG AUCCUGGAACGUGAUCAUGUUCGUGUGUUUUGAGCAGUUGAAA AGGGAGCUGUCUAAGUCAAGGCAAACGAUGGAUUGUGCCACCUG A' |
| 117 | mol_type = RNA origin = synthetic construct | AUGGGGGGUCUUACUGCAUCAGACGUUCAUCCCACACUGGGGGU GCAGCUCUUCAGUGCGGGCAUCGCCGCGUGCCUCGCGAUGUCA UUACGUUUCCCCUGGAUACAGCUAAGGUGCGCCUGCAGGUCCAG GGCGAAUGCCCAACUUCCUCCGUAAUCCGUUACAAAGGCGUGUU GGGCACCAUCACAGCCGUCGUGAAGACCGAGGGACGUAUGAAAC UUUACAGCGGGCUCCCUGCCGGGCUGCAACGGCAGAUCAGCUCC GCUUCCCUCCGUAUCGGACUAUACGACACAGUGCAGGAAUUCCU UACGGCUGGAAAAGAGACGGCACCUAGCUUGGGCAGCAAAAUCU UGGCAGGGCUCACUACAGGUGGCGUUGCUGUCUUUAUCGGACAG CCUACUGAGGUAGUGAAGGUCCGUCUCCAAGCUCAAUCCCACCU GCACGGCAUCAAACCUCGAUACACCGGCACUUAUAACGCCUACA GGAUUAUCGCUACUACAGAAGGCCUUACUGGGCUGUGGAAGGGG ACAACACCUAAUUUAAUGCGGUCGGUUAUCAUCAAUUGCACUGA GCUCGUGACCUACGAUCUCAUGAAGGAAGCGUUUGUGAAAAACA ACAUUCUGGCAGAUGACGUCCCCUGCCACUUGGUGUCUGCUCUC AUCGCCGGAUUUUGUGCCACCGCCAUGUCUUCCCCUGUUGACGU UGUGAAAACAAGAUUUAUCAAUUCUCCUCCAGGUCAAUAUAAAA GUGUCCCCAAUUGUGCCAUGAAGGUGUUCACAAAUGAGGGCCCA ACGGCAUUCUUCAAGGGGCUCGUCCCUUCCUUUCUUCGACUGGG GUCGUGGAACGUCAUCAUGUUUGUAUGCUUUGAACAAUUGAAA CGGGAGCUGUCCAAGUCCCGGCAGACAAUGGACUGUGCCACUUA G |
| 118 | mol_type = RNA origin = synthetic construct | AUGGGCGGCCUGACAGCUUCUGAUGUGCAUCCUACACUGGGGGUGU GCAACUUUUCAGUGCGGGAAUCGCUGCUUGCCUCGCCGACGUCA UUACCUUUCCCUUAGACACAGCAAAGGUCCGCCUGCAGGUCCAA GGCGAGUGUCCUACUUCCUCCGUCAUUCGAUACAAGGGUGUGCU GGGAACCAUCACCGCUGUUGUAAAAACAGAAGGCGUAUGAAGC UUUACAGCGGACUGCCAGCCGGUUUACAGAGGCAGAUCAGCUCU GCGUCGCUGCGUAUCGGGCUCUAUGACACCGUCCAAGAGUUCCU |

-continued

| SEQ ID NO | | RNA Sequence |
|---|---|---|
| | | AACAGCAGGGAAGGAGACAGCGCCCAGCCUGGGGGAGUAAAAUCC |
| | | UCGCAGGACUCACAACAGGUGGUGUCGCCGUGUUCAUUGGACAG |
| | | CCAACUGAGGUGGUGAAGGUCCGACUGCAGGCCCAGUCCCACCU |
| | | CCACGGGAUCAAACCUCGCUACACCGGGACGUACAACGCUUAUA |
| | | GAAUCAUCGCCACCACAGAAGGGCUCACAGGACUCUGGAAGGGG |
| | | ACAACACCUAAUUUGAUGCGAUCUGUUAUUAUUAAUUGUACUG |
| | | AACUCGUGACUUAUGAUCUCAUGAAGGAGGCCUUUGUGAAAAAC |
| | | AACAUCCUGGCCGACGACGUCCCAUGUCACCUGGUAUCUGCACU |
| | | GAUCGCCGGAUUCUGUGCAACCGCCAUGUCAUCUCCUGUUGACG |
| | | UUGUCAAGACACGCUUCAUAAACUCUCCUCCGGGUCAGUAUAAA |
| | | AGUGUCCCCAAUUGUGCCAUGAAAGUAUUUACCAACGAAGGCCC |
| | | AACCGCAUUCUUUAAGGGGCUUGUGCCAUCUUUUCUGCGGCUGG |
| | | GCUCCUGGAAUGUCAUCAUGUUCGUGUGUUUCGAACAAUUAAAA |
| | | AGAGAGCUGUCGAAGUCCCGGCAGACGAUGGACUGCGCCACUUA |
| | | G |
| 119 | mol_type = RNA origin = synthetic construct | AUGGGGGGUCUCACAGCUAGUGACGUUCAUCCUACACUCGGAGU |
| | | GCAGCUCUUCAGUGCAGGAAUCGCCGCUUGCCUUGCAGACGUUA |
| | | UCACCUUUCCUCUUGACACCGCUAAGGUCCGACUGCAGGUCCAA |
| | | GGCGAGUGUCCCACCUCCUCCGUAAUCAGAUACAAGGGUGUCCU |
| | | GGGGACAAUCACCGCAGUCGUAAAGACAGAGGGCCGUAUGAAAC |
| | | UUUACAGCGGGCUCCCGGCAGGAUUGCAGCGCCAGAUCAGCUCC |
| | | GCAUCUCUGAGAAUUGGUCUCUACGACACUGUUCAAGAAUUCCU |
| | | AACAGCCGGAAAGGAGACUGCACCCAGUCUGGGAAGUAAAAUAC |
| | | UAGCCGGGCUCACCACAGGCGGCGUUGCUGUAUUCAUAGGACAG |
| | | CCUACCGAAGUAGUCAAGGUCAGACUUCAGGCUCAGUCUCAUCU |
| | | GCACGGAAUCAAGCCCCGUUAUACCGGAACUUAUAAUGCUUACA |
| | | GGAUCAUCGCCACCACAGAAGGCUUAACUGGACUUUGGAAGGGG |
| | | ACCACACCUAAUUUAAUGCGUUCCGUUAUAAUCAACUGCACCGA |
| | | GCUAGUGACUUACGACCUCAUGAAGGAGGCAUUUGUGAAAAACA |
| | | ACAUCCUGGCAGAUGACGUUCCUUGUCACUUAGUGUCUGCACUC |
| | | AUCGCCGGAUUUUGUGCAACCGCCAUGUCCAGUCCCGUCGAUGU |
| | | CGUUAAGACUCGGUUCAUUAACUCCCCUCCGGGCCAAUACAAAU |
| | | CUGUCCCUAACUGUGCCAUGAAAGUAUUUACAAACGAGGGUCCU |
| | | ACAGCCUUCUUUAAGGGGCUCGUCCCGUCUUUUCUCCGGCUAGG |
| | | CUCGUGGAACGUUAUCAUGUUUGUGUGUUUCGAACAACUAAAA |
| | | AGAGAGCUUUCCAAAUCCAGGCAAACCAUGGAUUGCGCAACUUG |
| | | A |
| 120 | mol_type = RNA origin = synthetic construct | AUGGGGGGCCUGACAGCUUCCGACGUCCACCCCACAUUGGGAGU |
| | | UCAGCUCUUCAGUGCAGGAAUCGCCGCUUGCCUUGCCGAUGUCA |
| | | UUACUUUUUCCUUUGGAUACCGCUAAGGUGCGCCUGCAAGUCCAG |
| | | GGCGAGUGUCCUACUUCUUCUGUGAUUCGAUACAAGGGCGUCUU |
| | | AGGAACUAUUACAGCCGUCGUGAAAACCGAAGGUCGUAUGAAGC |
| | | UCUACAGUGGGCUGCCAGCCGGACUGCAGCGGCAGAUAAGCUCA |
| | | GCUUCUCUCCGAAUCGGACUGUACGACACCGUUCAGGAGUUUCU |
| | | UACUGCCGGGAAGGAAACCGCACCCAGUCUGGGGAGCAAAAUUC |
| | | UUGCCGGGCUCACCACAGGCGGCGUCGCCGUCUUCAUCGGACAG |
| | | CCUACCGAAGUCGUGAAGGUGCGACUGCAAGCCCAGUCACACCU |
| | | GCAUGGCAUCAAGCCACGUUAUACUGGAACUUACAACGCUUACA |
| | | GGAUUAUCGCCACCACUGAAGGCCUUACUGGACUCUGGAAGGGG |
| | | ACAACUCCUAAUUUAAUGCGAUCAGUUAUCAUUAACUGCACAGA |
| | | GCUCGUUACUUAUGACCUUAUGAAGGAAGCAUUCGUGAAAAACA |
| | | ACAUCUUAGCAGACGACGUCCCCUGUCACCUGGUAUCUGCACUA |
| | | AUCGCCGGAUUUUGUGCUACCGCCAUGUCAUCCCCUGUGGACGU |
| | | CGUAAAGACGCGAUUCAUAAAUUCUCCUCCCGGUCAAUACAAAU |
| | | CGGUCCCCAAUUGUGCCAUGAAAGUGUUCACAAACGAGGGGCCA |
| | | ACCGCCUUUUUCAAAGGGCUUGUGCCCUCUUUUCUGCGACUCGG |
| | | CUCCUGGAAUGUCAUCAUGUUCGUGUGCUUCGAACAGCUAAAAA |
| | | GGGAGCUGUCUAAAUCCAGGCAAACAAUGGACUGUGCUACUUAA |
| 121 | mol_type = RNA origin = synthetic construct | AUGGGCGGUCUUACAGCAAGCGACGUUCAUCCCACACUCGGGGU |
| | | GCAGCUCUUUAGUGCGGGAAUCGCCGCUUGCCUCGCCGACGUGA |
| | | UAACCUUUCCGUUGGACACAGCCCAAAGUACGCCUUCAAGUCCAG |
| | | GGCGAGUGCCCAACUUCUUCCGUGAUUCGAUAUAAAGGCGUGUU |
| | | GGGAACCAUUACUGCCGUCGUGAAGACCGAAGGCCGCAUGAAGU |
| | | UAUACAGCGGGCUGCCCGCUGGGUUGCAGAGGCAGAUAAGCUCU |
| | | GCCUCCCUGCGUAUCGGCUUGUAUGACACGGUUCAAGAAUUCCU |
| | | CACUGCCGGGAAGGAGACCGCCCCCAGCUUGGGCAGCAAAAUCC |
| | | UGGCCGGGCUCACUACAGGCGGCGUGGCGUGUAUUUAUUGGACAA |
| | | CCUACCGAAGUUGUUAAGGUACGACUUCAAGCUCAAUCUCACCU |
| | | GCACGGAAUUAAACCGCGCUACACUGGAACUUACAACGCUUAUC |
| | | GAAUUAUUGCCACUACAGAAGGCUUAAACAGGACUUUGGAAGGG |
| | | GACGACCCCUAAUUUAAUGCGGUCGGUUAUCAUCAAUUGCACCG |
| | | AAUUGGUGCAUACGAUCUUAUGAAAGAGGCUUUCGUGAAAAA |
| | | CAACAUCUUGGCAGAUGACGUUCCUUGUCACUUAGUAUCCGCAU |

| SEQ ID NO | | RNA Sequence |
|---|---|---|
| | | UAAUCGCCGGAUUCUGUGCUACUGCCAUGUCCUCCCCUGUUGAU<br>GUUGUCAAGACAAGGUUCAUAAAUUCGCCUCCUGGCCAAUAUAA<br>AAGUGUCCCCAAUUGUGCCAUGAAAGUCUUCACCAACGAAGGGC<br>CUACCGCCUUCUUUAAGGGGCUCGUCCCGUCUUUUCUGCGUCUG<br>GGGUCCUGGAACGUGAUCAUGUUUGUGUGUUUUGAGCAAUUGA<br>AAAGAGAGCUGUCGAAGUCCAGACAGACGAUGGACUGUGCUACA<br>UGA |
| 122 | mol_type = RNA origin = synthetic construct | AUGGGUGGACUGACCGCUUCGGACGUUCACCCUACCCUGGGAGU<br>GCAGCUCUUCAGUGCAGGAAUCGCCGCGUGCCUCGCCGAUGUCA<br>UUACUUUUCCUUUAGAUACAGCUAAAGUGCGGCUGCAAGUCCAA<br>GGAGAAUGCCCCACAUCCUCAGUCAUUCGAUACAAAGGCGUUUU<br>GGGGACCAUCACUGCCGUGGUGAAAACAGAGGGCCGAAUGAAAC<br>UCUACAGCGGGCUGCCAGCCGGAUUGCAGAGGCAGAUCAGCUCC<br>GCAUCUCUGCGAAUCGGGUUGUACGACACAGUUCAGGAGUUUCU<br>GACUGCCGGAAAGGAGACCGCACCUAGUUUGGGCAGUAAAAUCC<br>UGGCCGGACUCACUACAGGUGGCGUCGCCGUAUUUAUCGGGCAG<br>CCCACCGAAGUUGUGAAGGUCCGGCUGCAGGCUCAGUCUCACCU<br>ACACGGGAUUAAGCCACGCUACACUGGGACAUACAACGCUUAUA<br>GGAUCAUCGCCACCACUGAAGGUCUUACGGGACUUUGGAAAGGC<br>ACAACACCCAACCUAAUGCGAUCUGUUAUCAUCAAUUGUACUGA<br>GCUGGUCACUUACGAUCUGAUGAAAGAAGCGUUUGUGAAAAAC<br>AACAUUCUCGCAGAUGACGUUCCAUGUCAUCUAGUGUGUCCGCACU<br>CAUCGCCGGGUUCUGUGCAACCGCCAUGUCCAGCCCUGUUGACG<br>UCGUUAAGACAAGAUUUAUUAAUUCUCCACCAGGCCAAUACAAA<br>AGCGUCCCUAACUGUGCCAUGAAAGUGUUCACAAACGAGGGCCC<br>UACUGCCUUCUUUAAGGGGCUGGUUCCCUCCUUUCUGCGACUCG<br>GAUCCUGGAAUGUCAUCAUGUUCGUAUGCUUUGAGCAAUUGAA<br>AAGAGAGUUGUCUAAGUCAAGACAAACCAUGGACUGCGCCACAU<br>GA |
| 123 | mol_type = RNA origin = synthetic construct | AUGGGCGGCCUAACCGCGAGUGACGUUCACCCUACUUUAGGGGU<br>GCAGCUUUUCAGCGCAGGCAUCGCAGCCUGCCUCGCUGACGUCA<br>UUACAUUUCCCCUCGACACCGCCAAGGUCCGCCUGCAAGUUCAG<br>GGUGAAUGUCCGACUUCCUCCGUCAUUCGUUAUAAAGGCGUGCU<br>CGGGACCAUUACCGCUGUGGUGAAGACCGAAGGCCGCAUGAAAC<br>UGUAUAGCGGGCUGCCUGCGGGUCUCCAGAGACAAAUCAGCUCA<br>GCCUCUCUCCGUAUCGGCCUAUACGAUACAGUUCAAGGAAUUCUU<br>AACGGCCGGGAAAGAAACCGCACCUUCUCUGGGGAAGCAAAAUUC<br>UCGCCGGGCUCACUACAGGCGGCGUCGCCGUCUUCAUCGGCCAA<br>CCAACUGAAGUUGUUAAGGUACGACUGCAAGCUCAAAGUCACCU<br>UCACGGCAUCAAGCCUCGCUACACUGGCACUUACAAUGCUUACA<br>GGAUUAUCGCUACAACCGAAGGCCUAACUGGACUCUGGAAGGGG<br>ACAACACCCAAUUUGAUGCGGUCUGUUAUUAUCAACUGCACAGA<br>ACUCGUGACAUACGAUCUCAUGAAGGAAGCUUUCGUGAAGAAUA<br>ACAUCCUGGCUGAUGAUGUCCCUUGCCACCUCGUAUCUGCUCUG<br>AUCGCAGGAUUUUGUGCUACCGCUAUGUCAAGCCCUGUCGACGU<br>CGUAAAAACACGGUUUAUAAACUCCCCCCCUGGCCAGUACAAGU<br>CUGUCCCUAAUUGUGCCAUGAAAGUCUUCACCAAUGAAGGCCCC<br>ACUGCCUUUUUCAAGGGGCUCGUGCCCUCCUUUCUGCGGCUCGG<br>GUCCUGGAAUGUCAUCAUGUUUGUGUGUUUUGAGCAACUGAAA<br>AGGGAGUUAAGUAAAUCCAGGCAGACCAUGGACUGCGCCACAUG<br>A |
| 124 | mol_type = RNA origin = synthetic construct | AUGGGCGGUCUGACAGCAUCCGACGUGCAUCCUACUCUGGGGGU<br>GCAGCUCUUCAGCGCCGGGAUUGCCGCGUGCCUCGCUGAUGUUA<br>UUACUUUUCCCCUGGACACCGCUAAGGUCCGUCUGCAAGUUCAG<br>GGCGAGUGCCCCACCUCUUCUGUAAUUCGCUAUAAAGGCGUCCU<br>UGGAACCAUAACUGCUGUUGUGAAGACUGAAGGCCGUAUGAAGC<br>UCUAUAGCGGGCUGCCUGCGGGCCUGCAGAGGCAGAUCAGCUCC<br>GCCUCCCUCCGUAUCGGCCUGUACGACACUGUCCAAGAAUUCCU<br>CACUGCUGGAAAAGAAACUGCACCCAGUCUGGGGGAGUAAGAUCC<br>UCGCCGGGCUUACUACAGGUGGCGUCGCUGUCUUUAUUGGACAG<br>CCAACAGAGGUCGUGAAGGUGCGACUGCAGGCUCAAAGCCACCU<br>GCAUGGAAUUAAACCUCGCUACACUGGGAACCUAUAACGCCUAUA<br>GGAUUAUCGCAACCACCGAAGGUUUAACUGGGCUCUGGAAGGGA<br>ACAACUCCUAAUCUAAUGCGAUCAGUUAUUAUCAAUUGCACUGA<br>ACUCGUUACUUAUGAUCUCAUGAAGGAAGCCUUUGUGAAAAAU<br>AAUAUAUUGGCGGACGACGUCCCUUGUCACCUGGUAUCCGCACU<br>UAUCGCCGGAUUUUGUGCUACCGCUAUGUCCAGCCCUGUCGAUG<br>UUGUUAAAACAAGAUUUAUAAACUCUCCCCCCUGGUCAAUAUAAA<br>AGUGUUCCUAACUGUGCCAUGAAGGUCUUCACUAACGAAGGCCC<br>CACAGCUUUUUUUAAGGGGCUUGUUCCCUCCUUUUUGCGGCUGG<br>GUUCUUGGAAUGUGAUCAUGUUCGUCUGUUUUGAACAGCUGAA<br>AAGGGAGCUAUCCAAAUCCAGACAGACGAUGGACUGUGCCACCU<br>GA |

-continued

| SEQ ID NO | | RNA Sequence |
|---|---|---|
| 125 | mol_type = RNA origin = synthetic construct | AUGGGUGGUCUGACUGCUAGUGAUGUGCAUCCAACACUGGGGGU GCAACUUUUCAGUGCUGGGAUCGCCGCCUGCCUCGCCGACGUUA UAACUUUUCCGCUGGAUACCGCCAAGGUGCGCCUACAGGUUCAG GGCGAGUGUCCUACCUCUUCAGUGAUUCGAUAUAAAGGCGUCUU GGGUACCAUCACUGCUGUGGGUGAAGACUGAAGGCCGCAUGAAGC UCUACAGCGGCCUGCCAGCGGGCUUACAGAGGCAGAUCAGCUCC GCUUCCCUGCGCAUCGGCCUGUACGACACAGUCCAAGAAUUUCU UACUGCCGGGAAGGAAACCGCUCCAAGUUUGGGGUCCAAAAUUC UCGCCGGGCUCACCACAGGUGGUGUCGCUGUCUUUAUUGGCCAG CCUACCGAAGUGGUGAAGGUCCGACUCCAAGCUCAGUCCCAUCU CCACGGAAUUAAGCCUCGGUACACCGGGACUUACAAUGCUUAUA GAAUCAUCGCUACCACAGAAGGAUUAACUGGACUUUGGAAGGGC ACGACACCCAAUUUGAUGCGGUCAGUCAUUAUCAACUGCACAGA GUUGGUUACCUAUGAUCUCAUGAAGGAAGCCUUUGUGAAAAAU AACAUUCUGGCAGACGACGUUCCAUGUCACCUGGUUUCUGCAUU AAUCGCUGGGUUUUGUGCUACCGCCAUGUCAUCUCCUGUCGACG UUGUGAAAACCCGGUUUAUAAAUUCACCACCUGGCCAGUAUAAA AGCGUUCCCAAUUGUGCCAUGAAGGUGUUCACAAAUGAGGGCCC UACCGCAUUCUUCAAAGGGCUCGUCCCAUCCUUUCUCCGUCUAG GAUCCUGGAAUGUCAUAAUGUUCGUCUGUUUUGAACAGUUAAA AAGGGAACUGAGUAAAUCCAGGCAAACAAUGGACUGCGCUACCU GA |
| 126 | mol_type = RNA origin = synthetic construct | AUGGGAGGUCUGACUGCAAGCGACGUACACCCAACUCUAGGAGU GCAGCUCUUUAGUGCAGGAAUUGCCGCUUGUCUCGCUGAUGUCA UUACUUUUCCCUUGGAUACCGCUAAGGUCCGUCUGCCAGGUCCAG GGCGAGUGUCCUACUUCAUCUGUCAUUCGUUAUAAAGGCGUAUU GGGAACCAUUACAGCAGUCGUGAAAACUGAGGGCCGCAUGAAGC UCUACAGUGGGCUUCCAGCUGGCCUGCAGCGACGAUCAGCUCG GCGUCCCUGCGUAUUGGCCUAUACGACACAGUCCAAGAGUUCCU CACAGCUGGGAAGGAGACCGCGCCAAGUUUGGGCAGCAAAAUAC UCGCCGGUCUCACAACAGGCGGCGUGGCCGUAUUCAUUGGACAG CCCACUGAGGUCGUUAAGGUACGACUACAGGCUCAGUCUCAUCU CCAUGGGAUAAAACCUCGCUAUACUGGCACAUACAAUGCUUAUC GAAUCAUCGCAACAACCGAAGGCCUCACAGGGCUGUGGAAAGGG ACGACACCUAACUUAAUGCGGUCAGUGAUCAUCAACUGCACUGA ACUGGUGACCUACGAUCUGAUGAAGGAAGCUUUCGUAAAGAAU AACAUUCUGGCAGACGACGUCCCAUGUCAUCUAGUAUCCGCGUU AAUCGCCGGAUUUUGUGCCACUGCUAUGUCUUCCCUGUCGAUG UUGUGAAGACACGAUUCAUAAACUCUCCUCCCGGCCAAUACAAA UCUGUCCCUAAUUGUGCCAUGAAGGUCUUCACAAACGAGGGUCC AACAGCCUUUUUUAAGGGGCUCGUUCCUUCGUUUCUUCGGCUUG GGUCCUGGAAUGUGAUUCAUGUUUGUGUGUUUGAACAAUUGAA GAGAGAGCUCUCUAAGUCCAGGCAGACAAUGGAUUGUGCCACCU AG |
| 127 | mol_type = RNA origin = synthetic construct | AUGGGUGGACUGACAGCCAGCGAUGUGCACCCUACGCUCGGAGU UCAGCUCUUUAGCGCCGGCAUCGCCGCCUGCCUUGCCGAUGUCA UUACAUUUCCUCUAGACACUGCUAAGGUACGCCUGCAGGUCCAA GGAGAAUGUCCAACAUCAUCCGUAAUUCGGUACAAAGGUGUAUU GGGGACCAUCACCGCUGUCGUGAAGACUGAGGGCCGCAUGAAAC UUUACAGCGGGCUGCCAGCGGGCCUGCAGAGGCAAAUAAGCUCU GCAUCCCUGCGCAUCGGCCUGUACGACACAGUUCAGGAAUUUCU UACUGCCGGGAAGGAGACUGCACCCAGUCUGGGGAGCAAAAUUC UCGCCGGCCUCACUACAGGCGGCGUAGCCGUAUUCAUAGGACAA CCUACCGAAGUCGUCAAGGUAAGACUGCAGGCCCAAUCACAUCU GCAUGGGAUCAAGCCACGCUACACCGGGACAUACAAUGCCUAUA GGAUUAUCGCCACAACCGAAGGCUUAACUGGGCUCUGGAAGGGG ACAACCCCUAAUUUAAUGCGAUCAGUUAUCAUUAAUUGUACGGA ACUGGUGACAUACGACCUCAUGAAGGAAGCUUUUGUAAAAAAU AACAUCCUGGCAGACGACGUCCCAUGUCAUUUGGUCUCUGCAUU AAUCGCCGGAUUUUGUGCCACCGCUAUGUCAAGCCCUGUCGAUG UUGUCAAGACGCGGUUCAUAAAUUCCCCUCCCGGCCAGUACAAA AGUGUUCCUAACUGUGCCAUGAAGGUGUUUCACCAACGAAGGCCU CACUGCAUUCUUCAAGGGGUUGGUUCCUUCCUUUCUGCGGCUCG GAUCCUGGAAUGUCAUCAUGUUUGUGUGUUUCGAGCAGCUGAA AAGAGAGCUCUCUAAGUCUAGACAAACAAUGGACUGCGCAACCU GA |
| 128 | mol_type = RNA origin = synthetic construct | AUGGGGGGUCUCACAGCUUCUGACGUUCAUCCAACACUGGGAGU GCAGCUCUUUAGCGCAGGAAUUGCCGCUUGUCUCGCCGACGUCA UAACUUUUCCCUUAGACACCGCUAAGGUCCGCCUGCAGGUCCAG GGCGAAUGUCCUACAUCUUCAGUGAUCCGCUAUAAAGGCGUCUU GGGAACCAUCACUGCAGUCGUGAAGACCGAAGGCCGUAUGAAGC UGUACAGCGGACUGCCGGCCAGGGGCUCCAGAGGCAAAUAAGUUCC |

-continued

| SEQ ID NO | | RNA Sequence |
|---|---|---|
| | | GCAUCACUGCGAAUUGGUCUGUAUGACACCGUUCAGGAAUUCCU |
| | | GACAGCCGGAAAAGAAACAGCACCUAGCUUGGGUAGCAAAAUUC |
| | | UGGCCGGUCUCACCACAGGCGGCGUUGCUGUUUUCAUAGGACAG |
| | | CCCACCGAGGUAGUAAAGGUGCGACUUCAGGCACAGAGUCAUCU |
| | | GCACGGCAUCAAACCGCGCUACACGGGCACUUACAACGCUUAUA |
| | | GGAUCAUCGCCACUACAGAAGGCCUAACUGGUCUGUGGAAGGGC |
| | | ACAACACCUAAUUUAAUGCGAUCUGUUAUUAUCAAUUGUACUGA |
| | | ACUCGUAACAUAUGACCUCAUGAAGGAAGCCUUUGUAAAAAACA |
| | | ACAUCCUCGCAGAUGACGUCCCUUGCCAUUUGGUUUCAGCUCUA |
| | | AUAGCAGGAUUUUGUGCUACUGCCAUGUCUUCUCCCGUCGACGU |
| | | UGUAAAGACACGAUUCAUUAAUUCUCCACCUGGUCAGUAUAAAU |
| | | CUGUCCCUAAUUGUGCAAUGAAAGUCUUCACAAACGAAGGCCCA |
| | | ACCGCAUUCUUCAAAGGGCUUGUGCCUUCCUUUCUGCGACUCGG |
| | | CUCCUGGAACGUUAUCAUGUUCGUGUGCUUCGAACAACUGAAGC |
| | | GGGAGCUGUCAAAAUCCAGGCAGACAAUGGACUGUGCCACAUGA |
| 129 | mol_type =<br>RNA<br>origin =<br>synthetic<br>construct | AUGGGCGGGCUCACAGCAAGCGACGUCCAUCCUACACUGGGUGU |
| | | GCAGCUCUUCAGUGCAGGAAUAGCCGCCUGUCUCGCCGAUGUUA |
| | | UUACUUUUCCCUUAGAUACGGCAAAGGUCCGCCUUCAAGUCCAG |
| | | GGCGAGUGCCCAACAUCAUCUGUCAUACGUUAUAAGGGCGUAUU |
| | | GGGCACCAUCACAGCCGUGGUGAAAACCGAAGGACGGAUGAAGC |
| | | UCUAUAGCGGACUGCCAGCAGGGCUACAAAGGCAGAUCAGCUCA |
| | | GCCUCUCUACGGAUCGGAUUGUACGACACUGUCCAAGAAUUCCU |
| | | CACUGCGGGGAAGGAAACAGCACCCAGUUUGGGGAGUAAAAUCC |
| | | UGGCCGGUCUCACCACAGGCGGCGUCGCCGUCUUCAUUGGACAG |
| | | CCUACAGAGGUGGUGAAGGUUCGACUGCAAGCCCAAAGUCACCU |
| | | GCACGGAAUCAAGCCACGCUACACUGGAACUUAUAACGCUUACA |
| | | GGAUUAUCGCCACCACCGAAGGGCUCACUGGGCUGUGGAAGGGG |
| | | ACAACUCCUAACUUGAUGCGGUCUGUCAUUAUCAACUGCACCGA |
| | | AUUGGUGACUUACGAUCUCAUGAAAGAAGCUUUUGUGAAAAAC |
| | | AACAUCCUUGCAGACGACGUUCCUUGUCACCUGGUGUCCGCACU |
| | | CAUCGCCGGAUUCUGUGCCCACCGCUAUGUCUAGCCCUGUCGACG |
| | | UUGUCAAAACACGUUUUAUAAACUCUCCGCCCGGCCAGUACAAA |
| | | AGCGUCCCCAACUGUGCCAUGAAGGUGUUCACCAACGAGGGUCC |
| | | CACUGCCUUCUUCAAGGGUCUGGUUCCUUCUUUUCUGCGGCUCG |
| | | GAUCUUGGAAUGUGAUCAUGUUCGUCUGCUUUGAACAAUUAAA |
| | | ACGGGAGCUGUCCAAGAGUAGACAAACGAUGGACUGCGCCACGU |
| | | GA |

EQUIVALENTS

Those skilled in the art will recognize or be able to ascertain using no more than routine experimentation, many equivalents to the specific embodiments of the present invention described herein. Such equivalents are intended to be encompassed by the following claim.

All publications, patents, and patent applications mentioned in this specification are herein incorporated by reference into the specification to the same extent as if each individual publication, patent or patent application was specifically indicated to be incorporated herein by reference.

The invention claimed is:

1. A pharmaceutical composition comprising:
   a synthetic mRNA comprising the nucleotide sequence set forth in SEQ ID NO: 6;
   wherein the synthetic mRNA is packaged in a lipid nanoparticle (LNP).

2. The pharmaceutical composition of claim 1, wherein the LNP comprises (C14-4: non-cationic lipids (NCL): Cholesterol:PEG/Lipid Conjugate) at a molar ratio of (35:16: 46.5:2.5), (50:10:38.5:1.5) or (56.5:10:31.8:1.7).

3. The pharmaceutical composition of claim 1, wherein the LNP comprises (SM-102:NCL:Cholesterol:PEG/Lipid Conjugate) at a molar ratio of (50:10:38.5:1.5), (48.3:9.1: 40.5:2.1) or (46.6:10.4:41.2:1.8).

4. The pharmaceutical composition of claim 1, wherein all uridine nucleotides of the synthetic mRNA are substituted with pseudouridines.

5. The pharmaceutical composition of claim 1, wherein all uridine nucleotides of the synthetic mRNA are substituted with N1-Methylpseudouridines.

6. A pharmaceutical composition comprising:
   a synthetic mRNA comprising the nucleotide sequence set forth in SEQ ID NO: 3;
   wherein the synthetic mRNA is packaged in a lipid nanoparticle (LNP).

7. The pharmaceutical composition of claim 6, wherein the LNP comprises (C14-4: non-cationic lipids (NCL): Cholesterol:PEG/Lipid Conjugate) at a molar ratio of (35:16: 46.5:2.5), (50:10:38.5:1.5) or (56.5:10:31.8:1.7).

8. The pharmaceutical composition of claim 6, wherein the LNP comprises (SM-102:NCL:Cholesterol:PEG/Lipid Conjugate) at a molar ratio of (50:10:38.5:1.5), (48.3:9.1: 40.5:2.1) or (46.6:10.4:41.2:1.8).

9. The pharmaceutical composition of claim 6, wherein all uridine nucleotides of the synthetic mRNA are substituted with pseudouridines.

10. The pharmaceutical composition of claim 6, wherein all uridine nucleotides of the synthetic mRNA are substituted with N1-Methylpseudouridines.

11. A pharmaceutical composition comprising:
    a synthetic mRNA comprising the nucleotide sequence set forth in SEQ ID NO: 4;
    wherein the synthetic mRNA is packaged in a lipid nanoparticle (LNP).

12. The pharmaceutical composition of claim 11, wherein the LNP comprises (C14-4: non-cationic lipids (NCL): Cholesterol:PEG/Lipid Conjugate) at a molar ratio of (35:16: 46.5:2.5), (50:10:38.5:1.5) or (56.5:10:31.8:1.7).

13. The pharmaceutical composition of claim 11, wherein the LNP comprises (SM-102:NCL:Cholesterol:PEG/Lipid Conjugate) at a molar ratio of (50:10:38.5:1.5), (48.3:9.1: 40.5:2.1) or (46.6:10.4:41.2:1.8).

14. The pharmaceutical composition of claim 11, wherein all uridine nucleotides of the synthetic mRNA are substituted with pseudouridines.

15. The pharmaceutical composition of claim 11, wherein all uridine nucleotides of the synthetic mRNA are substituted with N1-Methylpseudouridines.

* * * * *